US009410168B2

(12) United States Patent
Silverman et al.

(10) Patent No.: US 9,410,168 B2
(45) Date of Patent: *Aug. 9, 2016

(54) BIOREFINERY SYSTEM, METHODS AND COMPOSITIONS THEREOF

(71) Applicant: Calysta, Inc., Menlo Park, CA (US)

(72) Inventors: Joshua A. Silverman, Los Altos Hills, CA (US); Sol M. Resnick, Encinitas, CA (US); Michael Mendez, San Diego, CA (US); Renee M. Saville, Mountain View, CA (US); Sungwon Lee, Fremont, CA (US); Luan Nguyen, San Ramon, CA (US)

(73) Assignee: Calysta, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/813,804

(22) Filed: Jul. 30, 2015

(65) Prior Publication Data

US 2015/0353971 A1 Dec. 10, 2015

Related U.S. Application Data

(63) Continuation of application No. 13/941,027, filed on Jul. 12, 2013, now Pat. No. 9,371,549.

(60) Provisional application No. 61/671,542, filed on Jul. 13, 2012.

(51) Int. Cl.
| | |
|---|---|
| *C12P 7/64* | (2006.01) |
| *C12N 15/74* | (2006.01) |
| *C12P 5/00* | (2006.01) |
| *C10L 1/02* | (2006.01) |
| *C10L 1/04* | (2006.01) |
| *C10G 3/00* | (2006.01) |
| *C12N 9/16* | (2006.01) |
| *C12N 9/00* | (2006.01) |
| *C12N 1/16* | (2006.01) |
| *C12N 1/20* | (2006.01) |
| *C12N 9/10* | (2006.01) |
| *C10G 47/00* | (2006.01) |

(52) U.S. Cl.
CPC . *C12P 7/649* (2013.01); *C10G 3/00* (2013.01); *C10G 3/50* (2013.01); *C10G 47/00* (2013.01); *C10L 1/02* (2013.01); *C10L 1/04* (2013.01); *C12N 1/16* (2013.01); *C12N 1/20* (2013.01); *C12N 9/1029* (2013.01); *C12N 9/16* (2013.01); *C12N 9/93* (2013.01); *C12N 15/74* (2013.01); *C12P 5/00* (2013.01); *C12P 7/6409* (2013.01); *C12P 7/6463* (2013.01); *C12Y 301/02* (2013.01); *C12Y 602/01003* (2013.01); *C10G 2300/1014* (2013.01); *C10L 2200/0469* (2013.01); *C10L 2270/02* (2013.01); *C10L 2270/04* (2013.01); *C10L 2290/26* (2013.01); *C12Y 203/01039* (2013.01); *C12Y 604/01002* (2013.01); *Y02E 50/13* (2013.01); *Y02E 50/343* (2013.01); *Y02P 20/52* (2015.11); *Y02P 30/20* (2015.11)

(58) Field of Classification Search
None
See application file for complete search history.

(56) References Cited

U.S. PATENT DOCUMENTS

| | | | |
|---|---|---|---|
| 4,269,940 A * | 5/1981 | Patel | C07D 301/02 435/148 |
| 6,492,135 B1 | 12/2002 | Larsen | |
| 6,689,601 B2 | 2/2004 | Koffas et al. | |
| 6,818,424 B2 | 11/2004 | DiCosimo et al. | |
| 7,026,464 B2 | 4/2006 | Dicosimo et al. | |
| 7,098,005 B2 | 8/2006 | Dicosimo et al. | |
| 7,579,163 B2 | 8/2009 | Eriksen et al. | |
| 7,799,550 B2 | 9/2010 | Moen et al. | |
| 8,062,392 B2 | 11/2011 | Bryan et al. | |
| 8,093,306 B2 | 1/2012 | Blevins et al. | |
| 8,129,154 B2 | 3/2012 | Burk et al. | |
| 8,129,155 B2 | 3/2012 | Trawick et al. | |
| 8,153,850 B2 | 4/2012 | Hall et al. | |
| 8,168,686 B2 | 5/2012 | Blevins et al. | |
| 8,173,044 B1 | 5/2012 | Cheiky et al. | |
| 8,177,870 B2 | 5/2012 | Herrema et al. | |
| 8,592,198 B2 | 11/2013 | Moen et al. | |
| 2003/0003528 A1 | 1/2003 | Brzostowicz et al. | |
| 2005/0054030 A1 | 3/2005 | Schnoor et al. | |
| 2005/0163802 A1 | 7/2005 | Jorgensen et al. | |
| 2006/0057726 A1 | 3/2006 | Sharpe | |
| 2008/0026005 A1 | 1/2008 | Miguez et al. | |
| 2008/0057554 A1 | 3/2008 | Huhnke et al. | |
| 2009/0263877 A1 | 10/2009 | Eriksen et al. | |

(Continued)

FOREIGN PATENT DOCUMENTS

| | | |
|---|---|---|
| EP | 0 296 484 A2 | 12/1988 |
| EP | 1 265 982 B1 | 9/2004 |

(Continued)

OTHER PUBLICATIONS

Stein LY et al. Genome sequence of obligate methanotroph Methylosinus trichosporium strain OB3b. 2010. Journal of Bacteriology. vol. 192, No. 24. p. 6497-6498.*

Henstra et al., "Microbiology of synthesis gas fermentation for biofuel production," *Current Opinion in Biotechnology* 18:200-206 (2007).

Jahnke, "The effects of growth temperature on the methyl sterol and phospholipid fatty acid composition of *Methylococcus capsulatus* (Bath)," *FEMS Microbiology Letters* 93:209-212 (1992).

(Continued)

*Primary Examiner* — Paul Holland
(74) *Attorney, Agent, or Firm* — Seed IP Law Group PLLC

(57) ABSTRACT

The present disclosure relates to bioengineering approaches for producing biofuel and, in particular, to the use of a $C_1$ metabolizing microorganism reactor system for converting $C_1$ substrates, such as methane or methanol, into biomass and subsequently into biofuels, bioplastics, or the like.

19 Claims, 6 Drawing Sheets

(56) References Cited

U.S. PATENT DOCUMENTS

| | | |
|---|---|---|
| 2010/0068772 A1 | 3/2010 | Downey |
| 2010/0221813 A1 | 9/2010 | Miguez et al. |
| 2010/0248344 A1 | 9/2010 | Schroder et al. |
| 2010/0297749 A1 | 11/2010 | Aravanis et al. |
| 2011/0165639 A1 | 7/2011 | Ascon et al. |
| 2011/0236919 A1 | 9/2011 | Zahn et al. |
| 2012/0003705 A1 | 1/2012 | Jin et al. |
| 2012/0116138 A1 | 5/2012 | Goodall et al. |
| 2012/0142983 A1 | 6/2012 | Vermeiren et al. |
| 2013/0189763 A1 | 7/2013 | Dalla-Betta et al. |
| 2014/0024872 A1 | 1/2014 | Silverman et al. |

FOREIGN PATENT DOCUMENTS

| | | | |
|---|---|---|---|
| EP | 1 497 409 B1 | 5/2006 | |
| EP | 1 183 326 B1 | 3/2007 | |
| EP | 1 478 376 B1 | 9/2010 | |
| EP | 1 419 234 B1 | 3/2011 | |
| EP | 2 427 200 B1 | 4/2014 | |
| WO | 01/60974 A2 | 8/2001 | |
| WO | 02/18617 A2 | 3/2002 | |
| WO | 03/016460 A1 | 2/2003 | |
| WO | 03/068003 A1 | 8/2003 | |
| WO | 03/072133 A2 | 9/2003 | |
| WO | 03/089625 A2 | 10/2003 | |
| WO | 2007/136762 A2 | 11/2007 | |
| WO | WO 2007136762 A2 * | 11/2007 | ............... C10L 1/02 |
| WO | 2009/009391 A2 | 1/2009 | |
| WO | WO 2009009391 A2 * | 1/2009 | ............. C07C 67/03 |
| WO | 2009/140695 A1 | 11/2009 | |
| WO | WO 2009140695 A1 * | 11/2009 | ............... C10L 1/02 |
| WO | 2009/151342 A1 | 12/2009 | |
| WO | 2010/128312 A2 | 10/2010 | |
| WO | 2011/038132 A1 | 3/2011 | |
| WO | 2012/045022 A2 | 4/2012 | |
| WO | 2012/088071 A2 | 6/2012 | |
| WO | 2014/012055 A1 | 1/2014 | |

OTHER PUBLICATIONS

Kaluzhnaya et al., "Taxonomic Characterization of New Alkaliphilic and Alkalitolerant Methanotrophs from Soda Lakes of the Southeastern Transbaikal Region and description of *Methylomicrobium buryatense* sp.nov.," *System. Appl. Microbiol.* 24:166-176 (2001).

Kosa et al., "Lipids from heterotrophic microbes: advances in metabolism research," *Trends in Biotechnology* 29(2):53-61 (Feb. 2011).

Lee et al., "Heterologous Co-expression of *accA, fabD*, and Thioesterase Genes for Improving Long-Chain Fatty Acid Production in *Pseudomonas aeruginosa* and *Escherichia coli*," *Appl Biochem Biotechnol* 167:24-38 (2012).

Schrader et al., "Methanol-based industrial biotechnology: current status and future perspectives of methylotrophic bacteria," *Trends in Biotechnology* 27(2):107-115 (Feb. 1, 2009).

Summons et al., "Carbon isotopic fractionation in lipids from methanotrophic bacteria: Relevance for interpretation of the geochemical record of biomarkers," *Geochimica et Cosmochimica Acta.* 58(13):2853-2863 (1994).

Chen, "A microbial polyhydroxyalkanoates (PHA) based bio- and materials industry," *Chem. Soc. Rev.* 38:2434-2446, 2009.

Fang et al., "Characterization of methanotrophic bacteria on the basis of intact phospholipid profiles," *FEMS Microbiology Letters* 189:67-72, 2000.

Folch et al., "A Simple Method for the Isolation and Purification of Total Lipides From Animal Tissues," *J. Biol. Chem.* 226(1):497-509, May 1957.

Hanson et al., "Methanotrophic Bacteria," *Microbiological Reviews* 60(2):439-471, Jun. 1996.

Helm et al., "Characterizing a stable methane-utilizing mixed culture used in the synthesis of a high-quality biopolymer in an open system," *Journal of Applied Microbiology* 101:387-395, 2006.

Höfer et al., "Production of functionalized polyhydroxyalkanoates by genetically modified *Methylobacterium extorquens* strains," *Microbial Cell Factories* 9:70, 2010, 13 pages.

Kim et al., "Creating auxotrophic mutants in *Methylophilus methylotrophus* AS1 by combining electroporation and chemical mutagenesis," *Appl. Microbiol. Biotechnol.* 48:105-108, 1997.

Madison et al., "Metabolic Engineering of Poly(3-Hydroxyalkanoates): From DNA to Plastic," *Microbiology and Molecular Biology Reviews* 63(1):21-53, Mar. 1999.

Marx et al., "Development of improved versatile broad-host-range vectors for use in methylotrophs and other Gram-negative bacteria," *Microbiology* 147:2065-2075, 2001.

McDonald et al., "Molecular Ecology Techniques for the Study of Aerobic Methanotrophs," *Applied and Environmental Microbiology* 74(5): 1305-1315, Mar. 2008.

Ramsay et al., "Production of Poly-(β-Hydroxybutyric-Co-β-Hydroxyvaleric) Acids," *Applied and Environmental Microbiology* 56(7):2093-2098, Jul. 1990.

Stolyar et al., "Role of multiple gene copies in particulate methane monooxygenase activity in the methane-oxidizing bacterium *Methylococcus capsulatus* Bath," *Microbiology* 145:1235-1244, 1999.

Templeton et al., "Variable carbon isotope fractionation expressed by aerobic $CH_4$-oxidizing bacteria," *Geochimica et Cosmochimica Acta* 70:1739-1752, 2006.

Toyama et al., "Construction of insertion and deletion *mxa* mutants of *Methylobacterium extorquens* AM1 by electroporation," *FEMS Microbiology Letters* 166:1-7, 1998.

Vuilleumier et al., "Genome Sequence of the Haloalkaliphilic Methanotrophic Bacterium *Methylomicrobium alcaliphilum* 20Z," *Journal of Bacteriology* 194(2):551-552, Jan. 2012.

Zellner et al., "A study of three anaerobic methanogenic bioreactors reveals that syntrophs are diverse and different from reference organisms," *FEMS Microbiology Ecology* 22:295-301, 1997.

Keeling et al., "Monthly Atmospheric $^{13}C/^{12}C$ Isotopic Ratios for 11 SIO Stations," Trends: A Compendium of Data on Global Change. Carbon Dioxide Information Analysis Center, Oak Ridge National Laboratory, U.S. Department of Energy, Oak Ridge, Tenn., U.S.A. (3 pages) (Feb. 16, 2010).

Kendall et al., "Resources on Isotopes—Periodic Table—Carbon," Isotope Tracers Project, Menlo Park, Calif. (4 pages) http://wwwrcamnl.wr.usgs.gov/isoig/period/c_iig (1995).

Park et al., "Metabolic Fractionation of $C^{13}$ & $C^{12}$ in Plants," *Plant Physiology* 36(2):133-138 (Mar. 1961).

\* cited by examiner

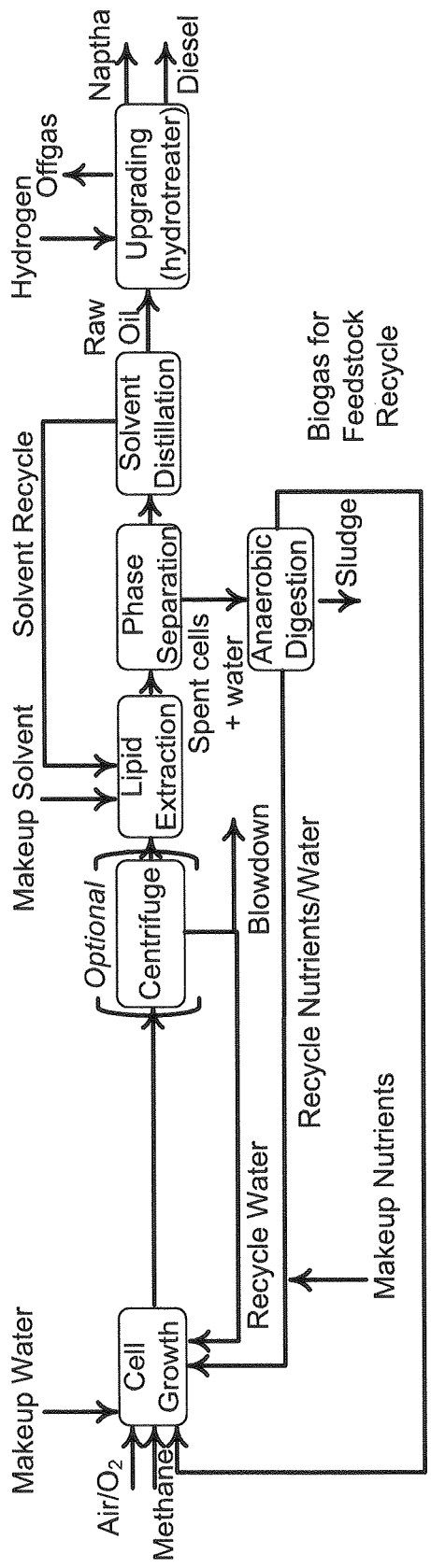
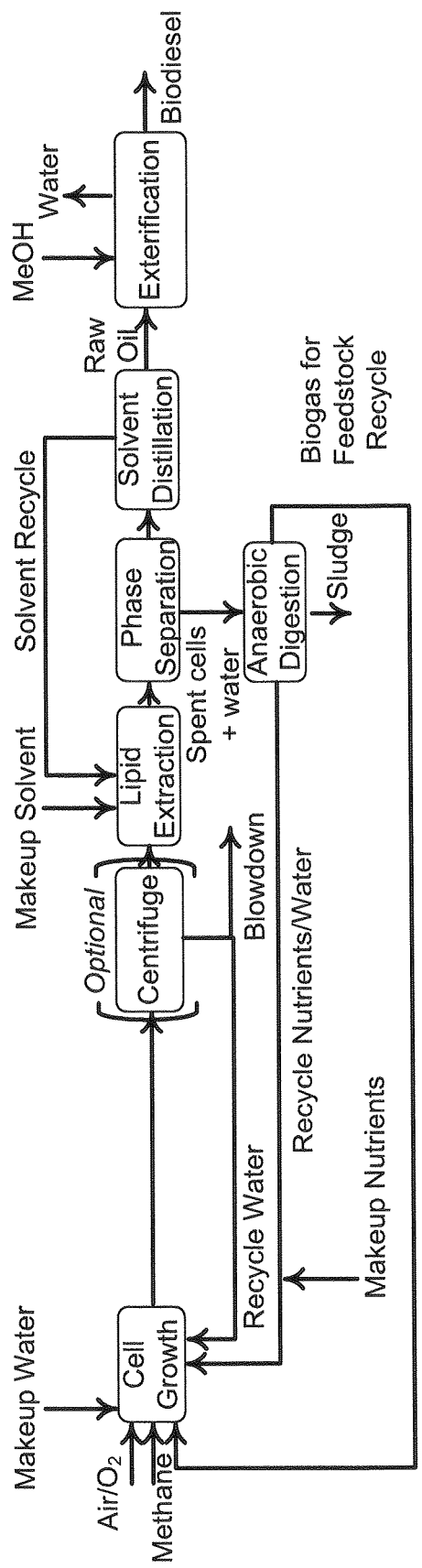
Fig. 1
Fig. 2

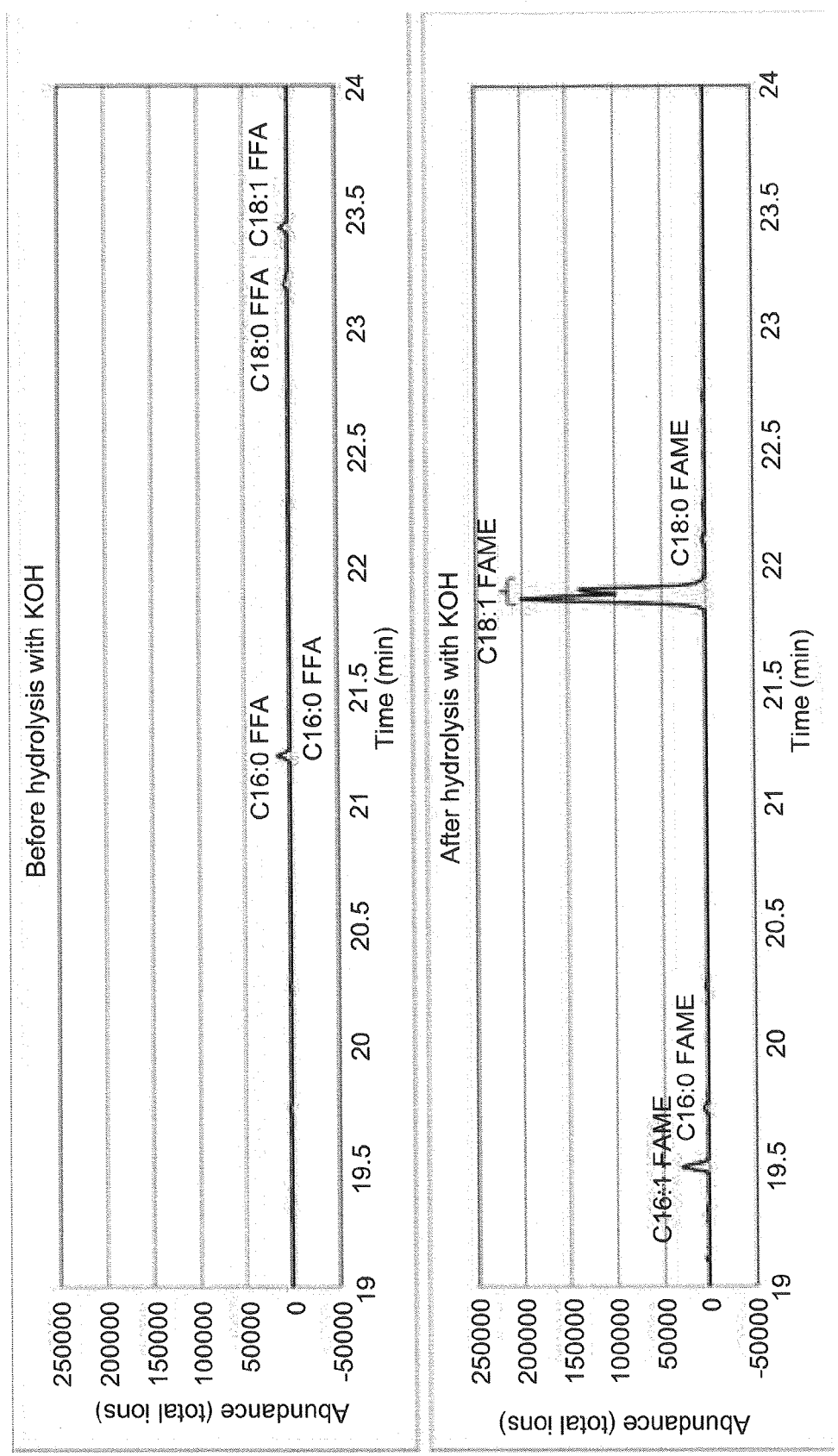

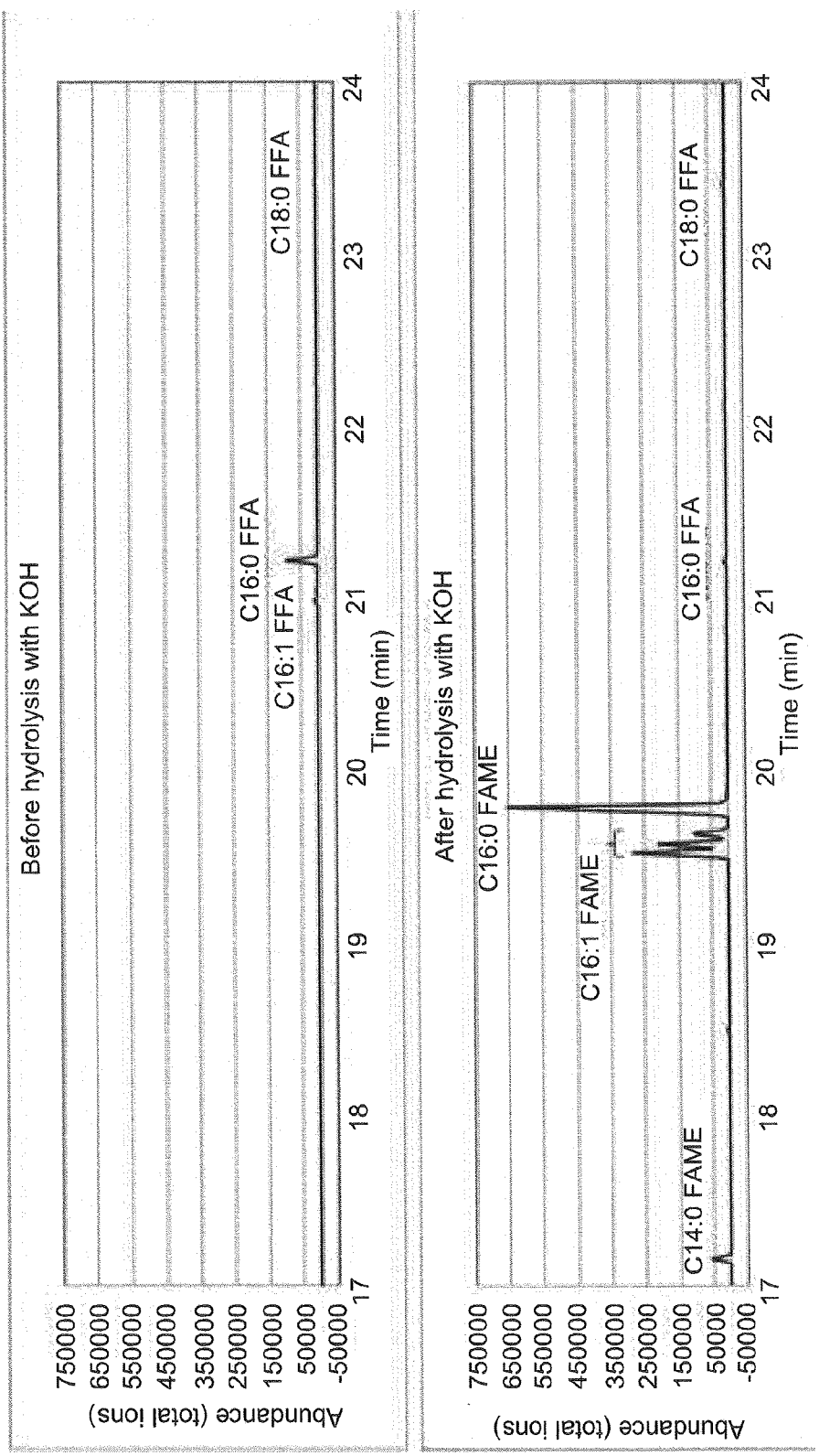

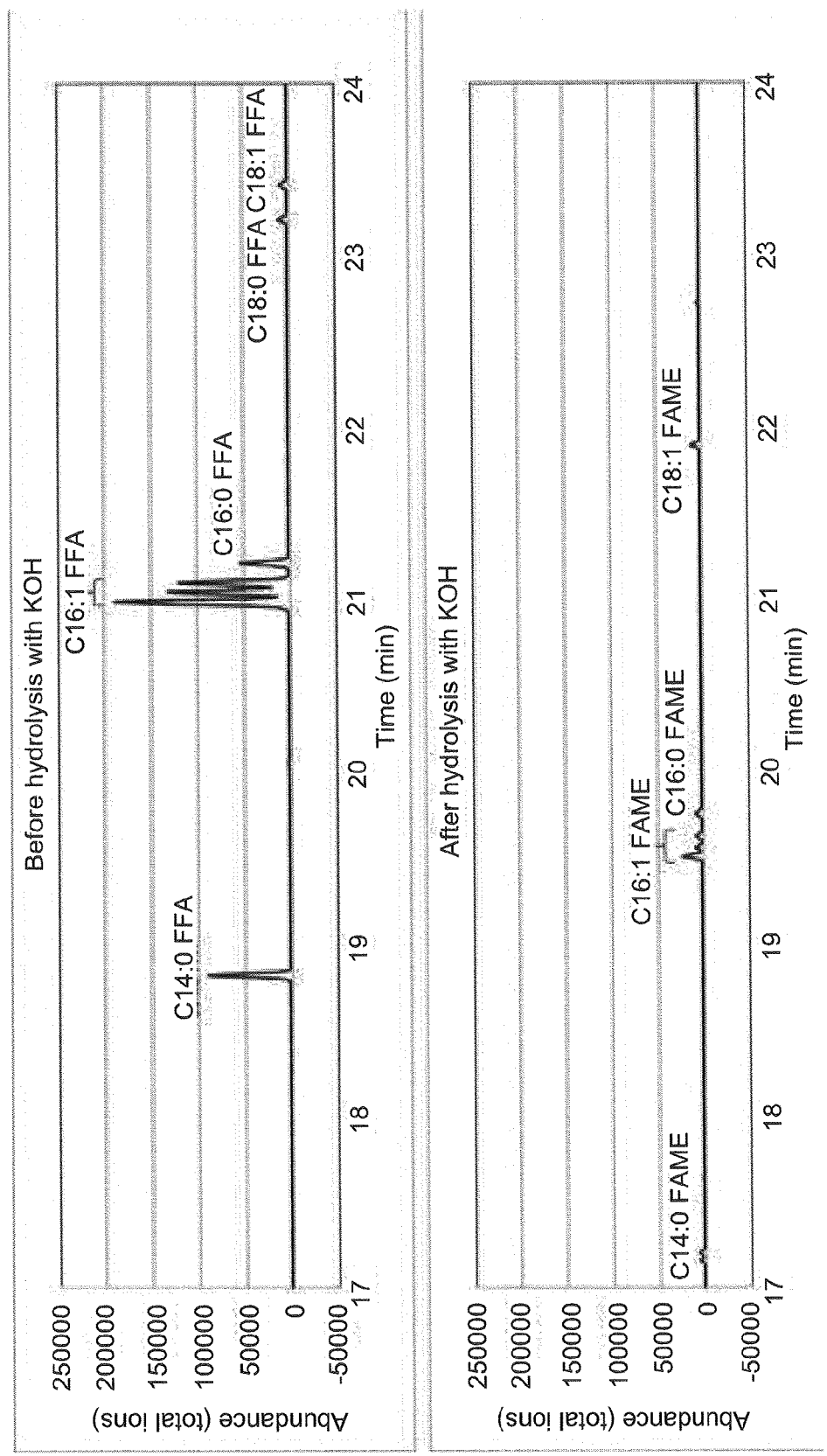

BIOREFINERY SYSTEM, METHODS AND COMPOSITIONS THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200206_404C1_SEQUENCE_LISTING.txt. The text file is 146 KB, was created on Aug. 19, 2015, and is being submitted electronically via EFS-Web.

BACKGROUND

1. Technical Field

The present disclosure relates to bioengineering approaches for producing biofuel and, in particular, to the use of a $C_1$ metabolizing microorganism reactor system for converting $C_1$ substrates, such as methane or methanol, into biomass and subsequently into biofuels, bioplastics, or the like.

2. Description of the Related Art

With the ever increasing depletion of fossil fuel deposits, the increasing production of greenhouse gases and recent concerns about climate change, substituting biofuels (e.g., ethanol, biodiesel) for fossil fuels has become an industrial focus. But, biofuels generated to date have their own difficulties and concerns. First generation biofuels are derived from plants (e.g., starch; cane sugar; and corn, rapeseed, soybean, palm, and other vegetable oils), but these fuel crops compete with crops grown for human and animal consumption. The amount of farm land available is not sufficient to satisfy both global food and fuel needs. Therefore, second generation biofuels are being produced from, for example, cellulose or algae. But, technical difficulties in production, along with the high cost of production, have not made second generation biofuels any more cost-effective or accessible.

Third or next generation biofuels made from alternative feedstocks (i.e., not sugar, corn, algae) are needed. In this regard, methane is one of the most abundant domestic carbon feedstocks and is sourced primarily from natural gas. The recent rise in domestic production of methane (from 48 bft$^3$/day in 2006 to 65 bft$^3$/day in 2012) has driven the cost of natural gas to record lows (from about $14.00/MMBTU in 2006 to about $2.50/MMBTU in 2012). Domestic natural gas is primarily produced by hydraulic fracturing ("fracking"), but methane can also be obtained from other sources, such as landfills and sewage. In addition, capturing methane sources will have a significant environmental benefit since methane has a 23× greater greenhouse gas contribution relative to $CO_2$.

But, methane's volatility makes transportation and direct usage as a fuel problematic. For this reason, there is a strong incentive to convert the gas to a liquid form to allow for easy transport to the point of use. Two main approaches are currently being pursued: liquefaction leading to liquefied natural gas (LNG) and chemical conversion to convert gas-to-liquid (GTL) (Patel, 7th World Congress of Chemical Engineering, Glasgow, Scotland, UK, 2005). The Fischer-Tropsch (F-T) process is currently the most prevalent GTL approach for converting methane from natural gas to higher-order hydrocarbons (Patel, 2005). Note that the F-T process takes syngas as an input which is produced from natural gas by steam reforming (syngas can also be sourced from coal gasification, by high-temperature reaction with water and oxygen). The F-T process yields petroleum products consistent with today's fuel supply, but suffers from a number of drawbacks, including low yields, poor selectivity (making downstream utilization complex), and requires significant capital expenditure and scale to achieve economical production (Spath and Dayton, December 2003 NREL/TP-510-34929). The massive scale required for an F-T plant (more than $2 B capital cost for a typical plant [Patel, 2005]) also represents a significant limitation due to the large amount of methane feedstock required to supply continuous operation of such a plant. As methane transportation is prohibitively expensive in most cases, such a plant must be co-located with either a large gas source or a pipeline. An additional cost and scaling factor is the economics of gas-scrubbing technologies (Spath and Dayton, 2003), as F-T catalysts are highly sensitive to common contaminants in natural gas that survive the syngas conversion process.

F-T plants have been in operation semi-continuously since 1938. Several companies are currently investigating introduction of new plants given the current availability and price of methane discussed above. However, despite significant research and development over the last 70+ years, the limitations of F-T technology prevent broad adoption of commercial GTL processes. The requirements for ready access to large volumes of clean gas, combined with massive capital investment, currently limit natural gas based F-T plants to successful operation in only a few locations world-wide (Spath and Dayton, 2003). The high minimum processing requirement for a GTL or LNG plant, combined with the high cost of transport, result in smaller methane sources being referred to as 'stranded' gas (for example, natural gas produced at off-shore oil wells, or methane off-gas from landfills). In the current absence of efficient small-scale conversion technologies, such stranded gas sources are typically vented to atmosphere or flared, as methane accumulation presents a significant safety risk.

In view of the limitations associated with the production of first, second and next generation biofuels, there is clearly a need in the art for new methods of efficiently and cost-effectively producing alternative fuels without taxing the environment or competing with food production. The present invention solves this problem by providing efficient and cost-effective methods for producing biofuels and other products using bioengineering.

BRIEF SUMMARY

In one aspect, the present disclosure provides a $C_1$ metabolizing non-photosynthetic microorganism biomass having a $\delta^{13}C$ of less than about −30‰, or ranging from about −40‰ to about −60‰. In other aspects, the present disclosure provides an oil composition or a biofuel composition having molecules comprising hydrogen and carbon atoms, wherein the hydrogen and carbon atoms are at least about 50% to about 99% of the weight of the composition and wherein the $\delta^{13}C$ of the composition ranges from about −35‰ to about −50‰, −45‰ to about −35‰, or about −50‰ to about −40‰, or about −45‰ to about −65‰, or about −60‰ to about −70‰, or about −30‰ to about −70‰.

In certain embodiments, the present disclosure provides $C_1$ metabolizing microorganisms that are prokaryotes or bacteria, such as *Methylomonas, Methylobacter, Methylococcus, Methylosinus, Methylocystis, Methylomicrobium, Methanomonas, Methylophilus, Methylobacillus, Methylobacterium, Hyphomicrobium, Xanthobacter, Bacillus, Paracoccus, Nocardia, Arthrobacter, Rhodopseudomonas,* or *Pseudomonas*. In further embodiments, $C_1$ metabolizing bacteria are a methanotroph or a methylotroph. Exemplary methanotrophs include *Methylomonas, Methylobacter, Methylococcus,*

*Methylosinus, Methylocystis, Methylomicrobium, Methanomonas,* or a combination thereof.

Exemplary methanotroph species include *Methylomonas* sp. 16a (ATCC PTA 2402), *Methylosinus trichosporium* OB3b (NRRL B-11,196), *Methylosinus sporium* (NRRL B-11,197), *Methylocystis parvus* (NRRL B-11,198), *Methylomonas methanica* (NRRL B-11,199), *Methylomonas albus* (NRRL B-11,200), *Methylococcus capsulatus* Bath (NCIMB 11132), *Methylobacter capsulatus* Y (NRRL B-11,201), *Methylobacterium organophilum* (ATCC 27,886), *Methylomonas* sp. AJ-3670 (FERM P-2400), *Methylomicrobium alcaliphilum, Methylocella silvestris, Methylacidiphilum infernorum, Methylibium petroleiphilum, Methylococcus capsulatus* Bath, or high growth variants thereof.

Exemplary methylotroph species include *Methylobacterium extorquens, Methylobacterium radiotolerans, Methylobacterium populi, Methylobacterium chloromethanicum, Methylobacterium nodulans,* or a combination thereof.

In still further embodiments, the present disclosure provides $C_1$ metabolizing microorganisms that are syngas metabolizing bacteria, such as *Clostridium, Moorella, Pyrococcus, Eubacterium, Desulfobacterium, Carboxydothermus, Acetogenium, Acetobacterium, Acetoanaerobium, Butyribaceterium, Peptostreptococcus,* or any combination thereof. Exemplary syngas metabolizing bacteria include *Clostridium autoethanogenum, Clostridium ljungdahli, Clostridium ragsdalei, Clostridium carboxydivorans, Butyribacterium methylotrophicum, Clostridium woodii, Clostridium neopropanologen,* or any combination thereof.

In certain other embodiments, $C_1$ metabolizing microorganisms are eukaryotes such as yeast, including *Candida, Yarrowia, Hansenula, Pichia, Torulopsis,* or *Rhodotorula*.

In further embodiments, the $C_1$ metabolizing non-photosynthetic microorganism is a recombinant microorganism comprising a heterologous polynucleotide encoding a fatty acid producing enzyme, a formaldehyde assimilation enzyme, or a combination thereof. In certain embodiments, the heterologous polynucleotide encodes a thioesterase, a malonyl CoA-acyl carrier protein transacylase, an acetyl-CoA carboxylase, or any combination thereof. For example, the thioesterase may be a codon optimized *E. coli* tesA lacking a periplasmic targeting sequence; the malonyl CoA-acyl carrier protein transacylase may be a codon optimized *E. coli* fabD; and the acetyl-CoA carboxylase may be a codon optimized *E. coli* accA, accB, accC, accD, or any combination thereof. In certain further embodiments, the $C_1$ metabolizing microorganism further comprises a mutation that minimizes or eliminates fatty acid-CoA ligase activity.

BRIEF DESCRIPTION OF THE DRAWINGS

FIG. 1 shows an exemplary conceptual model of a $C_1$ metabolizing microorganism reactor system for methane capture and conversion into an alkane fuel in accordance with certain embodiments of this disclosure.

FIG. 2 shows an exemplary conceptual model of a $C_1$ metabolizing microorganism reactor system for methane capture and conversion into biodiesel in accordance with certain embodiments of this disclosure.

FIGS. 4A and 4B show GC/MS chromatograms of an oil composition extracted from *M. trichosporium* before (A) and after (B) hydrolysis and transesterification with KOH in toluene:methanol.

FIGS. 5A and 5B show GC/MS chromatograms of an oil composition extracted from *M. capsulatus* before (A) and after (B) hydrolysis and transesterification with KOH in toluene:methanol.

FIGS. 6A and 6B show GC/MS chromatograms of an oil composition extracted from *Methylomonas* sp. 16a before (A) and after (B) hydrolysis and transesterification with KOH in toluene:methanol.

DETAILED DESCRIPTION

Figure 3A:
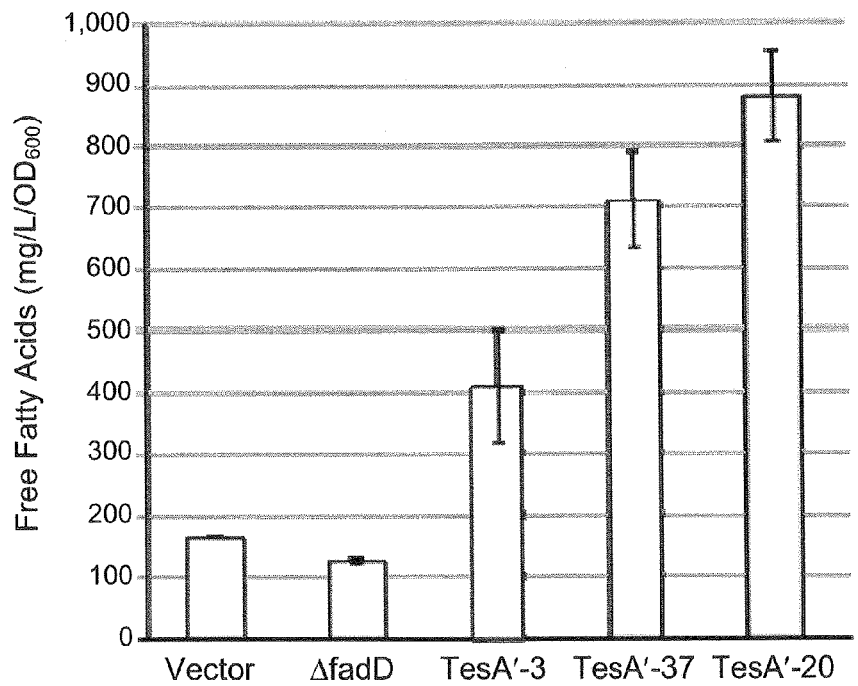
FIGS. 3A and 3B show that recombinant *Methylobacter capsulatus* expressing TesA' (TesA gene from *E. coli* with the periplasmic targeting sequence removed) causes (A) an increase in in free fatty acid production, and (B) the increase was primarily due to increased levels of C16:0 and C18:0 lipids.

The instant disclosure provides compositions, methods and systems for generating biofuels and bioplastics, in which $C_1$ metabolizing microorganisms are cultured to generate biomass maximized for bio-oil accumulation. For example, a methane-to-biofuel fermentation process is provided, which is a scalable commercial process. This new approach can use, for example, methylotroph or methanotroph bacteria as a new host system to generate biomass for biofuel in the form of, for example, esterified biodiesel or alkane fuels for hydrotreatment, or for bioplastics in form of polyhydroalkanoates (PHAs). Furthermore, an oil composition of interest can be obtained from methylotroph or methanotroph bacteria because these organisms can accumulate significant quantities of membrane lipids under conditions described herein and, moreover, these microorganisms produce high membrane content.

By way of background, methane from a variety of sources, including natural gas, represents an abundant domestic resource. Chemical approaches developing gas-to-liquids (GTL) technology to improve the use of methane as a fuel have met with only limited success to date despite significant investment. In contrast, little effort has been expended to deploy modern bioengineering approaches toward GTL process development. Several limitations, most notably the cost of sugar feedstocks, have prevented the economical production of biofuels using microbial systems. Exploiting inexpensive, domestically abundant carbon feedstocks, such as methane, represents an economically sustainable biofuel production alternative. New production microorganisms have been developed with new bioengineering tools and techniques to provide an industrial-scale GTL bioprocess as described herein. Furthermore, fuel properties following refining and upgrading of extracted lipids demonstrate the drop-in potential for applications such as diesel, gasoline, jet fuel, or olefins.

In one aspect, the present disclosure provides a method for making fuel by refining an oil composition derived from a $C_1$ metabolizing non-photosynthetic microorganism in a refining unit to produce fuel. Additionally, this disclosure provides a method for making fuel by converting biomass from a culture primarily comprising a $C_1$ metabolizing non-photosynthetic microorganism into an oil composition and refining the oil composition into a fuel. In another aspect, this disclosure provides a biorefinery that includes a processing unit in which an oil composition is derived from a $C_1$ metabolizing non-photosynthetic microorganism; and a refining unit for refining the oil composition to produce a fuel.

In still another aspect, the instant disclosure provides an oil composition or biofuel composition derived therefrom having molecules comprising hydrogen and carbon atoms, wherein the hydrogen and carbon atoms are at least about 50% to about 99% of the weight of the composition and wherein the $\delta^{13}C$ of the composition is less than −30‰ or ranges from about −70‰ to about −35‰, or, when blended with a fuel component to produce a fuel product, ranges from about −37‰ to about −10‰. In a related aspect, the instant disclosure provides a biomass having a $\delta^{13}C$ of less than −30‰ or ranging from about −35‰ to about −50‰, −45‰ to about −35‰, or about −50‰ to about −40‰, or about −45‰ to about −65‰, or about −60‰ to about −70‰, or about −30‰ to about −70‰.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means ±20% of the indicated range, value, or structure, unless otherwise indicated. The term "consisting essentially of" limits the scope of a claim to the specified materials or steps, or to those that do not materially affect the basic and novel characteristics of the claimed invention. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

As used herein, "$C_1$ substrate" or "$C_1$ compound" refers to any carbon containing molecule or composition that lacks a carbon-carbon bond. Exemplary $C_1$ substrates include natural gas, unconventional natural gas, syngas, methane, methanol, formaldehyde, formic acid or a salt thereof, carbon monoxide, carbon dioxide, methylated amines (e.g., methylamine, dimethylamine, trimethylamine, etc.), methylated thiols, methyl halogens (e.g., bromomethane, chloromethane, iodomethane, dichloromethane, etc.), cyanide, or any combination thereof.

As used herein, "$C_1$ metabolizing microorganism" or "$C_1$ metabolizing non-photosynthetic microorganism" refers to any microorganism having the ability to use a $C_1$ substrate as a source of energy or as its primary source of energy and biomass, and may or may not use other carbon substrates (such as sugars and complex carbohydrates) for energy and biomass. For example, a $C_1$ metabolizing microorganism may oxidize a $C_1$ substrate, such as methane or methanol. $C_1$ metabolizing microorganisms include bacteria (such as methanotrophs and methylotrophs) and yeast. In certain embodiments, a $C_1$ metabolizing microorganism does not include a photosynthetic microorganism, such as algae. In certain embodiments, the $C_1$ metabolizing microorganism will be an "obligate $C_1$ metabolizing microorganism," meaning its sole source of energy are $C_1$ substrates. In further embodiments, a $C_1$ metabolizing microorganism (e.g., methanotroph) will be cultured in the presence of a $C_1$ substrate feedstock (i.e., using the $C_1$ substrate as a source of energy).

As used herein, the term "methylotrophic bacteria" refers to any bacteria capable of oxidizing any compound in any form (e.g., solid, liquid, gas) that contains at least one carbon and that do not contain carbon-carbon bonds. In certain embodiments, a methylotrophic bacterium may be a methanotroph. For example, "methanotrophic bacteria" refers to any methylotrophic bacteria that have the ability to oxidize methane as a source of carbon and energy, which may be the primary source of carbon and energy. Exemplary methanotrophic bacteria include *Methylomonas, Methylobacter, Methylococcus, Methylosinus, Methylocystis, Methylomicrobium,* or *Methanomonas.* In certain embodiments, the methylotrophic bacterium is an "obligate methylotrophic bacterium," which refers to bacteria that are limited to the use of $C_1$ substrates for the generation of energy. In certain embodiments, methylotrophic bacteria are "facultative methanotrophic bacteria" that are naturally able to use multi-carbon substrates, such as acetate, pyruvate, succinate, malate, or ethanol, in addition to $C_1$ substrates as their carbon and energy source. Facultative methanotrophs include some species of *Methylocella, Methylocystis, Methylocapsa* (e.g., *Methylocella silvestris, Methylocella palustris, Methylocella tundrae, Methylocystis daltona* SB2, *Methylocystis bryophila,* and *Methylocapsa aurea* KYG), and *Methylobacterium organophilum* (ATCC 27,886).

As used herein, the term "CO utilizing bacterium" refers to a bacterium that naturally possesses the ability to oxidize carbon monoxide (CO) as a source of carbon and energy. Carbon monoxide may be utilized from "synthesis gas" or "syngas", a mixture of carbon monoxide and hydrogen produced by gasification of any organic feedstock, such as coal, coal oil, natural gas, biomass, or waste organic matter. CO utilizing bacteria does not include bacteria that must be genetically modified for growth on CO as its carbon source.

As used herein, "syngas" refers to a mixture comprising carbon monoxide (CO) and hydrogen ($H_2$). Syngas may also include $CO_2$, methane, and other gases in smaller quantities relative to CO and $H_2$.

"Growth" is defined as an increase in cell mass. This may occur through cell division (replication) and the formation of new cells during "balanced growth," or during "unbalanced growth" when cellular mass increases due to the accumulation of a specific compound or polymer, such as certain lipids. In the latter case, growth may be manifest as an increase in cell size due to the accumulation of a biopolymer within the cell.

During "balanced cell growth," all of the feedstocks (electron donors and electron acceptors) and all of the nutrients are present in the ratios required to make all of the macromolecular components of a cell. That is, no feedstock or nutrient limits the synthesis of proteins, complex carbohydrate polymers, fats, or nucleic acids. In contrast, during "unbalanced cell growth," a feedstock or nutrient needed to make one or more of a cell's macromolecules is not present in an amount or ratio required for balanced growth. Accordingly, this feedstock or nutrient becomes limiting and is referred to as a "limiting nutrient."

Some cells may still achieve net growth under unbalanced conditions, but the growth is unbalanced and polymers that can be synthesized in the absence of the limiting feedstock or nutrient will accumulate. These polymers include lipids or intracellular storage products, such as the polydroxyalkanoates (PHAs), including polyhydroxybutyrate (PHB), polyhydroxyvalerate (PHV), and polyhydroxyhexanoate (PHHx)-glycogen, or secreted materials, such as extracellular polysaccharide. Such oil compositions are useful in the production of bioplastics.

Exemplary balanced and unbalanced growth conditions may differ in the nitrogen content in the media. For example, nitrogen constitutes about 12% of dry cell weight, which means that 12 mg/L nitrogen must be supplied (e.g., in a nitrate or ammonium salt form, along with a feedstock and other nutrients in the required stoichiometric ratios) to grow 100 mg/L dry cell weight. Without wishing to be bound by theory, this assumes that fixation of atmospheric nitrogen into ammonia (i.e., via nitrogen fixation) does not represent a significant source of nitrogen for biosynthetic intermediates or cellular constituents. If other feedstock and nutrients are available in the quantities needed to produce 100 mg/L of dry cell weight, but less than 12 mg/L nitrogen is provided, then unbalanced cell growth may occur, with accumulation of polymers that do not contain nitrogen. If nitrogen is subsequently provided, the stored polymer may serve as feedstock for the cell, allowing balanced growth, with replication and production of new cells.

As used herein, the term "growth cycle" as applied to a cell or microorganism refers to the metabolic cycle through which a cell or microorganism moves in culture conditions. For example, the cycle may include various stages, such as a lag phase, an exponential phase, the end of exponential phase, and a stationary phase.

The term "exponential growth", "exponential phase growth", "log phase" or "log phase growth" refer to the rate at which microorganisms are growing and dividing. For example, during log phase, microorganisms are growing at their maximal rate given their genetic potential, the nature of the medium, and the conditions under which they are grown. Microorganism rate of growth is constant during exponential phase and the microorganism divides and doubles in number at regular intervals. Cells that are "actively growing" are those that are growing in log phase. In contrast, "stationary phase" refers to the point in the growth cycle during which cell growth of a culture slows or even ceases. The term "growth-altering environment" refers to energy, chemicals, or living things that have the capacity to either inhibit cell growth or kill cells. Inhibitory agents may include mutagens, drugs, antibiotics, UV light, extreme temperature, pH, metabolic byproducts, organic chemicals, inorganic chemicals, bacteria, viruses, or the like.

As used herein, "high growth variant" refers to an organism, microorganism, bacterium, yeast, or cell capable of growth with a $C_1$ substrate, such as methane or methanol, as the sole or primary carbon and energy source and which possesses an exponential phase growth rate that is faster than the parent, reference or wild-type organism, microorganism, bacterium, yeast, or cell—that is, the high growth variant has a faster doubling time and consequently a high rate of growth and yield of cell mass per gram of $C_1$ substrate metabolized as compared to a parent cell (see, e.g., U.S. Pat. No. 6,689,601).

As used herein, "biofuel" refers to a fuel at least partially derived from "biomass."

As used herein, "biomass" or "biological material" refers to organic material having a biological origin, which may include one or more of whole cells, lysed cells, extracellular material, or the like. For example, the material harvested from a cultured microorganism (e.g., bacterial or yeast culture) is considered the biomass, which can include cells, cell membranes, cell cytoplasm, inclusion bodies, products secreted or excreted into the culture medium, or any combination thereof. In certain embodiments, biomass comprises the $C_1$ metabolizing microorganisms of this disclosure together with the media of the culture in which the $C_1$ metabolizing microorganisms of this disclosure were grown. In other embodiments, biomass comprises a $C_1$ metabolizing microorganisms (whole or lysed or both) of this disclosure recovered from a culture grown on a $C_1$ substrate (e.g., natural gas, methane).

In still other embodiments, biomass comprises the spent media supernatant from a culture of $C_1$ metabolizing microorganism cultured on a $C_1$ substrate. Such a culture may be considered a renewable resource.

As used herein, "oil composition" refers to the lipid content of a biomass (e.g., bacterial culture), including fatty acids, fatty acid esters, triglycerides, phospholipids, polyhyroxyalkanoates, isoprenes, terpenes, or the like. An oil composition of a biomass may be extracted from the rest of the biomass material by methods described herein, such as by hexane or chloroform extraction. In addition, an "oil composition" may be found in any one or more areas of a culture, including the cell membrane, cell cytoplasm, inclusion bodies, secreted or excreted into the culture medium, or any combination thereof. An oil composition is neither natural gas nor crude petroleum.

As used herein, the term "host" refers to a cell or microorganism (e.g., methanotroph) that may be genetically modified with an exogenous nucleic acid molecule to produce a polypeptide of interest (e.g., thioesterase [tesA], acetyl-CoA carboxylase [accABCD], malonyl-CoA-ACP transacylase [fabD]). In certain embodiments, a host cell may optionally already possess or be modified to include other genetic modifications that confer desired properties related or unrelated to the lipid biosynthesis (e.g., deleted, altered or truncated long-chain fatty acid-CoA ligase [fadD]). For example, a host cell may possess genetic modifications that minimize or reduce the degradation of fatty acids, minimize or reduce production of host cell growth inhibitors, provide high growth, tolerance of contaminants or particular culture conditions (e.g., acid tolerance, biocide resistance), ability to metabolize additional carbon substrates, or ability to synthesize further desirable products or intermediates.

As used herein, "recombinant" or "non-natural" refers to an organism, microorganism, cell, nucleic acid molecule, or vector that has at least one genetic alteration or has been modified by the introduction of a heterologous nucleic acid molecule, or refers to a cell that has been altered such that the expression of an endogenous nucleic acid molecule or gene can be controlled. Recombinant also refers to a cell that is derived from a cell or is progeny of a cell having one or more such modifications. Genetic alterations include, for example, modifications introducing expressible nucleic acid molecules encoding proteins or enzymes, or other nucleic acid molecule additions, deletions, substitutions or other functional alteration of a cell's genetic material. For example, recombinant cells may express genes or other nucleic acid molecules that are not found in identical form within the native cell (i.e., unmodified or wild type cell), or may provide an altered expression pattern of endogenous genes, such genes that may otherwise be over-expressed, under-expressed, minimally expressed, or not expressed at all.

Recombinant methods for expression of exogenous or heterologous nucleic acids in microbial organisms are well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999). Exemplary exogenous proteins or enzymes to be expressed include thioesterase, one or more acetyl-CoA carboxylases, malonyl-CoA-ACP transacylase, or any combination thereof. Genetic modifications to nucleic acid molecules encoding enzymes, or functional fragments thereof, can confer a biochemical or metabolic capability to a recombinant cell that is altered from its naturally occurring state.

As used herein, the term "endogenous" or "native" refers to a gene, protein, compound or activity that is normally present in a host cell. The term "homologous" or "homolog" refers to a molecule or activity from an exogenous (non-native) source that is the same or similar molecule or activity as that found in or derived from a host cell, species or strain.

As used herein, "heterologous" nucleic acid molecule, construct or sequence refers to a nucleic acid molecule or portion of a nucleic acid molecule sequence that is not native to a cell in which it is expressed, a nucleic acid molecule or portion of a nucleic acid molecule native to a host cell that has been altered or mutated, or a nucleic acid molecule with an altered expression as compared to the native expression levels under similar conditions. For example, a heterologous control sequence (e.g., promoter, enhancer) may be used to regulate expression of a gene or a nucleic acid molecule in a way that is different than the gene or a nucleic acid molecule that is normally expressed in nature or culture. In certain embodiments, a heterologous nucleic acid molecule may be homologous to a native host cell gene, but may have an altered expression level or have a different sequence or both. In other embodiments, heterologous or exogenous nucleic acid molecules may not be endogenous to a host cell or host genome, but instead may have been added to a host cell by conjugation, transformation, transfection, electroporation, or the like, wherein the added molecule may integrate into the host genome or can exist as extra-chromosomal genetic material (e.g., plasmid or other self-replicating vector).

In certain embodiments, more than one heterologous or exogenous nucleic acid molecule can be introduced into a host cell as separate nucleic acid molecules, as a polycistronic nucleic acid molecule, as a single nucleic acid molecule encoding a fusion protein, or any combination thereof, and still be considered as more than one heterologous or exogenous nucleic acid. For example, a $C_1$ metabolizing microorganism can be modified to express two or more heterologous or exogenous nucleic acid molecules, which may be the same or different, that encode one or more thioesterases as disclosed herein. In certain embodiments, multiple copies of a thioesterase (TE) encoding polynucleotide molecule are introduced into a host cell, which may be two, three, four, five, six, seven, eight, nine, ten or more copies of the same TE or different TE encoding polynucleotides.

When two or more exogenous nucleic acid molecules are introduced into a host $C_1$ metabolizing microorganism, it is understood that the two more exogenous nucleic acid molecules can be introduced as a single nucleic acid molecule (e.g., on a single vector), on separate vectors, integrated into the host chromosome at a single site or multiple sites, and each of these embodiments is still to be considered two or more exogenous nucleic acid molecules. Thus, the number of referenced heterologous nucleic acid molecules or protein activities refers to the number of encoding nucleic acid molecules or the number of protein activities, not the number of separate nucleic acid molecules introduced into a host cell.

The "percent identity" between two or more nucleic acid sequences is a function of the number of identical positions shared by the sequences (i.e., % identity=number of identical positions/total number of positions×100), taking into account the number of gaps, and the length of each gap that needs to be introduced to optimize alignment of two or more sequences. The comparison of sequences and determination of percent identity between two or more sequences can be accomplished using a mathematical algorithm, such as BLAST and Gapped BLAST programs at their default parameters (e.g., Altschul et al., *J. Mol. Biol.* 215:403, 1990; see also BLASTN at www.ncbi.nlm.nih.gov/BLAST).

A "conservative substitution" is recognized in the art as a substitution of one amino acid for another amino acid that has similar properties. Exemplary conservative substitutions are well known in the art (see, e.g., WO 97/09433, p. 10; Lehninger, Biochemistry, $2^{nd}$ Edition; Worth Publishers, Inc. NY:N.Y. (1975), pp. 71-77; Lewin, Genes IV, Oxford University Press, NY and Cell Press, Cambridge, Mass. (1990), p. 8).

As used herein, "overexpressed" when referring to a gene or a protein means an increase in expression or activity of the gene or protein. Increased expression or activity includes expression or activity of a gene or protein being increased above the level of a wild-type (non-genetically engineered) control or reference microorganism. A gene or protein is overexpressed if the expression or activity is in a microorganism where it is not normally expressed or active. A gene or protein is overexpressed if the expression or activity is extended or present longer in the recombinant microorganism than in a wild-type control or reference microorganism.

"Inhibit" or "inhibited," as used herein, refers to an alteration, reduction, down regulation, abrogation or deletion, directly or indirectly, in the expression of a target gene or in the activity of a target molecule (e.g., long-chain fatty acid-CoA ligase) relative to a control, endogenous or reference molecule, wherein the alteration, reduction, down regulation or abrogation is statistically, biologically, industrially, or clinically significant.

As used herein, "biorefinery" refers to a facility that integrates biomass conversion processes and equipment to produce fuels from biomass.

As used herein, "refinery" refers to an oil refinery, or aspects thereof, at which oil compositions (e.g., biomass, biofuel, or fossil fuels such as crude oil, coal or natural gas) may be processed. Exemplary processes carried out at such refineries include cracking, transesterification, reforming, distilling, hydroprocessing, isomerization, or any combination thereof.

Biofuel Production Systems

The systems for generating biofuels of the instant disclosure may include separate units (e.g., close or adjacent to each other, or not), integrated units, or the system itself may be interconnected and partially or fully integrated. The systems of this disclosure may use biomass from a microorganism grown in an integrated biorefinery to generate fuel compositions and fuel products, particularly biofuels. In certain embodiments, a biorefinery uses a single biomass or a mixed biomass to generate fuel (e.g., diesel fuel, jet fuel, gasoline), such as a $C_1$ metabolizing microorganism (e.g., a methanotroph such as *Methylosinus trichosporium* OB3b, *Methylococcus capsulatus* Bath, *Methylomonas* sp. 16a, *Methylomonas methanica*, *Methylomicrobium alcaliphilum*, or a high growth variants thereof) as the biomass.

An exemplary biorefinery system is illustrated in FIG. 1. Such a system can perform one or more of the following steps: culturing a microorganism strain of interest (e.g., a methanotroph, methylotroph or yeast) which may have one or more improved properties (e.g., recombinant, higher growth rate, ability to grow in high pH, improved utilization of nutrients, temperature stability, increased biomass yield), recovering a product such as an oil composition (e.g., fatty acids, triglycerides, phospholipids, isoprenes, terpenes, PHA, or any combination thereof) from the microorganism, and refining the oil composition to produce plastic precursors or one or more fuels, such as jet fuel, diesel fuel, gasoline, or a combination thereof. Different biofuel compositions and products can be produced by the system simultaneously or in series. For example, the system can include a hydrotreating plant or unit that can convert the oil composition to jet fuel and diesel. The system can also include a petroleum refinery that can convert the crude oil and products from the hydrotreating plant to gasoline. For example, the production of jet fuel and diesel fuel can result in additional products, such as naphtha and light hydrocarbons, including propane, that are then used for generating gasoline. Exemplary light hydrocarbons include methane, ethane, propane, butane, pentane, butanol, and isobutanol. In another example, production of gasoline can result in additional products, such as diesel, which can be used for producing jet fuel.

An alternative exemplary biorefinery system is illustrated in FIG. 2. Such a system can perform one or more of the following steps: culturing a microorganism strain of interest (e.g., a methanotroph, methylotroph or yeast) which may have one or more improved properties (e.g., recombinant, higher growth rate, ability to grow in high pH, improved utilization of nutrients, temperature stability, increased biomass yield), recovering a product such as an oil composition (e.g., fatty acids, fatty acid esters, triglycerides, phospholipids, isoprenes, terpenes, PHA, or any combination thereof) from the microorganism, and modifying the oil composition to produce a biodiesel composition. For example, the system can include an esterification plant or unit that can convert the oil composition to biodiesel by reaction with an alcohol. Exemplary alcohols include methanol, ethanol, propanol, butanol, or longer chain fatty alcohols.

In some embodiments, the systems disclosed herein use bacteria, such as methylotrophs or methanotrophs, or yeast as the microorganism. The bacteria or yeast can be harvested and separated from the culture media (if not grown as, for example, a biofilm), resulting in a bacterial or yeast paste. The bacterial or yeast biomass may optionally be dried prior to obtaining an oil composition from the biomass. In certain embodiments, the bacterial or yeast biomass remains wet to some extent and need not be fully dried before the oil composition is derived, separated, or extracted. Bacterial or yeast oil compositions may be extracted from the biomass and be separated from the bacterial or yeast solids or sludge.

Extraction of an oil composition may be accomplished using various different methods or solvents (e.g., a polar solvent, a non-polar solvent, a neutral solvent, an acidic solvent, a basic solvent, hexane, or a combination thereof), such as hexane or acidic methanol or chloroform/methanol mix, in processes such as those described in more detail herein or other extraction methods known in the art.

In certain embodiments, a $C_1$ metabolizing microorganism (e.g., methanotroph) oil composition contained within a harvested biomass is separated from the biomass using high-shear contact with an organic solvent (e.g., hexane) and a conditioning agent. By way of background, the oil dissolves into hexane, or other similar solvents, forming a solution of miscella, whereas water and cellular solids do not dissolve and can be separated from the miscella. The immiscibility of water and hexane is used to produce the desired separation. In certain embodiments, following high-shear mixing, the oil composition/hexane/water mixture is sent to a decanter where it separates into two distinct liquids: a lighter hexane and oil composition phase (miscella), and a heavier water and spent solids phase. In still further embodiments, the miscella from the decanter is fed into a distillation process where the oil composition is separated from the solvent, which allows recovery and reuse of the solvent, and purifies the oil to a point where it is ready for downstream processing. Distillation, for example, takes advantage of the difference in boiling points of the solvent and oil to separate the two components.

In certain embodiments, an oil composition of the present disclosure is refined. Refining may include cracking, transesterification, reforming, distilling, hydroprocessing, isomerization, or a combination thereof. Optionally, refining can involve removal of contaminants. For example heteroatoms and metals can be removed by hydrotreating (e.g., hydrodenitrogenation (HDN), hydrodeoxygenation (HDO), hydrodesulfurization (HDS), hydrodemetallization (HDM)). Hydrotreatment may also be saturation of olefins, distillate hydrotreating, vacuum gas oil hydrotreating, fixed-bed residue hydrotreating, or a combination thereof. Hydrotreatment of an oil composition can produce jet fuel or diesel. The oil composition can also be refined by cracking, such as catalytic cracking to produce gasoline. Representative cracking processes may include catalytic cracking, fluid catalytic cracking, steam cracking, hydrocracking, thermal cracking, thermal catalytic cracking, or a combination thereof. The refining by hydrotreating and cracking can occur concurrently (both processes occurring) or alternatively (one or the other is occurring). The refining processes can also be subsequent to each other, for example, products produced by hydrotreatment, can then be processed by cracking. Products from one refining process (e.g., $H_2$) can also be further used by another refining process. The refining processes can be separate units of the system, or in the same unit. Moreover, the bacterial or yeast solids or sludge can be used to produce fuels, animal feed, or energy, such as methane released from digestion of the solids or sludge.

In certain embodiments, the instant disclosure provides a biorefinery comprising (a) a processing unit in which an oil composition is derived from a $C_1$ metabolizing non-photosynthetic microorganism; and (b) a refining unit for refining the oil composition to produce a fuel. In further embodiments, the biorefinery may further comprise a controlled culturing unit for culturing a $C_1$ metabolizing non-photosynthetic microorganism in the presence of a feedstock comprising a $C_1$ substrate, wherein the cultured bacteria produce the oil composition.

Exemplary controlled culturing units include a fermentor, a bioreactor, a hollow fiber cell, packed bed bioreactor, or the like. In further embodiments, the culture may be grown in the form of liquid-phase fermentation or solid phase fermentation. For example, bacteria, such as methylotrophs or methanotrophs, may be cultured in a bioreactor containing balanced media, or unbalanced media that has limiting quantities of phosphorus, nitrogen, trace elements, oxygen, or any combination thereof, so that certain lipids or other polymers of interest (e.g., PHAs) accumulate in the cells.

In certain embodiments, cultures include a bacterial community, including a variety of methylotrophs or methanotrophs that produce the highest levels of an oil composition of interest (i.e., high w/w ratios of lipids to biomass). A range of bioreactor configurations may be used, including sequencing membrane bioreactors and a continuous multistage dispersed growth configuration. In certain embodiments, a bioreactor is operated to select for bacteria that efficiently produce an oil composition of interest from methane, e.g., bioreactor conditions may select against bacteria that either do not produce an oil composition of interest from methane or produce such a composition inefficiently.

In further embodiments, the present disclosure provides a controlled culturing unit in which a $C_1$ substrate (e.g., methane or syngas) is delivered in a gas phase to microbial biofilms in solid phase fermentation. In other embodiments, balanced or unbalanced growth conditions are established in solid phase fermentation. In still other embodiments, methylotrophs or methanotrophs are grown under balanced growth conditions, harvested and separated from liquid phase, and transferred to a solid phase fermentation chamber where $C_1$ substrate is delivered under unbalanced conditions (e.g., nitrogen is not included) and the bacteria consume the substrate to generate an oil composition of interest.

In certain embodiments, the instant disclosure provides a biorefinery comprising (a) a controlled culturing unit for culturing a $C_1$ metabolizing non-photosynthetic microorganism in the presence of a feedstock comprising a $C_1$ substrate, wherein the cultured bacteria produce the oil composition; (b) a processing unit in which an oil composition is derived or extracted from a $C_1$ metabolizing non-photosynthetic microorganism; and (c) a refining unit for refining the oil composition to produce a fuel. In further embodiments, the feedstock $C_1$ substrate used in the biorefinery is methane, methanol, formaldehyde, formic acid or a salt thereof, carbon monoxide, carbon dioxide, syngas, a methylamine, a methylthiol, or a methylhalogen.

In further biorefinery embodiments, the $C_1$ metabolizing non-photosynthetic microorganism is a methanotroph or methylotroph, the feedstock $C_1$ substrate is natural gas or methane, and the bacteria are cultured under aerobic conditions. In further embodiments, the methanotroph is *Methylosinus trichosporium* OB3b, *Methylococcus capsulatus* Bath, *Methylomonas* sp. 16a, *Methylomonas methanica*, *Methylomicrobium alcaliphilum*, any combination thereof, or a high growth variant thereof, and the methylotroph is *Methylobacterium extorquens*, *Methylobacterium radiotolerans*, *Methylobacterium populi*, *Methylobacterium chloromethanicum*, *Methylobacterium nodulans*, any combination thereof, or a high growth variant thereof. In certain other embodiments, the $C_1$ metabolizing non-photosynthetic microorganism is an obligate $C_1$ metabolizing non-photosynthetic microorganism, such as an obligate methanotroph or methylotroph.

In further embodiments, the $C_1$ metabolizing non-photosynthetic microorganism is a recombinant microorganism comprising a heterologous polynucleotide encoding a fatty acid producing enzyme, a formaldehyde assimilation enzyme, or a combination thereof. For example, biosynthesis of free fatty acids (FFAs), which can be used as precursors for the production of fuels or other high value chemicals, can be enhanced by introducing a thioesterase (TE) gene into a $C_1$ metabolizing non-photosynthetic microorganism of this disclosure (e.g., *Methylosinus trichosporium* OB3b, *Methylococcus capsulatus* Bath, *Methylomonas* sp. 16a, *Methylomonas methanica*). Biosynthesis of FFAs can also be enhanced by optionally introducing more than one TE gene, malonyl CoA-acyl carrier protein transacylase (FabD, also referred to as MCT) gene, one or more genes from the acetyl-CoA carboxylase operon (AccABCD), or any combination thereof. In certain embodiments, the production of FFAs can be improved by over-expressing a malonyl CoA-acyl carrier protein transacylase (FabD, also referred to as MCT) since the first committed step of fatty acid biosynthesis is the conversion of acetyl-CoA to malonyl-CoA by an adenosine triphosphate (ATP)-dependent acetyl-CoA carboxylase followed by the conversion of malonyl-CoA to malonyl-ACP through the FabD enzyme.

In further embodiments, a $C_1$ metabolizing non-photosynthetic microorganism is a recombinant microorganism comprising a genetic modification that minimizes or reduces the degradation of fatty acids. For example, a $C_1$ metabolizing non-photosynthetic microorganism is a recombinant microorganism comprising one or more mutations that truncate or knock-out long-chain fatty acid-CoA ligase activity encoded by one or more endogenous fadD genes.

The nucleic acid sequences encoding wild-type FadD proteins are the reference standard starting point for designing mutant fadD genes. For example, the wild-type FadD protein sequence encoded by *M. trichosporium* OB3b, *M. capsulatus* Bath, *M. methanica*, *M. extorquens*, and *C. ljungdahlii* are provided in GenBank Accession Nos. EFH00931.1, YP_114021.1, YP_004512148.1, YP_002964871.1, and YP_003782065.1, respectively. In certain embodiments, a nucleic acid molecule of a fadD gene encoding any one of above-noted proteins is individually modified to mutate fadD. In Example 2 herein, the fadD gene from various $C_1$ metabolizing microorganism were synthesized to incorporate several stop mutations and frame shifts in the 5'-region of the gene from *M. trichosporium* OB3b (SEQ ID NO.:1), *M. methanica* (SEQ ID NO.:35), *M. extorquens* (SEQ ID NO.:52), and *C. ljungdahlii* (SEQ ID NO.:85). For the *M. capsulatus* fadD gene, a nucleic acid molecule comprising an internal deletion was synthesized so that the remaining 5' and 3' ends of the gene could be joined to maintain the original reading frame (SEQ ID NO.:18).

For certain $C_1$ metabolizing microorganisms wherein the fadD gene sequence is not known (e.g., *Clostridium autoethanogenum*), the genome can be sequenced and the fadD homolog to *E. coli* is identified via a tblastn search (a search of the translated nucleotide gene sequences with the protein sequence of the *E. coli* FadD). For example, a nucleic acid molecule of the *C. autoethanogenum* fadD gene is synthesized to incorporate several stop mutations and frame shifts in the 5'-region of the gene.

In certain embodiments, a mutant fadD nucleic acid molecule is cloned into a plasmid expression vector (and optionally lacking a $C_1$ metabolizing microorganism origin of replication and encoding antibiotic resistance) for conjugation, electroporation, or transformation into a $C_1$ metabolizing microorganism using methods described herein. In certain embodiments, a fadD mutant incorporates into a host cell genome by homologous recombination and results in recombinant cells that lack or have minimal long-chain fatty acid-CoA ligase activity.

In certain embodiments, any one or all of the TE, MCT, and Acc genes introduced into $C_1$ metabolizing microorganisms of this disclosure can be over-expressed and the $C_1$ metabolizing microorganisms may optionally have a mutation that minimizes or eliminates fatty acid-CoA ligase activity (e.g., a fadD knock-out).

In certain embodiments, the biorefinery processing unit is capable of deriving the oil composition by a wet extraction, a supercritical fluid extraction, dry extraction, thermal extraction (e.g., steam stripping, hydrothermal liquefaction, pressure cooking), enzymatic hydrolysis (e.g., of the cell wall), pulsed electric field extraction, microbubbles, hollow fiber extraction, or the like. In further embodiments, the wet extraction comprises use of a polar solvent, a non-polar solvent, a neutral solvent, an acidic solvent, a basic solvent, hexane, or a combination thereof. In certain embodiments, an oil composition is derived or extracted from a cell membrane of the $C_1$ metabolizing non-photosynthetic microorganism or may be recovered from a culture supernatant if secreted or excreted, or a combination thereof. In further embodiments, the biorefinery further comprises a second processing unit, wherein the second processing unit is a waste processing unit for processing residual matter from the refined oil composition, which includes an anaerobic digester, an aerobic digester, or both. In still further embodiments, the biorefinery further comprises a conduit for delivering at least one product from the waste processing unit for use in culturing or maintaining the $C_1$ metabolizing non-photosynthetic microorganism.

In still further embodiments, the biorefinery processing unit further comprises a controlled culturing unit, wherein the controlled culturing unit is a solid phase fermentation unit in which the culturing and processing (e.g., extraction) can occur in the same unit or even the same chamber. In certain embodiments, the biorefinery combined culturing/processing unit includes supercritical fluid extraction, such as by supercritical fluid comprising $CO_2$, methanol, or $H_2O$.

In certain aspects, any of the aforementioned biorefineries are integrated.

$C_1$ Metabolizing Microorganisms

The $C_1$ metabolizing microorganisms of the instant disclosure may be natural, strain adapted (e.g., performing fermentation to select for strains with improved growth rates and increased total biomass yield compared to the parent strain), or recombinantly modified to produce lipids of interest (e.g., genetically altered to express a fatty acid producing enzyme, a formaldehyde assimilation enzyme, or a combination thereof) or to have increased growth rates or both. In certain embodiments, the $C_1$ metabolizing microorganisms are not $C_1$ metabolizing non-photosynthetic microorganisms, such as algae or plants.

In certain embodiments, the present disclosure provides $C_1$ metabolizing microorganisms that are prokaryotes or bacteria, such as *Methylomonas, Methylobacter, Methylococcus, Methylosinus, Methylocystis, Methylomicrobium, Methanomonas, Methylophilus, Methylobacillus, Methylobacterium, Hyphomicrobium, Xanthobacter, Bacillus, Paracoccus, Nocardia, Arthrobacter, Rhodopseudomonas*, or *Pseudomonas*.

In further embodiments, the $C_1$ metabolizing bacteria are a methanotroph or a methylotroph. Exemplary methanotrophs include *Methylomonas, Methylobacter, Methylococcus, Methylosinus, Methylocystis, Methylomicrobium, Methanomonas, Methylocella*, or a combination thereof. Exemplary methylotrophs include *Methylobacterium extorquens, Methylobacterium radiotolerans, Methylobacterium populi, Methylobacterium chloromethanicum, Methylobacterium nodulans*, or a combination thereof.

In certain embodiments, methanotrophic bacteria are genetically engineered with the capability to convert a $C_1$ substrate feedstock into an oil composition. Methanotrophic bacteria have the ability to oxidize methane as a carbon and energy source. Methanotrophic bacteria are classified into three groups based on their carbon assimilation pathways and internal membrane structure: type I (gamma proteobacteria), type II (alpha proteobacteria, and type X (gamma proteobacteria). Type I methanotrophs use the ribulose monophosphate (RuMP) pathway for carbon assimilation whereas type II methanotrophs use the serine pathway. Type X methanotrophs use the RuMP pathway but also express low levels of enzymes of the serine pathway. Methanotrophic bacteria include obligate methanotrophs, which can only utilize $C_1$ substrates for carbon and energy sources, and facultative methanotrophs, which naturally have the ability to utilize some multi-carbon substrates as a carbon and energy source.

Exemplary facultative methanotrophs include some species of *Methylocella, Methylocystis*, and *Methylocapsa* (e.g., *Methylocella silvestris, Methylocella palustris, Methylocella tundrae, Methylocystis daltona* strain SB2, *Methylocystis bryophila*, and *Methylocapsa aurea* KYG), *Methylobacterium organophilum* (ATCC 27,886), *Methylibium petroleiphilum*, or high growth variants thereof. Exemplary obligate methanotrophic bacteria include *Methylococcus capsulatus* Bath (NCIMB 11132), *Methylomonas* sp. 16a (ATCC PTA 2402), *Methylosinus trichosporium* OB3b (NRRL B-11,196), *Methylosinus sporium* (NRRL B-11,197), *Methylocystis parvus* (NRRL B-11,198), *Methylomonas methanica* (NRRL B-11,199), *Methylomonas albus* (NRRL B-11,200), *Methylobacter capsulatus* Y (NRRL B-11,201), *Methylomonas flagellata* sp. AJ-3670 (FERM P-2400), *Methylacidiphilum infernorum* and *Methylomicrobium alcaliphilum*, or high growth variants thereof.

In still further embodiments, the present disclosure provides $C_1$ metabolizing microorganisms that are syngas metabolizing bacteria, such as *Clostridium, Moorella, Pyrococcus, Eubacterium, Desulfobacterium, Carboxydothermus, Acetogenium, Acetobacterium, Acetoanaerobium, Butyribaceterium, Peptostreptococcus*, or any combination thereof. Exemplary syngas metabolizing bacteria include *Clostridium autoethanogenum, Clostridium ljungdahli, Clostridium ragsdalei, Clostridium carboxydivorans, Butyribacterium methylotrophicum, Clostridium woodii, Clostridium neopropanologen*, or any combination thereof.

In certain other embodiments, $C_1$ metabolizing microorganisms are eukaryotes such as yeast, including *Candida, Yarrowia, Hansenula, Pichia, Torulopsis*, or *Rhodotorula*.

In certain other embodiments, the $C_1$ metabolizing non-photosynthetic microorganism is an obligate $C_1$ metabolizing non-photosynthetic microorganism, such as an obligate methanotroph or methylotroph. In further embodiments, the $C_1$ metabolizing non-photosynthetic microorganism is a recombinant microorganism comprising a heterologous polynucleotide encoding a fatty acid producing enzyme, a formaldehyde assimilation enzyme, or a combination thereof. In certain embodiments, any one or all of the TE, MCT, and Acc genes introduced into a $C_1$ metabolizing microorganism of this disclosure can be over-expressed and the $C_1$ metabolizing microorganisms may optionally have a mutation that minimizes or eliminates fatty acid-CoA ligase activity (e.g., a fadD knock-out).

Each of the microorganisms of this disclosure may be grown as an isolated culture, with a heterologous organism that may aid with growth, or one or more of these bacteria may be combined to generate a mixed culture. In still further embodiments, $C_1$ metabolizing non-photosynthetic microorganisms of this disclosure are obligate $C_1$ metabolizing non-photosynthetic microorganisms.

Any one of the aforementioned $C_1$ metabolizing microorganisms can be used as a parent or reference host cell to make a recombinant $C_1$ metabolizing microorganisms of this disclosure.

Codon Optimization

Expression of recombinant proteins may be difficult outside their original host. For example, variation in codon usage bias has been observed across different species of bacteria (Sharp et al., *Nucl. Acids. Res.* 33:1141, 2005). Over-expression of recombinant proteins even within their native host may also be difficult. In certain embodiments, nucleic acid molecules (e.g., nucleic acids encoding thioesterase, fabD, accABCD) to be introduced into a host as described herein may be subjected to codon optimization prior to introduction into the host to ensure protein expression is effective or enhanced. Codon optimization refers to alteration of codons in genes or coding regions of nucleic acids before transformation to reflect the typical codon usage of the host without altering the polypeptide encoded by the non-natural DNA molecule. Codon optimization methods for optimum gene expression in heterologous hosts have been previously described (see, e.g., Welch et al., *PLoS One* 4:e7002, 2009; Gustafsson et al., *Trends Biotechnol.* 22:346, 2004; Wu et al., *Nucl. Acids Res.* 35:D76, 2007; Villalobos et al., *BMC Bioinformatics* 7:285, 2006; U.S. Patent Publication Nos. 2011/0111413 and 2008/0292918; disclosure of which methods are incorporated herein by reference, in their entirety).

Similarly, exogenous nucleic acid molecules of this disclosure encoding polypeptide variants may be designed using the phylogenetic-based methods described in the references noted above (U.S. Pat. No. 8,005,620; Gustafsson et al.; Welch et al.; Villalobos et al.; Minshull et al.). Each variant polypeptide generated by these methods will retain at least 50% activity (preferably 100% or more activity) and have a polypeptide sequence that is at least 90%, at least 91%, at least 92%, at least 93%, at least 94%, at least 95%, at least 96%, at least 97%, at least 98%, at least 99% identical, or 100% identical to a reference or parental wild-type polypeptide sequence. In certain embodiments, variant polypeptides will include at least one amino acid substitution (e.g., 1, 2, 3, 5, 6, 7, 8, 9 or 10 or more or up to 20, 25, or 30 substitutions) at a pre-determined position relative to a reference or parental wild-type enzyme, provided that a variant retains an activity of interest (e.g., thioesterase activity or fatty acid production).

In certain embodiments, an *E. coli, Cinnamomum camphorum, Umbellularia californica, Streptoccus pyogenes, Ricinius communis,* or *Jatropha curcus* thioesterase is codon optimized for expression in a $C_1$ metabolizing microorganism of this disclosure (e.g., methanotroph, methylotroph, *Clostridium*). In further embodiments, any one or more of the codon optimized thioesterase sequences are introduced (e.g., transformed, conjugated, electroporated) into a $C_1$ metabolizing microorganism of this disclosure. Exemplary codon optimized thioesterase sequences are set forth in (1) SEQ ID NOS.:3-13 for *M. trichosporium* OB3b; (2) SEQ ID NOS.:20-30 for *M. capsulatus* Bath; (3) SEQ ID NOS.:37-47 for *M. methanica*; (4) SEQ ID NOS.:54-64 for M. extorquens; (5) SEQ ID NOS.:70-80 for *C. autoethanogenum*; and (6) SEQ ID NOS.:87-97 for *C. ljungdahlii.*

In certain embodiments, an *E. coli* malonyl CoA-acyl carrier protein transacylase (fabD) sequence is codon optimized for expression in a $C_1$ metabolizing microorganism of this disclosure (e.g., methanotroph, methylotroph, *Clostridium*). In further embodiments, any one or more of the codon optimized fabD sequences are introduced (e.g., transformed, conjugated, electroporated) into a $C_1$ metabolizing microorganism of this disclosure. Exemplary codon optimized fabD sequences are set forth in (1) SEQ ID NO.:2 for *M. trichosporium* OB3b; (2) SEQ ID NO.:19 for *M. capsulatus* Bath; (3) SEQ ID NO.:36 for *M. methanica*; (4) SEQ ID NO.:53 for *M. extorquens*; (5) SEQ ID NO.:69 for *C. autoethanogenum*; and (6) SEQ ID NO.:86 for *C. ljungdahlii.*

In certain embodiments, one or more acetyl-CoA carboxylase sequence (e.g., accA, accB, accC, and accD from *E. coli*) is codon optimized for expression in a $C_1$ metabolizing microorganism of this disclosure (e.g., methanotroph, methylotroph, *Clostridium*). In further embodiments, any one or more of the codon optimized Acc sequences are introduced (e.g., transformed, conjugated, electroporated) into a $C_1$ metabolizing microorganism of this disclosure. In other embodiments, a codon optimized accA is introduced or a codon optimized accABCD is introduced. Exemplary codon optimized accA, accB, accC, and accD sequences are set forth, respectively, in (1) SEQ ID NOS.:14-17 for *M. trichosporium* OB3b; (2) SEQ ID NOS.:31-34 for *M. capsulatus* Bath; (3) SEQ ID NOS.:48-51 for *M. methanica*; (4) SEQ ID NOS.:65-68 for *M. extorquens*; (5) SEQ ID NOS.:81-84 for *C. autoethanogenum*; and (6) SEQ ID NOS.:98-101 for *C. ljungdahlii.*

Transformation Methods

Any of the recombinant $C_1$ metabolizing microorganisms or methanotrophic bacteria described herein may be transformed to comprise at least one exogenous nucleic acid to provide the host with a new or enhanced activity (e.g., enzymatic activity) or may be genetically modified to remove or substantially reduce an endogenous gene function using any of a variety of methods known in the art.

Transformation refers to the introduction of a nucleic acid molecule (e.g., exogenous or heterologous nucleic acid molecule) into a host cell. The transformed host cell may carry the exogenous or heterologous nucleic acid molecule extra-chromosomally or integrated in the chromosome. Integration into a host cell genome and self-replicating vectors generally result in genetically stable inheritance of the transformed nucleic acid molecule. Host cells containing the transformed nucleic acid molecules are referred to as "non-naturally occurring" or "genetically engineered" or "recombinant" or "transformed" or "transgenic" cells (e.g., bacteria).

Expression systems and expression vectors useful for the expression of heterologous nucleic acids in $C_1$ metabolizing microorganisms (e.g., methanotrophic bacteria) are known.

Electroporation of $C_1$ metabolizing bacteria is described herein and has been previously described in, for example, Toyama et al., *FEMS Microbiol. Lett.* 166:1, 1998; Kim and Wood, *Appl. Microbiol. Biotechnol.* 48:105, 1997; Yoshida et al., *Biotechnol. Lett.* 23:787, 2001, and U.S. Patent Appl. Pub. No. 2008/0026005.

Bacterial conjugation, which refers to a particular type of transformation involving direct contact of donor and recipient cells, is more frequently used for the transfer of nucleic acid molecules into $C_1$ metabolizing bacteria. Bacterial conjugation involves mixing "donor" and "recipient" cells together in close contact with each other. Conjugation occurs by formation of cytoplasmic connections between donor and recipient bacteria, with unidirectional transfer of newly synthesized donor nucleic acid molecules into the recipient cells. A recipient in a conjugation reaction is any cell that can accept nucleic acids through horizontal transfer from a donor bacterium. A donor in a conjugation reaction is a bacterium that contains a conjugative plasmid, conjugative transposon, or mobilized plasmid. The physical transfer of the donor plasmid can occur through a self-transmissible plasmid or with the assistance of a "helper" plasmid. Conjugations involving $C_1$ metabolizing bacteria is described herein and have been previously described in Stolyar et al., *Mikrobiologiya* 64:686, 1995; Motoyama et al., *Appl. Micro. Biotech.* 42:67, 1994; Lloyd et al., *Arch. Microbiol.* 171:364, 1999; PCT Publication No. WO 02/18617; and Ali et al., *Microbiol.* 152:2931, 2006.

Expression of heterologous nucleic acids in $C_1$ metabolizing bacteria is known in the art (see, e.g., U.S. Pat. No. 6,818,424, U.S. Patent Appl. Pub. No. 2003/0003528). Mu transposon based transformation of methylotrophic bacteria has been described (Akhverdyan et al., *Appl. Microbiol. Biotechnol.* 91:857, 2011). A mini-Tn7 transposon system for single and multicopy expression of heterologous genes without insertional inactivation of host genes in *Methylobacterium* has been described (U.S. Patent Appl. Pub. No. 2008/0026005).

Various methods for inactivating, knocking-out, or deleting endogenous gene function in $C_1$ metabolizing bacteria may be used. Allelic exchange using suicide vectors to construct deletion/insertion mutants in slow growing $C_1$ metabolizing bacteria have also been described herein and in, for example, Toyama and Lidstrom, *Microbiol.* 144:183, 1998; Stolyar et al., *Microbiol.* 145:1235, 1999; Ali et al., *Microbiol.* 152:2931, 2006; Van Dien et al., *Microbiol.* 149:601, 2003.

Suitable homologous or heterologous promoters for high expression of exogenous nucleic acid molecules may be utilized. For example, U.S. Pat. No. 7,098,005 describes the use of promoters that are highly expressed in the presence of methane or methanol for heterologous gene expression in $C_1$ metabolizing bacteria. Additional promoters that may be used include deoxy-xylulose phosphate synthase methanol dehydrogenase operon promoter (Springer et al., *FEMS Microbiol. Lett.* 160:119, 1998); the promoter for PHA synthesis (Foellner et al., *Appl. Microbiol. Biotechnol.* 40:284, 1993); the pyruvate decarboxylase promoter (Tokuhiro et al., *Appl. Biochem. Biotechnol.* 131:795, 2006); or promoters identified from native plasmid in methylotrophs (EP 296484). Non-native promoters include the lac operon Plac promoter (Toyama et al., *Microbiol.* 143:595, 1997) or a hybrid promoter such as Ptrc (Brosius et al., *Gene* 27:161, 1984).

In certain embodiments, promoters or codon optimization are used for high constitutive expression of exogenous polynucleotides encoding one or more lactate production enzymes in host methanotrophic bacteria. Regulated expression of an exogenous nucleic acid in a host methanotrophic bacterium may also be utilized. In certain embodiments, regulated expression of exogenous nucleic acids encoding one or more thioesterase, acetyl-CoA carboxylase, or malonyl-CoA-ACP transacylase enzymes may be desirable to optimize lipid production by the non-naturally occurring methanotrophic bacteria. For example, an inducible/regulatable system of recombinant protein expression in methylotrophic and methanotrophic bacteria as described in, for example, U.S. Patent Appl. No. US 2010/0221813 may be used.

Recombinant $C_1$ Metabolizing Microorganisms

As noted herein, any of the recombinant $C_1$ metabolizing microorganisms (e.g., methanotrophic bacteria) described herein may be used as a parent or reference host cell to make recombinant $C_1$ metabolizing microorganisms. In certain embodiments, the instant disclosure provides a recombinant $C_1$ metabolizing non-photosynthetic microorganism, wherein the microorganism comprises a heterologous nucleic acid sequence related to fatty acid biosynthesis and wherein expression heterologous nucleic acid sequence leads to accumulation of an increased level of fatty acids or an overexpression of fatty acids in the recombinant $C_1$ metabolizing microorganism as compared to a parent or reference $C_1$ metabolizing non-photosynthetic microorganism.

In certain embodiments, a recombinant $C_1$ metabolizing non-photosynthetic microorganism comprises a heterologous polynucleotide encoding a fatty acid producing enzyme, a formaldehyde assimilation enzyme, or any combination thereof. In further embodiments, the heterologous polynucleotide encodes a thioesterase, a malonyl CoA-acyl carrier protein transacylase, an acetyl-CoA carboxylase, or any combination thereof. For example, a thioesterase may be an *E. coli, Cinnamomum camphorum, Umbellularia californica, Streptoccus pyogenes, Ricinius communis,* or *Jatropha curcus* thioesterase. Exemplary fabD, accA, accB, accC, and accD genes may be from *E. coli* or any other organism of choice.

In further embodiments, the recombinant $C_1$ metabolizing non-photosynthetic microorganism comprises a heterologous nucleic acid sequence codon optimized for efficient expression in the $C_1$ metabolizing non-photosynthetic microorganism. In certain embodiments, any one or more of thioesterase, fabD, accA, accB, accC, and accD are codon optimized for a $C_1$ metabolizing non-photosynthetic microorganism. In one embodiment, a codon optimized thioesterase is an *E. coli* tesA lacking a periplasmic targeting sequence.

In yet other embodiments, any of the aforementioned recombinant $C_1$ metabolizing non-photosynthetic microorganisms further comprises a mutation that minimizes or eliminates fatty acid-CoA ligase activity.

Exemplary organisms for use in making recombinant $C_1$ metabolizing non-photosynthetic microorganisms of this disclosure include bacteria or yeast. In certain embodiments, the parent or reference $C_1$ metabolizing bacteria used to make a recombinant $C_1$ metabolizing bacteria of this disclosure is a methanotroph or methylotroph, such as a *Methylomonas* sp. 16a (ATCC PTA 2402), *Methylosinus trichosporium* OB3b (NRRL B-11,196), *Methylosinus sporium* (NRRL B-11,197), *Methylocystis parvus* (NRRL B-11,198), *Methylomonas methanica* (NRRL B-11,199), *Methylomonas albus* (NRRL B-11,200), *Methylobacter capsulatus* Y (NRRL B-11,201), *Methylococcus capsulatus* Bath (NCIMB 11132), *Methylobacterium organophilum* (ATCC 27,886), *Methylomonas* sp. AJ-3670 (FERM P-2400), *Methylomicrobium alcaliphilum, Methylocella silvestris, Methylacidiphilum infernorum, Methylibium petroleiphilum, Methylobacterium extorquens, Methylobacterium radiotolerans, Methylobacterium populi, Methylobacterium chloromethanicum, Methylobacterium nodulans,* or any combination thereof.

In further embodiments, a parent or reference $C_1$ metabolizing bacteria used to make a recombinant $C_1$ metabolizing bacteria of this disclosure is a syngas metabolizing bacteria, such as *Clostridium autoethanogenum, Clostridium ljungdahli, Clostridium ragsdalei, Clostridium carboxydivorans, Butyribacterium methylotrophicum, Clostridium woodii, Clostridium neopropanologen,* or a combination thereof.

Culture Methods and Methods of Making Oil Compositions

A variety of culture methodologies may be used for the microorganisms, bacteria and yeast described herein. For example, $C_1$ metabolizing microorganisms (such as methanotroph or methylotroph bacteria) may be grown by batch culture or continuous culture methodologies. In certain embodiments, the cultures are grown in a controlled culture unit, such as a fermentor, bioreactor, hollow fiber cell, or the like. Generally cells in log phase are often responsible for the bulk production of a product or intermediate of interest in some systems, whereas stationary or post-exponential phase production can be obtained in other systems.

A classical batch culturing method is a closed system in which the media composition is set when the culture is started and is not altered during the culture process. That is, media is inoculated at the beginning of the culturing process with one or more microorganisms of choice and then are allowed to grow without adding anything to the system. As used herein, a "batch" culture is in reference to not changing the amount of a particular carbon source initially added, whereas control of factors such as pH and oxygen concentration can be monitored and altered during the culture. In batch systems, metabolite and biomass compositions of the system change constantly up to the time the culture is terminated. Within batch cultures, cells (e.g., bacteria such as methylotrophs) will generally move from a static lag phase to a high growth logarithmic phase to a stationary phase where growth rate is reduced or stopped (and will eventually lead to cell death if conditions do change).

A fed-batch system is a variation on the standard batch system in which a carbon substrate of interest is added in increments as the culture progresses. Fed-batch systems are useful when cell metabolism is likely to be inhibited by catabolite repression and when it is desirable to have limited amounts of substrate in the media. Since it is difficult to measure actual substrate concentration in fed-batch systems, an estimate is made based on changes of measurable factors such as pH, dissolved oxygen, and the partial pressure of waste gases. Batch and fed-batch culturing methods are common and known in the art see, e.g., Thomas D. Brock, Biotechnology: A Textbook of Industrial Microbiology, 2$^{nd}$ Ed. (1989) Sinauer Associates, Inc., Sunderland, Mass.; Deshpande, *Appl. Biochem. Biotechnol.* 36:227, 1992).

Continuous cultures are "open" systems in the sense that defined culture media is continuously added to a bioreactor while an equal amount of used ("conditioned") media is removed simultaneously for processing. Continuous cultures generally maintain the cells at a constant high, liquid phase density where cells are primarily in logarithmic growth phase. Alternatively, continuous culture may be practiced with immobilized cells (e.g., biofilm) where carbon and nutrients are continuously added and valuable products, by-products, and waste products are continuously removed from the cell mass. Cell immobilization may be achieved with a wide range of solid supports composed of natural materials, synthetic materials, or a combination thereof.

Continuous or semi-continuous culture allows for the modulation of one or more factors that affect cell growth or end product concentration. For example, one method may maintain a limited nutrient at a fixed rate (e.g., carbon source, nitrogen) and allow all other parameters to change over time. In other embodiments, several factors affecting growth may be continuously altered while cell concentration, as measured by media turbidity, is kept constant. The goal of a continuous culture system is to maintain steady state growth conditions while balancing cell loss due to media being drawn off against the cell growth rate. Methods of modulating nutrients and growth factors for continuous culture processes and techniques for maximizing the rate of product formation are well known in the art (see Brock, 1992).

In certain embodiments, culture media includes a carbon substrate as a source of energy for a $C_1$ metabolizing microorganism. Suitable substrates include $C_1$ substrates, such as methane, methanol, formaldehyde, formic acid (formate), carbon monoxide, carbon dioxide, methylated amines (methylamine, dimethylamine, trimethylamine, etc.), methylated thiols, or methyl halogens (bromomethane, chloromethane, iodomethane, dichloromethane, etc.). In certain embodiments, culture media may comprise a single $C_1$ substrate as the sole carbon source for a $C_1$ metabolizing microorganism, or may comprise a mixture of two or more $C_1$ substrates (mixed $C_1$ substrate composition) as multiple carbon sources for a $C_1$ metabolizing microorganism.

Additionally, some $C_1$ metabolizing organisms are known to utilize non-$C_1$ substrates, such as sugar, glucosamine or a variety of amino acids for metabolic activity. For example, some *Candida* species can metabolize alanine or oleic acid (Sulter et al., *Arch. Microbiol.* 153:485, 1990). *Methylobacterium extorquens* AM1 is capable of growth on a limited number of $C_2$, $C_3$, and $C_4$ substrates (Van Dien et al., *Microbiol.* 149:601, 2003). Alternatively, a $C_1$ metabolizing microorganism may be a recombinant variant having the ability to utilize alternative carbon substrates. Hence, it is contemplated that a carbon source in culture media may comprise a mixture of carbon substrates, with single and multi-carbon compounds, depending on the $C_1$ metabolizing microorganism selected.

In certain embodiments, the instant disclosure provides a method for making fuel, comprising converting biomass from a culture primarily comprising a $C_1$ metabolizing non-photosynthetic microorganism into an oil composition and refining the oil composition into a fuel. In certain embodiments, the $C_1$ metabolizing non-photosynthetic microorganism is an obligate $C_1$ metabolizing non-photosynthetic microorganism, such as an obligate methanotroph or methylotroph. In further embodiments, the $C_1$ metabolizing non-photosynthetic microorganism is a recombinant microorganism comprising a heterologous polynucleotide encoding a fatty acid producing enzyme, a formaldehyde assimilation enzyme, or a combination thereof. In certain embodiments, any one or all of the TE, MCT, and Acc genes introduced into $C_1$ metabolizing microorganisms of this disclosure can be over-expressed and the $C_1$ metabolizing microorganisms may optionally have a mutation that minimizes or eliminates fatty acid-CoA ligase activity (e.g., a fadD knock-out). In further embodiments, the oil composition is derived or extracted from a cell membrane of the $C_1$ metabolizing non-photosynthetic microorganism (e.g., methylotroph, methanotroph, yeast) or may be recovered from a culture supernatant if secreted or excreted, or a combination thereof.

In further embodiments, the step of converting biomass into an oil composition comprises extracting the oil composition, such as by wet extraction, supercritical fluid extraction, dry extraction, thermal extraction (e.g., steam stripping, hydrothermal liquefaction, pressure cooking), enzymatic hydrolysis (e.g., of the cell wall), pulsed electric field extraction, microbubbles, hollow fiber extraction, or the like. Exemplary extraction methods are known in the art, such as the Folch chloroform:methanol (2:1 v/v) (CM solution) method (see Folch et al., *J. Biol. Chem.* 226:497, 1957), or a modified method thereof (see Example 3); the Hara and Radin hexane:isopropanol (HIP) extraction method (see Hara and Radin, *Anal. Biochem.* 90:420, 1978); the Bligh and Dyer chloroform:methanol:water method (see Bligh and Dyer, *Canadian J. Biochem. Physiol.* 37:911, 1959); or the like. Other exemplary extraction methods include solid phase extraction columns (Pinkart et al., *J. Microbiol. Meth.* 34:9, 1998), single step reactive extraction (Nelson, *All Graduate Theses and Dissertations*. Paper 642, digitalcommons.usu.edu/etd/642), an α-hydroxysulfonic acid extraction (U.S. Patent Pub. No. 2013/0144078), high temperature and pressure extraction (U.S. Patent Pub. No. 2012/0110898), or accelerated solvent extraction (ASE), soxhlet, ultrasonic extraction and oscillator extraction methods (see Liu et al., *J. Earth Sci.* 21:300, 2010). Each of these extraction methods are incorporated herein by reference in their entireties, and can be used in any of the aforementioned methods or biorefinery systems described herein.

In certain embodiments, the instant disclosure provides a method for making fuel by refining an oil composition (e.g., in a refining unit) to produce fuel, wherein the oil composition is derived from a $C_1$ metabolizing non-photosynthetic microorganism, such as a methylotroph or methanotroph. In further embodiments, the method further comprises extracting the oil composition or use of a processing unit for extracting the oil composition from the $C_1$ metabolizing non-photosynthetic microorganism. In still further embodiments, the method comprises (a) culturing $C_1$ metabolizing bacteria in the presence of a feedstock comprising a $C_1$ substrate in a controlled culturing unit, wherein the cultured bacteria produce an oil composition; (b) extracting the oil composition from the cultured bacteria or extracting the oil composition in a processing unit; and (c) refining the extracted oil composition or refining the oil composition in a refining unit to produce fuel. In certain embodiments, the feedstock $C_1$ substrate is methane, methanol, formaldehyde, formic acid, carbon monoxide, carbon dioxide, a methylamine, a methylthiol, or a methylhalogen.

In any of the aforementioned methods of making fuel or biofuel, the $C_1$ metabolizing non-photosynthetic microorganism is a methanotroph, methylotroph or *Clostridium*, the feedstock $C_1$ substrate is natural gas, syngas or methane, and the bacteria are cultured under aerobic or anaerobic conditions. In further embodiments, the methanotroph is *Methy-* losinus trichosporium OB3b, *Methylococcus capsulatus* Bath, *Methylomonas* sp. 16a, *Methylomonas methanica*, *Methylomicrobium alcaliphilum*, any combination thereof, or a high growth variant thereof; the methylotroph is *Methylobacterium extorquens*, *Methylobacterium radiotolerans*, *Methylobacterium populi*, *Methylobacterium chloromethanicum*, *Methylobacterium nodulans*, any combination thereof, or a high growth variant thereof; and the *Clostridium* is *Clostridium autoethanogenum*, *Clostridium ljungdahli*, *Clostridium ragsdalei*, *Clostridium carboxydivorans*, *Clostridium woodii*, *Clostridium neopropanologen*, or any combination thereof, or a high growth variant thereof. In certain other embodiments, the $C_1$ metabolizing non-photosynthetic microorganism is an obligate $C_1$ metabolizing non-photosynthetic microorganism, such as an obligate methanotroph, methylotroph or *Clostridium*.

In any of the aforementioned methods of making fuel or biofuel, the $C_1$ metabolizing non-photosynthetic microorganism is a methanotroph, the feedstock $C_1$ substrate is natural gas or methane, and the bacteria are cultured under aerobic conditions. In further embodiments, the $C_1$ metabolizing non-photosynthetic microorganism is a methanotroph, the $C_1$ substrate is natural gas or methane, and the bacteria are cultured with limiting quantities of phosphorus, nitrogen, trace elements, oxygen, or any combination thereof.

Fuel Compositions and Fuel Products

Figure 7:
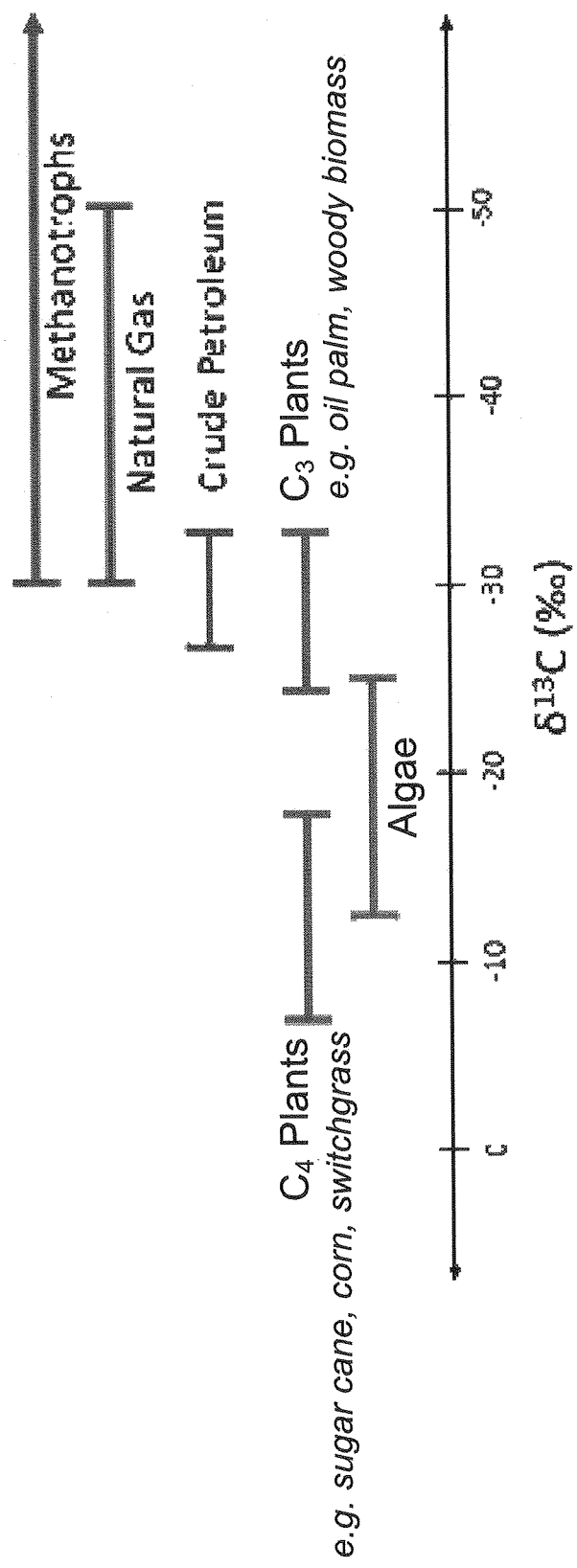
FIG. 7 shows a schematic of the $\delta^{13}C$ distribution of various carbon sources.

By way of background, stable isotopic measurements and mass balance approaches are widely used to evaluate global sources and sinks of methane (see Whiticar and Faber, *Org. Geochem.* 10:759, 1986; Whiticar, *Org. Geochem.* 16: 531, 1990). To use $\delta^{13}C$ values of residual methane to determine the amount oxidized, it is necessary to know the degree of isotopic fractionation caused by microbial oxidation of methane. For example, aerobic methanotrophs can metabolize methane through a specific enzyme, methane monooxygenase (MMO). Methanotrophs convert methane to methanol and subsequently formaldehyde. Formaldehyde can be further oxidized to $CO_2$ to provide energy to the cell in the form of reducing equivalents (NADH), or incorporated into biomass through either the RuMP or Serine cycles (Hanson and Hanson, *Microbiol. Rev.* 60:439, 1996), which are directly analogous to carbon assimilation pathways in photosynthetic organisms. More specifically, a Type I methanotroph uses the RuMP pathway for biomass synthesis and generates biomass entirely from $CH_4$, whereas a Type II methanotroph uses the serine pathway that assimilates 50-70% of the cell carbon from $CH_4$ and 30-50% from $CO_2$ (Hanson and Hanson, 1996). Methods for measuring carbon isotope compositions are provided in, for example, Templeton et al. (*Geochim. Cosmochim. Acta* 70:1739, 2006), which methods are hereby incorporated by reference in their entirety. The $^{13}C/^{12}C$ stable carbon ratio of an oil composition from a biomass (provided as a "delta" value ‰, $\delta^{13}C$) can vary depending on the source and purity of the $C_1$ substrate used (see, e.g., FIG. 7).

Oil compositions produced using the $C_1$ metabolizing non-photosynthetic microorganisms and methods described herein, as well as biofuel compositions derived therefrom, may be distinguished from oil and fuels produced from petrochemicals or from photosynthetic microorganisms or plants by carbon fingerprinting. In certain embodiments, a biomass, an oil composition, or a biofuel derived from the biomass or oil composition has a $\delta^{13}C$ of less than –30‰, less than –31‰, less than –32‰, less than –33‰, less than –34‰, less than –35‰, less than –36‰, less than –37‰, less than –38‰, less than –39‰, less than –40‰, less than –41‰, less than –42‰, less than –43‰, less than –44‰, less than –45‰, less than –46‰, less than –47‰, less than –48‰, less than –49‰, less than –50‰, less than –51‰, less than –52‰, less than –53‰, less than –54‰, less than –55‰, less than –56‰, less than –57‰, less than –58‰, less than –59‰, less than –60‰, less than –61‰, less than –62‰, less than –63‰, less than –64‰, less than –65‰, less than –66‰, less than –67‰, less than –68‰, less than –69‰, or less than –70‰.

In certain embodiments, a $C_1$ metabolizing microorganism biomass comprises an oil composition, wherein the biomass has a $\delta^{13}C$ of about –35‰ to about –50‰, –45‰ to about –35‰, or about –50‰ to about –40‰, or about –45‰ to about –65‰, or about –60‰ to about –70‰, or about –30‰ to about –70‰. In further embodiments, the biomass oil composition comprises at least 50% fatty acids or comprises at least 50% free fatty acids. In still further embodiments, the biomass oil composition comprises a mixture of diacylglycerides and triacylglycerides. In yet further embodiments, the biomass oil composition comprises a majority (more than 50% w/w) of fatty acids having carbon chain lengths ranging from C14 to C18 or from C16 to C18, or a majority of fatty acids having carbon chain lengths of less than C16. In further embodiments, the biomass oil composition comprises more than 50% w/w terpenoid or isoprenoid compounds, wherein the terpenoid may be farnesene or limonene.

In further embodiments, a $C_1$ metabolizing non-photosynthetic microorganism biomass has a $\delta^{13}C$ of less than about –30‰, or ranges from about –40‰ to about –60‰. In certain embodiments, the biomass comprises a recombinant $C_1$ metabolizing non-photosynthetic microorganism together with the spent media, or the biomass comprises a spent media supernatant composition from a culture of a recombinant $C_1$ metabolizing non-photosynthetic microorganism, wherein the $\delta^{13}C$ of the biomass is less than about –30‰. In certain other embodiments, the an oil composition is extracted or concentrated from a biomass, which can comprise recombinant $C_1$ metabolizing non-photosynthetic microorganisms together with the spent media from a culture, or a spent media supernatant composition from a culture of a recombinant $C_1$ metabolizing non-photosynthetic microorganism.

In certain embodiments, biomass is of a recombinant $C_1$ metabolizing non-photosynthetic microorganism comprises a heterologous polynucleotide encoding a fatty acid producing enzyme, a formaldehyde assimilation enzyme, or any combination thereof. In further embodiments, the heterologous polynucleotide encodes a thioesterase, a malonyl CoA-acyl carrier protein transacylase, an acetyl-CoA carboxylase, or any combination thereof. For example, a thioesterase may be an *E. coli, Cinnamomum camphorum, Umbellularia californica, Streptoccus pyogenes, Ricinius communis*, or *Jatropha curcus* thioesterase. Exemplary fabD, accA, accB, accC, and accD genes may be from *E. coli* or any other organism of choice.

In further embodiments, biomass is of a recombinant $C_1$ metabolizing non-photosynthetic microorganism comprising a heterologous nucleic acid sequence codon optimized for efficient expression in the $C_1$ metabolizing non-photosynthetic microorganism. In certain embodiments, any one or more of thioesterase, fabD, accA, accB, accC, and accD are codon optimized for a $C_1$ metabolizing non-photosynthetic microorganism. In one embodiment, a codon optimized thioesterase is an *E. coli* tesA lacking a periplasmic targeting sequence.

In yet other embodiments, any of the aforementioned biomass is of a recombinant $C_1$ metabolizing non-photosynthetic microorganism further comprises a mutation that minimizes or eliminates fatty acid-CoA ligase activity.

Exemplary organisms for use in generating biomass is of a recombinant $C_1$ metabolizing non-photosynthetic microorganisms of this disclosure include bacteria or yeast. In certain embodiments, biomass is of a $C_1$ metabolizing bacteria from a methanotroph or methylotroph, such as a *Methylomonas* sp. 16a (ATCC PTA 2402), *Methylosinus trichosporium* OB3b (NRRL B-11,196), *Methylosinus sporium* (NRRL B-11, 197), *Methylocystis parvus* (NRRL B-11,198), *Methylomonas methanica* (NRRL B-11,199), *Methylomonas albus* (NRRL B-11,200), *Methylobacter capsulatus* Y (NRRL B-11,201), *Methylococcus capsulatus* Bath (NCIMB 11132), *Methylobacterium organophilum* (ATCC 27,886), *Methylomonas* sp. AJ-3670 (FERM P-2400), *Methylomicrobium alcaliphilum*, *Methylocella silvestris*, *Methylacidiphilum infernorum*, *Methylibium petroleiphilum*, *Methylobacterium extorquens*, *Methylobacterium radiotolerans*, *Methylobacterium populi*, *Methylobacterium chloromethanicum*, *Methylobacterium nodulans*, or any combination thereof.

In further embodiments, biomass is of a $C_1$ metabolizing bacteria from a recombinant $C_1$ metabolizing bacteria of this disclosure is a syngas metabolizing bacteria, such as *Clostridium autoethanogenum*, *Clostridium ljungdahli*, *Clostridium ragsdalei*, *Clostridium carboxydivorans*, *Butyribacterium methylotrophicum*, *Clostridium woodii*, *Clostridium neopropanologen*, or a combination thereof.

In certain embodiments, an oil composition has a $\delta^{13}C$ of about −35‰ to about −50‰, −45‰ to about −35‰, or about −50‰ to about −40‰, or about −45‰ to about −65‰, or about −60‰ to about −70‰, or about −30‰ to about −70‰. In further embodiments, an oil composition comprises at least 50% w/w fatty acids or comprises at least 50% w/w free fatty acids. In still further embodiments, an oil composition comprises a mixture of diacylglycerides and triacylglycerides. In yet further embodiments, an oil composition comprises a majority of fatty acids having carbon chain lengths ranging from C14 to C18 or from C16 to C18, or a majority of fatty acids having carbon chain lengths of less than C16. In further embodiments, an oil composition comprises more than 50% w/w terpenoid or isoprenoid compounds, wherein the terpenoid compounds may be farnesene, limonene, or both.

In certain embodiments, a biofuel derived from a biomass or an oil composition has a $\delta^{13}C$ of about −35‰ to about −50‰, −45‰ to about −35‰, or about −50‰ to about −40‰, or about −45‰ to about −65‰, or about −60‰ to about −70‰, or about −30‰ to about −70‰. In certain other embodiments, a biofuel derived from an oil composition has a $\delta^{13}C$ of about −35‰ to about −50‰, −45‰ to about −35‰, or about −50‰ to about −40‰, or about −45‰ to about −65‰, or about −60‰ to about −70‰, or about −30‰ to about −70‰.

In further embodiments, a biofuel comprises at least 50% w/w fatty acid methyl esters (FAMEs). In related embodiments, a biofuel comprises at least 50% FAMEs, wherein the majority of FAMEs have carbon chain lengths of C14-C18, C16-C18, or less than C16. In still further embodiments, a biofuel comprises at least 50% w/w fatty acid ethyl esters (FAEEs). In related embodiments, a biofuel comprises at least 50% FAEEs, wherein the majority of FAEEs have carbon chain lengths of C14-C18, C16-C18, or less than C16. In yet further embodiments, a biofuel comprises at least 50% w/w hydrogenated terpenoids, such as farnesane or limonane. In certain embodiments, the majority of hydrogenated terpenoids are comprised of farnesane, limonane, or both. In certain embodiments, a biofuel comprises a hydrogenated biomass. In certain embodiments, the majority of the hydrogenated biomass comprises a mixture of linear and branched alkanes. In certain embodiments, a biofuel comprises a majority of fatty acids having carbon chain lengths ranging from C14 to C18 or from C16 to C18, or a majority of fatty acids having carbon chain lengths of less than C16. In further embodiments, a biofuel comprises more than 50% w/w terpenoid or isoprenoid compounds, wherein the terpenoid may be farnesene or limonene.

In certain embodiments, an oil composition of a $C_1$ metabolizing microorganism (which may optionally be an extract or isolate from the $C_1$ metabolizing microorganism biomass) comprises hydrogen and carbon atoms of at least about 50% to about 80% of the weight of the composition, and wherein the $\delta^{13}C$ of the composition is less than about −35‰ or less than about −36‰ or less than about −37‰ or less than about −38‰ or less than about −39‰ or less than about −40‰. In certain embodiments, an oil or biofuel composition derived therefrom comprises molecules having hydrogen and carbon atoms, wherein the hydrogen and carbon atoms are at least 50%, at least 55%, at least 60%, at least 65%, at least 70%, at least 75%, or at least 80%, or at least 90%, or at least 95% of the weight of the composition and wherein the $\delta^{13}C$ of the composition ranges from about −30‰ to about −70‰, or wherein the $\delta^{13}C$ in the biomass decreases as cell density increases by about −5‰ to about −20‰, or wherein the $\delta^{13}C$ of the biomass was higher than $CO_2$ produced at the same time by an average of 5‰ to 15‰ when cultured in the presence or absence of copper.

In further embodiments, an oil composition of a $C_1$ metabolizing microorganism of this disclosure (which may optionally be extracted or isolated from the $C_1$ metabolizing microorganism biomass) comprises hydrogen and carbon atoms at about at least 85%, 90%, 91%, 92%, 93%, 94%, 95%, 96%, 97%, 98%, 99%, or 100% of the weight of the composition. In certain embodiments, an oil composition or a biofuel composition derived therefrom comprises molecules having hydrogen and carbon atoms, wherein the hydrogen and carbon atoms are at least about 90% of the weight of the composition and wherein the $\delta^{13}C$ of the composition ranges from about −40‰ to about −55‰.

A fuel component, as described herein and known in the art, can be a fossil fuel or a mixing blend for generating a fuel product. For example, a mixture for fuel or biofuel blending may be a hydrocarbon mixture that is suitable for blending with another hydrocarbon mixture to generate a fuel or biofuel product. For example, a mixture of light alkanes may not have a certain octane number to be suitable for a type of fuel; however, it can be blended with a high octane mixture to generate a fuel product. In certain embodiments, a biomass, an oil composition or biofuel derived therefrom of this disclosure is a fuel or biofuel component after being refined.

In certain embodiments, a biofuel composition comprises molecules having hydrogen and carbon atoms, wherein the hydrogen and carbon atoms are at least 80% of the weight of the composition and wherein the $\delta^{13}C$ distribution of the composition ranges from about −37‰ to about −10‰, or wherein the $\delta^{13}C$ distribution in the biomass increases as cell density increases from −22‰ to −9‰, or wherein the $\delta^{13}C$ composition of the biomass was higher than $CO_2$ produced at the same time by an average of 5‰ to 15‰ when cultured in the presence or absence of copper.

A biofuel product as described herein is a product generated by blending an oil composition or a biofuel composition derived therefrom of the instant disclosure with a fuel or biofuel component. In some instances, a biofuel product has a $\delta^{13}C$ distribution of greater than −60‰ or greater than −50‰ or greater than −40‰ or greater than −30‰, provided the oil composition or biofuel composition derived therefrom portion of the blend is not derived from a photosynthetic microorganism or a plant. In certain embodiments, the fuel component used for blending is a petroleum-based composition or a fuel additive (e.g., oxygenates like methanol, ethanol, isopropanol; ethers such as methyl tert-butyl ether, tertiary amyl methyl ether; antioxidants such as butylated hydroxytoluene, ethylene diamine; anti-knock agents such as tetraethyllead, ferrocene toluene; lead scavengers such as tricresyl phosphate; dyes; or the like). For example, an oil composition of a $C_1$ metabolizing microorganism can be blended with a fuel component prior to refining (e.g., transesterification; cracking) in order to generate a fuel product as described herein. In still other embodiments, an oil composition is a liquid or a solid, and is refined into a fuel additive for use in producing a biofuel product. In certain embodiments, an oil composition comprises a terpene, terpenoid, isoprene, or an isopreniod. In still other embodiments, a biofuel product has an octane number of 85-120 or an octane number greater than 90.

EXAMPLES

Example 1

Culture and Bioreactor Conditions for Lipid Production by $C_1$ Metabolizing Microorganisms Exemplary $C_1$ metabolizing microorganisms of the instant disclosure (methanotrophs, methylotrophs, clostridia) were cultured in tubes, in vials, in bottles, on plates, or in a bioreactor (fermentation). Growth conditions, media, and carbon source for various microorganisms are described in this example.
*Methylosinus trichosporium* Strain OB3b (NCIMB 11131); *Methylomonas* sp. Strain 16a (ATCC PTA-2402); or *Methylomonas methanica*

For serum bottles, the bacteria were cultured at 30° C. in Higgins minimal nitrate salts medium (NSM; Cornish et al., *J. Gen. Microbiol.* 130:2565, 1984; Park et al., *Biotechnol. Bioeng.* 38:423, 1991) or MM-W1 medium. The headspace composition was adjusted to a 1:1 volume of methane:air. The bottles were shaken at a rate of 200-250 rpm. Alternatively, the culture was maintained on NSM-media plates containing 1.5% w/v agar grown in a gas-tight chamber containing a 1:1 (v/v) methane:air gas mixture, or in the presence of methanol vapor (via 0.5 mL methanol in the lid of parafilm-sealed plates) or on NSM-media plates supplemented with 0.5% methanol. Plates were incubated inverted in a humidified chamber at 30° C.

The composition of the NSM medium used was as follows: 1.0 g $MgSO_4*7H_2O$, 0.20 g $CaCl_2*6H_2O$, 2.0 ml chelated iron solution (0.1 g ferric (III) ammonium citrate or 0.5 g ferric (III) chloride; 0.2 g EDTA, sodium salt; 0.3 ml HCl, concentrated; 100.0 ml distilled deionized $H_2O$), 1.0 g $KNO_3$, 0.5 ml trace element solution (500.0 mg EDTA, 200.0 mg $FeSO_4.7H_2O$, 10.0 mg $ZnSO_4*7H_2O$, 3.0 mg $MnCl_2*4H_2O$, 30.0 mg $H_3BO_3$, 20.0 mg $CoCl_2*6H_2O$, 1.0 mg $CaCl_2*2H_2O$, 2.0 mg $NiCl_2*6H_2O$, 3.0 mg $Na_2MoO_4*2H_2O$, 1.0 L distilled water), 0.272 g $KH_2PO_4$, 0.717 g $Na_2HPO_4*12H_2O$, optionally 12.5 g purified agar (e.g., Oxoid L28 or Bacto™ agar; used when making plates), 1.0 L distilled deionized water, pH adjusted to 6.8 and autoclaved at 121° C. for 15 minutes.

For fermentation, a 2-liter bioreactor containing 1 L of sterilized defined media MM-W1 was inoculated with cells from serum bottle batch cultures (10-20% v/v) grown in MM-W1 supplied with a 1:1 (v/v) mixture of methane and air. The composition of medium MM-W1 used was as follows: 0.8 mM $MgSO_4*7H_2O$, 10 mM $NaNO_3$, 0.14 mM $CaCl_2$, 1.2 mM $NaHCO_3$, 2.35 mM $KH_2PO_4$, 3.4 mM $K_2HPO_4$, 20.7 µM $Na_2MoO_4*2H_2O$, 1 µM $CuSO_4*5H_2O$, 10 µM $Fe^{III}$—Na-EDTA, and 1 mL per liter of trace metals solution (containing, per liter 500 mg $FeSO_4*7H_2O$, 400 mg $ZnSO_4*7H_2O$, 20 mg $MnCl_2*7H_2O$, 50 mg $CoCl_2*6H_2O$, 10 mg $NiCl_2*6H_2O$, 15 mg $H_3BO_3$, 250 mg EDTA). Phosphate, bicarbonate, and $Fe^{III}$—Na-EDTA were added after the media was autoclaved and cooled. Bicarbonate was added up to 0.1% (w/v) in certain fermentations. The reactor contents were stirred with an overhead impeller at a constant 750 rpm. The culture was fed with a constant methane sparging at about 60 mL/min to about 120 mL/min, while concentrated oxygen (at least 85%) was supplied at a variable rate of about 10-100 mL/min to maintain a dissolved oxygen level of about 40% to about 80% (relative to air saturation of the media).

Temperature in the bioreactor was maintained at 30° C. and pH was maintained at 7.1±0.1 using automated addition of 0.5M NaOH and 0.5M HCl, along with other additions, to the culture about every 4 hours to about 24 hours (corresponding to an $OD_{600}$ increase of approximately 5 OD units). The other additions alternated between a metal addition (10 µM $CuSO4$, 5 µM $FeSO4$, 5 µM $Fe^{III}$—Na-EDTA final concentrations) and a nutrient addition (5.75 mM $KxHyPO4$, 10 mM $NaNO3$). Under these conditions, essentially linear growth was observed, with an effective biomass generation rate of about 2.7 to about 3.3 grams dry cell weight per liter per day to an $OD_{600}$ of greater than 20. Culture biomass was harvested by centrifugation, washed once in MM-W1 media, and recovered biomass was either frozen at −80° C. or used immediately for fractionation of cellular components (e.g., lipid extraction).

A semi-continuous fermentation approach can also be applied to maintain biomass productivity and reduce time associated with fermentation shut-down and start-up (i.e., turn-around time or lead time).

Harvesting of the bacterial biomass was performed at approximately 12-24 hour intervals, as the culture density approached (but before entering) stationary phase. Approximately half of the bioreactor volume was removed by transferring to a separate container via centrifugal pump. An equal volume of sterilized or recycled media was then returned to the bioreactor such that the optical density of the reactor was approximately half of its initial value. The bioreactor fermentation was continued according to the above protocol so that multiple cycles of growth and biomass recovery could be carried out during a single fermentation run.
*Methylococcus capsulatus* Bath (NCIMB 11132)

The bacteria were cultured at 42° C. in serum bottles containing Higgins minimal nitrate salts medium (NSM) or MM-W1 medium. The headspace composition was adjusted to a 1:1 volume of methane:air. The bottles were shaken at a rate of 200-250 rpm. Alternatively, the culture was maintained on NSM-media plates solidified with 1.5% w/v agar grown in a gas-tight chamber containing a 1:1 (v/v) methane:air gas mixture. Plates were incubated inverted in the chamber at 42° C.

For fermentation, a 3-liter bioreactor containing 1.25 L sterilized media MMF1.1 was inoculated with cells from serum bottle batch cultures (10-20% v/v) grown in the same media supplied with a 1:1 (v/v) mixture of methane and air. The composition of medium MMF1.1 was as follows: 0.8 mM $MgSO_4*7H_2O$, 40 mM $NaNO_3$, 0.14 mM $CaCl_2$, 6 mM $NaHCO_3$, 4.7 mM $KH_2PO_4$, 6.8 mM $K_2HPO_4$, 20.7 µM $Na2MoO_4*2H_2O$, 6 µM $CuSO_4*5H_2O$, 10 µM $Fe^{III}$—Na-EDTA, and 1 mL per liter of trace metals solution (containing, per liter 500 mg $FeSO_4*7H_2O$, 400 mg $ZnSO_4*7H_2O$, 20 mg $MnCl_2*7H_2O$, 50 mg $CoCl_2*6H_2O$, 10 mg $NiCl_2*6H_2O$, 15 mg $H_3BO_3$, 250 mg EDTA). Phosphate, bicarbonate, and $Fe^{III}$—Na-EDTA were added after media was autoclaved and cooled. The reactor contents were stirred with an overhead impeller at a constant 750 rpm. The culture was fed with a constant methane sparging at about 60 to about 200 mL/min, while concentrated oxygen (>85%) was supplied at a variable rate of 15-90 mL/min and the dissolved oxygen level was maintained below 10% (relative to air saturation of the media).

Temperature in the bioreactor was maintained at 44° C. and pH was maintained at 7.0±0.1 using automated addition of 0.5M NaOH and 0.5M HCl, along with additions of copper and iron (5 µM CuSO4, 5 µM $FeSO_4$, 10 µM $Fe^{III}$—Na-EDTA final concentration) to the culture every 3-6 hours (corresponding to an $OD_{600}$ increase of approximately 3-5 OD units after reaching OD 5). Under these conditions, essentially linear growth was observed, with effective biomass generation rate of more than 5 grams dry cell weight per liter per day to an $OD_{600}$ of greater than 10. Culture biomass was harvested by centrifugation, the cells washed once in MM-W1 media and cell pellets were either frozen at −80° C. or used immediately for fractionation of cellular components.

Nutrient depletion was recognized as an issue that could limit the growth yield during fermentation. To avoid limitation of nutrients, mainly nitrogen and phosphate, nutrient feeds composed of 2-fold concentrated MMF1.1 were initiated after culture $OD_{600}$ exceeded 5. The nutrient feed was initiated at dilution rates corresponding to approximately half of the cultures' growth rate to avoid wash-out and to maintain an increase in OD while expanding the culture volume. The bioreactor fermentation was continued according to the above protocol so that multiple cycles of growth and biomass recovery could be carried out during a single fermentation run.

*Methylobacterium extorquens* or *Methylosinus trichosporium* Strain OB3b (NCIMB 11131)

The bacteria is cultured at 30° C. in tubes containing Higgins minimal nitrate salts medium (NSM) supplemented with 0.5% methanol. The tubes are shaken at a rate of 200-250 rpm. Alternatively, the cultures are maintained on NSM-media plates containing 1.5% w/v agar grown in the presence of methanol vapor (via 0.5 mL methanol in the lid of parafilm-sealed plates) or supplemented with 0.5% methanol. Plates are incubated inverted in a humidified chamber under normal atmosphere at 30° C.

For fermentation, a 2-liter bioreactor containing 1 L defined media MM-W1 is inoculated with cells from culture tube batch culture (10-20% v/v). The composition of medium MM-W1 was as described above. The reactor contents are stirred with an overhead impeller at a constant 800 rpm. The culture is fed with an initial bolus of methanol to a final concentration of 0.5% and variable methanol feed, while pure oxygen was supplied at a variable rate of 30-100 mL/min to maintain a dissolved oxygen level of 60-90% (relative to air saturation of the media).

Temperature in the bioreactor was maintained at 30° C. and pH was maintained at 7.1±0.1 using automated addition of 0.5M NaOH and 1M HCl, along with the metal and nutrient additions as described above. Under these conditions, essentially linear growth is observed, with effective biomass generation rate 2.7 to 3.3 grams dry cell weight per liter per day to an $OD_{600}$ of greater than 20. Culture biomass was harvested by centrifugation, the cells washed once in MM-W1 media and cell pellets were either frozen at −80° C. or used immediately for fractionation of cellular components.

A semi-continuous fermentation approach can also be applied to maintain biomass productivity and reduce time associated with fermentation shut-down and start-up (i.e., turn-around time or lead time).

Harvesting of the accumulated bacterial biomass was performed at approximately 12-24 hour intervals, as the culture density approached (but before entering) stationary phase. Approximately half of the bioreactor volume was removed by transferring to a separate container via centrifugal pump. An equal volume of fresh or recycled media was then returned to the bioreactor such that the optical density of the reactor was approximately half of its initial value. The bioreactor fermentation was continued according to the above protocol so that multiple cycles of growth and biomass recovery was carried out during a single fermentation run.

*Clostridium autoethanogenum* and *Clostridium ljungdahlii*

The *Clostridium* bacteria are cultivated anaerobically in 100 mL modified PETC medium (ATCC medium 1754) at 37° C. in plastic-coated 500 ml-Schott Duran® GL45 bottles with butyl rubber stoppers and 200 kPa steel mill waste gas. Growth is monitored by measuring the optical density at 600 nm ($OD_{600}$).

The modified PETC medium contains (per liter) 1 g $NH_4Cl$, 0.4 g KCl, 0.2 g $MgSO_4*7H_2O$, 0.8 g NaCl, 0.1 g $KH_2PO_4$, 20 mg $CaCl_2*2H_2O$, 10 ml trace elements solution (see below), 10 ml Wolfe's vitamin solution (see below), 2 g $NaHCO_3$, and 1 mg resazurin. After the pH is adjusted to 5.6, the medium is boiled, dispensed anaerobically, and autoclaved at 121° C. for 15 min. Steel mill waste gas (composition: 44% CO, 32% $N_2$, 22% $CO_2$, 2% $H_2$) or equivalent synthetic mixtures are used as a carbon source. The media has a final pH of 5.9 and is reduced with cysteine-HCl and $Na_2S$ at a concentration of 0.008% (w/v).

The trace elements solution contains 2 g nitrilotriacetic acid (adjusted to pH 6 with KOH before addition of the remaining ingredients), 1 g $MnSO_4$, 0.8 g $Fe(SO_4)_2$ $(NH_4)_2*6H_2O$, 0.2 g $CoCl_2*6H_2O$, 0.2 mg $ZnSO_4*7H_2O$, 20 mg $CuCl_2*2H_2O$, 20 mg $NiCl_2*6H_2O$, 20 mg $Na_2MoO_4*2H_2O$, 20 mg $Na_2SeO_4$, and 20 mg $Na_2WO_4$ per liter.

Wolfe's vitamin solution (Wolin et al., *J. Biol. Chem.* 238: 2882, 1963) contains (per liter) 2 mg biotin, 2 mg folic acid, 10 mg pyridoxine hydrochloride, 5 mg thiamine-HCl, 5 mg riboflavin, 5 mg nicotinic acid, 5 mg calcium D-(+)-pantothenate, 0.1 mg vitamin B12, 5 mg p-aminobenzoic acid, and 5 mg thioctic acid.

a. *Clostridium autoethanogenum* Fermentation

Fermentation of *Clostridium autoethanogenum* is conducted using methods similar to those described in, for example, U.S. Patent Appl. No. 2011/0300593. Briefly, a 2-liter bioreactor containing 1.3 L Solution A (3.083 g $NH_4Ac$; 0.61 g $MgCl_2*6H_2O$; 0.294 g $CaCl_2*2H_2O$; 0.15 g KCl; 0.12 g NaCl (optional); up to 1 L with distilled water) is sparged with $N_2$ gas. An 85% solution of $H_3PO_4$ (2.025 mL, 30 mM) is added and the pH adjusted to 5.3 using concentrated, aqueous $NH_4OH$. Then 13.5 mL Solution B (20.0 mg Biotin; 20.0 mg Folic acid; 10.0 mg pyridoxine HCl; 50.0 mg thiamine*HCl; 50.0 mg Riboflavin; 50.0 mg nicotinic acid; 50.0 mg calcium D-(*)-pantothenate; 50.0 mg vitamin B12; 50.0 mg p-aminobenzoic acid; 50.0 mg thioctic acid; up to 1 L with distilled water) is added and the solution sparged with $N_2$ gas. Chromium (II) chloride is added until the oxidation-reduction potential (ORP) of the solution decreases to approximately −200 mV, wherein resazurin (1.35 mL of a 2 g/L solution) is added. Sodium polysulfide (5.4 mL of a 3M solution, see below) is added and the solution sparged with $N_2$ and then CO containing gas (1% $H_2$; 13% $N_2$; 71% CO; 15% $CO_2$). A metal sulfide solution (150 mL, see below) is added and the solution sparged a further 30 minutes, before inoculation with an actively growing *C. autoethanogenum* culture at a level of approximately 5% (v/v).

The sodium polysulfide solution is prepared in a 500 ml flask that is charged with $Na_2S$ (93.7 g, 0.39 mol) and 200 ml $H_2O$. The solution is stirred until the salt dissolves and sulfur (25 g, 0.1 mol) is added under constant $N_2$ flow. After stirring at room temperature for 2 hours, the sodium polysulfide solution (about 4 M with respect to Na and about 5 M with respect to sulfur), now a clear reddish brown liquid, is transferred into $N_2$ purged serum bottles, and wrapped in aluminum foil.

The chromium (II) solution is prepared in a 1 L three necked flask that is fitted with a gas tight inlet and outlet to allow working under inert gas and subsequent transfer of the desired product into a suitable storage flask. The flask is charged with $CrCl_3*6H_2O$ (40 g, 0.15 mol), zinc granules [20 mesh] (18.3 g, 0.28 mol), mercury (13.55 g, 1 mL, 0.0676 mol) and 500 mL distilled water. Following flushing with $N_2$ for one hour, the mixture is warmed to about 80° C. to initiate the reaction. Following two hours of stirring under a constant $N_2$ flow, the mixture is cooled to room temperature and continuously stirred for another 48 hours by which time the reaction mixture turns into a deep blue solution. The solution is transferred into $N_2$ purged serum bottles and stored at 4° C. for future use.

The metal sulfide solution is prepared by adding about 950 mL Solution A into a 1 L fermenter and sparging with $N_2$ gas. An 85% solution of $H_3PO_4$ (1.5 mL, 30 mM) is added and the pH adjusted to 5.3 using concentrated aqueous $NH_4OH$. Solution B (10 mL) is added and the solution sparged with $N_2$. Chromium (II) chloride is added until the oxidation-reduction potential (ORP) of the solution decreases to approximately −200 mV, wherein resazurin (1 mL of a 2 g/L solution) is added. Solution C (1/10; 10 ml $FeCl_3$; 5 ml $CoCl_2$; 5 ml $NiCl_2$; 1 ml $H_3BO_3$; 1 ml $Na_2MoO_4$; 1 ml $MnCl_2$; 1 ml $Na_2WO_4$; 1 ml $ZnCl_2$; 1 ml $Na_2SeO_3$; into 1 L media) is added, then sodium polysulfide (2 mL of a 3M solution) is added, and then the solution is sparged with $N_2$ gas.

Fermentation of a substrate comprising CO by *C. autoethanogenum* under batch conditions in the presence of polysulfide results in a substantially increased rate of accumulation and a final biomass accumulation of approximately 4 g/L over a 2-3 day period. For example, following a short lag phase of approximately 1 day, the biomass can increase from about 0.5 g/L up to at least 3.5 g/L over approximately 36 hours of fermentation. Furthermore, acetate is not produced during the growth phase in the presence of polysulfide (as is typically found in batch fermentations) and in certain circumstances some of the acetate is consumed, such that there is a net decrease in the amount of acetate in the fermenter. Culture biomass was harvested by centrifugation, the cells washed once in media and cell pellets were either frozen at −80° C. or used immediately for fractionation of cellular components.

A semi-continuous fermentation approach can also be applied to maintain biomass productivity and reduce time associated with fermentation shut-down and start-up (i.e., turn-around time or lead time).

Harvesting of the accumulated bacterial biomass was performed at approximately 12-24 hour intervals, as the culture density approached (but before entering) stationary phase. Approximately half of the bioreactor volume was removed by transferring to a separate container via centrifugal pump. An equal volume of fresh or recycled media was then returned to the bioreactor such that the optical density of the reactor was approximately half of its initial value. The bioreactor fermentation was continued according to the above protocol so that multiple cycles of growth and biomass recovery was carried out during a single fermentation run.

b. *Clostridium ljungdahlii* Fermentation

Fermentation of *Clostridium ljungdahlii* is performed using similar methods to those described in, for example, U.S. Pat. Nos. 5,173,429 and 5,593,886. Briefly, batch fermentations are conducted using a biologically pure culture of *C. ljungdahlii*. Preparation of the medium ((1) 80.0 mL of a salt comprising $KH_2PO_4$ 3.00 g/L, $K_2HPO_4$ 3.00 g/L, $(NH_4)_2SO_4$ 6.00 g/L, NaCl 6.00 g/L, $MgSO_4*2H_2O$ 1.25 g/L; (2) 1.0 g of yeast extract; (3) 1.0 g of trypticase; (4) 3.0 ml of PFN (Pfenning) trace metal solution comprising $FeCl_2*4H_2O$ 1500 mg, $ZnSO_4*7H_2O$ 100 mg, $MnCl_2*4H_2O$ 30 mg, $H_3BO_3$ 300 mg, $CoCl_2*6H_2O$ 200 mg, $CuCl_2*H_2O$ 10 mg, $NiCl_2*6H_2O$ 20 mg, $NaMoO_4*2H_2O$ 30 mg, $Na_2SeO_3$ 10 mg, and distilled water up to 1 L; (5) 10.0 ml of B vitamins comprising Pyridoxal HCl 10 mg, Riboflavin 50 mg, Thiamine HCl 50 mg, Nictotinic acid 50 mg, Ca-D-Pantotheinate 50 mg, Lipoic acid 60 mg, p-aminobenzoic acid 50 mg, Folic acid 20 mg, Biotin 20 mg, cyanocobalamin 50 mg, and distilled water up to 1 L; (6) 0.5 g of cysteine HCl; (7) 0.06 g $CaCl_2*2H_2O$; (8) 2.0 g $NaHCO_3$; (9) 1.0 mL resazurin (0.01%); and (10) 920.0 mL distilled water) is carried out anaerobically in an atmosphere of 80% nitrogen and 20% $CO_2$. The pH of the medium is controlled during fermentation and maintained at 5.0 with HCl. If required, adjustments to the pH are made with sterile 10% NaOH or 1.0% acetic acid solution. The medium is transferred to 157.5 mL serum bottles and sealed with butyl rubber stoppers and aluminum seals. The bottles are then autoclaved at 121° C. for 20 minutes.

Approximately 48 hours before commencing the experiment, a seed culture is prepared from a stock culture of the *C. ljungdahlii* in a bottle similar to those as described above. The seed culture is grown in a shaker incubator at 37° C. and shaken at 100 rpm. Reducing solutions (2.0 ml $Na_2S$, 2.5% solution and 2.0 ml cysteine-HCl, 3.5% solution) are added to the culture, which is placed in the shaker incubator for approximately 15 minutes to allow for complete oxygen removal and temperature acclimation. Unlike the procedure used for isolating a biologically pure culture of the organism, addition of methane inhibitors is not required in batch fermentations.

Fermentation with *C. ljungdahlii* is performed in a New Brunswick Scientific Bioflow IIc 2.5-liter fermenter containing nutrient media at 37° C., and a constant fluid level of 1.5 liters is maintained while the fluid is agitated at variable rates of up to 1,000 revolutions per minute with gas introduced at a rate of approximately 500 cubic centimeters per minute. Optimal gas retention times are in the range of three minutes. The gas feed is varied with its uptake by the bacteria, which is in turn a function of the cell density.

Harvesting of the accumulated bacterial biomass was performed at approximately 12-24 hour intervals, as the culture density approached (but before entering) stationary phase. Approximately half of the bioreactor volume was removed by transferring to a separate container via centrifugal pump. An equal volume of fresh or recycled media was then returned to the bioreactor such that the optical density of the reactor was approximately half of its initial value. The bioreactor fermentation was continued according to the above protocol so that multiple cycles of growth and biomass recovery was carried out during a single fermentation run.

Example 2

$C_1$ Metabolizing Microorganisms Engineered for Enhanced Lipid Production

Host cells were engineered to possess genetic modifications to minimize or reduce the degradation of fatty acids—by knocking-out long-chain fatty acid-CoA ligase activity encoded by the endogenous fadD gene. Furthermore, biosynthesis of free fatty acids (FFAs) was enhanced by introducing a thioesterase (TE) gene into a methanotroph of this disclosure (*Methylococcus capsulatus*). Such recombinant alterations are further described in this example.

Recombinant Nucleic Acid Molecules

The nucleic acid sequences encoding wild-type FadD proteins were the reference standard starting point for designing mutant fadD genes. For example, the wild-type FadD protein sequence encoded by *M. trichosporium* OB3b, *M. capsulatus* Bath, *M. methanica, M. extorquens*, and *C. ljungdahlii* are provided in GenBank Accession Nos. EFH00931.1, YP_114021.1, YP_004512148.1, YP_002964871.1, and YP_003782065.1, respectively. Hence, a nucleic acid molecule of the fadD genes encoding the above-noted proteins were individually synthesized to incorporate several stop mutations and frame shifts in the 5'-region of the gene from *M. trichosporium* OB3b (SEQ ID NO.:1), *M. methanica* (SEQ ID NO.:35), *M. extorquens* (SEQ ID NO.:52), and *C. ljungdahlii* (SEQ ID NO.:85). For the *M. capsulatus* fadD gene, a nucleic acid molecule comprising an internal deletion was synthesized so that the remaining 5' and 3' ends of the gene could be joined to maintain the original reading frame (SEQ ID NO.:18).

For *C. autoethanogenum*, the genome is sequenced and the fadD homolog to *E. coli* is identified via a tblastn search (a search of the translated nucleotide gene sequences with the protein sequence of the *E. coli* FadD). A nucleic acid molecule of the *C. autoethanogenum* fadD gene is synthesized to incorporate several stop mutations and frame shifts in the 5'-region of the gene.

The mutant fadD nucleic acid molecules are individually cloned into a plasmid vector (lacking a methanotroph or clostridia origin of replication and encoding kanamycin resistance) for conjugation, electroporation, or transformation into a $C_1$ metabolizing microorganism using methods described herein. Such a vector (that does not replicate in a $C_1$ metabolizing microorganism) ensures that any kanamycin resistant $C_1$ metabolizing microorganism will have the resistance gene incorporated into the host cell genome due to homologous recombination and replacement of the endogenous fadD gene with the above-noted fadD mutants (such that the recombinant cells would lack or have minimal long-chain fatty acid-CoA ligase activity).

In addition, one or more selected thioesterase sequences, a malonyl CoA-acyl carrier protein transacylase (fabD) sequence, and an acetyl-CoA carboxylase sequence (e.g., accA, accB, accC, and accD from *E. coli*) were codon optimized and synthesized with appropriate promoters. One or more thioesterase genes and an acetyl-CoA carboxylase gene (e.g., accA or accABCD) are then cloned into an appropriate expression vector and conjugated, electroporated or transformed into wild-type or fadD-knockout $C_1$ metabolizing microorganisms as described herein.

Codon optimized thioesterase sequences are set forth in (1) SEQ ID NOS.:3-13 for *M. trichosporium* OB3b; (2) SEQ ID NOS.:20-30 for *M. capsulatus* Bath; (3) SEQ ID NOS.:37-47 for *M. methanica*; (4) SEQ ID NOS.:54-64 for *M. extorquens*; (5) SEQ ID NOS.:70-80 for *C. autoethanogenum*; and (6) SEQ ID NOS.:87-97 for *C. ljungdahlii*. Codon optimized fabD sequences are set forth in (1) SEQ ID NO.:2 for *M. trichosporium* OB3b; (2) SEQ ID NO.:19 for *M. capsulatus* Bath; (3) SEQ ID NO.:36 for *M. methanica*; (4) SEQ ID NO.:53 for *M. extorquens*; (5) SEQ ID NO.:69 for *C. autoethanogenum*; and (6) SEQ ID NO.:86 for *C. ljungdahlii*. Codon optimized accA, accB, accC, and accD sequences are set forth, respectively, in (1) SEQ ID NOS.:14-17 for *M. trichosporium* OB3b; (2) SEQ ID NOS.:31-34 for *M. capsulatus* Bath; (3) SEQ ID NOS.:48-51 for *M. methanica*; (4) SEQ ID NOS.:65-68 for *M. extorquens*; (5) SEQ ID NOS.: 81-84 for *C. autoethanogenum*; and (6) SEQ ID NOS.:98-101 for *C. ljungdahlii*.

Conjugation

The procedure for conjugating plasmids from *Escherichia coli* into *M. trichosporium* OB3b or *M. methanica* was based on the method developed by Martin and Murrell (*FEMS Microbiol. Lett.* 127:243, 1995), while the procedure for conjugating plasmids from *E. coli* into *M. capsulatus* was based on the method reported by Ali and Murrell (*Microbiology* 155:761, 2009).

Briefly, a mobilizable plasmid containing one or more genes of interest (e.g., mutant fadD, MCT, one or more TE, one or more Acc) and encoding kanamycin resistance was first transformed into *E. coli* S 17-1 using standard electroporation methods. Transformation was confirmed by selection of kanamycin-resistant colonies on LB-agar containing 30 μg/mL kanamycin. Transformed colonies were inoculated into LB media containing 30 μg/mL kanamycin and shaken overnight at 37° C. A 10 mL aliquot of the overnight culture was then collected on a sterile 47 mm nitrocellulose filter (0.2 mm pore size). The *E. coli* donor cells were washed on the filter with 50 mL sterile NSM media to remove residual media and antibiotic.

In parallel, a sample of the *M. trichosporium* OB3b, *M. methanica*, or *M. capsulatus* Bath recipient strains were separately inoculated into 100 mL serum bottles containing 20-50 mL NSM media. The headspace of the bottles was then flushed with a 1:1 mixture of oxygen and methane, and the bottles were sealed with butyl rubber septa and crimped. The bottles were shaken continuously in a 30° C. (*M. trichosporium* OB3b, *M. methanica*) or a 45° C. (*M. capsulatus* Bath) incubator until reaching an $OD_{600}$ of approximately 0.3. The cells were then collected on the same filter as the *E. coli* donor strain. The filter was again washed with 50 mL of sterile NSM media. The filter was placed (cells up) on an NSM agar plate containing 0.2% yeast extract and incubated for 24 h at 30° C. (*M. trichosporium* OB3b, *M. methanica*) or 37° C. (*M. capsulatus* Bath) in the presence of a 1:1 mixture of methane and air. After 24 h, cells were re-suspended in 10 mL sterile (NSM) medium before being concentrated by centrifugation. The harvested cells were re-suspended in 1 mL sterile NSM media and aliquots (100 μL) were spread onto NSM agar plates containing 10 μg/mL kanamycin.

The plates were incubated in sealed chambers containing a 1:1 mixture of methane and air and maintained at 30° C. (*M. trichosporium* OB3b, *M. methanica*) or 45° C. (*M. capsulatus* Bath). The gas mixture was replenished every 2 days until colonies formed, typically after 7-14 days. Colonies were streaked onto NSM plates containing kanamycin to confirm kanamycin resistance as well as to further isolate transformed methanotroph cells from residual *E. coli* donor cells.

Electroporation—*Methanobacterium*

The procedure for introducing plasmids into *M. extorquens* is based on the procedure described by Ueda et al., *Appl. Environ. Microbiol.* 57:924, 1991. Briefly, wild-type (wt) *M. extorquens* is cultured at 30° C. in NSM media supplemented with 0.5% methanol. Cells of *M. extorquens* NR-2 grown to the mid-log phase ($1.4 \times 10^9$/ml) are harvested by centrifugation at 6,000×g for 10 min and washed with electroporation buffer (10 mM Tris-HCl, 2 mM $MgCl_2 \cdot 6H_2O$, 10% [wt/vol] sucrose [pH 7.5]). Cells are re-suspended in the same buffer at a cell concentration of $7.0 \times 10^{10}$/ml. The cell suspension and vector (70 μg/mL) are mixed at a ratio of 9:1 (vol/vol) in a tube, and then 10 μL is transferred into a space between the electrodes of a chamber where it is equilibrated for 3 minutes. After being subjected to 10 pulses of a 10 kV/cm electric field for 300 μsec/pulse, a 5 μL aliquot of the mixture is transferred to a clean tube and 0.2 mL NSM medium is added. The cell suspension is then incubated for 2 h at 30° C. to allow expression of the antibiotic resistance genes prior to plating on NSM plates containing 0.5 methanol and 20 μg/mL kanamycin.

The plates were incubated at 30° C. until colonies formed. Colonies were streaked onto duplicate plates to confirm kanamycin resistance as well as to further isolate transformed methylotroph cells from residual *E. coli* donor cells.

Electroporation—*Clostridium*

Transformation methods for *C. autoethanogenum* or *C. ljungdahlii* are performed as described in U.S. Patent Pub. No. 2011/0236941, or using a modified protocol for *C. tyrobutyricum* (Zhu et al., *Biotechnol. Bioeng.* 90:154, 2005). Briefly, to make competent cells, a 50 mL culture of *C. autoethanogenum* is subcultured to fresh media for 3 consecutive days according to the culturing conditions described herein. These cells are used to inoculate 50 mL PETC media containing 40 mM DL-threonine at an $OD_{600}$ of 0.05. When the culture reaches an $OD_{600}$ of 0.4, the cells are transferred into an anaerobic chamber and harvested at 4,700×g and 4° C. The culture is washed twice with ice-cold electroporation buffer (270 mM sucrose, 1 mM $MgCl_2$, 7 mM sodium phosphate, pH 7.4) and finally suspended in a volume of 600 μl fresh electroporation buffer. This mixture is transferred into a pre-cooled electroporation cuvette with a 0.4 cm electrode gap containing 1 μg of vector (lacking a *Clostridium* origin of replication and containing a nucleic acid molecule of interest and encoding clarithromycin resistance) and immediately pulsed using the Gene pulser Xcell electroporation system (Bio-Rad) with the following settings: 2.5 kV, 600 μl, and 25 μF. Time constants of 3.7-4.0 ms are achieved. The culture is transferred into 5 ml fresh media. Regeneration of the cells is monitored at a wavelength of 600 nm using a Spectronic Helios Epsilon Spectrophotometer (Thermo) equipped with a tube holder. After an initial drop in biomass, the cells start growing again. Once the biomass has doubled from that point, the cells are harvested, suspended in 200 μl fresh media and plated on selective PETC plates (containing 1.2% Bacto™ Agar (BD)) with 4 μg/μl clarithromycin. After 4-5 days of incubation with 30 psi steel mill gas at 37° C., colonies are clearly visible.

Alternatively, after the electroporation pulse, the cells are transferred into 5 mL prewarmed medium in a Hungate tube and incubated at 37° C. until growth is visible (measured in Hungate tubes in a photometer). Aliquots of the transformants are inoculated into 5 mL liquid medium and spread onto clarithromycin-containing plates to develop mutant colonies.

The selected recombinant colonies are used to inoculate 2 ml PETC media containing 4 μg/μl clarithromycin. When growth occurs, the culture is scaled up into 5 ml and later 50 ml PETC media containing 4 μg/μl clarithromycin and 30 psi steel mill gas as the carbon source.

Recombinant $C_1$ Metabolizing Bacteria

Transformation is confirmed by resistance of the cells to antibiotic selection, and gene expression is confirmed by PCR, northern blot, western blot, or ELISA methods. For example, to verify transfer, plasmid DNA can be isolated and subjected to PCR using the illustra PuReTaq Ready-To-Go™ PCR Beads (GE Healthcare) using standard conditions (95° C. for 5 min; 32 cycles of 95° C. for 30 s, 50° C. for 30 s, and 72° C. for 1 min; 72° C. for 10 min). As a further control, 1 μl each of the isolated plasmids are re-transformed into *E. coli* XL1-Blue MRF' Kan (Stratagene, La Jolla, Calif.), from where the plasmids can be isolated cleanly and verified by restriction digests.

Methods for identifying homologous recombination events are well-established in the art, such as PCR and sequencing using unique primers in the genome and the vector to confirm proper insertion. Recombinant bacteria identified as having a proper insertion are then grown in the absence of selective pressure (e.g., without kanamycin or clarithromycin) for several generations, and kanamycin-sensitive clones are identified by replica plating (or equivalent technique). Approximately 50% of the kanamycin-sensitive revertants should possess the mutated form of the target gene in place of wild-type, which is confirmed by PCR and sequencing. Loss of fadD expression or function can be verified by one or more of (1) PCR and sequencing, (2) northern blot analysis, and (3) assaying for acyl-CoA synthetase activity.

For acyl-CoA synthetase activity, the method of, for example, Kameda et al. (*J. Biol. Chem.* 256:5702, 1981) can be used by growing cells to mid-log phase in NSM with antibiotics as required, harvesting cells by centrifugation, washing twice with NSM, suspending the cells to a density of $1.2 \times 10^9$ cells/mL in 10 mM Tris-HCl, pH 7.5, and then lysing by three cycles of sonication on ice. Reaction mixtures are prepared, in a total volume of 0.5 ml, to include 200 mM Tris-HCl, pH 7.5, 2.5 mM ATP, 8 mM MgCl, 2 mM EDTA, 20 mM NaF, 0.1% Triton® X-100, 10 pM [$^3$H]oleate, 0.5 mM coenzyme A, and cell extract. The enzyme reactions are initiated with the addition of coenzyme A, incubated at 35° C. for 10 minutes, and terminated by the addition of 2.5 ml isopropyl alcohol:n-heptane:1M $H_2SO_4$ (40:10:1). The radioactive oleic acid is removed by organic extraction using n-heptane, while oleoyl-CoA formed during the reaction remains in the aqueous fraction to be quantified by scintillation counting. Protein concentrations in the enzyme extracts are determined using the Bradford assay with bovine serum albumin as a standard.

Production of Fatty Acids from $C_1$ Substrates ($CH_4$ and CO)

For methanotrophs, wild-type or fadD-knockout *M. trichosporium* OB3b, *M. methanica*, *M. extorquens*, or *M. capsulatus* Bath transformed with a vector containing genes encoding one or more thioesterase genes or overexpressing acetyl-CoA carboxylase genes are used to inoculate 100 mL serum bottles or culture tubes containing 20-50 mL NSM media and 10 μg/mL kanamycin. For *M. extorquens*, the media is supplemented with 0.5% methanol as a carbon source, whereas the bottle headspace is flushed with a 1:1 mixture of oxygen and methane as the carbon source for *M. trichosporium* OB3b, *M. methanica*, and *M. capsulatus* Bath. The bottles are sealed with butyl rubber septa and crimped. The bottles or tubes are then shaken continuously at a rate of 200-250 rpm during incubation at 30° C. (*M. trichosporium* OB3b, *M. methanica*, *M. extorquens*) or 42-45° C. (*M. capsulatus* Bath).

For Clostridia, wild-type or fadD-knockout *C. autoethanogenum* or *C. ljungdahlii* transformed with a vector containing genes encoding one or more thioesterase enzymes and with or without acetyl-CoA carboxylase genes are used to inoculate 2 ml PETC media containing 4 μg/μl clarithromycin. When growth occurs, the culture is scaled up into 5 ml and later 50 ml PETC media containing 4 μg/μl clarithromycin and 30 psi steel mill gas as the carbon source. The bottles are then shaken continuously at a rate of 200-250 rpm during incubation at 37° C.

Quantification of fatty acids produced by the recombinant $C_1$ metabolizing bacteria is performed using a gas chromatograph/mass spectrometer (GC/MS). Fatty acids in the cell culture are extracted by vortexing vigorously with butyl acetate containing undecanoic acid as an internal standard for GC/MS analysis of the extract. After brief centrifugation of the mixture, a small portion of the organic layer was transferred to a separate vial, followed by addition of an equal volume of N,O-Bis(trimethylsilyl)trifluoroacetamide. The sample was analyzed by GC with a mass spectrometer detector (HP 5792) using an Agilent HP-5MS GC/MS column (30.0 m×250 µM×0.25 µM film thickness). A split ratio of 20:1 at 250° C. was used for the injector and helium was the carrier gas at a flow of 1.2 mL/min. The oven temperature was held at 60° C. for the 1 minute, followed by a temperature gradient increase of 19° C./min until reaching a temperature of 250° C. The concentration of fatty acids in the cell culture was calculated using selective ion mode based on the calibration curves of fatty acid standards. Since methane was the only carbon source provided to the cells, all fatty acids produced must have been derived from methane.

Results

The fatty acid profile of *M. capsulatus* Bath was altered by knocking out fadD and by introducing and expressing an *E. coli* thioesterase gene. First, the *E. coli* thioesterase gene with the periplasmic targeting sequence removed (TesA') was synthesized using three different codon compositions (TesA'-3, SEQ ID NO:102; TesA'-37, SEQ ID NO:103; and TesA'-20, SEQ ID NO:104) designed to generate variants with differing expression levels. The TesA' variants were cloned into an IncP-based plasmid (comprising an Inc-P oriV and oriT) and operatively connected to a promoter that functions in methanotrophs. The recombinant expression vector containing TesA' was transformed into *M. capsulatus* as described herein. *M. capsulatus* cultures in a 5 mL volume in 150 mL sealed serum bottles were grown with 40 mL methane and 80 mL oxygen for 5 days. After the growth stage, 1 mL of each culture was assayed for fatty acid concentration and composition using GC/MS as described herein. Measured free fatty acid values were normalized to $OD_{600}$ by culture. Note that the C16:1 fraction is comprised of at least three different isomers with the most abundant being Δ9-cis palmitoleic acid (data not shown).

In parallel, a homolog of the *E. coli* acyl coenzyme A (CoA) synthetase (fadD) was recombinantly knocked-out with SEQ ID NO:18 in the *M. capsulatus* genome as described herein and confirmed by PCR analysis. FadD knockout has been shown in several other microbial strains to increase free fatty acid levels (see, e.g., Lennen et al., *Trends Biotechnol.* 12:659, 2012). The *M. capsulatus* fadD knockout mutant did not show a significant increase in free fatty acid levels, which indicates that one or more additional FadD homologs may be present in the *M. capsulatus* genome, but lipid profile was shifted since there was an increase C 18:0 lipids.

Figure 3B:
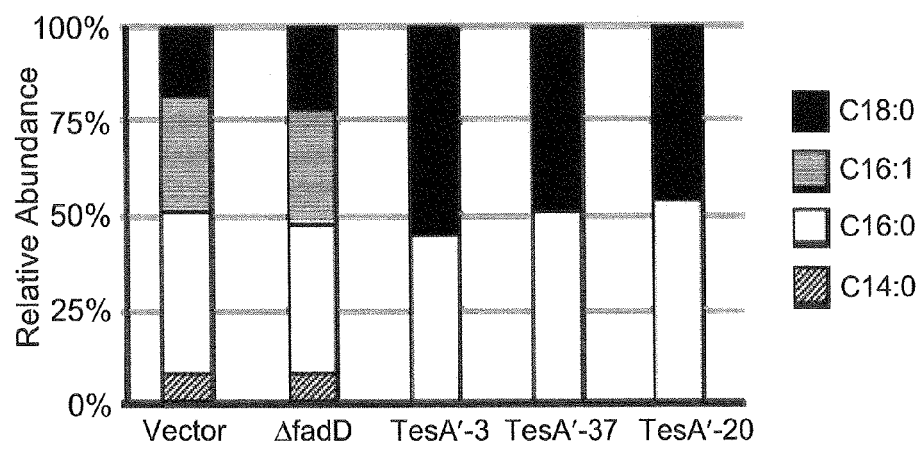

The free fatty acid pools in the transformed cells increased dramatically (see FIG. 3A), with the increase primarily attributed to increased levels of C16:0 and C18:0 lipids (see FIG. 3B).

Example 3

Lipid Extracting from $C_1$ Metabolizing Microorganisms

The oil composition contained within a harvested bacterial biomass was extracted using a modified version of Folch's extraction protocol (Folch et al., *J. Biol. Chem.* 226:497, 1957), performed at 20° C. (i.e., room temperature) and in an extraction solution made up of one volume methanol in two volumes chloroform (CM solution). About 5 g wet cell weight (WCW) of either fresh bacterial biomass (or bacterial biomass stored at −80° C. and subsequently thawed) was used for extractions. A 100 mL CM solution was added to the cell material and the mixture was extracted vigorously in a separatory funnel. After at least 10 minutes, three phases were resolved. The organic phase containing extracted lipids settled at the bottom of the separatory funnel, which was drained into a clean glass bottle. The middle layer contained primarily lysed cellular materials and could be separated from the light water phase containing salts and other soluble cellular components.

Optionally, solids in the water phase can be concentrated using a centrifuge or other mechanical concentration equipment. The water removed from the solids may be recycled, while the solids, with some residual water, can be fed to a solids processing unit.

To enhance the lipid extraction efficiency, a second extraction step was carried out by adding an additional 100 mL fresh CM solution directly into the separatory funnel containing the remaining lysed cell mass and residual water. The mixture was again mixed thoroughly, the phases allowed to separate, and the bottom organic phases from the two extractions were pooled. The pooled organic phases were then washed with 100 mL deionized water in a separatory funnel to remove any residual water-soluble material. The separated organic fraction was again isolated from the bottom of the separatory funnel and solvent was removed by rotary evaporation with heat, preferably in the absence of oxygen, or by evaporation at 55° C. under a stream of nitrogen.

TABLE 1

Extracted Lipid Content from Three Different Methanotrophs

| Batch No. | Reference Strain | Lipid Fraction (g/g DCW)* |
|---|---|---|
| 68C | *Methylosinus trichosporium* OB3b | 40.1 |
| 62A | *Methylococcus capsulatus* Bath | 10.3 |
| 66A | *Methylomonas* sp. 16a | 9.3 |

*Grams of extracted material per gram of dry cell weight (DCW)

The solidified oil compositions extracted from the harvested cultures of *M. trichosporium* OB3b, *Methylococcus capsulatus* Bath, and *Methylomonas* sp. 16a were each weighed and are shown as the weight fraction of the original dry cell weight (DCW) in Table 1. These data show that a significant fraction of the DCW from these $C_1$ metabolizing microorganisms is made up of lipids.

The oil composition from *Methylomonas* sp. 16a biomass was also extracted using hexane:isopropanol (HIP) extraction method of Hara and Radin (*Anal. Biochem.* 90:420, 1978). Analysis of the oil composition extracted using the HIP method showed that the oil composition was essentially identical to the oil composition extracted using the modified Folch method (data not shown).

Example 4

Fatty Acid Methyl Ester Conversion of Lipids from $C_1$ Metabolizing Microorganisms The lipid fractions extracted from *M. capsulatus* Bath, *M. trichosporium* OB3b, and *Methylomonas* sp. 16a culture biomass in the form of dry solids were individually hydrolyzed with potassium hydroxide (KOH) and converted into fatty acid methyl esters (FAMEs) via reaction with methanol in a single step. About 5 g of extracted solid lipids in a 10 mL glass bottle were dissolved with 5 mL of 0.2 M KOH solution of toluene:methanol (1:1 v/v). The bottle was agitated vigorously and then mixed at 250 rpm at 42° C. for 60 minutes, after which the solution was allowed to cool to ambient temperature and transferred to a separatory funnel. Approximately 5 mL distilled water and 5 mL CM solution were added to the separatory funnel, mixed, and then the phases were allowed to separate by gravity or by centrifugation (3,000 rpm, 25° C.) for 5 minutes. The top aqueous layer was removed, which contains dissolved glycerol phosphate esters, while the heavy oil phase (bottom) was collected and concentrated to dryness by rotary evaporation or by a constant nitrogen stream.

Analysis of FFAs and FAMEs found in lipids from each methanotroph culture was performed using a gas chromatograph/mass spectrometer (GC/MS). The solids collected before and after the hydrolysis/transesterification step were dissolved in 300 μL butyl acetate containing undecanoic acid as an internal standard for GC/MS analysis. The resulting solution was centrifuged for 5 minutes at 14,000 rpm to remove insoluble residues. The same volume equivalent of N,O-Bis(trimethylsilyl)trifluoroacetamide was added to the supernatant from the centrifugation step and vortexed briefly. Samples were loaded on an GC equipped with mass spectrometer detector (HP 5792), and an Agilent HP-5MS GC/MS column (30.0 m×250 μm×0.25 μm film thickness) was used to separate the FFAs and FAMEs. Identity of FFAs and FAMEs was confirmed with retention time and electron ionization of mass spectra of their standards. The GC/MS method utilized helium as the carrier gas at a flow of 1.2 mL/min. The injection port was held at 250° C. with a split ratio of 20:1. The oven temperature was held at 60° C. for 1 minute followed by a temperature gradient comprising an 8° C. increase/min until 300° C. The % area of each FFA and FAME was calculated based on total ions from the mass detector response.

The solid residue collected before and after hydrolysis/transesterification were analyzed for FFAs and FAMEs by GC/MS (see Table 2). Also, chromatograms from the GC/MS analysis are provided in FIGS. 4-6.

TABLE 2

Relative composition of FFA and FAME in Extracted Lipids Before and After KOH Hydrolysis/Esterification

| Fatty Acid Type | M. capsulatus Bath | | M. trichosporium OB3b | | Methylomonas sp. 16a | |
|---|---|---|---|---|---|---|
| | With hydrolysis % Area | Without hydrolysis % Area | With hydrolysis % Area | Without hydrolysis % Area | With hydrolysis % Area | Without hydrolysis % Area |
| C14:0 FFA | — | — | — | — | — | 12.9 |
| C16:0 FFA | 0.5 | 84.1 | — | 43.7 | — | 8.1 |
| C16:1 FFA | — | 13.4 | — | — | — | 76.1 |
| C18:0 FFA | 0.4 | 2.5 | — | 31.2 | — | 1.3 |
| C18:1 FFA | — | — | — | 25.1 | — | 1.5 |
| C14:0 FAME | 3.4 | — | — | — | 7.2 | — |
| C16:0 FAME | 54.4 | — | 1.4 | — | 14.7 | — |
| C16:1 FAME | 41.3 | — | 6.8 | — | 61.3 | — |
| C18:0 FAME | — | — | 1.0 | — | N.D. | — |
| C18:1 FAME | — | — | 90.8 | — | 16.8 | — |

* — = Not detectable; % Area MS detector response-Total ions

As is evident from Table 2, and FIGS. 4-6, extracted oil compositions before hydrolysis/transesterification have abundant free fatty acids and additional fatty acids present as (most likely) di- and tri-acyl glycerides (which are not detected on the GC/MS trace), but the FFAs are converted into fatty acid methyl esters of various lengths after hydrolysis/transesterification. These data indicate that oil compositions from the $C_1$ metabolizing microorganisms of this disclosure can be refined and used to make high-value molecules.

Example 5

Biofuel Production Using Oil Compositions from $C_1$ Metabolizing Microorganisms The extracted oil compositions from $C_1$ metabolizing microorganisms can be processed at a co-located refinery or transported to a distant refinery. A refinery is used to convert triglycerides from bio-renewable feeds (such as fats, greases, and methanotroph oils) into a mixture of liquid hydrocarbon fuels, primarily biodiesel and biojet fuel, a high quality synthetic paraffinic kerosene (SPK). The process requires hydrogen, which can be produced on-site using methane reforming or is provided by co-locating the fermentation facility at an existing refinery.

The refinery can be run in a Mixed Mode, wherein the output is a mixture of biodiesel and biojet fuel, or a Diesel Mode, wherein the output is primarily biodiesel.

During refining, fatty acids and glycerides are converted to SPK in three steps. First, raw feedstocks are treated to remove catalyst contaminants and water as needed. In the second step, fatty acid chains are transformed into n-paraffins in a hydrotreater. An example is oleic acid conversion to n-octadecane via the hydrogenation and deoxygenation reactions in the hydrotreater. For most bio-oils, fats, and greases, the hydrotreater liquid product is mainly a $C_{15}$-$C_{18}$ n-paraffin composition. In the third step of the process, these long straight-chain paraffins are hydrocracked into shorter branched paraffins. The hydrocracked products fall mainly in the kerosene boiling range.

The produced SPK preferably meets or exceeds all jet fuel fit-for-purpose specifications except density. The high H-to-C ratio of SPK, which gives its excellent thermal stability and low particulate emission attribute, means a lower density hydrocarbon composition: 760-770 kg/m$^3$ compared to the minimum ASTM specification value of 775 kg/m$^3$. But, this is not an issue with petroleum jet fuel:SPK blends (e.g., 50/50).

Example 6

Stable Carbon Isotope Distribution in Lipids from $C_1$ Metabolizing Microorganisms Dry samples of *M. trichosporium* biomass and lipid fractions were analyzed for carbon and nitrogen content (% dry weight), and carbon ($^{13}$C) and nitrogen ($^{15}$N) stable isotope ratios via elemental analyzer/continuous flow isotope ratio mass spectrometry using a CHNOS Elemental Analyzer (vario ISOTOPE cube, Elementar, Hanau, Germany) coupled with an IsoPrime100 IRMS (Isoprime, Cheadle, UK). Samples of methanotrophic biomass cultured in fermenters or serum bottles were centrifuged, resuspended in deionized water and volumes corresponding to 0.2-2 mg carbon (about 0.5-5 mg dry cell weight) were transferred to 5×9 mm tin capsules (Costech Analytical Technologies, Inc., Valencia, Calif.) and dried at 80° C. for 24 hours. Similarly, previously extracted lipid fractions were suspended in chloroform and volumes containing 0.1-1.5 mg carbon were transferred to tin capsules and evaporated to dryness at 80° C. for 24 hours. Standards containing 0.1 mg carbon provided reliable $\delta^{13}$C values.

The isotope ratio is expressed in "delta" notation (‰), wherein the isotopic composition of a material relative to that of a standard on a per million deviation basis is given by $\delta^{13}C$ (or $\delta^{15}N$)=$(R_{Sample}/R_{Standard}-1) \times 1,000$, wherein R is the molecular ratio of heavy to light isotope forms. The standard for carbon is the Vienna Pee Dee Belemnite (V-PDB) and for nitrogen is air. The NIST (National Institute of Standards and Technology) proposed SRM (Standard Reference Material) No. 1547, peach leaves, was used as a calibration standard. All isotope analyses were conducted at the Center for Stable Isotope Biogeochemistry at the University of California, Berkeley. Long-term external precision for C and N isotope analyses is 0.10‰ and 0.15‰, respectively.

*M. trichosporium* strain OB3b was grown on methane in three different fermentation batches, *M. capsulatus* Bath was grown on methane in two different fermentation batches, and *Methylomonas* sp. 16a was grown on methane in a single fermentation batch. The biomass from each of these cultures was analyzed for stable carbon isotope distribution ($\delta^{13}C$ values; see Table 3).

TABLE 3

Stable Carbon Isotope Distribution in Different Methanotrophs

| Methanotroph | Batch No. | EFT (h)† | $OD_{600}$ | DCW* | $\delta^{13}C$ Cells |
|---|---|---|---|---|---|
| Mt OB3b | 68A | 48 | 1.80 | 1.00 | −57.9 |
| | | 64 | 1.97 | 1.10 | −57.8 |
| | | 71 | 2.10 | 1.17 | −58.0 |
| | | 88 | 3.10 | 1.73 | −58.1 |
| | | 97 | 4.30 | 2.40 | −57.8 |
| | | 113 | 6.00 | 3.35 | −57.0 |
| | | 127 | 8.40 | 4.69 | −56.3 |
| Mt OB3b | 68B | 32 | 2.90 | 1.62 | −58.3 |
| | | 41 | 4.60 | 2.57 | −58.4 |
| | | 47 | 5.89 | 3.29 | −58.0 |
| | | 56 | 7.90 | 4.41 | −57.5 |
| Mt OB3b | 68C | 72 | 5.32 | 2.97 | −57.9 |
| | | 79.5 | 5.90 | 3.29 | −58.0 |
| | | 88 | 5.60 | 3.12 | −57.8 |
| | | 94 | 5.62 | 3.14 | −57.7 |
| Mc Bath | 62B | 10 | 2.47 | 0.88 | −59.9 |
| | | 17.5 | 5.80 | 2.06 | −61.0 |
| | | 20 | 7.32 | 2.60 | −61.1 |
| | | 23 | 9.34 | 3.32 | −60.8 |
| | | 26 | 10.30 | 3.66 | −60.1 |
| Mc Bath | 62A | 10 | 2.95 | 1.05 | −55.9 |
| | | 13.5 | 3.59 | 1.27 | −56.8 |
| | | 17.5 | 5.40 | 1.92 | −55.2 |
| | | 23 | 6.08 | 2.16 | −57.2 |
| | | 26 | 6.26 | 2.22 | −57.6 |
| Mms 16a | 66B | 16 | 2.13 | 0.89 | −65.5 |
| | | 18 | 2.59 | 1.09 | −65.1 |
| | | 20.3 | 3.62 | 1.52 | −65.5 |
| | | 27 | 5.50 | 2.31 | −66.2 |
| | | 40.5 | 9.80 | 4.12 | −66.3 |

*DCW, Dry Cell Weight is reported in g/L calculated from the measured optical densities ($OD_{600}$) using specific correlation factors relating OD of 1.0 to 0.558 g/L for Mt OB3b, OD of 1.0 to 0.355 g/L for Mc Bath, and OD of 1.0 to 0.42 g/L for Mms 16a. For Mt OB3b, the initial concentration of bicarbonate used per fermentation was 1.2 mM or 0.01% (Batch No. 68C) and 0.1% or 12 mM (Batch Nos. 68A and 68B).
†EFT = effective fermentation time in hours In addition, stable carbon isotope analysis was performed for biomass and corresponding lipid fractions (see Table 4) from strains *Methylosinus trichosporium* OB3b (Mt OB3b), *Methylococcus capsulatus* Bath (Mc Bath), and *Methylomonas* sp. 16a (Mms 16a) grown on methane in bioreactors as described in Example 1.

TABLE 4

Stable Carbon Isotope Distribution in Cells and Lipids

| Batch No. | Strain | $\delta^{13}C$ Cells | $\delta^{13}C$ Lipids |
|---|---|---|---|
| 68C | Mt OB3b | −57.7 | −48.6 |
| 62A | Mc Bath | −57.6 | −52.8 |
| 66A | Mms 16a | −64.4 | −42.2 |

Biomass from strains Mt OB3b, Mc Bath and Mms 16a were harvested at 94 h (3.14 g DCW/L), 26 h (2.2 g DCW/L) and 39 h (1.14 g DCW/L), respectively. The $\delta^{13}C$ values for lipids in Table 4 represent an average of duplicate determinations.

Example 7

Effect of Methane Source and Purity on Stable Carbon Isotope Distribution in Lipids To examine methanotroph growth on methane containing natural gas components, a series of 0.5-liter serum bottles containing 100 mL defined media MMS 1.0 were inoculated with *Methylosinus trichosporium* OB3b or *Methylococcus capsulatus* Bath from a serum bottle batch culture (5% v/v) grown in the same media supplied with a 1:1 (v/v) mixture of methane and air. The composition of medium MMS 1.0 was as follows: 0.8 mM $MgSO_4 \cdot 7H_2O$, 30 mM $NaNO_3$, 0.14 mM $CaCl_2$, 1.2 mM $NaHCO_3$, 2.35 mM $KH_2PO_4$, 3.4 mM $K_2HPO_4$, 20.7 µM $Na_2MoO_4 \cdot 2H_2O$, 6 µM $CuSO_4 \cdot 5H_2O$, 10 µM $Fe^{III}$—Na-EDTA, and 1 mL per liter of a trace metals solution (containing, per L: 500 mg FeSO4*7H$_2$O, 400 mg $ZnSO_4 \cdot 7H_2O$, 20 mg $MnCl_2 \cdot 7H2O$, 50 mg $CoCl_2 \cdot 6H_2O$, 10 mg $NiCl_2 \cdot 6H_2O$, 15 mg $H_3BO_3$, 250 mg EDTA). Phosphate, bicarbonate, and $Fe^{III}$—Na-EDTA were added after media was autoclaved and cooled. The final pH of the media was 7.0±0.1.

The inoculated bottles were sealed with rubber sleeve stoppers and injected with 60 mL methane gas added via syringe through sterile 0.45 µm filter and sterile 27 G needles. Duplicate cultures were each injected with 60 mL volumes of (A) methane of 99% purity (grade 2.0, Praxair through Alliance Gas, San Carlos, Calif.), (B) methane of 70% purity representing a natural gas standard (Sigma-Aldrich; also containing 9% ethane, 6% propane, 3% methylpropane, 3% butane, and other minor hydrocarbon components), (C) methane of 85% purity delivered as a 1:1 mixture of methane sources A and B; and (D) >93% methane (grade 1.3, Specialty Chemical Products, South Houston, Tex.; in-house analysis showed composition >99% methane). The cultures were incubated at 30° C. (*M. trichosporium* strain OB3b) or 42° C. (*M. capsulatus* Bath) with rotary shaking at 250 rpm and growth was measured at approximately 12 hour intervals by withdrawing 1 mL samples to determine $OD_{600}$. At these times, the bottles were vented and headspace replaced with 60 mL of the respective methane source (A, B, C, or D) and 60 mL of concentrated oxygen (at least 85% purity). At about 24 hour intervals, 5 mL samples were removed, cells recovered by centrifugation (8,000 rpm, 10 minutes), and then stored at −80° C. before analysis.

Analysis of carbon and nitrogen content (% dry weight), and carbon ($^{13}C$) and nitrogen ($^{15}N$) stable isotope ratios, for methanotrophic biomass derived from *M. trichosporium* strain OB3b and *M. capsulatus* Bath were carried out as described in Example 6. Table 5 shows the results of stable carbon isotope analysis for biomass samples from *M. capsu-* latus Bath grown on methane having different levels of purity and in various batches of bottle cultures.

TABLE 5

Stable Carbon Isotope Distribution of *M. capsulatus* Bath Grown on Different Methane Sources having Different Purity

| Methane* | Batch No. | Time (h)† | OD$_{600}$ | DCW (g/L) | $\delta^{13}$C Cells |
|---|---|---|---|---|---|
| A | 62C | 22 | 1.02 | 0.36 | −40.3 |
|   |     | 56 | 2.01 | 0.71 | −41.7 |
|   |     | 73 | 2.31 | 0.82 | −42.5 |
|   | 62D | 22 | 1.14 | 0.40 | −39.3 |
|   |     | 56 | 2.07 | 0.73 | −41.6 |
|   |     | 73 | 2.39 | 0.85 | −42.0 |
| B | 62E | 22 | 0.47 | 0.17 | −44.7 |
|   |     | 56 | 0.49 | 0.17 | −45.4 |
|   |     | 73 | 0.29 | 0.10 | −45.4 |
|   | 62F | 22 | 0.62 | 0.22 | −42.3 |
|   |     | 56 | 0.63 | 0.22 | −43.6 |
|   |     | 73 | 0.30 | 0.11 | −43.7 |
| C | 62G | 22 | 0.70 | 0.25 | −40.7 |
|   |     | 56 | 1.14 | 0.40 | −44.8 |
|   |     | 73 | 1.36 | 0.48 | −45.8 |
|   | 62H | 22 | 0.62 | 0.22 | −40.9 |
|   |     | 56 | 1.03 | 0.37 | −44.7 |
|   |     | 73 | 1.23 | 0.44 | −45.9 |

*Methane purity: A: 99% methane, grade 2.0 (min. 99%); B: 70% methane, natural gas standard (contains 9% ethane, 6% propane, 3% methylpropane, 3% butane); C: 85% methane (1:1 mix of A and B methane)
†Time = bottle culture time in hours The average $\delta^{13}$C for *M. capsulatus* Bath grown on one source of methane (A, 99%) was −41.2±1.2, while the average $\delta^{13}$C for *M. capsulatus* Bath grown on a different source of methane (B, 70%) was −44.2±1.2. When methane sources A and B were mixed, an intermediate average $\delta^{13}$C of −43.8±2.4 was observed. These data show that the $\delta^{13}$C of cell material grown on methane sources A and B are significantly different from each other due to the differences in the $\delta^{13}$C of the input methane. But, cells grown on a mixture of the two gasses preferentially utilize $^{12}$C and, therefore, show a trend to more negative $\delta^{13}$C values.

A similar experiment was performed to examine whether two different methanotrophs, *Methylococcus capsulatus* Bath and *Methylosinus trichosporium* OB3b, grown on different methane sources and in various batches of bottle cultures showed a difference in $\delta^{13}$C distribution (see Table 6).

TABLE 6

Stable Carbon Isotope Distribution of Different Methanotrophs Grown on Different Methane Sources of Different Purity

| Strain | Methane* | Batch No. | Time (h)† | OD$_{600}$ | DCW (g/L) | $\delta^{13}$C Cells |
|---|---|---|---|---|---|---|
| Mc Bath | A | 62I | 18 | 0.494 | 0.18 | −54.3 |
|   |   |   | 40 | 2.33 | 0.83 | −42.1 |
|   |   |   | 48 | 3.08 | 1.09 | −37.1 |
| Mc Bath | D | 62J | 18 | 0.592 | 0.21 | −38.3 |
|   |   |   | 40 | 1.93 | 0.69 | −37.8 |
|   |   |   | 48 | 2.5 | 0.89 | −37.8 |
| Mc Bath | D | 62K | 18 | 0.564 | 0.20 | −38.6 |
|   |   |   | 40 | 1.53 | 0.54 | −37.5 |
|   |   |   | 48 | 2.19 | 0.78 | −37.6 |
| Mt OB3b | A | 68D | 118 | 0.422 | 0.24 | −50.2 |
|   |   |   | 137 | 0.99 | 0.55 | −47.7 |
|   |   |   | 162 | 1.43 | 0.80 | −45.9 |
| Mt OB3b | A | 68E | 118 | 0.474 | 0.26 | −49.9 |
|   |   |   | 137 | 1.065 | 0.59 | −47.6 |
|   |   |   | 162 | 1.51 | 0.84 | −45.2 |
| Mt OB3b | D | 68F | 118 | 0.534 | 0.30 | −45.6 |
|   |   |   | 137 | 1.119 | 0.62 | −38.7 |
|   |   |   | 162 | 1.63 | 0.91 | −36.4 |
| Mt OB3b | D | 68G | 118 | 0.544 | 0.30 | −44.8 |
|   |   |   | 137 | 1.131 | 0.63 | −39.1 |
|   |   |   | 162 | 1.6 | 0.89 | −34.2 |

*Methane sources and purity: A: 99% methane (grade 2.0); D: >93% methane (grade 1.3)
†Time = bottle culture time in hours The average $\delta^3$C for *M. capsulatus* grown on a first methane source (A) was −44.5±8.8, while the average $\delta^{13}$C for *M. trichosporium* was −47.8±2.0 grown on the same methane source. The average $\delta^{13}$C for *M. capsulatus* grown on the second methane source (B) was −37.9±0.4, while the average $\delta^{13}$C for *M. trichosporium* was −39.8±4.5. These data show that the $\delta^{13}$C of cell material grown on a methane source is highly similar to the $\delta^{13}$C of cell material from a different strain grown on the same source of methane. Thus, the observed $\delta^{13}$C of cell material appears to be primarily dependent on the composition of the input gas rather than a property of a particular bacterial strain being studied.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to U.S. Patent Application No. 61/671,542, are incorporated herein by reference in their entirety. Aspects of the embodiments can be modified, if necessary, to employ concepts of the various patents, applications and publications to provide further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A biomass comprising whole and/or lysed cells of a methanotroph bacteria and, a $\delta^{13}C$ ranging from about −30‰ to about −70‰, wherein said methanotroph bacteria comprises a heterologous polynucleotide and wherein said methanotroph bacteria comprising said heterologous polynucleotide produce a biomass comprised of whole and/or lysed cells with a $\delta^{13}C$ ranging from about −30‰ to about −70‰ when cultured with a $C_1$ substrate.

2. The biomass of claim 1, wherein said $\delta^{13}C$ of said biomass ranges from about −40‰ to about −65‰.

3. The biomass of claim 1, wherein said methanotroph bacteria is selected from the group consisting of *Methylomonas* sp. 16a (ATCC PTA 2402), *Methylosinus trichosporium* OB3b (NRRL B-11,196), *Methylosinus sporium* (NRRL B-11,197), *Methylocystis parvus* (NRRL B-11,198), *Methylomonas methanica* (NRRL B-11,199), *Methylomonas albus* (NRRL B-11,200), *Methylobacter capsulatus* Y (NRRL B-11,201), *Methylococcus capsulatus* Bath (NCIMB 11132), *Methylobacterium organophilum* (ATCC 27,886), *Methylomonas* sp. AJ-3670 (FERM P-2400), *Methylomicrobium alcaliphilum*, *Methylocella silvestris*, *Methylacidiphilum infernorum*, *Methylibium petroleiphilum*, *Methylobacterium populi*, and any combination thereof.

4. The biomass of claim 1, wherein said methanotroph bacteria comprises a heterologous polynucleotide encoding a thioesterase, malonyl-CoA acyl carrier protein transacylase, acetyl-CoA carboxylase, and any combination thereof, and said methanotroph bacteria accumulates an increased level of fatty acids as compared to a wild-type methanotroph bacteria without said heterologous polynucleotide and grown under same conditions.

5. The biomass of claim 4, wherein said heterologous polynucleotide encoding said thioesterase is codon optimized for expression in said methanotroph bacteria.

6. The biomass of claim 5, wherein said heterologous polynucleotide encoding said thioesterase is an *E. coli* tesA lacking a periplasmic targeting sequence.

7. The biomass of claim 4, wherein said heterologous polynucleotide encoding said malonyl-CoA acyl carrier protein transacylase is an *E. coli* fabD, and wherein said heterologous polynucleotide is codon optimized for expression in said methanotroph bacteria.

8. The biomass of claim 4, wherein said heterologous polynucleotide encoding said acetyl-CoA carboxylase is an *E. coli* accA, accB, accC, accD, or any combination thereof, and wherein said heterologous polynucleotide is codon optimized for expression in said methanotroph bacteria.

9. The biomass of claim 4, wherein said methanotroph bacteria further comprises a mutation that minimizes or eliminates fatty acid-CoA ligase activity, wherein said mutation is in an endogenous fatty acid-CoA ligase gene.

10. A biomass comprising (a) a culture of said methanotroph bacteria of claim 1 together with a culture media in which said methanotroph bacteria were grown; (b) said methanotroph bacteria of claim 1 grown and recovered from said culture media; or (c) a spent media composition recovered from said culture of said methanotroph bacteria of (a), and wherein said biomass comprises a $\delta^{13}C$ ranging from about −30‰ to about −70‰.

11. The biomass of claim 10, wherein said biomass is said spent media composition recovered from said culture of said methanotroph bacteria of (a), and further comprising an oil composition that is extracted or concentrated from said spent media composition.

12. A method of producing biomass, comprising culturing methanotroph bacteria in a controlled culturing unit in the presence of a feedstock comprising a $C_1$ substrate under conditions and for a time sufficient to produce a biomass, wherein said methanotroph bacteria comprises a heterologous polynucleotide and wherein said biomass comprises whole and/or lysed cells of said methanotroph bacteria and a $\delta^{13}C$ range from about −30‰ to about −70‰.

13. The method of claim 12, wherein said methanotroph bacteria are cultured in a controlled culture unit selected from the group consisting of a fermentor, a bioreactor, a hollow fiber cell, a packed bed bioreactor, and combinations thereof.

14. The method of claim 12, wherein said feedstock comprising a $C_1$ substrate is natural gas or methane.

15. The method of claim 12, wherein said biomass comprises (a) a culture of said methanotroph bacteria together with a culture media in which said methanotroph bacteria were grown; (b) said methanotroph bacteria recovered from said culture media; of (c) a spent media composition recovered from said culture media comprising said methanotroph bacteria.

16. The method of claim 12, wherein said methanotroph bacteria is selected from the group consisting of *Methylomonas* sp. 16a (ATCC PTA 2402), *Methylosinus trichosporium* OB3b (NRRL B-11,196), *Methylosinus sporium* (NRRL B-11,197), *Methylocystis parvus* (NRRL B-11,198), *Methylomonas methanica* (NRRL B-11,199), *Methylomonas albus* (NRRL B-11,200), *Methylobacter capsulatus* Y (NRRL B-11,201), *Methylococcus capsulatus* Bath (NCIMB 11132), *Methylobacterium organophilum* (ATCC 27,886), *Methylomonas* sp. AJ-3670 (FERM P-2400), *Methylomicrobium alcaliphilum*, *Methylocella silvestris*, *Methylacidiphilum infernorum*, *Methylibium petroleiphilum*, *Methylobacterium populi*, and any combination thereof.

17. The method of 12, wherein said methanotroph bacteria are cultured in a bioreactor comprising balanced media.

18. The method of claim 12, wherein said methanotroph bacteria are cultured in a bioreactor comprising unbalanced media having limiting quantities of phosphorus, nitrogen, trace elements, oxygen relative to a balanced media, or any combination thereof.

19. The method of claim 12, wherein said $\delta^{13}C$ of said biomass ranges from about −40‰ to about −65‰.

* * * * *

SEQUENCE LISTING

<160> NUMBER OF SEQ ID NOS: 104

<210> SEQ ID NO 1
<211> LENGTH: 1731
<212> TYPE: DNA
<213> ORGANISM: Artificial Sequence
<220> FEATURE:
<223> OTHER INFORMATION: Mutated M. trichosporium fadD sequence

<400> SEQUENCE: 1

```
acccatgaca  dacgcatgac  tcgcgctcga  cccttacgcc  gcgcgtccct  gactcgcctc    60
ttaaaccgcc  gagcgtcgcg  ccggacatcg  atcccgccga  gccgcgcact  ctggtcgagg   120
tgtttcgtcg  cagcgtcgcc  gcgcattccg  acaaaatcgc  gctcgagagc  ttcggcgcga   180
cgctgacctt  cgcgcaattc  gacggcgccg  cgcgcgccat  cgccgccttt  ctgcaatcgc   240
agggcctgaa  gaagggcgat  cgcgtcgcga  tcatgtcgcc  caatgtgatg  gcctatccgc   300
cgatcatctt  cggcgtgctg  ctcgccggcg  gcgcggtggt  caacgtcaat  ccgctctaca   360
cgccgagcga  gctctccttt  cagatcaatg  attccggcgc  gcgcatcgtc  ttcgtgctgg   420
agaatttcgc  ccatacggtc  gaagccgcat  ggcccgacat  gtcgatcgat  ctcgcggtcg   480
tcgtcacgcc  aggcgatctg  ctcgggctca  aaggcaagct  cgtcgatttc  gtctcgcgct   540
atgtgaaatg  cgccgtgcgg  ccctatcagc  tgccgacgag  catgcgcttt  cgcgatatca   600
tgaagcaagg  ctcggcgcgc  tcgggcgcgc  gacgtctaga  tcgcaccgga  cgatctcgct   660
tttctgcaat  atacgggcgg  cacgaccggc  gtcgccaagg  gagcgatgct  gctccaccgc   720
aatgtcgcgg  ccaatgtggc  gcaagcgacc  gcctggctgc  atccgtttct  gctggaggcg   780
tccgggcgcg  agcggccgca  gaagatggtg  gcggcgctgc  cgctctagca  cattttcggc   840
ctcaccgcct  gtctgctggt  gctggtgcgc  atcggcggct  cctgcctgct  catcgccaat   900
ccgcgcgaca  tcgccggctt  cgtgaagacg  ctgcgcaagt  cgccgcttctc  gatgatctcc   960
ggcgtcaaca  cgctctatgc  ggcgctcgcc  gatcatccgt  aattcgcgca  ggtcgacttc  1020
tctcgcctcg  tcttctgcat  cgccggcggc  atggcgacga  ggacgtcgt  cgcgcgcaaa  1080
tggagagcga  tcaccggccg  cccgatcatc  gaaggctatg  gctctccga  gacctcgccg  1140
gtcgtcgcct  gcaacaggcc  cgatctcgag  taattctccg  gctcgatcgg  ctatccgcat  1200
ccctcgaccg  ccgtgtcgat  ccgcgcgccc  tcgggcgagc  cggttccgat  cggcgagcgc  1260
ggggagctgt  gcgtgaaggg  tccgcaggtg  atgccgggat  attggaatcg  ccccgcctag  1320
accgaggcgg  cgttcacgcc  ggacgggttt  tttcgcaccg  gcgatgtggc  gatcatgctg  1380
ccggacggac  aggtgaagct  cgtcgatcgt  ttgaagtaga  tgattctcgt  ctccggcttc  1440
aacgtctatc  cgaacgaggt  cgagaatgtg  ctggtgcagc  atcccaaggt  gaaggaggcg  1500
gcggtgatcg  gcgttcccga  tccgcattcg  ggctaggcgc  cgctcgcctt  catcgtgccg  1560
cgcgacgcca  gcgtcaccgg  ccaggagctg  catgatttct  gccgcaagac  gctgacgcac  1620
tataaggcgc  cgaagcattt  ctaattccgc  gacagcctgc  cgaagagcaa  tgtcggcaag  1680
gtgctgcggc  gcgtgctgcg  cgacgaggtg  caagcgcgag  ccgaatgagg  a           1731
```

<210> SEQ ID NO 2
<211> LENGTH: 927
<212> TYPE: DNA
<213> ORGANISM: Artificial Sequence
<220> FEATURE:
<223> OTHER INFORMATION: Codon optimized E. Coli FabD sequence

<400> SEQUENCE: 2

```
atgacgcaat  tcgctttcgt  tttcccggga  caaggttcgc  aaaactgttgg  aatgctcgct    60
gatatggccg  cctcgtaccc  gatcgtcgag  gaaacgttcg  ccgaggccag  cgcggcgctg   120
gggtacgacc  tgtgggccct  cacccagcag  ggcccggccg  aggaactcaa  caagacctgg   180
cagacgcagc  ctgccctcct  gaccgcctcg  gtcgcgctct  atcgtgtgtg  gcagcagcag   240
ggcggcaagg  cgcccgccat  gatggccggc  cacagcctgg  gcgagtactc  cgccctcgtg   300
```

```
tgcgcgggcg tgatcgactt cgcggacgcc gtccgcctgg tcgagatgcg cggcaagttc    360
atgcaggaag ccgtccccga gggcacgggc gctatggcgg cgatcatcgg cctcgacgat    420
gcctccatcg ccaaggcgtg cgaggaagcg gccgagggcc aggtcgtcag cccggtgaat    480
ttcaactcgc ccggtcaggt cgtcattgcc ggccataaag aggccgtcga gcgcgcgggc    540
gccgcgtgca aggccgccgg cgcgaagcgc gcgttgcccc tcccggtcag cgtcccgtcc    600
cattgcgcgc tgatgaagcc ggcggccgac aagctggccg tggagctcgc gaagatcacc    660
ttcaatgcgc cgaccgtccc ggtggtcaat aacgtcgacg tcaagtgcga acgaacggc     720 gatgccatcc gcgacgcgct cgtccggcag ctgtataacc cggtgcagtg gacgaagtcc    780
gtcgagtata tggcggcgca gggcgtggag cacctctatg aagtgggccc cggcaaggtc    840
ctcaccggcc tcaccaagcg catcgtggac ccctgacgg cctcggcgct gaatgagccc      900
tcggccatgg cggctgcgct ggagctg                                         927
```

```
<210> SEQ ID NO 3
<211> LENGTH: 549
<212> TYPE: DNA
<213> ORGANISM: Artificial Sequence
<220> FEATURE:
<223> OTHER INFORMATION: Codon optimized E. Coli TesA sequence with
      periplamic targeting sequence removed.

<400> SEQUENCE: 3
```

```
atggctgaca ccctcctgat tcttggcgat tccctctctg ctggttaccg tatgtccgcg    60
tccgctgcct ggcctgccct cctcaacgac aagtggcaga gcaagacgag cgtcgtcaat    120
gcgtcgatct cgggcgatac ctcgcaacag ggcctggcgc gcttgccggc cctgctcaag    180
cagcatcagc cgcgctgggt gctcgtcgag ctgggcggca acgatggact gcgcggcttc    240
cagccccagc agaccgagca acgctccgc cagatcctcc aagacgtcaa ggccgccaat    300
gcggagccgt gctgatgca gatccgcctc ccggcgaatt atggccgccg ctataacgaa    360
gcgttctcgg ccatctatcc gaagctggcg aaagagttcg acgtgcccct gctcccgttc    420
ttcatggaag aagtctacct gaagccgcag tggatgcaag acgatggcat ccatccgaac    480
cgggacgcgc agcccttcat cgccgactgg atggccaaac agctgcagcc cctcgtgaac    540
cacgactcg                                                            549
```

```
<210> SEQ ID NO 4
<211> LENGTH: 1146
<212> TYPE: DNA
<213> ORGANISM: Artificial Sequence
<220> FEATURE:
<223> OTHER INFORMATION: Codon optimized Cinnamomum camphorum
      thioesterase sequence

<400> SEQUENCE: 4
```

```
atggccacaa cttcacttgc ctctgccttt tgttcgatga agctgtcat gctcgcccgc    60 gatggacgtg gaatgaagcc gcgttcgtcg gacctccagc tccgagccgg caatgcgcag    120
acctccctga aaatgattaa cggcacgaag ttctcgtata ccgagtcgct gaagaagctc    180
ccggactgga gcatgctgtt cgcggtgatc accaccatct tctcggccgc tgagaagcaa    240
tggaccaatc tcgaatggaa gccgaagccg aatccgcccc agctgctgga cgaccacttc    300
ggcccccacg gcctcgtgtt ccgccgcacc ttcgccatcc gctcgtatga agtgggcccg    360
gaccgctcga ccagcatcgt cgccgtgatg aaccatttgc aggaagcggc gctcaatcat    420
```

```
gcgaagagtg tgggcatcct gggcgacggc ttcggtacga cgctggagat gagcaagcgc    480
gacctgatct gggtcgtcaa gcgcacgcac gtggcggtgg agcgttaccc cgcgtggggg    540
gacacggtcg aagtcgagtg ctgggtcggc gcctccggca caatggccg ccggcacgac     600 ttcctcgtgc gcgattgcaa gaccggtgag attctcaccc gctgcacgtc gctgagcgtc    660
atgatgaata ctcgcacccg ccgcctctcg aagatccctg aggaagtgag gggcgagatc    720
ggcccggcgt tcatcgacaa cgtggccgtc aaagatgagg agatcaagaa gccccagaag    780
ctcaacgact cgaccgcgga ttacatccag ggcggactga cgccgcgttg gaacgatctg    840
gacatcaacc agcacgtcaa caacatcaag tatgtggact ggatcctcga accgtcccc     900 gactcgatct tcgagagcca tcatatctcg tccttcacca tcgagtaccg cgcgagtgc     960 acgatggatt ccgtcctcca gtccctcacc acggttagcg gcggcagctc cgaggccggc    1020
ttggtctgcg agcatctgct gcagcttgag ggcggctccg aggtcctccg cgcgaaaacg    1080
gagtggcgcc ccaagctcac ggatagcttc cgcggcatct cggtgatccc ggcggagagc    1140
tcggtc                                                                1146

<210> SEQ ID NO 5
<211> LENGTH: 1146
<212> TYPE: DNA
<213> ORGANISM: Artificial Sequence
<220> FEATURE:
<223> OTHER INFORMATION: Codon optimized Umbellularia californica
      thioesterase sequence

<400> SEQUENCE: 5
atggccacta cctcccttgc ttctgccttt tgctcaatga aagctgtgat gctcgcccgt     60
gacggacgcg gtatgaagcc gcgctcgtcc gacctccagc tccgggccgg caacgcgccg    120
acctcgctca agatgattaa tggcactaag ttctcctata ccgagtcgct caagcgcctg    180
ccggattggt cgatgctgtt cgcggtcatc accacaatct tctcggccgc tgagaagcag    240
tggaccaact tggagtggaa gccgaagccg aagctgcccc agctcctgga cgaccatttc    300
ggcctccatg gcctggtgtt ccgcggacg ttcgccatcc gttcgtacga agtcggcccc     360
gaccgctcga cctccatcct ggcggtgatg aatcacatgc aagaggcgac gctcaaccat    420
gccaagtccg tcggtatcct gggcgatggc ttcggcacca ccctggagat gagcaagcgc    480
gatctcatgt gggtcgtccg ccgcacgcat gttgccgtgg agcgctatcc cacgtggggc    540
gacacggtcg aggtcgagtg ctggatcggg gcgtcgggaa ataacggcat gcgccgcgac    600
ttcctcgtcc gtgactgcaa gaccggcgag atcctcacgc gctgcacgtc gctgtcggtg    660
ctgatgaata cccgcacccg tagactgtcc accatccccg atgaagtgcg cggcgaaatc    720
ggcccggcct tcatcgacaa tgtcgccgtc aaagacgatg agatcaagaa gctgcagaag    780
ttgaacgact cgaccgcgga ctatatccag ggcggcctga cgccccgctg gaatgacctc    840
gacgtcaacc agcatgtcaa caatctcaag tacgtggcgt gggtgttcga acggtgccg     900 gacagtatct tcgagagcca ccacatttcc agcttcacgc tcgaatatcg tcgcgagtgc    960
acgcgcgact ccgtcctccg gtcgctgacc accgtgagcg gcggctcgtc ggaagcgggc    1020
ctggtctgcg atcacctcct gcagctggag ggcggctccg aggtcctccg cgcgaggacc    1080
gagtggcgtc cgaagctgac ggatagcttc cgcgggatca gcgtcatccc gccgagccc     1140 cgcgtg                                                                1146

<210> SEQ ID NO 6
```

```
<211> LENGTH: 750
<212> TYPE: DNA
<213> ORGANISM: Artificial Sequence
<220> FEATURE:
<223> OTHER INFORMATION: Codon optimized Streptococcus pyogenes acyl-ACP
      thioesterase sequence

<400> SEQUENCE: 6
atgggccttt cctatcaaga agaactcacc ctccccttcg agctctgcga cgtcaagtcc     60
gatatcaagc tgccgctgct gctcgactac tgcctgatgg tgagcggccg ccagtcggtc    120
cagctgggcc gttcgaacaa caatctgctg gttgactata agctcgtctg gatcgtgacc    180
gactatgaga tcaccatcca tcgcctcccg catttccagg aaacgattac catcgagaca    240
aaggccctct cgtacaacaa gttcttctgc taccgccagt tctatatcta tgaccaggag    300
ggctgcctgc tcgtcgatat cctcagctac ttcgcgctgc tgaatccgga tacgcgcaag    360
gtcgcgacca tccccgagga cctggtcgcg cccttcgaaa cggacttcgt caaaaagctc    420
caccgggtgc cgaagatgcc gctgttggag cagtcgatcg atcgcgacta ttatgtgcgc    480
tacttcgata tcgacatgaa tggtcacgtg aacaattcga agtatctcga ctggatgtac    540
gacgtcctgg gctgccagtt cctcaagacc atcagccgc tgaagatgac gctcaagtat     600
gtcaaagagg tcagccctgg cggacagatc acgtcctcgt accacctgga ccagctcacc    660
tcgtatcacc agatcatctc ggacggccag ctcaacgccc aggccatgat cgagtggcgc    720
gctattaagc agaccgagtc ggagactgat                                     750

<210> SEQ ID NO 7
<211> LENGTH: 1191
<212> TYPE: DNA
<213> ORGANISM: Artificial Sequence
<220> FEATURE:
<223> OTHER INFORMATION: Codon optimized Ricinus communis palmitoyl-acyl
      carrier protein thioesterase sequence

<400> SEQUENCE: 7
atgggaacat gctcgtatac catcaccctg ccgatccgct gcctgtctaa ttcgaacggc     60
catcacgacc cccataagca gaatctcaac aagatcaaga tcaacggcgc cagcacgagc    120
acgcgtccgc tgaagctcga tgcgccgtcg cagaccgtgg gcgtcgccac catttatctg    180
gcctccgtca gcgagaacct caccctcacc aagagggtca tgcggcagaa catccccacg    240
aagaagcagt acatcgaccc gcaccgccag ggcctgatga tcgagggcgg cgtcggctat    300
cgccagacga tcgtcatccg ttcgtatgaa gtcggccctg ataagaccgc gacgctggag    360
agtatcctct atctcctgca ggaaacggcc ctgaatcacg tgtggctgtc gggcctgctc    420
tccaatggct tcggcgccac gcatggcatg gtgaagaata acctgatctg gtggtgtcc    480 aagctccagg tccaggtcga ccattacccg atctggggcg aggtcgtcga gatcgatacc    540
tgggtccggg cgtccggcaa gaacggcatg aagcgtgact ggctgatccg ctcgcaggcc    600
acgggccatg ttttcgtccg cgcgacctcg acgtgggtca tgatgaacga gaaaactcgc    660
cgcctctcga agatgccgga agaagtgagg gccgagatct cccccgtggt catcgagaag    720
caagcgatca aggaagaggt gccggataag atcgcgaagc tcgacgataa ggctcgctac    780
gtcatctcga atttgaagcc gaagcgctcg gatctcgaca tgaaccatca cgtgaataac    840
gtgaaatatg tccgctggat gctggagatc ctccccggacc acttcctgga gtcgcatcag    900
ctctcgggca tcaccatgga gtatcgccgc gagtgcgggt cggccgacat tgtccagtcc    960
ctctgcgagc ccgacggtga cgagatcctg tccaacgaca tccccgtgct taacggattc   1020
```

```
agcctcgcgt cggagcccct gatggaaggc aacggcttcc tcgtcccct ggacaaggtc    1080 ccgctgaagt acacccacct cctgctcacg aagggtgaga gccagaatga agagatcgtc    1140
cgcggcaaga ccatttggaa gagaaactc tgcaccatgc ccttcagcac c              1191
```

<210> SEQ ID NO 8
<211> LENGTH: 1176
<212> TYPE: DNA
<213> ORGANISM: Artificial Sequence
<220> FEATURE:
<223> OTHER INFORMATION: Codon optimized Ricinus communis palmitoyl-acyl
      carrier protein thioesterase  sequence

<400> SEQUENCE: 8

```
atggcttcga aaggttccat ccgcctctac ttcccctgcg acttccgcaa caccctccag     60
aagaagaaca tgaagatgga catggtcatg gcccgctcgg gcttctccta ctcgctcaac    120
ccgatcgcgc cgaagatccc ccgcttctac gtggtcgcca acgcgtcgaa ccctcagcgg    180
gtcgacacga tcaatggcaa aaaggtgaac ggcattcacg tcgcggagag ctcgaattcg    240
tatgccgacc agaataagat gaacgcgacc gctggcctcg tcctggacgg caatgtcgac    300
catcagccgc tccacaagtg gctgttgggc cgtttcgtgg acgagcgcct ggtctatagt    360
caaaccttca tcatccgcag ctacgagatc ggtcccgata agaccgcgac catggagact    420
ctcatgaatc tgctccagga aaccgcgctc aatcatgtga cctcttcggg cctggcgggc    480
gatgggttcg gcgcgacgcg ggagatgtcg ctccggaagc tgatctgggt cgtcacgcgc    540
atccatatcc aggtccagcg ctattcctgc tggggcgatg tcgtcgagat cgacacgtgg    600
gtcgatggag cgggcaagaa tggcatgcgc agggattgga tcatccggga ctacaacacg    660
aaggagatca ttacccgcgc cacctcgacc tgggtcatca tgaaccgcga gacacgtaag    720
ctgtcgaaga tgccggaaca ggtgcgccag gaactggtgc cgttctatac caaccgcatc    780
gcgatcgcca aggaaaacaa cgacgtggag aagattgaca agctgaccga cgaaaccgcc    840
gagcgcatcc gtagcggcct cgcgccgcgc tggagcgata tggacgccaa ccagcatgtg    900
aacaatgtta agtatatcgg ctggatcctt gagagcgtcc cgatcaatgt cctcgaagat    960
tacaatctga cgtccatgac cctggagtat cgccgcgagt gccgccagag caacctcctg   1020
gagtcgctca cgtcgaccac ggagcattcg aataacaact cgtgcaaccg caaggcccac   1080
ctggagtata cgcacctcct gcgtatgcag gccgacaagg ccgagatcgt gcgtgcccgc   1140
accgagtggc agtccaagtc gaatcgcaag acgatc                             1176
```

<210> SEQ ID NO 9
<211> LENGTH: 1257
<212> TYPE: DNA
<213> ORGANISM: Artificial Sequence
<220> FEATURE:
<223> OTHER INFORMATION: Codon optimized Ricinus communis palmitoyl-acyl carrier protein thioesterase sequence

<400> SEQUENCE: 9

```
atggtcgcca ccgccgccgc cgctacctcc tcgttcttcc ccgtgccgtc ccagtccgct     60
gacgccaatt tcgataaggc ccggcgagc ctgggcggca tcaagctgaa atcgacgtcg    120
tgcagccggg gcctccaggt gaaggccaat gcgcaggcgc cgccgaagat caacggctcg    180
tcggtcggct tcaccacctc ggtggagaca gtgaagaatg acggcgacat gccgctcccg    240
cctcccccca ggaccttcat taatcagctc ccggactgga gtatgctcct ggccgcgatc    300
```

| | |
|---|---:|
| accaccatct tcctggcggc ggagaagcag tggatgatgc tcgactggaa gccccgccgt | 360 |
| ccggatatgc tcattgaccc gttcggaatc ggccgcatcg tccaggacgg cctgatcttc | 420 |
| cgccagaact tcagcatccg ctcgtatgag atcggcgccg accgcaccgc cagcatcgaa | 480 |
| accctgatga atcatctcca ggaaaccgcg ctcaaccacg tgaaaactgc gggcctcctt | 540 |
| ggcgatggct tcggctcgac cccggagatg tcgaagcgca atctgatctg ggtggtcacg | 600 |
| cgcatgcaag tcctggtcga ccgctacccg acctggggcg acgtcgtcca ggtcgacacc | 660 |
| tgggtgtcca gtcgggcaa gaacggaatg cgccgggatt ggtgcgttcg cgacagccgc | 720 |
| acgggtgaaa ccctgacgcg tgcgagctcg gtctgggtca tgatgaacaa gctgacgcgc | 780 |
| cgcctgtcga agatccccga ggaggtgcgt ggcgagattg agccgtattt cctcaactcg | 840 |
| gacccgatcg tcgacgagga ctcgcgcaag ctcccccaagc tggacgactc gaatgccgac | 900 |
| tatgtccgca agggcctcac gccgcgctgg tcggacctcg atatcaacca gcacgtcaac | 960 |
| aatgtgaagt atatcggctg gatcctggag agcgcgccac tgccgatcct cgaatcgcac | 1020 |
| gagctctcgg cgatcacgtt ggagtaccgt cgcgagtgcg tcgtgatag cgtcctgcag | 1080 |
| tccctgacgg ccgtgtccgg caacggcatc ggcaatctcg ggaacgcggg cgacatcgag | 1140 |
| tgccagcatc tcctgcgcct ggaagatggc gcggagatcg tccggggacg cacggagtgg | 1200 |
| cgccctaagt actctagcaa cttcggcatc atgggccaga tccccgtgga gtcggcc | 1257 |

<210> SEQ ID NO 10
<211> LENGTH: 1215
<212> TYPE: DNA
<213> ORGANISM: Artificial Sequence
<220> FEATURE:
<223> OTHER INFORMATION: Codon optimized Jatropha curcas acyl-ACP
      thioesterase sequence

<400> SEQUENCE: 10

| | |
|---|---:|
| atggctgttt tcacctaccg catcgccatg ctcccgattc gctgctcctc ctccaatagt | 60 |
| accaactcgc attcgcacga cccgaaccag cagaatctcc ataagatcaa gatcaatggg | 120 |
| tcggcgtcgg ccatgatgcc cctcaaggtc gacctcccgt cgagcctcac gatcacgagc | 180 |
| gtcgcccccg tggtcgagaa tctcagcctg accaaggagc agacgcgcca gaacatcccc | 240 |
| accaagaagc agtatatcga tccgcaccgc cagggcctca tcgtcgagga gggcgtgggc | 300 |
| taccgccaga ccgtcgtgat ccgctcgtat gaggtcggcc ccgataagac cgccaccctg | 360 |
| gagatcatcc tctgcttgct gcaagagact gccctgaacc acgtctggct ctcgggcctg | 420 |
| ctcagcaacg gcttcggcgc gacgcatgga atggtgcgca taatctcat ctgggtcgtg | 480 |
| tcgaagctcc aggtccaggt cgaccagtat cccatctggg gcgaggtcgt cgagatcgac | 540 |
| acgtgggtcg gcgcctccgg caagaacggt atgcgtcgcg actggctggt ccgctcgcag | 600 |
| gcgaccggtc aggtgttcgc gcgtgccacg tctacgtggg tgatgatgaa cgagaaaacg | 660 |
| cgccgtctgt cgaagatgcc cgaggaagtc cgggctgaga ttgcgccgtg gttcatcgag | 720 |
| aaacaggcga tcaaagaaga agtgcctgag aagatcgcga agctggacga caaggcccgc | 780 |
| tacgtcgtca ccaaccctcaa gcccaagcgc tcggacctgg atatgaacca gcacgtgaac | 840 |
| aatgtcaagt atgtgcgctg gatgctcgaa accctgccgg atcaattctt cgagaaccat | 900 |
| cagcttagcg gcatcacgct ggagtacaag cgggagtgcg gctcctcgga tatcgtggag | 960 |
| tcgttgtgcg agccggacga ggaggagggc atcatcaata ccggcctgaa gcagaacaat | 1020 |
| gacaagtcgc tgttcaacgg cttcagcctc ccgtcggaga ttatggaagg caacggattc | 1080 |

| | |
|---|---|
| ctgtcgtcgc tggaaaagac cccgctgaag tataccatc tcctcgttgc gaagggcaag | 1140 |
| acacagagcg aagagatcgt ccgcggcaag accatctgga agaagaagct gctcacgacc | 1200 |
| atgccgttct ccccg | 1215 |

<210> SEQ ID NO 11
<211> LENGTH: 1044
<212> TYPE: DNA
<213> ORGANISM: Artificial Sequence
<220> FEATURE:
<223> OTHER INFORMATION: Codon optimized Jatropha curcas acyl-ACP thioesterase sequence

<400> SEQUENCE: 11

| | |
|---|---|
| atggtgtcca cggccatctc gttctccctc ctccccatca agctcatcaa agaagaaacc | 60 |
| cgcatggctt ccgcggaccg ccgcaagaat tcgatcgtca agaattcgg ccatttcacg | 120 |
| tgccggtgcg cggcgatcga agcgcatc cagaagctca acaacttcct catcgatggc | 180 |
| ggcttcggct cgctggagca gaacggcctg atctatcgcc agaatatctt cattcgctcg | 240 |
| ttcgagatcg gcttcgaccg caagttgtcg ctggctgccc tcaccaattt cctccaggac | 300 |
| accgccctca accatgtccg catgatcggg ctgctggcgg ccggattcgg ctcgaccccg | 360 |
| gagatgtcga aaaggacct catctgggtc ctctgcaccc tccagatcct cgtcgatcgc | 420 |
| catccgtcgt ggctcgatgc ggtcgaggtc gacacctgga tgtaccccctc cggccagaac | 480 |
| ggccagggcc gcgattggct cgtgcgggac gccaagacgg gcaagcccct tgcccaggcg | 540 |
| agcagcgtga tggtgctgct gaacaagaaa cccgcaagc tgagtaagtt cacggaagag | 600 |
| atccgtgacg agatcgcccc tcacatgatg atggactgca accgatcat caatagccgc | 660 |
| aagatgctgc ccttcgacgt gaacaccgcc gactatgcgc gcacgggcct gaccccgggt | 720 |
| tggaacgatc tcgacctgaa tcagcatgtc aatcacgtcc aatatatcaa ttggattctc | 780 |
| cagaatgtcc tgcgctcgct catccagcac cacaagctga gcgacatcac gctggagtat | 840 |
| cgtaaggagt gcgatatcaa tagcatcctc cagttcctgt cgaagatcgt gaagaacggc | 900 |
| agcaaccatt cgaccgacac caacaacctc attgagctgg accactcgct gctgctggag | 960 |
| aatggctcgg agatcgcgag ggccaacacg atctggaagc cgcgtgaggt caataacttc | 1020 |
| aagaacgccg tttacactcc ggcg | 1044 |

<210> SEQ ID NO 12
<211> LENGTH: 1071
<212> TYPE: DNA
<213> ORGANISM: Artificial Sequence
<220> FEATURE:
<223> OTHER INFORMATION: Codon optimized Jatropha curcas acyl-ACP thioesterase sequence

<400> SEQUENCE: 12

| | |
|---|---|
| atggcttcca ccgcgatctc gttcctctcc attcccatca agctgatcaa agaagaaatg | 60 |
| cgcatggcct cggcgggtcg tcggaagaat acgatcgcgg cggagttcgg ccatttcacc | 120 |
| ttcggctccg ccaccgtgga gaagaaggtc cagaagtcga caacttcct catcgacggc | 180 |
| ggcttcggca gcctggagca gaacggactg atctaccgcc agaatatctt cgtccgctcg | 240 |
| ttcgagatcg gcttcgaccg caagctctcg ctggccgctc tgacgaattt cctgcaggac | 300 |
| accgcgctca ccactgcccg catgatcggc ctgctggccg agggcttcgg ctcgacgccg | 360 |
| gagatgatca gaaagacct gatttgggtg ctctgcaccc tccagatcct ggtcgacggc | 420 |
| taccccagct ggctcgacgt tgtcgaggtc gacacctgga tgtatccgag cggccagaac | 480 |

```
ggcctcggcc gcggctggct ggtgcgtgat ggcaagaccg gtcgctcgtt ggcgcagagt      540
tcgtctgtca tggtgagctt caataagaaa actcgcaagc tgagcaagct cgccaaggaa      600
atccgcgacg agatcgcccc gcacatgatg gactgcgatc cgatcatgaa caagaactcg      660
cggaagatcc tcccgttcga tgtgaacacc gccgactatg cccgcaccgg cctgaccccc      720
ggatggaacg aactggatct caatcagcat gtcaaccacg tccagtatat caactggatc      780
ctccagaatg tccgtccgag cctggtccaa catcacaagc tctcggcgat cacgctggag      840
tatcgcaaag agtgcgatat gaactcgatc ctccagtccc tctcgcgcat tgtcaagaat      900
ggcgggaaca cagcacggga caagaataac gtgatcgagc tcgaccattt cctgctcctg      960
gagaatggct cggagatcgc gcgcgccaac acgatctgga agccccgcga ggtgaataac     1020
ttcaagaatg tcgtccattc ccctgcggaa gagaatatct cgtcgatgaa c              1071
```

```
<210> SEQ ID NO 13
<211> LENGTH: 396
<212> TYPE: DNA
<213> ORGANISM: Artificial Sequence
<220> FEATURE:
<223> OTHER INFORMATION: Codon optimized E. Coli FadM sequence

<400> SEQUENCE: 13
atgcaaaccc agattaaggt ccgcggctac catctcgacg tctaccagca tgtgaataac       60
gcccgttatc tcgaattcct cgaagaagcg cgctgggacg gcctggagaa ctcggatagc      120
ttccagtgga tgaccgccca caatatcgcg ttcgtcgtgg tcaatatcaa catcaactat      180
cgccggccgg ctgtgctctc ggacctcctg accatcacct cgcagctcca gcagctgaac      240
ggcaagtcgg gaatcctgtc ccaggtgatc acgctggagc ccgagggcca ggtcgtcgcg      300
gatgccctga tcacgttcgt ttgcatcgac ctcaagacgc agaaagccct cgcgcttgag      360
ggcgagctgc gcgagaagct ggagcagatg gtcaag                                396
```

```
<210> SEQ ID NO 14
<211> LENGTH: 957
<212> TYPE: DNA
<213> ORGANISM: Artificial Sequence
<220> FEATURE:
<223> OTHER INFORMATION: Codon optimized E. Coli AccA sequence

<400> SEQUENCE: 14
atgtccctga acttcttgga tttcgaacag cccatcgccg aactggaagc gaagatcgac       60
tctctgaccg ccgtgagccg ccaagatgag aagctcgaca tcaacatcga cgaagaagtc      120
caccgcctcc gcgagaaatc ggtcgagctt acccgcaaga ttttcgcgga tctgggcgcg      180
tggcagatcg cccagctcgc gcgtcatccg cagcgcccgt acacgctcga ctatgttcgt      240
ctggccttcg acgagttcga cgagctcgcc ggtgatcgcg cgtatgccga cgataaggcc      300
atcgtcggcg catcgccag ctggatgga cgcccgtga tgatcatcgg ccatcagaaa        360
ggccgcgaga ctaaggagaa gatccgtcgc aacttcggca tgcctgcgcc cgaggggtat      420
cgcaaggccc tgcgcctcat gcagatggct gagcgcttca gatgcccat catcacgttc      480 atcgacaccc cgggcgcgta tccgggcgtg ggcgccgagg aacgcggcca gagcgaggcc      540
atcgcgcgga atctccggga gatgtcgcgc tcggagtcc cggtcgtgtg caccgtgatc      600
ggcgagggcg gctccggcgg cgcgctcgcg atcggcgtcg cgacaaggt caacatgctg      660 cagtattcga cgtactccgt catcagcccc gagggctgcg cgtcgatcct ctggaagtcg      720
```

```
gccgacaagg cgcccctcgc cgctgaggcc atgggcatca ttgccccgcg cctgaaagag    780
ctcaagctga tcgactcgat cattccggag ccgctgggtg gcgcgcaccg caatcccgag    840
gcgatggcgg cgtcgctgaa ggcgcagctg ctcgccgatc tcgccgacct ggacgtcctc    900
tcgaccgagg acctcaagaa tcgccgctac cagcgtctga tgtcctacgg ctatgct       957

<210> SEQ ID NO 15
<211> LENGTH: 468
<212> TYPE: DNA
<213> ORGANISM: Artificial Sequence
<220> FEATURE:
<223> OTHER INFORMATION: Codon optimized E. Coli AccB sequence

<400> SEQUENCE: 15
atggacattc gtaagatcaa aaagctcatc gaactcgtcg aggaaagcgg catctccgaa     60
ctggaaatct ctgagggcga agagtcggtg cgcatcagcc gcgcggcgcc tgccgcctcg    120
ttccccgtca tgcagcaggc ctacgcggcg cccatgatgc agcagccggc tcagtcgaac    180
gccgccgcgc cggccaccgt gccctcgatg aagcgccgg ctgcggcgga gatcagcggc    240
catatcgtgc gctcgccgat ggtcggcacc ttctatcgca cgccctcccc ggatgccaag    300
gccttcatcg aggtcggcca aaaggtcaac gttggagaca ccctgtgcat cgtcgaggcg    360
atgaagatga tgaatcagat cgaggccgac aagtcgggta cggtcaaggc catcctcgtg    420
gagtcgggcc agccggtcga gttcgacgag ccgctggtcg tgatcgag                 468

<210> SEQ ID NO 16
<211> LENGTH: 1347
<212> TYPE: DNA
<213> ORGANISM: Artificial Sequence
<220> FEATURE:
<223> OTHER INFORMATION: Codon optimized E. Coli AccC sequence

<400> SEQUENCE: 16
atgctggata agatcgttat agccaaccgt ggagaaatcg ccctgcgtat cctcagagcc     60
tgcaaagaac tcggtatcaa gaccgtcgcg gtgcatagct cggccgaccg cgacctcaag    120
cacgtgctgc tggccgacga aacggtctgc attggccccg ccccctcggt caagtcctat    180
ctcaatatcc cggcgatcat ctcggcggct gagatcaccg gggcggtcgc gatccacccc    240
ggctatggct tcctgtccga gaatgccaac ttcgcggagc aagtcgagcg ttcgggcttc    300
atcttcatcg gccccaaggc cgaaacgatc cgccttatgg agacaaggt gtcggcgatc    360 gcggcgatga aaaaggctgg cgtgccgtgc gtgccgggct cggatggccc gctgggcgac    420
gacatggata agaaccgggc catcgcgaag cgtatcggct atccggtcat tatcaaggcc    480
tccggcggcg gcggcggccg cggcatgcgc gtcgtccgcg gtgacgccga gctggcgcag    540
tcgattagca tgactcgcgc cgaggcgaaa gcggcgttct cgaatgacat ggtgtatatg    600
gagaagtact tggagaaccc ctcgccacgt cgagatccagg tgctcgcgga tggccagggc    660
aacgccatct atctcgcgga gcgcgattgc tcgatgcagc ggcgccacca gaaggtcgtc    720
gaggaagcgc ccgcccccgg gcatcacgcc gagctgcgcc gctatatcgg tgagcgctgc    780
gccaaggcgt gcgtcgatat cggatatcgc ggcgccggaa ccttcgagtt cctcttcgag    840
aacggcgagt tctatttcat cgagatgaat accgcatcc aggtcgagca tcccgttacc    900
gagatgatca ccgcgtcga tctgatcaaa gagcagctgc gcatcgccgc tggccagccg    960
ctgtcgatca gcaagaagag ggtccatgtg agggggccacg ccgtcgagtg ccgcatcaat   1020
gccgaggacc cgaacacgtt cctcccgtcc cccggcaaga ttacgcgctt ccatgcgccc   1080
```

```
ggcggcttcg gcgtccggtg ggagagccat atctacgcgg gctacaccgt gccgccgtac    1140
tacgacagca tgatcggcaa gctcatctgc tatggcgaga ccgcgacgt cgcgatcgcc    1200 cgcatgaaga acgccctcca ggaactcatc atcgacggga tcaagacgaa tgtggacctc    1260
cagatccgca tcatgaacga cgagaacttc cagcatggcg caccaatat ccactacctg    1320 gaaaagaagc tgggcctgca ggaaaag                                        1347
```

<210> SEQ ID NO 17
<211> LENGTH: 912
<212> TYPE: DNA
<213> ORGANISM: Artificial Sequence
<220> FEATURE:
<223> OTHER INFORMATION: Codon optimized E. Coli AccD sequence

<400> SEQUENCE: 17

```
atgagctgga ttgaacgcat caagagtaat atcaccccca cccgcaaggc ctctatccct     60
gaaggcgtct ggaccaagtg cgactcgtgc ggccaggtcc tctatcgcgc cgagctggag    120
cgcaacctcg aagtctgccc caagtgcgat catcacatgc gcatgacggc gaggaatcgg    180
ctccattcgc tgctggacga gggcagcctc gtcgagctcg gctcggagct ggagccgaag    240
gacgtcctca gttccggga ttcgaagaag tacaaggacc gcctggccag cgcccagaag    300
gaaacgggcg agaaagatgc cctcgtcgtt atgaagggca ccctgtacgg catgccggtg    360
gtggccgctg cgttcgagtt cgcgttcatg ggcggcagca tgggctcggt cgtcggtgcc    420
cgcttcgtcc gtgcggtgga gcaggcgctt gaggataatt gcccgctgat ctgcttctcc    480
gcgtcgggcg gtgcgcgcat gcaagaagcg ctgatgtcgc tgatgcagat ggcgaaaacg    540
tccgccgccc tggccaagat gcaggagcgc ggactgccgt atatctcggt cctgacggac    600
ccgaccatgg ggggagtctc cgcgtccttc gcgatgctcg gcgacctgaa catcgccgag    660
ccgaaggccc tcatcggctt cgcgggcccc cgtgtcatcg agcagaccgt gcgcgagaag    720
ctccccgccg gcttccagcg cagcgagttc ctcatcgaaa agggcgcgat cgacatgatc    780
gtgcgtcgcc cggagatgcg cctcaagctc gcgtcgatct tggccaagct catgaacctc    840
ccggccccca accccgaggc gccccgcgag ggcgtcgtcg tgccgccggt gccggaccag    900
gagcccgagg ct                                                        912
```

<210> SEQ ID NO 18
<211> LENGTH: 2181
<212> TYPE: DNA
<213> ORGANISM: Artificial Sequence
<220> FEATURE:
<223> OTHER INFORMATION: Mutated Methylococcus capsulatus fadD sequence

<400> SEQUENCE: 18

```
gatcgtagtc gtcttcacag gtcatggctc gggtggcgga gttcatggga aggcggaggg     60
actgagtctt cgttcaaatc ggccgcactg ccggtggctg ggacgggaat gatagcgctg    120 ccatccctc gcccgaaagg cggctagatc gtcttcttga gccggtcctc ctcccgttgg     180
ccaacggtcg ctcgagtcgc gcattcgctg ccgcctgctc cgcgtccaac gcccaggca    240 cggatcgctg acgatggcgc gccccgccgc tgggaatcag cccggcgcca accccgact    300 cccacgccac cgtcgccatg ggatgccacc caaagcatgc gtttgaccgg ctgttcctcg    360
aactccgccg tatatcgccg ccggctcggt ttctgtcggc cactcatcga ccacccccc    420 caagggcttg acccgcataa atgggggggct acgcaggcgt agcgagatca gcgccacgca    480
```

```
cgttcgattc cgcggacttg cagtcgatga aggccggcct gtccaccagc agcggtcgcg    540
tttccaggaa gccagccgtt tcgttcttgg tctaccccac gatgatccga ggctcggtgt    600
acctcggcat ctcctgcaga gcaatggtgg gccggacggt cagcgtagcg ggctcgtttg    660
cggccatggc cgctccaaaa gccgttgcaa gagtgtcgta tttcacgata ttcccggcgc    720
tcccaaggca gaacgaaccg gtgacgcatc accagcccgg cgctcagaga gcgtcgtaaa    780
gtttacgacc ggcccagttt gaccgcgact ggcagggttt gcggctctgg gagaaagtca    840
tcgaactgcc tcgggcgcac gcctcctcaa attccttcaa ggcagcaggc ggcgctgcaa    900
cgacgccccc gaccgcaggg acctggaccg cgacgggaat cacggaccgt tcccgcctgg    960
aaccgggggc atcggagatg cttcagagga tatcctgtca ggcatccacc ccgcgctcca   1020
cttcaccctg ccgccgcagc tgccgcttca ctatttgct tatacgtgtc gtaggtcggt   1080
ttccatccgg tataggtggc gcagcccgaa acggccacgg cggacatcag cagtatcggt   1140
acgcttttca acatggtcat gaactcctcg ctcgaaaatt ccgtccttac agcccccagc   1200
ccagatccgg ggacaggaag acgcagccac tatatcaaaa ccgggttcac gccgaacact   1260
tcgccgattc gggaatatcc ggtgcttctg ttatgatcgc atcctccgat gagcgcgatg   1320
gcccgccgcc ctccccgaa cgaccgaatc cctgcgccga tcgacgtccc ggcacgcggt   1380
caccctcatc agacattttt cactctttga ctccccatcc tgatgcaatc gaccgaaact   1440
cccttttcct ttgccgatct ggcgatctct gcccccattc tccaggccat ccgcgaaatc   1500
ggctacgaga ctccctctcc catccaggcg gcgagcattc ccctctcct cgccggccat   1560 gatcttctgg gccaggcgca gaccggcacg gcaaaaccg ccgctttcgc cctgccgatc   1620
ctgaacggta tcgacctcga gcgccgcgag ccgcaagcgc tggtgctggc tccgacccgc   1680
gaactcgccc tgcaagtggc cgaggccttc cagagctatg cccgccacct gcccgatttc   1740
catatcctgc cgatctatgg cggccagtcg atggatgcac agttgcgtca tctgcgccgg   1800
ggagtccacg tcatcgtcgg cacccccggc cgggtgattg accacctgcg ccgcaagagc   1860
ctcaatctgg atggcctgcg caccccttgtt ctggacgaag ccgacgagat gctgcgaatg   1920
ggcttcatcg aagacgtcga gtggatcctc gagcacactc cgcccgagcg ccagatcgca   1980
ctgttctccg ccaccatgcc ggaagcgatc cgcagggtcg ccaagcgcca cctccgccat   2040
cccaaggagg ccaagatcga ggccaagacc gccacggtcg aggcaatcac ccagcgctac   2100
tggctgggtt cgggcgcgca caaactggac gccctgaccc gcatcctcga ggtcgaggac   2160
ttcgacgcca tgatcatctt c                                             2181

<210> SEQ ID NO 19
<211> LENGTH: 927
<212> TYPE: DNA
<213> ORGANISM: Artificial Sequence
<220> FEATURE:
<223> OTHER INFORMATION: Codon optimized E. Coli FadD sequence

<400> SEQUENCE: 19
atgactcagt tcgcgttcgt cttttccaggt caaggttcac aaacagtcgg tatgctcgca     60
gatatggccg cctcctaccc gatcgtcgaa gaaaccttcg cggaagcctc ggcggcactg    120
ggttacgacc tgtgggccct gacgcagcaa ggcccggccg aggaactgaa caagacctgg    180
cagacgcagc ccgctctgct gaccgcctct gtggccctgt atcgcgtttg cagcaacag    240 ggcgggaaag ctcctgcgat gatggcgggc cacagcttgg gggagtatag tgcgctggtc    300
tgtgccgggg tgatcgattt cgccgacgcg gtccggctgg tcgagatgcg cggcaagttc    360
```

-continued

```
atgcaggaag ccgtaccgga aggcaccggc gccatggccg cgataatcgg cctggacgac      420
gcctcgatcg cgaaggcgtg cgaagaagcc gccgagggcc aggttgtcag ccccgtgaac      480
ttcaactccc ccggacaggt cgtcatcgcc ggacacaaag aagccgtgga gcgggccgga      540
gcggcctgca aggctgcagg cgccaagcgc gccttgccgc tcccggtgtc ggtccccagc      600
cattgcgcgc tcatgaagcc cgctgccgat aagctggcgg tggagcttgc gaaaatcacg      660
ttcaacgccc ccaccgtgcc ggtggtaaac aacgtggacg tgaagtgcga accaatggc       720 gacgcgattc gggacgccct cgtgcgtcag ctgtataacc cggtgcagtg gacgaaatcg      780
gtcgagtaca tggcagccca gggcgtcgag catctctacg aagtcggccc ggggaaggtc      840
ctcaccggcc tgaccaagcg catcgtggat accctgacgg cgagcgcctt gaatgagccg      900
tccgcgatgg cagccgccct ggagctc                                         927

<210> SEQ ID NO 20
<211> LENGTH: 549
<212> TYPE: DNA
<213> ORGANISM: Artificial Sequence
<220> FEATURE:
<223> OTHER INFORMATION: Codon optimized E. Coli TesA sequence with
      periplasmic targeting sequence removed

<400> SEQUENCE: 20
atggcagata ccctccttat tcttggcgat tctctctcag ctggttaccg tatgtccgct       60
tccgccgcat ggcccgcccct gctcaatgac aaatggcaaa gcaagacctc ggtcgtgaat     120
gcctcgatct cgggcgacac cagccaacag gggctggcca ggctgcctgc gttgctgaag     180
cagcatcagc cgcgctgggt gctcgtggag ctgggcggca cgatggact gcgcggcttc      240 cagccccagc agaccgagca gacgctgcgg cagatcctgc aagacgtgaa agcggccaat     300
gcggagccgc tgctcatgca gatccgcctc ccggccaact acggccggcg gtacaacgaa     360
gccttcagcg ccatctaccc aaagctggcg aaagaattcg acgttccgct gttgcccttc     420
ttcatggaag aagtctatct gaagccgcag tggatgcagg acgatggcat ccatcccaac     480
cgcgacgcgc agccgtttat cgccgactgg atggccaaac agctgcagcc gctggtcaac     540
cacgacagc                                                             549

<210> SEQ ID NO 21
<211> LENGTH: 1146
<212> TYPE: DNA
<213> ORGANISM: Artificial Sequence
<220> FEATURE:
<223> OTHER INFORMATION: Codon optimized Cinnamomum camphorum
      thioesterase sequence

<400> SEQUENCE: 21
atggccacca ctagtcttgc ttcagccttt tgttctatga agccgtaat gttagcccgc        60 gatggtagag aatgaagcc gaggtcgtcg gacttgcagc tgcgagcggg caacgcccag      120
acctccctga agatgatcaa cggcaccaag ttcagctaca ccgagtcgtt gaaaaagctg      180
ccggactggt ccatgctgtt cgcggtcatc accaccatct tcagtgccgc ggagaagcag      240
tggaccaacc tggagtggaa gcccaagccg aatccgcctc agctgctgga cgaccacttc      300
ggcccacatg gcctcgtctt cgccgcacg ttcgccatcc gcagctacga agtcggcccg       360
gatcggtcga cctccatcgt ggccgtgatg aaccatctgc aagaagcggc gctgaatcac      420
gccaagtccg tgggaatcct gggtgacggt tcgggacga ccctggaaat gagcaagcgg       480
```

```
gatctcatct gggtggtgaa gcgcacccat gttgcggtcg aacggtaccc cgcgtggggg      540
gacaccgtcg aggtcgaatg ctgggtgggc gcctccggca ataacggacg ccgccacgat      600
ttcttggtgc gcgattgcaa aaccggcgaa attctgaccc ggtgcaccag cctgtcagtc      660
atgatgaaca cgcggacgcg ccgtctgagc aagatcccgg aagaagtcag gggcgagatc      720
ggtccggcat ttatcgataa tgtcgctgtt aaagatgaag agatcaagaa gccccagaag      780
ctcaacgact ccaccgccga ctacatccag ggcgggctga cgccccgttg aacgaccta       840 gacatcaacc agcatgtgaa caacattaaa tatgtcgact ggatcctgga gactgtgccg      900
gatagcatat cgaaagcca tcacatctcg tcgttcacga tcgaatatcg tcgggagtgc       960
acgatggaca gcgtcctgca gtcgttgacg accgtgagcg gcggttcctc cgaagcgggc     1020
ctcgtgtgcg aacacctcct ccagcttgag ggcgggtccg aggtcctgcg cgccaagacc     1080
gagtggcggc cgaaactgac agactcgttc cggggcatct ccgtgatccc cgcagagagc     1140
agcgtc                                                                1146
```

<210> SEQ ID NO 22
<211> LENGTH: 1146
<212> TYPE: DNA
<213> ORGANISM: Artificial Sequence
<220> FEATURE:
<223> OTHER INFORMATION: Codon optimized Umbellularia californica thioesterase sequence

<400> SEQUENCE: 22

```
atggccacca cctctctagc ttcagccttt tgttcaatga aagccgttat gctcgcacgc       60
gatggacgcg gaatgaagcc ccgcagcagc gacttgcagc tccgcgccgg caatgcaccg      120
accagcttga aaatgatcaa cggaactaag ttctcgtaca cagagtccct gaagagactg      180
ccggactggt ccatgctgtt cgcggtcatc accaccatct tctcggccgc ggaaaagcag      240
tggacgaacc tcgaatggaa gccgaagccg aaactgcccc agctgctcga cgaccacttc      300
gggctgcacg gcctcgtgtt ccggcgaacc ttcgccattc ggtcgtacga agttggcccg      360
gatcggagta cctcgattct ggccgtcatg aaccacatgc aagaagccac cctgaaccac      420
gccaaaagtg tgggtatcct cggtgacggc ttcggcacga ccctggaaat gagcaagcgg      480
gacttgatgt gggtcgtgcg taggacccat gtcgcggtcg aacgttatcc tacctggggg      540
gatacggtcg aggtcgagtg ttggataggc gcgtccggca ataacggcat gcgccgcgac      600
ttcctggtgc gcgactgcaa gacgggcgag atcttgaccc gctgcacctc gctgtcggtg      660
ctgatgaaca cccggacgcg gcgcctgagc accatccctg acgaagtccg aggcgagatc      720
ggccccgcct tcatcgacaa cgtggccgta aaagacgacg agataaagaa gctgcagaag      780
ctcaacgact ccaccgccga ctacatccag ggcggcctga cccccggtg aacgacctg       840 gatgtgaacc agcacgtcaa taatctgaag tacgttgcgt gggtgtttga acggtgccc      900 gatagcatct cgagtccca tcacatcagc tcgttcaccc tggagtatcg ccgggaatgc      960
acacgcgata gcgtgttgcg gtcgcttacc actgtcagcg ggggttcgtc cgaggccgga     1020
ctggtctgcg accatctcct ccagcttgag ggcgggtcgg aagtcctgcg cgcccggacg     1080
gaatggcgtc cgaagttgac ggactccttc cgtgggatct ccgtgatccc agccgaaccg     1140
cgcgtg                                                                1146
```

<210> SEQ ID NO 23
<211> LENGTH: 750
<212> TYPE: DNA

<213> ORGANISM: Artificial Sequence
<220> FEATURE:
<223> OTHER INFORMATION: Codon optimized Streptococcus pyogenes acyl-ACP thioesterase sequence

<400> SEQUENCE: 23

```
atgggcctgt cctaccaaga agaactgacc ctgccattcg aactctgcga cgtgaaatcc      60
gacatcaagc tgccgcttct tctggattat tgcctcatgg tgtctggccg gcagtccgtc     120
cagctgggcc gcagcaacaa caatctgctg gtcgactaca agctcgtctg atagtcacg      180
gactacgaga tcactatcca taggttgccg cacttccagg aaacgatcac gatcgaaacc     240
aaggccctgt cgtataacaa attcttttgt taccgccagt tctacatcta cgaccaggaa     300
ggctgcctgc tcgtcgacat cctgtcgtac ttcgcgctgc tgaaccccga tacgcgcaag     360
gtcgcgacca tccctgagga tctggtggcc cccttcgaaa ccgacttcgt gaagaaactc     420
catcgggtgc cgaagatgcc gttgctggag cagagtatcg accgtgacta ctacgttcgc     480
tacttcgaca tcgacatgaa tggacacgta aacaactcaa agtatctgga ttggatgtat     540
gatgtgctgg gctgccaatt cctcaagacc catcagccct gaagatgac cctgaaatat      600
gtgaaagaag tcagcccggg tggtcagatt accagctcgt atcacctcga ccaattgacc     660
agctaccacc agatcatctc ggacgggcag ctcaacgccc aggccatgat tgagtggcgg     720
gcaatcaagc agaccgagtc cgagacagat                                      750
```

<210> SEQ ID NO 24
<211> LENGTH: 1191
<212> TYPE: DNA
<213> ORGANISM: Artificial Sequence
<220> FEATURE:
<223> OTHER INFORMATION: Codon optimized Ricinus communis palmitoyl-acyl carrier protein thioesterase sequence

<400> SEQUENCE: 24

```
atgggcacat gttcttacac catcaccctc cccatccgct gcctcagtaa ctcgaacggc      60
caccatgatc cgcacaagca gaatctgaac aagatcaaga tcaatggcgc ctcgacctcc     120
acccggcctc tgaagcttga cgccccctcc cagacggtcg cgtcgccac catatacttg       180
gcgagcgtgt ccgagaacct caccctgacc aaagaagtca tgcgccagaa catcccgacc     240
aagaaacagt acatcgatcc ccaccgccag ggcctgatga tcgagggtgg cgtgggctat     300
aggcagacta ttgtcatccg cagctacgaa gtgggacccg acaaaacggc cactctggag     360
agcatcctgt atctgctcca ggaaaccgcc ctcaaccatg tgtggctgtc cggtctgctg     420
tccaatgggt tcgcgcgac gcacggcatg gtcaaaaaca acctgatttg ggtggtgagc     480
aagctgcaag tccaggtcga tcattatccg atctgggggg aagtggtgga gatcgacacc     540
tgggtccgcg cctccggcaa gaatggaatg aagcgggact ggctcattcg tagccaggca     600
acggggcacg tttttcgtgcg cgcgacgtcg acctgggtga tgatgaacga aaagaccaga     660
cggctctcca aaatgccgga agaagtccga gcggagataa gcccatggtt catcgagaag     720
caagcgatca agaagaagt acccgacaag atcgctaagt tggacgacaa ggcccggtac      780
gtaatctcaa acctgaaacc gaagcgctcc gacctcgata tgaaccacca tgttaacaat     840
gtcaaatacg tccggtggat gctggagatc ctgcccgacc actttctgga aagccatcag     900
ctatcgggga tcaccatgga gtatcggcgt gagtgcggct cggccgatat cgtgcagagc     960
ctgtgcgaac ggacggggga cgagatcctg tcgaatgaca tcccggtgct taacggcttc    1020
agtctggcca gcgagcctct gatggaaggt aatggattct tggtccccct ggataaggtc    1080
```

```
ccgctgaagt acacccactt gctgttgacg aagggcgagt cccagaacga agagatcgtg    1140
cgcggcaaga cgatctggaa gaaaaagctc tgcaccatgc cgttctcgac g             1191

<210> SEQ ID NO 25
<211> LENGTH: 1176
<212> TYPE: DNA
<213> ORGANISM: Artificial Sequence
<220> FEATURE:
<223> OTHER INFORMATION: Codon optimized Ricinus communis palmitoyl-acyl
      carrier protein thioesterase sequence

<400> SEQUENCE: 25
atggcatcta aaggctcgat caggttgtat ttcccctgtg actttcgtaa caccctgcag      60
aagaagaaca tgaagatgga tatggtcatg gcccgcagcg gattcagcta ttcgctcaac     120
ccgatcgcac caaaaatccc ccgcttctat gtcgtggcga acgccagcaa cccgcagcgg     180
gtggacacca tcaatggcaa aaaagtgaac ggtatccacg tggccgaatc ctccaactcg     240
tatgcggacc agaacaagat gaatgcgaca gccggcctcg tgctggacgg aacgtcgac      300 catcagccgc tccacaagtg gctgctgggg cggttcgtcg atgaacgcct ggtctactcg     360
cagaccttca tcatccgctc ctatgagata ggccccgaca gaccgccac catggaaacc      420 ctgatgaatc tgctgcagga aaccgcgttg aaccacgtaa ccagtagcgg cctcgctggc     480
gacggattcg gtgcgacgcg tgagatgtcc ctgcggaaac tgatctgggt ggtgacgcgc     540
attcatatcc aagtacagcg ctacagctgc tgggggacg ttgtcgagat cgacacctgg      600
gtggatggtg ccggcaagaa tggcatgcgt cgggattgga tcatccgcga ttacaatacg     660
aaagaaatca tcactcgcgc gacctcaacc tgggtgatta tgaaccgcga aacccggaaa     720
ctgtccaaga tgccggaaca ggttcgacag gaactcgtgc ccttctacac caacaggatc     780
gcgattgcca aggaaaacaa cgacgtcgag aagatcgaca agctcacgga cgagactgcc     840
gagcgcatca gaagcggctt ggcccctcgg tggtcggata tggatgccaa tcaacacgtc     900
aacaacgtga agtacatcgg ctggatcctg agtcggtcc cgatcaatgt ccttgaggac      960
tacaacctga cctcgatgac gctggagtac cgccgtgagt gccggcagtc caatctgttg    1020
gaatcgctga cgagcaccac cgaacattcc aacaacaata gctgcaaccg caaggcgcac    1080
ctggagtaca cgcatctcct gcggatgcag gctgacaagg ccgagatcgt ccgagcccgg    1140
accgaatggc agagtaagtc gaaccgcaag acgatc                              1176

<210> SEQ ID NO 26
<211> LENGTH: 1257
<212> TYPE: DNA
<213> ORGANISM: Artificial Sequence
<220> FEATURE:
<223> OTHER INFORMATION: Codon optimized Ricinus communis palmitoyl-acyl
      carrier protein thioesterase sequence

<400> SEQUENCE: 26
atggtcgcca cagccgccgc cgccacctcc tcattcttcc ccgttcctag ccaatccgca      60
gacgccaact tcgacaaagc gccagccagc ctgggggggca tcaaactgaa atccacgtcc    120
tgcagtcgcg gcctccaggt caaggccaac gcccaggcac cgcccaagat caatggtagc    180
agcgtgggct tcaccacgag cgtggaaacc gtgaagaacg acggcgacat gccctgcca     240 ccgcctccgc ggaccttcat caatcagttg cccgattggt ccatgctgct cgctgcgatt    300
acgacgatct tcctggcggc tgagaagcag tggatgatgc tggactggaa gccgcggcgc    360
```

```
cccgacatgc tcatcgaccc cttcggcatc ggccggatcg tccaggacgg gctcatcttc    420
cggcaaaact ttagcatccg gtcgtacgag atcggggcgg atcggaccgc gtcgatcgag    480
actctgatga accatttgca ggaaactgcc ctcaaccacg tgaaaaccgc cggtctgctg    540
ggggacggct tcggcagcac cccggaaatg agcaaaagga atctgatctg ggtcgtaacc    600
cggatgcaag ttctggtgga tcgctacccg acgtggggtg acgtcgtaca ggtcgatacg    660
tgggtgtcga agtcgggtaa gaacggcatg cgccgtgatt ggtgcgtgcg cgacagtcgc    720
acgggcgaaa ccttgacccg agccagctct gtctgggtca tgatgaacaa gctgacccgt    780
agactatcga agatcccccga agaagtccga ggggaaatcg agccgtattt cctgaactcc    840
gaccccatag tggacgaaga ttcccgcaag ctcccgaagc tggacgacag caatgcggac    900
tacgtccgca agggactgac gccgcgttgg tcagatcttg acatcaacca gcacgtgaat    960
aacgtcaagt acatcggctg gattctggag agcgcgccgc tcccgatcct cgaatcccac   1020
gagctttcgg ccatcaccct cgaatatcgc cgggaatgtg gccgggattc cgtcttgcag   1080
tcgttgaccg cggtgtccgg caacgggatt ggcaacctgg gcaacgccgg cgacatcgag   1140
tgccagcatc tgctgcgcct ggaagatggc gccgagatcg tgaggggacg caccgagtgg   1200
cgcccgaaat acagctcgaa tttcggaatc atgggccaga tccccgtgga gtcggcg     1257
```

<210> SEQ ID NO 27
<211> LENGTH: 1071
<212> TYPE: DNA
<213> ORGANISM: Artificial Sequence
<220> FEATURE:
<223> OTHER INFORMATION: Codon optimized Jatropha curcas acyl-ACP
      thioesterase sequence <400> SEQUENCE: 27

```
atggctagca cggctatctc cttcctctct atcccgatca aactcatcaa agaagaaatg     60
cgcatggcgt ccgccggacg gcggaagaac accatcgcag cggagttcgg ccacttcaca    120
ttcggctcgg cgaccgttga agaaggtgtg cagaaaagca caacttcct gatcgacggc     180 ggctttgggt cgctggagca gaacggtctt atctaccgtc aaaacatctt cgtccgcagc    240
ttcgaaatcg gtttcgatcg caagttgagc ctggcagccc tgaccaattt cttgcaggat    300
acggccctca accattgccg gatgattggc ctgttggccg aggggtttgg gtccaccccc    360
gaaatgatca agaaagacct gatctgggtc ctgtgtaccc tgcagattct cgtggacggc    420
tatccctcct ggctcgatgt ggtcgaagtc gatacgtgga tgtacccgtc gggacaaaac    480
ggcctggggc gcggctggct cgttcgcgac ggaaagactg gccggagcct ggcccagtcg    540
tccagcgtaa tggtgtccttt caacaaaaag acccgcaagc tgagtaagtt ggccaaagaa    600
attcgggacg agatagcgcc tcacatgatg gactgcgacc cgatcatgaa caagaactcc    660
cgtaagatcc tgccgttcga cgtcaatacg gcggactatg ccaggaccgg ccttaccccc    720
ggttggaatg aactggatct gaatcagcac gtcaaccatg tgcagtacat caactggatc    780
ctgcagaacg tgcgccccctc cctggtgcag caccataagc tctcagcgat cacccctggag    840 taccgaaaag aatgcgacat gaacagcatc ctgcagtcgc tctcgcggat cgtgaagaat    900 gcggcaacg actcgaccga caagaacaac gtgatcgaac tcgatcattt cctgctgctg    960
gagaacggca gtgagatcgc cagagccaat acgatctgga agccgcgcga ggtcaataac   1020
ttcaaaaatg tcgtccactc gccagccgaa gagaacatca gcagcatgaa c           1071
```

<210> SEQ ID NO 28

```
<211> LENGTH: 1215
<212> TYPE: DNA
<213> ORGANISM: Artificial Sequence
<220> FEATURE:
<223> OTHER INFORMATION: Codon optimized Jatropha curcas acyl-ACP
      thioesterase sequence

<400> SEQUENCE: 28
```

| | | |
|---|---|---|
| atggccgtgt tcacctaccg tatcgcaatg ctcccaatcc ggtgttcctc ttccaattcg | 60 |
| accaactccc atagccacga tccgaatcag cagaacttgc acaaaatcaa gatcaacggc | 120 |
| tccgcctcgg cgatgatgcc gctgaaggtt gacctcccca gcagcctgac gatcaccagc | 180 |
| gtggcccctg tggtggagaa cctgtccctg accaaagagc agacgcggca gaacattccc | 240 |
| accaagaagc agtacattga cccgcatcgt caggggctga tcgtagaaga gggcgtgggt | 300 |
| taccggcaga cagttgtcat ccgctcctac gaggtcggtc cggataagac ggccaccttg | 360 |
| gagatcattc tctgcctgtt gcaagaaacc gccctgaacc acgtctggct gagcggcctg | 420 |
| ctgagcaatg gcttcggagc cactcatggc atggtgcgca caacttgat ctgggtcgtc | 480 |
| agcaagctcc aggtccaagt cgatcagtat cccatctggg gcgaagtagt ggagatcgat | 540 |
| acgtgggtgg agcgagtgg caagaatggg atgcgcagag actggctggt ccggtcgcag | 600 |
| gcgaccggtc aggtctttgc acgcgcgacc tcgacgtggg tgatgatgaa cgaaaagacg | 660 |
| cgacgcctgt cgaaaatgcc ggaagaagtg agggccgaaa tcgcgccgtg gttcatcgag | 720 |
| aaacaggcca tcaaagaaga ggtcccggag aaaatcgcga gcttgacga caaggcccgc | 780 |
| tatgtggtga ccaacctgaa gccgaagcgg tccgacctcg acatgaacca acatgtcaac | 840 |
| aatgtgaaat atgtccgctg gatgctagaa accctgcccg accagttttt cgaaaatcac | 900 |
| cagctcagcg gaatcaccct ggaatacaag cgcgagtgcg gctcctcgga catcgtcgag | 960 |
| tcgctgtgcg agccggacga agaagagggc atcatcaaca ccggcctcaa gcagaacaac | 1020 |
| gataagagtc tgttcaatgg gttcagcctc ccttcggaga tcatggaagg gaacggcttc | 1080 |
| ctgtccagcc tggaaaagac cccgctgaag tacacccacc tccttgtggc taaaggcaag | 1140 |
| acccagtcag aggaaatcgt ccggggcaag actatatgga agaaaaagct gctgacaacg | 1200 |
| atgcccttct cgccg | 1215 |

```
<210> SEQ ID NO 29
<211> LENGTH: 1044
<212> TYPE: DNA
<213> ORGANISM: Artificial Sequence
<220> FEATURE:
<223> OTHER INFORMATION: Codon optimized Jatropha curcas acyl-ACP
      thioesterase sequence

<400> SEQUENCE: 29
```

| | | |
|---|---|---|
| atggtgtcaa ccgcgatctc ctttagcctc ctgcccatca aacttatcaa agaagaaacc | 60 |
| cgcatggcct ccgccgaccg gcgcaagaac agtatcgtca agaattcgg ccatttcacc | 120 |
| tgtcgctgcg cagccatcga aaagcgaatc cagaagctga taacttcct gatcgacggg | 180 |
| ggcttcggat ccctggagca aaatggcctg atctataggc aaaacatctt cattcggagc | 240 |
| tttgagatcg gtttcgaccg caagttgtcg ctggccgcgt tgaccaactt cctgcaggat | 300 |
| acagcgctca accatgtccg tatgataggc ctgctcgctg ccggcttcgg cagcaccccg | 360 |
| gagatgtcca agaaagacct gatctgggtg ctgtgcaccc tgcagatcct tgttgatcgg | 420 |
| cacccctctt ggctgatgc ggtcgaagtg gacacgtgga tgtaccctag cggccagaac | 480 |
| gggcagggca gagattggct cgtccgcgac gccaagacgg gcaagcccct cgcccaggcg | 540 |

```
tcgagcgtga tggtcctgct caacaagaaa acccgcaagc tgagcaagtt caccgaagag    600
attcgcgacg agatcgcccc acacatgatg atggactgca atccgatcat caactcgcgg    660
aagatgctcc cgttcgacgt aaataccgcc gactacgccc gcaccgggct aacgccgggt    720
tggaacgatt tggatctcaa tcagcatgtg aatcacgtgc agtacatcaa ctggatcctg    780
cagaacgtgc tccggtccct gatccagcat acaagctgt ccgacatcac tctggagtat    840
cgtaaggaat gcgacatcaa ctccatcttg cagttcctgt cgaagatcgt caagaacggc    900
agtaaccact cgaccgatac gaacaatttg attgagctcg accactcgct gctgctggag    960
aacggaagcg agatcgcgcg ggcgaacacg atctggaaac ccgggaagt caacaacttc    1020 aaaaacgccg tctacacccc ggca                                          1044
```

<210> SEQ ID NO 30
<211> LENGTH: 396
<212> TYPE: DNA
<213> ORGANISM: Artificial Sequence
<220> FEATURE:
<223> OTHER INFORMATION: Codon optimized E. Coli FadM sequence

<400> SEQUENCE: 30

```
atgcagaccc agatcaaagt gcgcggctac cacctcgacg tctatcagca cgttaacaac    60
gctcgttacc tcgaatttct ggaagaagcc cggtgggacg gcctgagaa cagcgactcg    120 ttccagtgga tgaccgcgca taacatcgcg ttcgtggtcg tcaacatcaa tatcaactac    180
cggcgcccgg ccgtactgtc ggaccttctc accattacga gccagctgca gcagctgaat    240
ggaaagtccg ggatcctgtc ccaagtgatc accctggaac ccgagggtca gtggtggca    300 gatgcgctga tcacgttcgt ctgcatcgat ctcaagaccc agaaagccct ggccttggaa    360
ggcgagttgc gcgagaagct ggagcagatg gtcaag                              396
```

<210> SEQ ID NO 31
<211> LENGTH: 957
<212> TYPE: DNA
<213> ORGANISM: Artificial Sequence
<220> FEATURE:
<223> OTHER INFORMATION: Codon optimized E. Coli AccA sequence

<400> SEQUENCE: 31

```
atgtccctga tttcctcga cttcgaacag cccatcgccg agcttgaagc caaaatcgac    60
agcctcaccg ccgtcagccg tcaagacgag aagctggaca ttaacatcga cgaagaggtt    120
catcggctcc gggagaagtc cgtcgaactg acccgcaaga tcttcgccga tctggggcc    180 tggcagatcg cccagctagc tcggcacccg cagcgcccct acacgctgga ctatgtacgg    240
ctcgcattcg acgagtttga tgagctcgct ggcgaccgcg cctacgcgga cgataaggcc    300
atcgtcggcg gcatcgctcg gctggacggt cgtccggtca tgatcatcgg ccaccaaaag    360
ggcagagaaa ccaaagaaaa gatccgccgt aacttcggca tgccagcgcc cgagggatac    420
cggaaggccc tgcggttgat gcagatggcc gaacgcttca gatgcccat catcacgttc    480 atcgataccc cggagccta tccgggcgtg ggtgccgagg aaaggggcca gtccgaagcg    540
attgcccgca acttgcgaga gatgtcgcgc ctggcgtgc cggtcgtgtg caccgtgatc    600
ggcgagggtg gcagcggcgg agcgctcgcc atcggcgtcg gggataaagt caacatgctg    660
cagtattcca cttactcggt gatcagtccc gaaggctgcg cctctatcct gtggaaaagc    720
gccgacaagg caccgctggc ggcagaggcc atggggatca ttgcgcctcg cctgaaagaa    780
```

| ctgaagctca tagactcgat catcccggag cccttgggcg gtgcgcatcg caacccggaa | 840 |
| gcgatggcgg cgagcctcaa ggcccagctg ttggcggacc tggccgacct tgatgtgctg | 900 |
| tcaaccgagg atctgaagaa tcggcgctac cagaggctga tgtcgtacgg gtacgcg | 957 |

<210> SEQ ID NO 32
<211> LENGTH: 468
<212> TYPE: DNA
<213> ORGANISM: Artificial Sequence
<220> FEATURE:
<223> OTHER INFORMATION: Codon optimized E. Coli AccB sequence

<400> SEQUENCE: 32

| atggacatca ggaaaatcaa gaaactcatt gaattggtcg aggaaagtgg cattagcgaa | 60 |
| ctggaaatca gcgagggtga ggaatccgtt cgcatcagcc gtgcggcgcc cgccgcgtcc | 120 |
| ttcccggtca tgcaacaggc ctatgcagcc cccatgatga gcagccagcc cagtcgaat | 180 |
| gccgcggccc ccgcgaccgt gccgagcatg aagcaccgg ctgccgccga gatctccgga | 240 |
| cacatcgtgc ggtcccctat ggtgggcacc ttttaccgca cgccgtcgcc ggatgcgaag | 300 |
| gccttcatcg aagtcgggca gaaagtgaac gtcggcgata cgctgtgcat agtcgaggcg | 360 |
| atgaagatga tgaaccagat cgaggccgac aagtcgggca ccgtcaaggc catcctggta | 420 |
| gagtcgggcc agcccgtgga gttcgacgaa ccgctggtcg tgatcgag | 468 |

<210> SEQ ID NO 33
<211> LENGTH: 1347
<212> TYPE: DNA
<213> ORGANISM: Artificial Sequence
<220> FEATURE:
<223> OTHER INFORMATION: Codon optimized E. Coli AccC sequence

<400> SEQUENCE: 33

| atgcttgaca aaatagtaat tgcgaataga ggggaaatag cgttgaggat cttgagggcc | 60 |
| tgcaaagaat tgggcatcaa gaccgttgcc gtccatagca gcgccgatcg ggacctcaaa | 120 |
| cacgtgttgc tggccgacga aaccgtgtgc atcgggcctg caccttccgt caagtcgtat | 180 |
| ctcaacatcc cggccattat ctccgctgcg gaaatcaccg gagccgtggc gatccacccg | 240 |
| ggctacggct tcctgagcga gaatgccaac ttcgccgaac aggtcgagcg gtcggggttt | 300 |
| atctttattg gccaaaggc cgaaaccatc cggctgatgg cgacaaagt gtctgcgatc | 360 |
| gccgccatga agaaagcggg agtgccctgc gtcccgggca gtgacggccc tctgggcgac | 420 |
| gacatggaca gaaccgcgc gatcgcgaag cgcatcggct acccggtaat catcaaagcg | 480 |
| agcggtgggg gtggtggacg tggtatgcgt gtggtcaggg gcgatgcgga gctcgcccag | 540 |
| agcatctcca tgacccgcgc tgaggccaag gccgccttct ccaacgatat ggtgtacatg | 600 |
| gagaagtacc tggaaaatcc ccggcacgtg gaaatccagg tcctggcaga cgggcaaggc | 660 |
| aacgcgatct acctggccga gcgggattgc tcgatgcaac gccggcatca gaaagtcgtt | 720 |
| gaagaagcgc cggcacccgg catcaccccc gagctgcgcc gctacatcgg cgagcggtgt | 780 |
| gccaaggcct gcgtcgacat cggctatcgg ggagcgggca ccttcgagtt cctgttcgag | 840 |
| aatggcgaat ctatttcat cgagatgaac acacgcatcc aggtcgagca tccggtgacc | 900 |
| gaaatgatca ccggggtgga cctgattaag aacagctgc gaatcgcagc cggccagccg | 960 |
| ctctcgatca gcaagaaga agtccacgtc cggggacacg ccgtggagtg ccgtatcaac | 1020 |
| gccgaggatc cgaacacgtt cctgccctcg cccggtaaga tcacgcgctt ccatgctccg | 1080 |
| ggtggattcg cgtccgctg ggagtcacac atctatgccg gctacacggt cccgccctac | 1140 |

```
tacgactcca tgatcggcaa gctgatctgt tatggcgaga accgcgatgt ggcgatcgcc    1200
cgcatgaaga acgcgctcca ggaactgatt atcgacggca tcaagactaa cgtggacctc    1260
cagatccgga tcatgaacga cgaaaacttc cagcacggcg gcacgaatat ccattacctg    1320
gagaagaaac tgggcctcca ggaaaag                                        1347

<210> SEQ ID NO 34
<211> LENGTH: 912
<212> TYPE: DNA
<213> ORGANISM: Artificial Sequence
<220> FEATURE:
<223> OTHER INFORMATION: Codon optimized E. Coli AccD sequence

<400> SEQUENCE: 34
atgagctgga tcgaacgcat taagtcaaac ataaccccca ccagaaaggc gagcattccc      60
gagggcgtat ggaccaagtg cgacagctgc ggtcaagtcc tgtatcgggc tgagttggag     120
cgaaatctgg aagtgtgtcc gaagtgcgac catcacatgc ggatgactgc caggaaccgt     180
ctgcacagtc tcctggacga agggtcgctc gtcgaactgg gctccgagct ggagccgaaa     240
gacgtgctga agttccggga ctcgaagaag tataaagatc ggctggcgtc cgcccagaaa     300
gaaaccggcg agaaagatgc gttggtcgtg atgaagggga cgctgtacgg catgccggtc     360
gtggcggcag ccttcgagtt tgccttcatg ggcggctcta tgggcagcgt ggtgggagcg     420
cggttcgtcc gcgctgtgga acaggcgctc gaagataact gcccgctgat ctgcttctcg     480
gcgtcggggg gtgcgcgcat gcaagaagcc ctgatgtccc tgatgcagat ggcgaaaacg     540
tccgccgcac tcgccaagat gcaggaacgc ggcctcccct acatctcggt gctgaccgat     600
ccgacgatgg gcggtgttag cgcctccttc gccatgctcg cgacctgaa catcgccgag     660 cccaaagccc tgatcggctt cgccggaccg cgggtcatcg aacagaccgt tcgcgagaag     720
ctcccctccg ggttccagcg ctcggagttc cttatcgaaa agggcgccat cgacatgatc     780
gtccgtcgcc ccgagatgcg gctgaagttg ccagcatcc tggccaagct gatgaatctt     840
cctgccccca accccgaggc accgcgcgag ggcgtcgtcg tgccgccagt gccggaccag     900
gaaccggaag cg                                                         912

<210> SEQ ID NO 35
<211> LENGTH: 1668
<212> TYPE: DNA
<213> ORGANISM: Artificial Sequence
<220> FEATURE:
<223> OTHER INFORMATION: Mutated Methylomonas methanica FadD sequence

<400> SEQUENCE: 35
atgatgggat tgggtaatgt cgacatattc tgctacgata gtttgcattg agcgtcccta      60
acaatttggt ttattttcca catggcaacc tgattacatc aattattatt cgataacctg     120
aatgctcgcg gcggattccg atgctattga gcataaggat agccgaatta gttttcgtca     180
actgagcgag ttagtagcac tccaggccaa agccctacaa agcctggatt tgaaacgcca     240
gcaacgtgtt gcaatttacc ttcctaaaca aatcgaaacc gtcagcagct tcctggccgt     300
ttccttggcc gggcggcgtg ttcgtgacgg taaatccggt actaaaggcg ccacaggtta     360
gccacatcct caacgactga aacgtcaaaa tactgatcac ctcaaaaagc cgcctgcata     420
gtttacagac agtactgcat gaatgaaccg atctacacac catcatcctg ttgatcatg     480 acgcgggcga cgttaaactc ccgtcgtggc aaattattga ctggcaaacc tacaaccgtt     540
```

```
tagccgactc ttatccacac catccggtta ccatgatcga caccgacatg gcggcgatct     600
tgtacacctc cggcagcacg ggcaaaccga aggcgtggt gttatctcat cgcaatatcg     660
tggccggcgc ccaaagtgtg gctgaatacc tgcaaattca ggcagacgac cgattgctcg     720
ccgtactacc ctttagtttc gactacgggc tgaatcaact aacgaccagc ctgttgaagg     780
gtgcaagttg cgtgttattg gactatttac tgcccaagga tgtgattaac gccctaggca     840
aataccaaat cacaggtctg gccgccgtcc cgcctttatg ggctcaactg gcggatttaa     900
actggccgga atccatcgat caacacttgc gctatatgac caactcgggc ggaaaaatgc     960
ccaaaaccgt actacaaaaa ctgcgctcta agcccccaa ttcaaagttt tttctgatgt    1020
atggcctgac ggaagccttc cgttcaacct atttaccacc cgagcaaatc gacattcgtc    1080
cggactccat gggtaaagcc atcccaaacg cggaaatcat ggtagtccgt gaggacggta    1140
gcctgtgcgc tccgcacgaa ccgggcgaac tggttcaccg cggctccctg tcagtcttg    1200
gttattggaa cgaccccgcc aaaaccgcgg aacgctttaa acccgctccc ggccaactat    1260
ccggcttacc cctgaccgaa atagccgtct ggtccggcga taccgtcacg atggatgagg    1320
atggtttttt gtattttgtc ggccgtaaag acgatatgat caaaacgtcc ggctacagag    1380
tgagtccgag tgaaattgaa gaagtcattt acgcctccgg attggttaag gaggctgcgg    1440
cgattgggat cgaacaccca aacctgggcc aggcggttgt cgttgtcgtt agcccacaac    1500
ctgatatgca attcgatcca caacaattga ttgattgctg caaaacccaa ctgccaaatt    1560
tcatggtacc cgcgcgaatt gaagagctca gcagcttacc gcgtaacccc aacggcaaaa    1620
tagatcgtaa aatgcttagc caacagtttg cccatttgtt tcagctga                1668
```

<210> SEQ ID NO 36
<211> LENGTH: 927
<212> TYPE: DNA
<213> ORGANISM: Artificial Sequence
<220> FEATURE:
<223> OTHER INFORMATION: Codon optimized E. Coli FabD sequence

<400> SEQUENCE: 36

```
atgacgcagt tcgctttcgt tttccccgga caaggatccc agaccgttgg tatgctcgct      60
gatatggccg cttcgtatcc gatcgtcgag gagactttcg cggaagcctc cgcggccctg     120
ggctacgatc tctgggccct cacccagcaa ggtccggcgg aagagttgaa taagacctgg     180
cagacgcagc ccgcgctgct caccgcgtcc gtggcgctgt atcgcgtgtg gcagcagcag     240
ggcggcaagg cccctgccat gatggcgggc cactcgctcg gcgagtattc ggccctggtc     300
tgcgccggcg tcatcgactt cgccgacgcc gtccgcctgg tcgagatgcg cggcaagttc     360
atgcaggagg ccgtccccga gggcaccggc gctatggccg ccatcatcgg cctcgacgac     420
gcgtcgatcg cgaaggcgtg cgaagaagcc gccgagggcc aggtcgtgag cccggtcaat     480
ttcaactcgc cgggtcaggt cgtcatcgcg ggccataaag aagcggtcga gcgtgccgga     540
gcggcgtgca aggccgcggg ggcgaagcgc gcgctcccgc tgccggtgtc ggtccccagc     600
cattgcgccc tcatgaagcc ggccgccgat aagctggccg tcgagctggc caagatcacg     660
ttcaacgccc cgaccgtccc cgtggtgaac aatgtcgacg tgaagtgcga acgaacggc     720
gacgccatcc gggacgcgct ggtgcgccag ctctataatc cggtccagtg gaccaagagc     780
gtggagtaca tggcggcgca gggcgtcgag cacctctacg aagtgggccc cggcaaggtc     840
ctcaccggcc tgaccaagcg cattgtcgac acgctgacgg cgtcggccct gaacgagccc     900
agcgcgatgg ccgcggcgct ggagctg                                         927
```

<210> SEQ ID NO 37
<211> LENGTH: 549
<212> TYPE: DNA
<213> ORGANISM: Artificial Sequence
<220> FEATURE:
<223> OTHER INFORMATION: Codon optimized E. Coli TesA sequence with periplasmic targeting sequence removed

<400> SEQUENCE: 37

```
atggctgata ccctcctcat tctcggcgac tccctctctg ctggttatcg tatgtccgct      60
tccgctgcct ggcctgcgct gctcaacgac aagtggcagt cgaaaaccag cgtcgtcaac     120
gcctcgatca gcggagacac gtcgcagcag ggcctcgccc gctgcccgc gctcctgaag      180
cagcaccagc cgcggtgggt cctggtggag ctgggcggca tgacggcct gcgtggcttc      240
cagccccagc agacggagca gaccctgcgc cagatcctgc aagacgtgaa ggccgccaac     300
gcggagccgc tcctcatgca gatccgcctg ccggcgaact acggccgccg ctataatgaa     360
gcgttctcgg cgatctaccc gaagctcgcg aaggaattcg acgtgccctt gctgccgttc     420
ttcatggagg aggtctatct caagccgcag tggatgcaag acgatggcat ccaccccaat     480
cgcgacgccc agccgttcat cgcggattgg atggccaagc agctccagcc gctggtcaac     540
catgattcg                                                             549
```

<210> SEQ ID NO 38
<211> LENGTH: 1146
<212> TYPE: DNA
<213> ORGANISM: Artificial Sequence
<220> FEATURE:
<223> OTHER INFORMATION: Codon optimized Cinnamomum camphorum thioesterase sequence

<400> SEQUENCE: 38

```
atggccacta cctcccttgc ttctgccttt tgctctatga agctgtgat gctcgcccgt      60
gatggacgcg gtatgaagcc gcggagctcg gatctccagc tgcgcgcggg caacgcgcag     120
acgtccctga agatgatcaa tggaccaag ttctcctata cggagtcgct gaagaagctg     180
ccggactggt ccatgctgtt cgcggtgatc accaccatct tcagcgccgc cgagaagcag     240
tggaccaacc tcgaatggaa gcccaagccg aatcccccgc agctcctcga tgatcatttc     300
ggcccccatg gcctggtgtt ccgccgtacg ttcgcgatcc gctcgtatga ggtcggcccg     360
gaccgctcca cctcgatcgt cgccgtcatg aatcatctcc aagaagcggc cctgaaccat     420
gccaaaagcg tcggcatcct gggcgacggc ttcggcacca ccctggagat gtcgaagcgc     480
gacctgatct gggtcgtcaa acgcacccac gtcgccgtgg agcgctaccc ggcctggggc     540
gataccgtcg aggtcgagtg ctgggtgggc gcctcgggca caacggccg tcgccacgac     600
ttcctggtcc gcgactgcaa aacgggagag atcctgaccc gctgcacaag cctgagcgtc     660
atgatgaata cccgcacgcg ccggctctcc aagatccccg aggaagtgcg cggtgagatc     720
ggacccgcgt tcatcgacaa cgtcgcggtc aaggacgaag agatcaagaa gccgcagaag     780
ctcaacgaca gtacggcgga ctatattcag ggcggcctga cccccgctg gaatgacctg     840
gacatcaacc agcatgtgaa caatatcaag tacgttgact ggatcctgga gactgtgccg     900
gactcgatct tcgagtcgca tcacatttcg tcgttcacga tcgagtatcg ccgcgagtgc     960
accatggatt cggtcctcca gtccttgacc acggtcagcg gcggcagctc ggaagcgggc    1020
ctcgtctgcg agcacctcct ccagctcgaa ggcggctccg aggtcctccg ggccaagacc    1080
```

```
gagtggcgtc ctaagctcac cgactcgttc cgcggcatct cggtcatccc tgccgagtcg    1140
agcgtg                                                               1146
```

<210> SEQ ID NO 39
<211> LENGTH: 1146
<212> TYPE: DNA
<213> ORGANISM: Artificial Sequence
<220> FEATURE:
<223> OTHER INFORMATION: Codon optimized Umbellularia californica
      thioesterase sequence

<400> SEQUENCE: 39

```
atggccacta cctcccttgc ttctgccttt tgctcgatga aagctgtgat gctcgcccgt      60
gatggacgag gaatgaagcc gcgctcgtct gacctccagc tgcgtgcggg caatgccccg     120
acctcgctca agatgatcaa cggcacgaag ttctcgtata ccgagtccct caagcgcctc     180
ccggactggt cgatgctgtt cgccgtcatc accacgatct tcagcgccgc ggaaaagcag     240
tggaccaacc tggagtggaa gccgaagccg aagctccccc agctgttgga tgatcacttc     300
ggcctgcacg gcctcgtgtt ccgccgcacc ttcgcgatcc gcagctacga ggtcggccct     360
gatcgcagca cctcgatcct ggcggtcatg aaccacatgc aagaagccac gctgaaccac     420
gccaagtccg tcggcatcct gggcgacggc ttcggcacca ccctcgaaat gagtaagcgc     480
gacctcatgt gggtcgtccg ccgcacccat gtcgccgtcg agcgttaccc gacctggggc     540
gacaccgtcg aggtcgagtg ctggattgga gcgtcgggca caatggcat gcgtcgcgac     600 ttcctcgtgc gcgattgcaa gaccggcgag attctgacgc gctgcacctc gctctcggtg     660
ctgatgaaca cccgcacccg ccgcctctcg accatcccgg acgaggtcag gggcgaaatc     720
ggccccgcgt tcatcgacaa cgtcgcggtg aaggacgacg agatcaaaaa gctgcagaag     780
ctcaacgact ccacggcgga ctatatccag ggcggcctga cgccccgctg gaatgacctg     840
gacgtcaacc agcatgtcaa taatctgaaa tacgtcgcct gggtgttcga cacagtgccc     900
gatagcatct tcgagagcca tcacatctcg tcgttcaccc tggagtatcg ccgggagtgc     960
acgcgggaca gcgtgctgcg gtcgctcacg accgtcagcg ggggctccag cgaagccggc     1020
ctcgtctgcg accacctcct gcagcttgag ggtggcagcg aagtcctccg tgcgcgcacg     1080
gagtggcgcc ccaagctcac ggattcgttc cgcggcatct cggtgattcc cgcggagccg     1140
cgcgtc                                                                1146
```

<210> SEQ ID NO 40
<211> LENGTH: 750
<212> TYPE: DNA
<213> ORGANISM: Artificial Sequence
<220> FEATURE:
<223> OTHER INFORMATION: Codon optimized Streptococcus pyogenes acyl-ACP
      thioesterase sequence

<400> SEQUENCE: 40

```
atgggactct cgtatcaaga agaactgacc ctgccttttcg agctttgcga cgtgaaatcg     60
gacatcaagc tgccgttgct gctcgattat tgcctgatgg tgtccggccg gcagtcggtc    120
cagctcggcc gcagcaacaa taatctcctc gtcgactaca agctcgtgtg atcgtgacc    180 gattacgaga ttacgatcca tcgcctcccg cacttccagg aaaccatcac catcgagaca    240
aaggccctgt cgtataacaa gttcttctgc taccgccagt tctatatcta cgatcaggaa    300
ggctgcctgc tcgtcgacat cctgtcctat ttcgcgctcc tcaatccgga cacccgcaag    360
gtcgccacga tccccgagga cctggtcgct cccttcgaaa ccgacttcgt gaagaaactc    420
```

-continued

```
caccgtgtgc cgaagatgcc gctgctggag cagtccatcg accgcgacta ctatgtccgc    480
tatttcgaca tcgatatgaa cggtcatgtc aacaactcga agtacctcga ttggatgtat    540
gacgtcctcg gctgccagtt cctcaagacg catcagccgc tcaagatgac cctgaaatat    600
gttaaggaag tctcgcccgg cggccagatc acgtcgtcgt accatctgga tcagctgacg    660
tcgtatcacc agatcatcag cgacggccag ctgaacgcgc aggccatgat cgagtggcgc    720
gcgattaagc agaccgagag cgagactgac                                     750
```

<210> SEQ ID NO 41
<211> LENGTH: 1191
<212> TYPE: DNA
<213> ORGANISM: Artificial Sequence
<220> FEATURE:
<223> OTHER INFORMATION: Codon optimized Ricinus communis palmitoyl-acyl carrier protein thioesterase sequence

<400> SEQUENCE: 41

```
atgggcactt gctcctatac catcaccctc ccgatccgct gcctctcgaa ttccaacggc     60
caccatgacc cccacaagca gaacctcaat aagatcaaga ttaatggcgc gtcgaccagc    120
acgcgcccgc tcaagctcga cgccccctcg cagaccgtgg gcgtggcgac catctacctg    180
gccagcgtgt cggagaatct gaccctgacg aaagaggtca tgcgccagaa catccccacc    240
aagaagcagt atatcgatcc ccatcgccag ggcctcatga tcgagggcgg agtgggctat    300
cgccagacga tcgtcatccg ctcctacgaa gtgggccctg acaagacggc cacgcttgag    360
tcgatcctgt atctgctcca ggaaaccgcg ctcaaccacg tgtggctgtc cggcctgctc    420
tcgaacggtt tcggcgcgac gcacggaatg gtcaagaaca acctcatctg ggtcgtgtcc    480
aagctgcaag tccaggtcga ccattacccg atctggggcg aggtcgtcga gatcgacacg    540
tgggtccgcg ctagcgggaa gaacggcatg aagcgcgatt ggctgatccg cagccaggcc    600
accggccacg tgttcgtccg cgccacctcg acctgggtga tgatgaatga gaaaacacgc    660
cggctctcga agatgccgga agaagtccgt gccgagatca gccccctggtt catcgagaag    720 caggcgatca aagaagaggt ccccgacaag atcgcgaagc tggacgataa ggcgcgttat    780
gttatctcga atctgaagcc gaagcgctct gacctcgaca tgaaccacca tgtcaataat    840
gtcaagtacg tccgctggat gctggagatc ctgccggacc atttcctgga gtcgcatcag    900
ctctcgggca ttacgatgga gtatcgccgt gagtgcggca gtgcggacat cgtccagagc    960
ctgtgcgagc cggacggcga tgagatcctg tccaacgaca tcccggtgct caacggcttc   1020
tcgctggcct cggagccgct catggaaggt aatggcttcc tggtcccgct ggataaggtg   1080
ccgttgaagt acacccatct gctcctcacg aagggcgagt cccagaacga agagatcgtc   1140
cggggcaaga cgatttggaa gaaaaagctc tgcaccatgc ccttctcgac c            1191
```

<210> SEQ ID NO 42
<211> LENGTH: 1176
<212> TYPE: DNA
<213> ORGANISM: Artificial Sequence
<220> FEATURE:
<223> OTHER INFORMATION: Codon optimized Ricinus communis palmitoyl-acyl carrier protein thioesterase sequence

<400> SEQUENCE: 42

```
atggcgtcca agggctcgat ccggctgtat ttcccctgcg atttccgtaa caccctccag     60
aagaagaata tgaagatgga catggtcatg gcgcggtcgg gcttctccta ctcgctcaat    120
```

| | |
|---|---|
| ccgatcgcgc ccaagattcc gcgcttctac gtggtcgcca atgccagcaa tccccagcgc | 180 |
| gtggatacga tcaacgggaa gaaagtgaac ggcatccatg tcgcggagtc gagcaatagt | 240 |
| tatgcggacc agaataagat gaacgctacg gccggactgg tcctcgacgg caatgtggat | 300 |
| caccagccgc tgcataagtg gctcctcggc cgcttcgtcg acgagcgcct cgtgtatagc | 360 |
| cagacgttca tcatccgttc gtatgagatc ggccctgaca agacggcgac catggaaacc | 420 |
| ctgatgaatc tcctgcagga aaccgcgctc aaccatgtca cctcgtcggg cctcgccggt | 480 |
| gacggcttcg gcgccacccg cgagatgtcg ctccgcaagc tgatctgggt ggttacccgc | 540 |
| atccacatcc aggtccagcg ttactcgtgc tggggcgatg tcgtcgagat cgacacgtgg | 600 |
| gtcgacggcg cgggcaagaa cggcatgcgt cgcgactgga tcatccgcga ttacaacacc | 660 |
| aaggaaatca tcacgcgcgc tacgtctacc tgggtgatca tgaaccgcga aacgcgcaag | 720 |
| ctgtccaaga tgccggagca agtccgccag gaactggtcc cgttctatac gaaccgcatc | 780 |
| gccatcgcga aagagaacaa cgacgtcgag aagattgaca agctgactga cgagacagcg | 840 |
| gagcgcatcc gctcgggcct ggcgccgcgc tggagcgaca tggacgccaa ccagcatgtg | 900 |
| aataatgtca agtatatcgg ctggatcctg gagtcggtcc ccatcaatgt ccttgaggat | 960 |
| tacaacctca cgagcatgac cctggagtat cgccgcgagt gcaggcagag caatttgctg | 1020 |
| gagtcgctca cctccaccac cgagcacagc aataacaact cgtgcaaccg caaggcccac | 1080 |
| ctggagtata cccacctcct ccgtatgcag gccgacaagg ccgagattgt gcgtgcccgg | 1140 |
| accgagtggc agtccaagtc gaaccgcaag accatc | 1176 |

<210> SEQ ID NO 43
<211> LENGTH: 1257
<212> TYPE: DNA
<213> ORGANISM: Artificial Sequence
<220> FEATURE:
<223> OTHER INFORMATION: Codon optimized Ricinus communis palmitoyl-acyl
carrier protein thioesterase sequence

<400> SEQUENCE: 43
atggtcgcca ccgccgccgc cgctaccagc tcgttcttcc ccgtcccgtc ccagtctgcc 60
gacgccaatt ttgataaggc gccggcctcg ctggggggca tcaagctcaa gtccacgtcg 120
tgcagtcgtg gcctccaggt caaggcgaat gcgcaggcgc ctccgaagat caacggctcc 180
tcggtgggtt tcacgaccag cgtggagaca gtgaagaatg acggcgacat gccgctgccg 240
ccgcctcccc gcacgttcat caaccagctg cccgattggt ccatgctcct ggcggccatc 300
accaccatct tcctggctgc ggagaagcag tggatgatgc tggactggaa gccccggcgc 360
ccggacatgt tgatcgaccc gttcggcatc ggccggattg tccaggacgg cctcatcttc 420
cgccagaatt tctccatccg ttcctatgag atcggcgcgg atcgcacggc ctcgatcgag 480
actctcatga accatctcca ggaaacggcg ctcaaccatg tgaaaaccgc cggtctgctc 540
ggcgatggct tcggctcgac cccggagatg agcaagcgca atctcatttg ggtggtgacc 600
cgcatgcaag ttctggtcga ccgctacccg acctggggcg acgtcgtcca ggtcgacacg 660
tgggtcagca aatcgggcaa gaacggaatg cgtcgcgatt ggtgcgtgcg cgactcgcgc 720
accggcgaaa cgctgacgcg tgcgagctcg gtgtgggtca tgatgaacaa gctcacccgc 780
cgcctctcga agatccccga ggaagtccgc ggagagatcg agccgtactt cctcaatagc 840
gacccgatcg tcgacgaaga ttcgcgcaag ctgccgaagc tggacgactc gaacgccgac 900
tacgtccgca agggcctcac gccccgctgg tcggatctgg acatcaacca gcacgtcaat 960

```
aatgtcaagt atatcggctg atcctggag tccgcgccgc ttcccatcct cgaatcgcat    1020
gagctgtcgg cgatcaccct ggagtatcgg cgtgagtgcg gcagggacag cgtcctgcag    1080
tcgctgaccg ccgtgtcggg caacggcatc ggcaacctcg gcaatgccgg cgacatcgag    1140
tgccagcacc tcctgcgcct cgaagatggc gcggagattg tgcgcggacg cacggagtgg    1200
cgccccaagt attcgtcgaa cttcggcatc atgggccaga tcccggtcga gagcgcg       1257
```

<210> SEQ ID NO 44
<211> LENGTH: 1215
<212> TYPE: DNA
<213> ORGANISM: Artificial Sequence
<220> FEATURE:
<223> OTHER INFORMATION: Codon optimized Jatropha curcas acyl-ACP thioesterase sequence

<400> SEQUENCE: 44

```
atggccgttt tcacctaccg catcgctatg ctccccatcc gctgcagctc gtctaactcc    60
accaattccc atagccacga cccgaaccag cagaacctcc acaagatcaa gatcaatggc    120
tcggcgagcg cgatgatgcc gctgaaggtc gatctgccct cctcgctcac gatcacgtcg    180 gtcgccccg tcgtggagaa cctctcgctg acgaaggaac aaactcggca gaatattccc    240
accaagaagc agtatatcga cccgcatcgc cagggcctga tcgtcgagga gggcgtgggc    300
taccgccaga cggtcgtgat ccggtcgtat gaggtcggac cggacaagac ggcgaccctg    360
gagatcattt tgtgcctcct gcaggaaacg cgctgaacc atgtctggct gtccggtctg    420
ctctcgaatg gcttcggcgc cacccacggc atggtccgca caatctcat ttgggtggtg    480 tcgaagctcc aggtccaggt cgatcagtat cccatctggg gcgaggtcgt ggagatcgac    540
acgtgggtcg gcgcctcggg taagaacgga atgcgtcgcg actggctcgt ccgcagccag    600
gcgacgggcc aggtttcgc ccgcgcgacc agtacgtggg tcatgatgaa tgagaaaaca    660
cgccgcctca gcaagatgcc ggaagaagtc cgcgcggaga tcgccccgtg gttcatcgag    720
aaacaggcca tcaagagga agtgccggag aagatcgcga agctcgacga taaggcccgc    780
tatgtggtga cgaacctgaa gcccaagcgc tccgacctgg acatgaacca gcatgtcaat    840
aacgtcaagt acgtgcgctg gatgctggaa accctcccgg atcagttctt cgagaatcat    900
cagttgtcgg gcatcaccct ggagtacaag cgtgagtgcg gctcgtcgga catcgtcgag    960
agcctgtgcg agcccgatga gaggagggc atcatcaaca ccggcctcaa gcagaacaac    1020
gacaagtcgc tgttcaatgg cttcagcctc ccgtcggaga tcatggaggg caacgggttc    1080
ctgtcgtcgc tggaaaagac cccgctcaag tatcccacc ttctcgtcgc gaagggcaag    1140
acccagtccg aggagatcgt gcgtggcaag accatctgga gaaaaagct cctcaccacc    1200 atgcctttct cgccg                                                    1215
```

<210> SEQ ID NO 45
<211> LENGTH: 1044
<212> TYPE: DNA
<213> ORGANISM: Artificial Sequence
<220> FEATURE:
<223> OTHER INFORMATION: Codon optimized Jatropha curcas acyl-ACP thioesterase sequence

<400> SEQUENCE: 45

```
atggttccca ccgccatctc tttctcgctc ctgcccatca agctcatcaa agaagaaact    60
cgcatggcct ccgcggaccg ccgcaagaac agcatcgtga aggagttcgg ccacttcacg    120
tgccgctgcg ccgcgatcga gaagcgcatc cagaagctga acaatttcct gattgacggc    180
```

```
ggcttcggct cgcttgagca gaatggcctc atctaccgcc agaatatctt catccggtcc      240
ttcgagatcg gcttcgaccg taagctgagc ctcgccgccc tcacgaattt cctccaggac      300
acggcgctga accatgtccg tatgattgga ctgctcgcgg ctggcttcgg gtccaccccg      360
gagatgtcga agaaagacct gatctgggtg ctctgcaccc tgcagatcct ggtcgaccgc      420
catccctcgt ggctcgacgc ggtcgaggtc gatacctgga tgtacccctc cggccaaaac      480
ggccagggcc gtgactggct ggtgcgggat gccaagacgg caagccgct ggcccaggcg      540 tcgagcgtga tggtcttgct caataagaaa acccgcaagc tcagcaagtt caccgaagag      600
atccgcgatg agatcgctcc gcacatgatg atggactgca atcccatcat taactcgcgc      660
aagatgctgc cgttcgacgt caacaccgcg gactatgcgc gcacgggcct cacgccgggt      720
tggaacgacc tcgatctcaa tcagcatgtc aaccacgtgc agtatatcaa ctggatcctc      780
cagaatgtgc tccgctcgct catccagcac ataagctgt cggacatcac cctggagtac      840
cgcaaggaat gcgatatcaa ctcgatcctg cagttcctct cgaagatcgt caagaacggc      900
tcgaaccact cgaccgacac caataacctg atcgagctgg atcattcgct gctcctggag      960
aatggcagcg agatcgcgcg cgccaacacc atctggaagc gcgcgaggt caataacttc      1020 aagaacgccg tctatacgcc tgcg                                            1044

<210> SEQ ID NO 46
<211> LENGTH: 1071
<212> TYPE: DNA
<213> ORGANISM: Artificial Sequence
<220> FEATURE:
<223> OTHER INFORMATION: Codon optimized Jatropha curcas acyl-ACP
      thioesterase sequence

<400> SEQUENCE: 46
atggcctcga ctgcgatctc cttcctctct atccccatta agcttatcaa agaagaaatg       60
cgcatggcgt ccgcgggccg ccgcaagaac accatcgcgg ccgagttcgg ccatttcacg      120
ttcggatccg cgaccgtcga agaaggtc cagaagtcga ataacttcct catcgacggc        180
ggcttcggct ccctggagca gaacgggctc atctaccgcc agaacatctt cgtgcgctcg      240
ttcgagattg gcttcgatcg gaagctgagc ctggcggctc tgaccaactt cctccaggac      300
acggcgctca tcattgccg catgatcggc ctgctcgccg agggcttcgg ctcgacgccg      360
gagatgatta agaaagatct catctgggtt ctgtgcacgc tgcagatcct ggtggatggc      420
tatccgtcgt ggctcgacgt ggtcgaggtc gatacgtgga tgtacccgag cggtcagaat      480
ggcctcggcc gtggctggct ggtccgcgac ggcaagacgg gtcgcagcct ggcccagtcg      540
agcagtgtga tggtgtcgtt caacaaaaag acccggaagc tctcgaagct ggccaaggaa      600
atcagggacg agatcgcccc tcacatgatg gactgcgacc cgatcatgaa caagaactcg      660
cgcaagatct tgcccttcga cgtcaacacc gcggattatg cccgcaccgg cctcaccccc      720
ggatggaatg agctggacct gaatcagcat gtcaatcacg tgcagtacat caattggatc      780
ctccagaacg tccgcccgtc cctcgtccaa caccataagc tctcggcgat cacgctggag      840
tatcgcaaag agtgcgacat gaattcgatc ctccagtcgc tcagccgcat cgtcaagaac      900
ggcggcaacg atagcaccga caagaacaac gtcatcgagc tggaccactt cctgctcctg      960
gagaacggct cggagatcgc ccgtgccaat accatctgga agccgcgtga ggtgaacaac      1020
ttcaagaatg tcgtgcatag ccccgccgaa gagaatatct cctcgatgaa t              1071
```

<210> SEQ ID NO 47
<211> LENGTH: 396
<212> TYPE: DNA
<213> ORGANISM: Artificial Sequence
<220> FEATURE:
<223> OTHER INFORMATION: Codon optimized E. Coli FadM sequence

<400> SEQUENCE: 47

```
atgcagaccc agatcaaagt gcgcggatat catctcgacg tttatcaaca tgtcaacaat      60
gctcgttacc tggagttctt ggaagaagcc cggtgggacg gcctggagaa ctcggactcg     120
ttccagtgga tgaccgcgca acatcgcc ttcgtcgtcg tgaatatcaa catcaattac      180
cgccgcccgg cggtgctgtc ggatctgctc acgatcacgt cccagctcca gcagctcaac     240
ggcaagtcgg gcatcctcag ccaggtcatt acgctggagc ccgagggcca ggtcgtcgcg     300
gatgccctga tcaccttcgt ctgcatcgac ctcaagaccc agaaagccct cgcgctggaa     360
ggcgagctcc gcgagaagct ggagcagatg gtgaag                              396
```

<210> SEQ ID NO 48
<211> LENGTH: 957
<212> TYPE: DNA
<213> ORGANISM: Artificial Sequence
<220> FEATURE:
<223> OTHER INFORMATION: Codon optimized E. Coli AccA sequence

<400> SEQUENCE: 48

```
atgtccctca atttcctcga cttcgaacaa cccatcgccg agctggaagc caagatcgat      60
tcgctcaccg ctgttagccg ccaggacgag aagctcgaca tcaacatcga cgaggaagtg     120
catcgcctcc gcgagaagtc cgtcgagctg acgcgcaaga tcttcgccga cctgggcgcc     180
tggcagatcg cccagctcgc gcgccacccg cagcgcccgt atacgctgga ttatgtgcgc     240
cttgccttcg acgagttcga cgagctggcc ggcgaccggg cgtatgcgga cgataaggcc     300
atcgtgggcg gcatcgcgag gctggacgga cgcccggtca tgatcatcgg ccatcagaaa     360
ggccgcgaaa cgaaggaaaa gattcgccgc aacttcggca tgccggcccc cgagggctac     420
cgcaaggccc tgcgcctcat gcagatggcg gagcgtttca agatgccgat cattaccttc     480
atcgacaccc ccgcgcgta tccggggtg ggtgccgagg aacggggcca gagcgaggcg     540
atcgctcgca acctccgcga gatgtcccgt ctgggcgtgc cggtcgtctg cacggtcatc     600
ggcgagggcg gctcggtgg cgccctcgcg atcggcgtcg cgacaaggt caatatgctc     660
cagtactcga cctatagcgt catctcgccc gagggctgcg cctcgatcct gtggaagtcg     720
gcggacaagg ccccgttggc ggctgaggcg atgggcatca tcgcccctcg cctcaaagaa     780
ctgaagctga tcgactcgat catcccggag ccgctgggcg agcgcaccg taaccccgag     840
gccatggcgg ccagcctgaa ggcgcagctc tcgcggatc tcgccgatct ggacgtcctc     900
tcgaccgagg atctgaagaa tcgccggtac cagcgcctga tgtcctacgg ctatgcg      957
```

<210> SEQ ID NO 49
<211> LENGTH: 468
<212> TYPE: DNA
<213> ORGANISM: Artificial Sequence
<220> FEATURE:
<223> OTHER INFORMATION: Codon optimized E. Coli AccB sequence

<400> SEQUENCE: 49

```
atggacattc ggaagatcaa gaaactcatc gaactcgtgg aagagagcgg aatctcggag      60
ctggaaatta gcgagggcga ggaatccgtc cgcatctccc gtgccgcccc cgcggcctcg     120
```

| | |
|---|---|
| ttcccggtga tgcagcaagc ctacgcggct ccgatgatgc agcagccggc gcagtcgaac | 180 |
| gcggctgcgc cggcgacggt ccCctcgatg gaagcccctg ccgcggcgga gatctcgggc | 240 |
| cacatcgtgc gctcccccat ggtcggcacc ttctatcgca cgccgtcgcc ggacgcgaag | 300 |
| gccttcatcg aggtcggtca gaaagtgaat gtcggcgata ccctctgcat cgtcgaggcc | 360 |
| atgaagatga tgaaccagat cgaggccgat aagagcggca ccgtcaaggc catcctggtc | 420 |
| gagtcgggcc agcccgtgga gttcgacgag ccgctggttg tcatcgag | 468 |

<210> SEQ ID NO 50
<211> LENGTH: 1347
<212> TYPE: DNA
<213> ORGANISM: Artificial Sequence
<220> FEATURE:
<223> OTHER INFORMATION: Codon optimized E. Coli AccC sequence

<400> SEQUENCE: 50

| | |
|---|---|
| atgcttgaca agatcgtgat cgccaatcgt ggagaaattg ctttgagaat cctgcgcgcc | 60 |
| tgcaaagaac tcggaatcaa gaccgtcgcg gtgcattcct cggccgaccg cgacctcaaa | 120 |
| cacgtcctgc tggcggatga aacggtctgc ataggccctg cgccgtcggt gaagtcgtac | 180 |
| ctcaacatcc cggccatcat ctctgccgcg gagatcaccg cgccgtcgc catccacccc | 240 |
| ggctatggct tcctgtcgga gaatgcgaac ttcgcggaac aggttgagag gtcgggcttc | 300 |
| attttcatcg gccccaaggc cgaaaccatc cgcctgatgg cgacaaggt gagcgcgatc | 360 |
| gcggcgatga agaaagcggg cgtgccctgc gtccccggca gcgacggccc tctcggcgac | 420 |
| gacatggata agaaccgcgc gattgcgaag cgcattggct atccggtgat catcaaggcc | 480 |
| tccggcggtg gtggcgggcg cggcatgcgg gtcgtgcgcg gcgacgcgga gctcgcccag | 540 |
| tcgatctcga tgactcgcgc cgaggccaag gctgccttct cgaacgatat ggtctatatg | 600 |
| gagaagtatc tggagaatcc gcggcacgtc gagatccagg tgctcgcgga cggccagggt | 660 |
| aatgccatct acctcgccga gcgcgattgc tccatgcagc gccgtcatca aaggtcgtc | 720 |
| gaggaagcgc cggcccccgg catcacccCg gagctgcgtc gctatatcgg cgagcgctgc | 780 |
| gcgaaggcct cgtgacat cggctatcgc ggcgccggca cgttcgagtt cctcttcgag | 840 |
| aacggggagt tctacttcat cgagatgaac acccgcatcc aggtcgagca tcccgtgacc | 900 |
| gagatgatca cggcgtgga cctgatcaag gaacagctcc gcatcgcggc tggtcagccg | 960 |
| ctctcgatca gcaagagga ggtccacgtc cgtggccacg cggtcgagtg ccgcatcaac | 1020 |
| gccgaggatc cgaacacgtt cctgccgtcg ccgggaaaga tcacgcgctt ccatgcccc | 1080 |
| ggcggcttcg gcgtccgctg ggagagccat atctatgccg gatatacggt cccgccgtat | 1140 |
| tacgattcca tgatcggcaa gctgatctgc tatggcgaga tcgggacgt cgccatcgcg | 1200 |
| cgcatgaaga acgctctcca agagctcatc atcgacggca tcaagaccaa tgtcgatctg | 1260 |
| cagattcgca tcatgaacga cgagaacttc agcacggcg gcaccaatat ccattacctg | 1320 |
| gagaagaagc tgggcctcca ggagaag | 1347 |

<210> SEQ ID NO 51
<211> LENGTH: 912
<212> TYPE: DNA
<213> ORGANISM: Artificial Sequence
<220> FEATURE:
<223> OTHER INFORMATION: Codon optimized E. Coli AccD sequence

<400> SEQUENCE: 51

| | |
|---|---|
| atgtcgtgga tcgagcgtat caagagcaat attaccccca cacggaaggc gagcatcccg | 60 |

```
gaaggcgtct ggactaagtg cgacagctgc ggccaggtcc tctatcgtgc cgagctggag    120
cgcaatctgg aagtgtgccc gaagtgcgac catcacatgc gcatgaccgc tcgcaaccgc    180
ctgcattccc tcctggatga aggctcgctc gtcgagctgg gctcggagct ggagcccaag    240
gacgtcctga agttccgcga ttccaagaag tataaggacc gctggcgtc ggcgcagaaa    300 gaaaccggcg agaaagacgc cctcgtcgtc atgaagggca ccctgtatgg catgccggtc    360
gttgccgcgg cgttcgagtt cgcgttcatg ggcggctcga tggggtcggt ggtcggcgcc    420
cgcttcgtcc gggcggtgga gcaggcgctt gaggacaact gcccgctgat ctgcttctcg    480
gcgagcggtg gtgcgcgcat gcaagaagcg ctcatgtccc tcatgcagat ggccaagacg    540
agtgccgctt tggccaagat gcaggaacgt ggcctcccct acatctcggt cctcacggac    600
ccgacgatgg gcgagtgtc cgcgtcgttc gcgatgctcg gcgatctcaa catcgccgag    660
ccgaaggccc tgatcggctt cgccggcccg cgcgtgatcg agcagaccgt gcgcgagaag    720
ctcccgcccg gcttccagcg ctcggagttc ctcatcgaga aggcgcgat cgacatgatc    780 gtccgccgcc cggagatgcg cctgaagctc gcctcgatcc tggccaagct catgaatctg    840
ccggctccga accccgaggc cccgcgcgag ggagtcgtgg tgcctccggt ccccgaccaa    900
gagcccgagg cg    912
```

<210> SEQ ID NO 52
<211> LENGTH: 1749
<212> TYPE: DNA
<213> ORGANISM: Artificial Sequence
<220> FEATURE:
<223> OTHER INFORMATION: Mutated Methylobacterium extorquens FadD
      sequence

<400> SEQUENCE: 52

```
atggcgtagg accggagcgc ggagcgtcct tggctggccg cctatccccc cggcattccc     60
gccgatatcg acgtcgattc cgtcggcacg gtggtcgatc tgttcgaccg cagcgtgctg    120
cgcttcgcct agcgcccggc gatcacctgc ttcggcgcgc agcctgcgct accgcgaggt    180
cggcgccgcg gcgcaggcgg tggcggcgtg gctcgcccgc caacggctac ggcaaggccg    240
gcaagggaag tgagaacggc agcgagacgg tgtggacgg catcggcgac cgcatcgcgg    300
tgatgatgcc caacgtcccg gcctgtcccg tctcgctgct cggcgtgctg gtggcgggct    360
gcaccgtcgt caacgtcaac ccgctctaca ccccgcgcga actcgccgcg cagatcaacg    420
attccggcgc ccgcgtcctc ttcgtgctgg agaacttctg ccacacggtc gcgcaggcgc    480
tgccgcagat gccgagcctg gagcggatcg tcgtggcagg ccccggcgac ctgctcgggc    540
tgaagggacg gatcgtcgat ctcgtctcgc ggcgggtgaa gcgggcggtg ccgccctaca    600
ccctgccggc cgggcggacc ctgcggttcg aggcggtggt gcgggcgggc gcggcctca    660 agcgcccctc ggtcgcgatc gatcccggcg acgtcgcctt cctgcaatat accggcggca    720
ccaccggcat cgccaaggcg gcgatgctga cccaccgcaa catcatggcc aatgtcgagc    780
agagccgggc gtggttccgc ggccggcgg gggaggggga cggacatgtg gcggtgacgg    840
cgctgccgct ctaccacatc ttcgcgctga cggcctgctt cctgttcttc ttccggctcg    900
gcggctgctg cctgctgatc ccgaacccgc gcgatctcga cggcttcgtg aagacgctca    960
gccgcacccg cttcaccaac ttcgccgggg tgaacacgct gttcaacgcg ctgaacaacc   1020
acccgaagat cggcacggtc gatttctcaa acgtggagta cgtggtcggc ggcggcatgg   1080
cggtgcagtc ggcggtggcc gcccgctgga aggcgatcac cggccagacc atcctcgaag   1140
```

```
gctacggcct gtcggagacc tcgccggtgg tgagcgtcaa cccgctcggg ctcgccaact    1200
ggaccgggac gattggttat ccgctgccct cgaccgaggt gacgatccgc gccgaggacg    1260
gcacggtgct gcccttcggc gtgcccggcg aactctgcgt gcgcgggccc caggtgatgg    1320
ccggctattg gaaccgcccg gaggagacgc gggcggcgat gaccgccgac ggcttcttcc    1380
gcaccggcga cgtggcggtg atgacgccgg acgggcagat ccgcatcgtc gaccggatga    1440
aggacatgat cctcgtctcc ggcttcaacg tctacccgaa cgaggtcgag gacgtgctcg    1500
ccacccatcc ggcggtggtc gaatgcgccg tggtcggcgc gccctgcggc gagagcggcg    1560
agatggtcgt cgcccatgtc gtcctgcgcg atccctctgt ggagccggac gcgctcaggg    1620
cgcatgcccg cgcgagcctc accggctaca aggtgccccg ccggatcgtg atccaggaca    1680
gcctgccgaa gaccaatgtc ggcaaggtgc tgcgccgggc cctgcgggac agcgggccgg    1740
cggcggtaa                                                            1749

<210> SEQ ID NO 53
<211> LENGTH: 927
<212> TYPE: DNA
<213> ORGANISM: Artificial Sequence
<220> FEATURE:
<223> OTHER INFORMATION: Codon optimized E. Coli FabD sequence

<400> SEQUENCE: 53
atgactcaat tcgccttcgt tttccccgga caaggatcgc agaccgttgg aatgctcgct     60
gatatggccg cctcctatcc catcgtcgag gaaaccttcg ccgaggcgag cgcggctctc    120
ggctatgatc tctgggccct gacccagcaa ggcccggccg aagagttgaa caagacctgg    180
cagacccagc cggccctgct gaccgcctcg gtggccctct atcgcgtgtg gcagcagcag    240
ggcggcaagg cgccggcgat gatggccggc cacagcctcg gcgagtactc ggcgcttgtc    300
tgcgcgggcg tcatcgactt cgcggacgcc gtccgcctgg tggagatgcg cggcaagttc    360
atgcaggaag ccgtcccgga aggcacgggc gcgatggcgg cgatcattgg cctcgacgac    420
gcctcgatcg cgaaggcgtg cgaagaagcg gccgagggcc aggtcgtgtc cccggtcaac    480
ttcaactcgc cgggtcaggt cgtgatcgcc ggccataaag aagcggtcga gcgcgccggc    540
gctgcctgca agccgccggc gcgaagcgg ccctgcccc tgccggtgag cgtgccgtcc    600
cactgcgcgc tgatgaagcc cgcggcggat aagctggccg tggagctcgc taagatcacg    660
ttcaacgcgc ctacggtccc ggtcgtcaat aatgtcgacg tgaagtgcga acgaatggt     720 gatgcgatcc gcgacgccct cgtgcgccag ctgtacaacc ccgtccagtg gaccaagtcc    780
gtggagtaca tggccgccca gggcgtcgag catctgtatg aggtcgggcc gggcaaggtc    840
ctcaccggcc tgaccaagcg tatcgtggac acgctcacgg cgtcggcgct caatgagccg    900
tcggccatgg cggcggccct ggagctg                                        927

<210> SEQ ID NO 54
<211> LENGTH: 549
<212> TYPE: DNA
<213> ORGANISM: Artificial Sequence
<220> FEATURE:
<223> OTHER INFORMATION: Codon optimized E. Coli TesA sequence with
      periplasmic targeting sequence removed

<400> SEQUENCE: 54
atggctgata ccctcctgat ccttggcgac tccctctctg ctggttatcg tatgtccgcg     60
tccgctgcct ggcctgcgct gctcaacgat aagtggcaga gcaagacgag cgtcgtgaac    120
```

| | |
|---|---|
| gcgagcatct cgggcgatac ctcgcagcag ggactggccc ggctccccgc cctcctcaag | 180 |
| cagcatcagc cccgctgggt gttggtcgag ctgggcggca acgacggcct gcgcggcttc | 240 |
| cagccgcagc agacggagca gaccctgcgc cagatcctcc aagacgtcaa ggccgccaat | 300 |
| gccgagccgc tgctgatgca gatccgcctg ccggcgaact acggccgccg ctataatgaa | 360 |
| gcgttctcgg ccatctatcc caagctcgcg aaagagttcg acgtccccct cctgccgttc | 420 |
| ttcatggaag aagtgtacct gaagccgcag tggatgcaag acgacggcat tcatcccaat | 480 |
| cgcgacgcgc agccgttcat cgccgattgg atggcgaaac agctccagcc gctcgtcaac | 540 |
| cacgactcg | 549 |

<210> SEQ ID NO 55
<211> LENGTH: 1146
<212> TYPE: DNA
<213> ORGANISM: Artificial Sequence
<220> FEATURE:
<223> OTHER INFORMATION: Codon optimized Cinnamomum camphorum
      thioesterase sequence

<400> SEQUENCE: 55

| | |
|---|---|
| atggccacaa cttcactcgc ttccgctttt tgttctatga aagccgttat gcttgcccga | 60 |
| gatggtagag gaatgaagcc gcgctccagc gatctccagc tgcgtgcggg caacgcgcag | 120 |
| acgtcgctga agatgattaa tggcacgaag ttctcgtaca ccgagtcgct caaaaagctc | 180 |
| ccggactggt cgatgctgtt cgccgtcatc accaccatct tctcggccgc ggagaagcag | 240 |
| tggaccaacc tggagtggaa gccgaagccg aatcccccgc agctcctcga cgatcacttc | 300 |
| ggcccgcatg gcctggtgtt ccgccgtact ttcgccatcc gctcgtatga agtgggcccc | 360 |
| gataggtcga cctcgatcgt cgcggtcatg aaccatctcc aagaagcggc gctgaaccac | 420 |
| gccaagtccg tgggcatact cggcgatgga ttcggaacca cgctggagat gtccaagcgc | 480 |
| gacctgatct gggtggtcaa gcggacccat gtcgccgtgg agcgctatcc cgcgtggggg | 540 |
| gacacggtcg aggtcgagtg ctgggtgggc gcgtcgggaa acaatggccg ccgccacgac | 600 |
| ttcctggttc gcgattgcaa gaccggcgag atcctgaccc gctgcacgtc gctgagtgtc | 660 |
| atgatgaata cgcgcacccg tcgcctcagc aagatccccg aagaggtccg gggcgagatc | 720 |
| ggcccggcgt tcatcgacaa tgtcgcggtc aaggacgaag agatcaaaaa gccgcagaag | 780 |
| ctcaatgaca gcaccgcgga ctatatccag ggtggcctca cgccccgttg gaacgacctg | 840 |
| gatatcaatc agcatgtcaa caacatcaag tatgtggatt ggatcctgga accgtcccg | 900 |
| gactcgatct tcgagagcca ccacatctcc tcgttcacca tcgagtaccg ccgcgaatgc | 960 |
| accatggaca cgctcctcca gtccctgacc acggtgtcgg gcggcagcag cgaggccggc | 1020 |
| ttggtgtgcg agcatctcct gcagctggag ggcggctccg aggtcctccg cgccaagacg | 1080 |
| gagtggcgcc ctaagctgac cgactcgttc cgcggcatct cggtgattcc cgccgagtcg | 1140 |
| tcggtc | 1146 |

<210> SEQ ID NO 56
<211> LENGTH: 1146
<212> TYPE: DNA
<213> ORGANISM: Artificial Sequence
<220> FEATURE:
<223> OTHER INFORMATION: Codon optimized Umbellularia californica
      thioesterase sequence

<400> SEQUENCE: 56

```
atggccacta ctagtctcgc ttcagccttt tgttctatga aagccgttat gctcgctcgc    60
gatggacgcg gaatgaagcc gcgttcctcc gatctgcagc tcagggccgg aaatgcgccg   120
acgtcgctca agatgatcaa cggcacgaag ttctcgtaca cggaaagcct gaagcggctc   180
cccgactggt cgatgctgtt cgccgtgatc acgaccatct tctcggccgc ggagaagcag   240
tggaccaatc tggagtggaa gccgaagccc aagctccccc agctcctcga cgaccacttc   300
ggcctgcatg gcctggtgtt ccgccgcacg ttcgcgatcc gctcctatga ggtcggcccg   360
gatcgctcga ccagcatcct ggcggtcatg aaccacatgc aggaagcgac cctgaaccat   420
gccaaaagcg ttggcatcct cggcgacggc ttcggcacca cgttggaaat gtcgaagcgc   480
gacctgatgt gggtcgtccg ccggacgcac gtcgcggtgg agcgttaccc gacctggggc   540
gacaccgtcg aggtcgagtg ctggatcggc gcgtcgggca ataacggcat gcgccgggac   600
ttcctcgtcc gggactgcaa gaccggcgag atcctcaccc gctgcacgag cctcagcgtc   660
ctgatgaata cccgcacgcg gcgcctgtcc accatcccgg acgaagtccg cggcgagatt   720
ggccccgcct tcatcgataa cgtcgctgtc aaagatgacg agatcaagaa gctccagaag   780
ctgaacgact cgaccgcgga ttatattcag ggtgggctga cccctcgctg aacgatctc   840 gacgtcaacc agcatgtgaa caatctgaag tatgtcgcct gggtgttcga aacggtcccg   900
gattcgattt tcgagtcgca ccatatcagc tcgttcaccc tggagtatcg ccgcgagtgc   960
acgcgcgact cggtcctccg tagcctgacc accgtgagcg gcggttcgtc cgaagccggg  1020
ctggtctgcg atcacctcct ccagctggag ggcggctccg aggtgctgcg cgcgcgcacc  1080
gagtggcgcc ccaagctgac ggacagcttc cgtggcatct cggtgatccc cgccgagccg  1140
cgcgtg                                                               1146

<210> SEQ ID NO 57
<211> LENGTH: 750
<212> TYPE: DNA
<213> ORGANISM: Artificial Sequence
<220> FEATURE:
<223> OTHER INFORMATION: Codon optimized Streptococcus pyogenes acyl-ACP
      thioesterase sequence

<400> SEQUENCE: 57
atgggcctct cgtaccaaga agaactcacc ctgcctttcg agctctgcga cgttaaatcg    60
gacatcaagc tgccgttgct gctggactac tgcctgatgg tgtcgggccg tcagtccgtc   120
cagctcggcc ggtcgaacaa caacctcctc gtggactaca agctcgtgtg gatcgtgacc   180
gattatgaga tcaccattca ccgcctgccc catttccagg aaacgatcac catcgaaacc   240
aaggctctct cgtacaataa gttcttctgc taccgccagt tctatatcta tgaccaggag   300
ggatgcctgc tcgtcgacat cctgagctat ttcgccctgc tcaatccgga cacccgcaag   360
gtcgcgacga tccccgagga tctcgtcgcg ccgttcgaga ctgatttcgt caaaaagctg   420
catcgcgtgc caagatgcc gctcctggag cagtcgatcg atcgcgacta ttatgtccgt   480
tatttcgaca tcgatatgaa tggccacgtc aacaactcga agtatctcga ctggatgtat   540
gacgtcctgg gctgccagtt cctcaagacg caccagccgc tgaagatgac gctgaagtac   600
gtgaaggaag tcagcccggg cggccagatc acctccagct atcatctgga ccagctcacg   660
tcgtatcatc agatcatctc cgatggtcag ctcaacgcgc aggccatgat cgagtggcgc   720
gccattaagc agaccgagtc ggagacagac                                     750

<210> SEQ ID NO 58
```

-continued

```
<211> LENGTH: 1191
<212> TYPE: DNA
<213> ORGANISM: Artificial Sequence
<220> FEATURE:
<223> OTHER INFORMATION: Codon optimized Ricinus communis palmitoyl-acyl
      carrier protein thioesterase sequence

<400> SEQUENCE: 58
atgggcactt gctcctatac catcaccctc cccatccgct gcctcagcaa cagtaacggc     60
caccacgacc cgcataagca gaacctgaat aagattaaga tcaatggggc ctcgacctcc    120
acccgccctc tcaagctgga tgccccgtcg cagaccgtcg gcgtcgcgac catctatctg    180
gcctcggttt cggagaatct gacgctcacg aaagaggtga tgcggcagaa catccccacg    240
aagaagcagt acatcgatcc gcatcgccag ggcctgatga tcgagggcgg agtgggctac    300
cgtcagacca tcgtgatccg cagctatgag gtcggaccgg acaagacggc gaccctggag    360
agcatcctgt atctcctcca ggaaacggcc ctgaaccatg tctggctttc gggcctcctc    420
tcgaacggct tcggcgcgac acatggcatg gtcaagaata atctgatctg ggtcgtgtcc    480
aagctccagg tccaggtcga ccattatccc atctggggcg aggtcgtcga gattgacacg    540
tgggtccgcg cgtcgggcaa gaacggcatg aagcgcgact ggctgattcg cagccaggcg    600
acgggccacg tgttcgtccg cgcgacctct acgtgggtca tgatgaacga aaagacccgc    660
cgcctctcga agatgcccga agaggtgcgc gctgagatct cgccgtggtt catcgagaag    720
caagccatca aggaagaggt gccggacaag atcgcgaagc tggatgataa ggcccgctat    780
gtcatcagca acctcaagcc gaagcgttcg gacctggata tgaaccacca tgtgaataac    840
gtgaaatatg tgcgctggat gctggagatc ctgccggacc acttcctgga gtcgcaccag    900
ctgtcgggca tcacgatgga gtaccgtcgg gagtgcggct cggcggacat cgtccagtcc    960
ctgtgcgagc ccgacggcga tgagatcttg tcgaatgaca tcccggtcct caatggtttc   1020
agcctcgcct cggagcccct gatggaaggc aacggcttcc tcgtcccgct cgacaaggtc   1080
cccctcaagt acacgcatct gctcctcacc aagggcgagt cccagaacga agagatcgtg   1140
cgcggtaaga ccatctggaa gaagaaactg tgcacgatgc cgttctccac c            1191

<210> SEQ ID NO 59
<211> LENGTH: 1176
<212> TYPE: DNA
<213> ORGANISM: Artificial Sequence
<220> FEATURE:
<223> OTHER INFORMATION: Codon optimized Ricinus communis palmitoyl-acyl
      carrier protein thioesterase sequence

<400> SEQUENCE: 59
atggcctcca aaggtagcat ccgcctctat ttcccctgcg atttccggaa caccctccag     60
aagaagaaca tgaagatgga catggtcatg gcccgcagcg gcttctcgta ttcgctcaat    120
ccgatcgccc cgaagatccc ccgcttctat gtcgtcgcca atgcgtcgaa cccgcagcgc    180
gtcgacacga tcaacggcaa gaaagtgaac ggaatccacg tggcggagag ctccaactcg    240
tacgccgacc agaacaagat gaatgccaca gcggggctgg tcctggacgg caacgtggat    300
caccagcccc tccataagtg gctcctcggc cgtttcgtgg acgagcgcct cgtctattcg    360
cagacgttca tcatccgctc ctatgagatc ggaccggata agaccgccac tatggaaacg    420
ctgatgaatc tcctgcagga aaccgcgctc aatcacgtga cgagctcggg cctcgcgggc    480
gatggcttcg gcgcgacccg cgagatgagc ctccgcaagc tcatctgggt cgtgacccgc    540
atccatattc aggttcagcg ctattcgtgc tggggcgacg tggtcgagat cgacacgtgg    600
```

| | |
|---|---|
| gtggacggcg ctggcaagaa cggcatgcgt cgcgattgga ttatccgcga ctacaatacc | 660 |
| aaggagatca tcacccgtgc gacgtccacg tgggtcatca tgaacaggga aacccggaag | 720 |
| ctgtccaaga tgccggagca agtccgccag gaactggtcc ccttctacac caatcgcatc | 780 |
| gcgattgcga aagagaacaa cgacgtcgag aagatcgaca agctgaccga cgaaacggcg | 840 |
| gagcgcatcc gctcgggcct ggcccctcgc tggtcggata tggacgcgaa ccagcacgtg | 900 |
| aacaatgtca agtacatcgg ctggatcctg gagtcggtcc cgatcaacgt ccttgaggat | 960 |
| tacaatctca cgtcgatgac cctggagtac cgtcgtgagt gccgccagtc taacctgttg | 1020 |
| gagtcgctga cctcgaccac cgagcatagt aataacaatt cgtgcaaccg gaaggcccat | 1080 |
| ctggagtata cccatctgct ccgcatgcag gccgacaagg ccgagatcgt ccgcgctcgc | 1140 |
| acggagtggc agtccaagag caatcgcaag accatc | 1176 |

<210> SEQ ID NO 60
<211> LENGTH: 1257
<212> TYPE: DNA
<213> ORGANISM: Artificial Sequence
<220> FEATURE:
<223> OTHER INFORMATION: Codon optimized Ricinus communis palmitoyl-acyl
carrier protein thioesterase sequence

<400> SEQUENCE: 60

```
atggtcgcta ccgccgccgc tgccacctcc tccttcttcc ccgtcccgtc ccagtcagcc     60
gatgcgaatt tcgataaggc gcctgcctcg ctcggcggca tcaagctcaa gtcgacgagc    120
tgctcgcgcg gcctccaggt caaggcgaac gcgcaggccc ctccgaagat caatggcagc    180
tcggtgggct tcacgactag cgtggaaacc gtcaagaatg atggcgacat gccgctgccg    240
ccgccgcccc gcacgttcat caaccagctg ccggactggt ccatgctcct cgccgcgatc    300
acgaccatct tccttgcggc ggagaagcag tggatgatgc tggactggaa gccgcgccgc    360
cccgacatgc tgatcgatcc cttcggcatc ggccgcatcg tgcaggacgg cctcattttc    420
cgccagaact tctcgatccg ctcctatgag attggcgcgg atcgcaccgc gtcgatcgag    480
acactcatga atcatctcca ggaaaccgcg ctcaaccatg tcaagacggc cggcctgctg    540
ggcgatggat tcggcagcac cccggagatg tcgaagcgga acctgatctg ggtcgtgacg    600
cgcatgcaag ttttggtcga ccgctacccc acctggggtg acgtcgtcca ggtcgacacc    660
tgggtgtcca agtccggcaa aaatggcatg cgccgcgact ggtgcgtccg cgactcgcgc    720
acgggagaaa cgctgacccg tgcgagctcg gtctgggtga tgatgaacaa gctcacccgg    780
cgtctgtcga agatcccgga agaggtcagg ggcgagatcg agccctactt cctcaactcg    840
gacccgatcg tggatgagga cagtcgtaag ctcccgaaac tggacgactc gaacgcggac    900
tatgtccgca agggcctcac gccgcgctgg tctgacctgg acatcaacca gcacgtgaac    960
aatgtcaagt acatcggctg gatcctggag tcggccccgc tccccatcct ggagtcgcac   1020
gagctgagcg ccattaccct ggagtatcgg cgcgagtgcg gccgcgacag cgtgctgcag   1080
tcgctgaccg ccgtcagcgg caacggcatc ggcaacctcg gcaatgcggg cgacatcgag   1140
tgccagcatc tcctccgtct ggaagatggg gccgagatcg tccgcggtcg taccgagtgg   1200 cgccccgaagt attcgtccaa cttcggcatc atggggcaga tcccggtcga gtcggcc    1257
```

<210> SEQ ID NO 61
<211> LENGTH: 1215
<212> TYPE: DNA
<213> ORGANISM: Artificial Sequence
<220> FEATURE:
<223> OTHER INFORMATION: Codon optimized Jatropha curcas acyl-ACP
      thioesterase sequence

<400> SEQUENCE: 61

| | | | | | |
|---|---|---|---|---|---|
| atggccgtgt | tcacctatcg | tatcgccatg | ctccctatcc | gctgctcctc | ctcgaatagc | 60 |
| accaactcgc | atagccacga | tccgaaccag | cagaatctcc | acaagatcaa | gattaacggc | 120 |
| tcggcgtccg | ccatgatgcc | gctcaaggtc | gatctgccga | gctcgctcac | gatcacctcc | 180 |
| gtggcgcccg | tggtggagaa | tctcagcctc | acgaaagagc | agacccgcca | gaacatcccg | 240 |
| acgaagaagc | aatacatcga | ccccatcgc | cagggcctga | tcgtcgagga | gggcgtgggc | 300 |
| tatcggcaga | ccgtcgtgat | ccgctcgtat | gaagtcggac | cggataagac | cgctacccct | 360 |
| gagatcatcc | tctgcctcct | gcaggaaact | gcgctcaacc | atgtgtggct | gtccggcctc | 420 |
| ctgtcgaatg | gcttcggcgc | cacccacggc | atggtccgca | caacctcat | ttgggtcgtc | 480 |
| agcaagctcc | aggtccaggt | cgatcagtat | ccgatctggg | gtgaggtcgt | cgagatcgac | 540 |
| acgtgggtcg | gcgcctcggg | caagaacggc | atgcccgca | ctggctggt | ccgctcgcag | 600 |
| gccacgggcc | aggtgttcgc | gcgcgccacc | tcgacctggg | tcatgatgaa | cgagaaaacc | 660 |
| cgtcggctga | gcaagatgcc | ggaagaagtc | cgcgcggaga | tcgcgccctg | gttcatcgag | 720 |
| aagcaggcga | tcaaagaaga | ggtgcccgag | aagatcgcca | gctcgacga | caaggcccgt | 780 |
| tacgtcgtca | ccaatttgaa | gccgaagcgc | tccgacctgg | acatgaacca | gcacgtgaat | 840 |
| aacgtgaagt | acgtccgctg | gatgctggaa | accctgccgg | accagttctt | cgagaatcac | 900 |
| cagctctcgg | gaatcacgct | ggagtacaag | cgcgagtgcg | gctcgtcgga | catcgtcgag | 960 |
| tctctgtgcg | agccggatga | agaagagggc | atcatcaata | ccgggctcaa | gcaaaacaac | 1020 |
| gacaagtcgc | tgttcaatgg | cttcagtctc | ccctccgaga | tcatggaagg | caacggtttc | 1080 |
| ctgtcgtcgc | tggagaaaac | cccgctcaag | tatacgcatc | tgctcgttgc | gaagggcaag | 1140 |
| acgcagtcga | agagatcgt | gcgcggcaag | accatttgga | agaaaaagct | gctcacgacg | 1200 |
| atgccgttct | cgccc | | | | | 1215 |

<210> SEQ ID NO 62
<211> LENGTH: 1044
<212> TYPE: DNA
<213> ORGANISM: Artificial Sequence
<220> FEATURE:
<223> OTHER INFORMATION: Codon optimized Jatropha curcas acyl-ACP
      thioesterase sequence

<400> SEQUENCE: 62

| | | | | | |
|---|---|---|---|---|---|
| atggtcagca | ccgcgatctc | cttctccctc | ctcccgatca | agctcattaa | agaagaaacc | 60 |
| cgcatggcct | cggcggaccg | ccgcaagaac | agtatcgtga | aggaattcgg | ccatttcacg | 120 |
| tgccgctgcg | ctgccatcga | gaagcggatc | cagaagctca | caacttcct | gatcgacggc | 180 |
| ggcttcggct | ccctggagca | gaacggcctg | atctaccgtc | agaatatctt | cattcgctcg | 240 |
| ttcgagatcg | gcttcgaccg | caagctcagc | ctggccgcgc | tgacgaactt | cctccaggat | 300 |
| accgcgctca | tcatgtccg | catgatcggc | ctcctcgccg | ctggcttcgg | atcgaccccg | 360 |
| gagatgtcca | agaaagacct | catctgggtg | ctctgcacgc | tgcagatcct | cgtcgatcgc | 420 |
| caccgtcgt | ggctggacgc | cgtcgaggtc | gacacctgga | tgtaccccag | cggccaaaat | 480 |
| ggccagggc | gtgactggct | cgttcgcgat | gccaagactg | gcaagcccct | ggcgcaggcg | 540 |
| tcgtcggtca | tggtcctgct | gaacaagaaa | acgcgcaagc | tctccaagtt | caccgaagag | 600 |

-continued

```
atccgcgacg agatcgcgcc gcacatgatg atggactgca atccgattat caactcgcgc    660
aagatgctgc ccttcgacgt caacaccgcg gattatgccc gtaccggcct gacccccggt    720
tggaacgacc tcgatctcaa tcagcacgtg aatcacgtcc agtatatcaa ctggatcctc    780
cagaatgtgc tgcggagctt gatccagcat cacaagctct cggatatcac cctggagtat    840
cgcaaggaat gcgacatcaa ttcgatcctg cagttcctgt cgaagatcgt caagaacggc    900
agcaatcatt cgacggacac caataacctg atcgagctcg accattcgct cctgctggag    960
aacggctcgg agatcgccag ggcgaacacg atctggaagc cgcgcgaggt gaacaacttc    1020
aagaacgccg tgtatacgcc tgcg                                           1044
```

<210> SEQ ID NO 63
<211> LENGTH: 1071
<212> TYPE: DNA
<213> ORGANISM: Artificial Sequence
<220> FEATURE:
<223> OTHER INFORMATION: Codon optimized Jatropha curcas acyl-ACP
      thioesterase sequence

<400> SEQUENCE: 63

```
atggcctcga ccgcgatctc gttcctctcc atcccgatca agcttatcaa agaagaaatg     60
cgtatggcct ccgcgggccg ccgcaagaac accattgcgg cggagttcgg ccacttcacg    120
ttcggcagcg cgaccgtcga agaaaagtc cagaagtcga ataacttcct catcgacggc    180
ggcttcggct cgctggagca gaacggactg atctaccggc agaacatctt cgtccgctcc    240
ttcgagatcg gcttcgatcg caagctgagc ctcgcggccc tgaccaattt cctgcaggac    300
accgcgctca ccattgccg catgatcggg ctcctcgctg agggtttcgg ctccacgccg    360
gagatgatca aaaaggactt gatctgggtg ctgtgcacgc tccagatcct cgtcgacggc    420
tatccgagct ggctcgatgt ggtcgaggtc gacacctgga tgtatccctc gggccagaat    480
ggactgggcc gtggctggct cgtccgcgac ggtaagaccg gccgcagcct ggcccagtcg    540
tcatcggtca tggtgtcctt caataagaaa acccggaagc tgtcgaagct ggcgaaggaa    600
atccgcgacg agatcgcccc tcacatgatg gattgcgacc cgatcatgaa caagaactcg    660
cgcaagatcc tcccgttcga cgtgaatacg gcggactatg ctcgcacggg cctcacgccc    720
ggctggaatg aactggatct gaaccagcac gtgaaccatg tccagtacat caactggatc    780
ctccagaacg tgcgcccgtc gctcgtccag catcataagc tctcggccat acgctggag    840 tatcgcaaag agtgcgacat gaactccatc ctgcaatcgc tctcgcgcat cgtgaagaac    900
ggcggcaacg acagcaccga taagaataac gtcatcgagc tcgaccactt cctcctgctg    960
gagaatggca gtgagattgc ccgtgccaat accatctgga agccccgcga ggtcaataac    1020
ttcaagaacg ttgtccattc gcccgccgaa gagaatatct ctagcatgaa c             1071
```

<210> SEQ ID NO 64
<211> LENGTH: 396
<212> TYPE: DNA
<213> ORGANISM: Artificial Sequence
<220> FEATURE:
<223> OTHER INFORMATION: Codon optimized E. Coli FadM sequence

<400> SEQUENCE: 64

```
atgcaaaccc agatcaaggt ccgcggatac catctcgatg tctatcagca tgtcaataac    60
gcccgttatc tcgaattcct cgaagaggcg cggtgggacg gcctggagaa ctcggactcg    120
ttccagtgga tgacggccca caacattgcg ttcgtggtgg tcaatatcaa catcaattac    180
```

```
cgccgcccgg cggtcctgtc cgatctgctc acgatcacct cgcagctcca gcagctgaac    240
ggcaagtcgg gcatcctcag ccaggtcatc acgctggagc ccgagggcca ggtcgtggcc    300
gacgctctga tcaccttcgt gtgcatcgac ctcaagaccc agaaagcgct ggccctcgaa    360
ggcgagctgc gcgagaagtt ggagcagatg gttaag                              396
```

<210> SEQ ID NO 65
<211> LENGTH: 957
<212> TYPE: DNA
<213> ORGANISM: Artificial Sequence
<220> FEATURE:
<223> OTHER INFORMATION: Codon optimized E. Coli AccA sequence

<400> SEQUENCE: 65

```
atgtcgctca acttcctgga cttcgaacaa cccatcgccg agctcgaagc gaagatcgat     60
tccctcaccg ccgtcagccg ccaggatgag aagctcgaca tcaatatcga cgaggaggtg    120
catcgcctgc gggagaagtc cgtcgagctc acccgcaaga tcttcgccga tctgggcgcg    180
tggcagatcg ctcagctcgc gcgtcatccg cagcgcccgt acacgctgga ctatgtgcgc    240
ctggcgttcg acgagttcga cgagctgggg gtgatcgcg cctacgccga tgacaaggcc    300
atcgtcggcg catcgcgcg tctggacggc cgtccggtga tgatcatcgg ccaccagaaa    360
ggccgcgaaa ccaaagagaa gatccgccgc aacttcggca tgcctgcccc cgagggctat    420
cgcaaggccc tccgcctcat gcagatggcc gagcgcttca gatgccgat tatcaccttc    480 atcgatacgc cgggcgcgta tccgggcgtc ggagccgagg aacgcggcca gagcgaggcg    540
atcgcgcgca atctccgcga gatgtcgcgc ctgggcgtcc ccgttgtctg caccgtgatc    600
ggcgagggcg gctcgggcgg tgccttggcc atcgcgtcg gcgacaaggt caacatgctc    660
cagtattcca cgtacagcgt catcagcccc gaggggtgcg cgtcgattct ctggaagtcg    720
gcggacaagg ctccgctcgc ggctgaggcg atgggcatca ttgcgccgcg cctgaaagaa    780
ctgaagctca tcgactcgat catcccggag cccctgggcg gagcccaccg taaccccgag    840
gccatggcgg cgtcgctgaa ggcccagctg ctcgcggacc tggcggacct cgatgtgctc    900
tcgaccgagg acctgaagaa taggcgctat cagcggctga tgtcgtacgg ctatgcg       957
```

<210> SEQ ID NO 66
<211> LENGTH: 468
<212> TYPE: DNA
<213> ORGANISM: Artificial Sequence
<220> FEATURE:
<223> OTHER INFORMATION: Codon optimized E. Coli AccB sequence

<400> SEQUENCE: 66

```
atggacattc gcaaaatcaa gaaactcatc gaactggtcg aggaaagcgg catttcggaa     60
ctggagatct cggaaggtga agagtcggtg cgtatctcgc gcgcggcccc tgcggcgtcg    120
ttccccgtca tgcagcaagc gtatgccgct ccgatgatgc agcagccggc gcagtccaat    180
gcggcggccc cggccaccgt cccgagcatg aagcgccgg cggccgctga gatctcgggc    240
catatcgtgc gcagccccat ggtcggaacg ttctaccgca cccgtccccc cgacgcgaag    300
gccttcatcg aagttggcca aaaggtcaac gtgggcgata cgctctgcat cgtcgaggcc    360
atgaagatga tgaaccagat cgaggccgat aagtccggca ccgtgaaggc catcctggtc    420
gagtcgggcc agcccgtcga gttcgacgag ccgctcgtcg tgatcgag                 468
```

<210> SEQ ID NO 67
<211> LENGTH: 1347

<210> SEQ ID NO 67
<211> LENGTH: 1347
<212> TYPE: DNA
<213> ORGANISM: Artificial Sequence
<220> FEATURE:
<223> OTHER INFORMATION: Codon optimized E. Coli AccC sequence

<400> SEQUENCE: 67

| | |
|---|---|
| atgttggata gatcgtcat cgccaatcgc ggagaaatag ccctcaggat tctcagagct | 60 |
| tgcaaagaac tcggaatcaa gactgtcgcg gtccactcca gcgcggaccg cgatctcaag | 120 |
| catgtcctgc tggcggacga aacggtctgc atcggccccg ccccctcggt caagtcctat | 180 |
| ctgaacatcc ccgccatcat ctctgccgcg gagatcaccg gggcggtggc tatccacccc | 240 |
| ggctacggct cctctcgga gaatgccaac ttcgcggaac aggtcgagcg ctcgggcttc | 300 |
| atcttcatcg gcccgaaggc cgagacaatt cgcctgatgg cgacaaggt gtcggccatc | 360 |
| gcggccatga gaaagcgggg cgtcccgtgc gtgccgggct cggacggccc ctcggcgac | 420 |
| gacatggata gaaccgcgc gatcgcgaag cgcatcggct acccggtcat catcaaggcc | 480 |
| agcggtggcg gcgcggccg tgcatgcgcg gtcgtgcgcg gtgacgcgga gctcgcgcag | 540 |
| tcgatctcca tgacccgggc tgaggccaag gccgccttct cgaacgacat ggtgtatatg | 600 |
| gagaagtacc tcgaaaatcc gcggcacgtt gagattcagg tcctgccga cgggcagggc | 660 |
| aatgcgatct atctggcgga gcgcgattgc tccatgcagc gtcgccatca aaggtcgtc | 720 |
| gaggaagcgc cggctccggg tattacccc gagcttcgcc gctatatcgg cgagcgctgc | 780 |
| gcgaaggcct gcgtggacat tggctatcgc ggcgcgggca cgttcgagtt cctgttcgag | 840 |
| aacggcgagt tctacttcat cgagatgaac acgcgcatcc aggtcgagca cccggtgacc | 900 |
| gagatgatca cgggcgtgga cctgatcaag gaacagctcc gcatcgccgc gggccagccc | 960 |
| ctgagcatca gcaagaaga ggtgcacgtc cggggccatg cggtggagtg ccgcatcaac | 1020 |
| gccgaggacc cgaataccct cctcccgtcg ccgggcaaga tcacccgctt ccatgcccct | 1080 |
| ggcggcttcg gagtccgctg ggagtccat atctacgccg gctataccgt cccgccctat | 1140 |
| tatgattcga tgatcggaaa gctcatctgc tacggcgaga ccgtgacgt ggcgatcgcg | 1200 |
| cgtatgaaga cgccctgca ggaactgatc atcgacggca tcaagaccaa tgtcgacctc | 1260 |
| cagatccgca tcatgaacga cgagaatttc agcatggcg gcaccaacat ccattacctg | 1320 |
| gagaagaaac tgggcctgca agagaag | 1347 |

<210> SEQ ID NO 68
<211> LENGTH: 912
<212> TYPE: DNA
<213> ORGANISM: Artificial Sequence
<220> FEATURE:
<223> OTHER INFORMATION: Codon optimized E. Coli AccD sequence

<400> SEQUENCE: 68

| | |
|---|---|
| atgagctgga tcgaacgcat caaaagcaac attacccta cccgcaaggc ttccatcccc | 60 |
| gagggcgtct ggacgaagtg cgactcgtgc ggccaggtcc tctaccgcgc ggagctggag | 120 |
| cgcaacctcg aagtctgccc caagtgcgac catcacatgc gcatgacggc gcgcaatcgc | 180 |
| ctgcacagcc tgctggacga gggttccctc gtggagctgg atcggagtt ggagccgaag | 240 |
| gatgtcctca agttccgcga ctcgaagaag tataaggatc ggctggcgtc ggcccagaaa | 300 |
| gaaacgggcg agaaagacgc cctcgtggtc atgaagggca ccctctatgg catgccggtc | 360 |
| gtcgcggcgg cgttcgagtt cgccttcatg ggcggctcga tgggctcggt cgtcggcgct | 420 |
| cgcttcgtcc gggcggtgga gcaggccctg gaagataatt gcccgctgat ctgcttctcg | 480 |

```
gcgagcggtg gcgctcgtat gcaagaagcc ctgatgtcgc tcatgcagat ggccaagacc    540
tccgccgccc tggcgaagat gcaggaacgc gggctcccgt acatctccgt gctcaccgac    600
ccgaccatgg gcggcgtgtc ggcgtcgttc gccatgctcg cgacctgaa catcgccgag     660 ccgaaggccc tcatcggctt cgccggaccg cgcgtcatcg agcagacggt gcgcgagaag    720
ctgcccccgg gcttccagag gtcggagttc ctgatcgaga agggcgcgat cgacatgatc    780
gtgcgccgtc cggagatgcg cctcaagctg gcgtcgatcc tcgccaagct gatgaacctc    840
ccggccccga accccgaggc gccccgtgag ggcgtggtcg ttccgcccgt cccggaccag    900
gaacccgagg cg                                                        912
```

<210> SEQ ID NO 69
<211> LENGTH: 744
<212> TYPE: DNA
<213> ORGANISM: Artificial Sequence
<220> FEATURE:
<223> OTHER INFORMATION: Codon optimized E. Coli FabD sequence

<400> SEQUENCE: 69

```
atgacacagt tcgcattcgt attcccagga caaggatcac agacagttgg aatgttagca     60
gatatggcag catcataccc aatagtagag gaaacatttg cagaggcatc agcagcatta    120
ggatacgact tatgggcact aacacaacag ggaccagcag aagagttaaa caagacatgg    180
cagacacagc cagcactatt aacagcatca gtagcattat acagggtatg gcagcaacag    240
ggtggaaagg caccagcaat gatggcagga cactcattag agagtattc agcattagta     300 tgcgcaggag taatagactt cgcagacgca gtaaggttag tagagatgag gggaaagttt    360
atgcaggaag cagtaccaga gggaacagga gcaatggcag ctataatagg attagatgac    420
gcatcaatag caaaggcatg cgaggaggca gcagagggac aggtagtatc accagtaaac    480
ttcaactcac caggacaagt agtaatagca ggacacaaag aggcagtaga gagagctgga    540
gcagcatgta aggcagctgg agcaaaaagg gcattaccat taccagtatc agtaccatca    600
cattgcgcat taatgaagcc agcagcagac aagttagcag tagagttagc aaagataaca    660
ttcaacgcac caacagtacc agtagtaaac aatgtagatg taaagtgcga aacaaacggt    720
gacgcaataa gggacgcatt agta                                           744
```

<210> SEQ ID NO 70
<211> LENGTH: 549
<212> TYPE: DNA
<213> ORGANISM: Artificial Sequence
<220> FEATURE:
<223> OTHER INFORMATION: Codon optimized E. Coli TesA sequence with
      periplasmic targeting sequence removed

<400> SEQUENCE: 70

```
atggcagaca cattattaat attaggagac tcattatcag ctggatacag aatgtcagca     60
tcagcagcat ggccagcatt attaaatgac aagtggcaga gtaagacatc agtagtaaac    120
gcatcaatat ctggagatac atcacagcaa ggattagcaa ggctaccagc attactaaag    180
cagcaccagc ctagatgggt attagtgagg cttggaggaa atgatggatt aaggggattc    240
cagccacagc agacagagca gacattaagg cagatattac aagacgtaaa ggcagcaaac    300
gcagagccat tactaatgca gataaggtta ccagcaaact acggaagaag gtataacgaa    360
gcattctcag caatataccc aaagttagca aaagagtttg acgtaccact attaccattc    420
tttatggaag aagtatactt aaagcccag tggatgcaag atgacggaat acatccaaac    480
```

| | |
|---|---|
| agggacgcac agccattcat agcagattgg atggcaaaac agttacagcc attagtaaac | 540 |
| cacgactca | 549 |

<210> SEQ ID NO 71
<211> LENGTH: 1146
<212> TYPE: DNA
<213> ORGANISM: Artificial Sequence
<220> FEATURE:
<223> OTHER INFORMATION: Codon optimized Cinnamomum camphorum
      thioesterase sequence

<400> SEQUENCE: 71

| | |
|---|---|
| atggcaacaa catcattagc atcagcattt tgcagtatga agcagtaat gttagcaagg | 60 |
| gacggaaggg gaatgaagcc taggtcatca gatttacagt taagggcagg aaacgcacag | 120 |
| acatcattaa agatgataaa tggaacaaag ttctcataca cagagtcatt aaagaaatta | 180 |
| ccagactggt caatgttatt cgcagtaata acaacaatat tctcagcagc agagaagcag | 240 |
| tggacaaact agagtggaa gccaaagcca aacccaccac agttattaga cgatcacttc | 300 |
| ggaccacacg gattagtatt taggagaaca ttcgcaataa gatcatacga ggtaggacca | 360 |
| gacaggtcta catcaatagt agctgtaatg aaccatttac aagaagcagc attaaaccac | 420 |
| gcaaagtcag ttggaatact aggtgacgga ttcggaacaa cattagagat gtcaaaaagg | 480 |
| gacctaatat gggtagtaaa agaaacacat gtagcagtag aaaggtaccc agcatgggga | 540 |
| gacacagtag aggtagagtg ctgggtagga gcatcaggaa ataacggaag gagacacgac | 600 |
| ttcttagtaa gggattgcaa gacaggtgag atactaacaa gatgcacatc attatcagta | 660 |
| atgatgaaca ctaggacaag gagactttca agataccag aagaagtaag gggagagata | 720 |
| ggaccagcat tcatagacaa cgtagcagta aaagatgaag agataaagaa gccacaaaag | 780 |
| ttaaacgatt caacagcaga ctatatacag ggaggattaa caccaaggtg gaatgactta | 840 |
| gacataaacc agcacgtaaa caatataaaa tatgtagact ggatactaga cacagtacca | 900 |
| gattcaatat tcgagtcaca ccatatatca tcatttacaa ttgagtacag aagagagtgc | 960 |
| acaatggact cagtattaca gtcattaaca acagtatctg gaggatcatc agaggctgga | 1020 |
| ctagtatgtg agcacttatt acagttagag ggaggatcag aggtattaag ggcaaagaca | 1080 |
| gagtggaggc caaagttaac agatagtttt aggggaatat cagtaatacc agcagagtca | 1140 |
| tcagta | 1146 |

<210> SEQ ID NO 72
<211> LENGTH: 1146
<212> TYPE: DNA
<213> ORGANISM: Artificial Sequence
<220> FEATURE:
<223> OTHER INFORMATION: Codon optimized Umbellularia californica
      thioesterase sequence

<400> SEQUENCE: 72

| | |
|---|---|
| atggcaacaa caagtttagc atcagcattt tgcagtatga aggcagtaat gttagcaagg | 60 |
| gacggaaggg gaatgaagcc aaggtcatca gatttacagt taagggcagg aaacgcacca | 120 |
| acatcattaa agatgataaa cggaacaaag ttctcataca cagagtcact aaaaagatta | 180 |
| ccagactggt caatgctttt tgcagtaata acaacaatat tctcagcagc agagaagcaa | 240 |
| tggacaaact agaatggaa gccaaagcca aagttaccac agttattaga cgatcacttt | 300 |
| ggattacacg gattagtatt cagaagaaca ttcgctataa ggtcttatga ggtaggacca | 360 |
| gacaggtcaa catcaatact agcagtaatg aaccacatgc aagaagcaac attaaaccac | 420 |

```
gcaaagtcag ttggaatact aggagatgga ttcggaacaa cattagagat gtcaaaaagg    480
gacttaatgt gggtagtaag aagaacacac gtagcagtag aaaggtaccc aacatgggga    540
gacacagtag aggtagagtg ctggatagga gcatcaggta ataacggaat gagaagggac    600
ttcttagtaa gggactgcaa gacaggagag atactaacaa ggtgcacttc attatcagta    660
ctaatgaata caaggacaag aaggctatca acaataccag atgaagtaag gggagaaata    720
ggaccagcat tcatagacaa tgtagcagta aaagacgatg agataaagaa attacagaag    780
ttaaacgact caacagcaga ttacatacag ggaggattaa caccctaggtg gaacgactta   840 gacgtaaatc agcacgtaaa caacttaaag tacgtagcat gggtatttga gacagtacca    900
gactcaatat tcgagtcaca ccatatatca tcattcacat tagagtatag aagagagtgt    960
acaagggatt cagtattaag gtcattaaca acagtatctg gaggatcatc agaggctgga   1020
ttagtatgcg accatctatt acagttagag ggaggatcag aggtattaag ggcaaggaca   1080
gagtggaggc caaagttaac agactcattc aggggaatat cagtaatacc agcagagcca   1140
agggta                                                              1146

<210> SEQ ID NO 73
<211> LENGTH: 750
<212> TYPE: DNA
<213> ORGANISM: Artificial Sequence
<220> FEATURE:
<223> OTHER INFORMATION: Codon optimized Streptococcus pyogenes acyl-ACP
      thioesterase sequence

<400> SEQUENCE: 73
atgggattat catatcaaga gagttaaca ttaccatttg agttatgcga cgtaaagtca      60
gacataaagt taccattact attagattat tgcttaatgg tatctggaag gcaatcagta    120
cagttaggaa gatcaaacaa caacttatta gtagactata agttagtatg gatagtaaca    180
gactacgaga taacaataca caggttacca cacttccaag agacaataac aatagagaca    240
aaggcattat catacaacaa gttttttctgt tacaggcagt tctacatata cgaccaagag    300
ggatgcttac tagtagacat actatcatac ttcgcattac taaacccaga tacaagaaag    360
gtagcaacaa taccagagga tttagtagca ccattcgaaa cagactttgt aaagaaatta    420
cacagggtac caaagatgcc attactgaga cagtcaatag ataggggacta ctatgtaagg    480 tacttcgaca tagacatgaa tggacatgta aacaactcaa agtacttaga ctggatgtac    540
gacgtattag gttgccagtt cttaaagaca caccagccat taaagatgac attaaaatac    600
gtaaaagaag tatcacctgg aggacagata acttcatcat atcatttaga tcagttaaca    660
tcataccacc agataatatc agatggacag ttaaatgcac aggcaatgat agagtggaga    720
gcaataaagc agacagagag tgagacagac                                    750

<210> SEQ ID NO 74
<211> LENGTH: 1191
<212> TYPE: DNA
<213> ORGANISM: Artificial Sequence
<220> FEATURE:
<223> OTHER INFORMATION: Codon optimized Ricinus communis palmitoyl-acyl
      carrier protein thioesterase sequence

<400> SEQUENCE: 74
atgggaacat gctcatacac aataacatta ccaataagat gcttatcaaa ctcaaacgga      60
caccacgacc cacataagca gaacttaaac aagataaaga taaatggagc atctacatca    120
```

| | |
|---|---:|
| acaaggccat taaagttaga cgcaccatca cagacagttg gagtagcaac aatatactta | 180 |
| gcatcagtat cagagaactt aactttaaca aaagaagtaa tgagacagaa ataccaaca | 240 |
| aagaagcagt acatagatcc acacaggcag ggattaatga tagagggtgg agtaggatat | 300 |
| aggcagacaa tagtaataag atcttacgag gtaggaccag acaagacagc aacattagag | 360 |
| tcaatactat acttattaca agagacagca ttaaaccacg tatggttatc aggactatta | 420 |
| tcaaacggat tcggagcaac acatggaatg taaagaata acctaatatg ggtagtatca | 480 |
| aagttacagg tacaggtaga ccactaccca atatggggag aggtagtaga gatagacaca | 540 |
| tgggtaaggg caagtggaaa gaacggaatg aaaagggact ggttaataag atcacaagca | 600 |
| acaggacatg tatttgtaag ggcaacatca acatgggtaa tgatgaatga gaaaactaga | 660 |
| aggctatcaa agatgccaga ggaagtaagg gcagagatat caccatggtt catagagaag | 720 |
| caagcaataa aagaagaagt acctgataag attgctaagt tagacgacaa ggcaaggtat | 780 |
| gtaatatcaa acttaaagcc aaaaagatca gacttagaca tgaaccatca cgtaaacaat | 840 |
| gtaaaatatg taaggtggat gttagagata ttaccagatc acttcttaga gtcacaccag | 900 |
| ttaagtggaa taacaatgga gtacaggaga gagtgtggat cagcagacat agtacagtca | 960 |
| ttatgcgagc cagacggaga tgagatacta tcaaacgata taccagtact aaatggattt | 1020 |
| tcattagcat cagagccatt aatgcaagga acggattct tagtaccatt agataaggta | 1080 |
| ccattaaagt acacacactt actattaaca aagggagagt cacagaacga agagatagta | 1140 |
| aggggaaaga caatatggaa gaaaaagtta tgcacaatgc cattctcaac a | 1191 |

<210> SEQ ID NO 75  
<211> LENGTH: 1176  
<212> TYPE: DNA  
<213> ORGANISM: Artificial Sequence  
<220> FEATURE:  
<223> OTHER INFORMATION: Codon optimized Ricinus communis palmitoyl-acyl carrier protein thioesterase sequence

<400> SEQUENCE: 75

```
atggcatcaa agggatcaat aaggctatac tttccatgcg acttcaggaa cacactacag     60
aagaagaata tgaagatgga catggtaatg gcaaggtcag gattttcata ctcattaaac    120
ccaatagcac caaagatacc aaggttctat gtagtagcaa atgcatcaaa tccacagagg    180
gtagatacaa taaacggaaa gaaagtaaac ggaatacacg tagcagagtc atcaaactca    240
tacgcagacc agaataagat gaacgcaaca gcaggattag tattagacgg aaacgtagat    300
catcagccat tacacaagtg gttattaggt aggttcgtag acgagaggtt agtatattca    360
cagacattca taataagatc atacgagata ggaccagaca agacagcaac aatggagaca    420
ttaatgaact tattacaaga gacagcatta aaccacgtaa catcaagtgg attagcagga    480
gatggattcg gagcaacaag agagatgtca ttaagaaagc taatatgggt agtaacaagg    540
atacacatac aggtacaaag gtactcatgc tggggagatg tagtagagat agatacatgg    600
gtagacggag ctggaaagaa cggaatgaga agggactgga taataaggga ttacaacaca    660
aaagaaataa taacaagggc aacatcaaca tgggtaataa tgaataggga aactagaaag    720
ttatcaaaga tgccagaaca ggtaaggcag gaattagtac cattctacac aaataggata    780
gcaatagcaa aagagaataa cgacgttgag aagatagata agttaacaga cgagacagca    840
gaaaggataa ggtctggatt agcaccaaga tggagtgaca tggacgcaaa ccagcacgta    900
aacaacgtaa agtacatagg atggatacta gagtcagtac caataaacgt attagaggac    960
```

| tataacttaa cttcaatgac attagagtac agaagagagt gcaggcagtc aaacttatta | 1020 |
| gagtcattaa catcaacaac agagcattca acaacaatt cttgtaacag gaaagcacac | 1080 |
| ttagagtata cacacttact aagaatgcaa gcagacaagg cagagatagt aagggcaagg | 1140 |
| acagagtggc agtcaaagtc aaacagaaag acaata | 1176 |

<210> SEQ ID NO 76  
<211> LENGTH: 1257  
<212> TYPE: DNA  
<213> ORGANISM: Artificial Sequence  
<220> FEATURE:  
<223> OTHER INFORMATION: Codon optimized Ricinus communis palmitoyl-acyl carrier protein thioesterase sequence

<400> SEQUENCE: 76

| atggtagcaa cagcagcagc agcaacatca tcattctttc cagtaccatc acagtcagca | 60 |
| gatgcaaaact tcgataaggc accagcatca ttaggaggaa taaagttaaa gtcaacttca | 120 |
| tgctcaaggg gactacaggt taaggcaaac gcacaggcac caccaaagat aaacggatca | 180 |
| tctgtaggat ttacaacatc agtagagaca gtaaagaacg acggagacat gccattacca | 240 |
| ccaccaccaa gaacattcat aaaccagtta ccagattggt caatgttatt agcagcaata | 300 |
| acaacaatat tcttagcagc agagaagcaa tggatgatgt tagattggaa gccaagaagg | 360 |
| ccagacatgt taatagaccc atttggaata ggaaggatag tacaagacgg attaatattc | 420 |
| aggcagaatt tctcaataag atcatacgag ataggagcag acaggacagc atcaatagag | 480 |
| acattaatga atcacttaca ggaaacagca ttaaaccatg taaagacagc aggactatta | 540 |
| ggtgacggat tcggatcaac accagagatg tcaaaaagaa acctaatatg ggtagtaaca | 600 |
| agaatgcaag tattagtaga taggtatcca acatggggag atgtagtaca ggtagacaca | 660 |
| tgggtatcaa agagtggaaa gaacggaatg agaagggact ggtgcgtaag ggactcaagg | 720 |
| acaggagaga cactaacaag ggcatcatca gtatgggtaa tgatgaataa gttaacaaga | 780 |
| aggctatcaa agataccaga agaagtaagg ggagagatag agccatactt cttaaactca | 840 |
| gacccaatag tagacgaaga ttctaggaaa ttaccaaagt tagacgattc aaacgcagac | 900 |
| tacgtaagga aaggattaac acctaggtgg agtgatttag acataaatca gcacgtaaac | 960 |
| aatgtaaagt acataggatg gattttagag tcagcaccat taccaatact agagtcacac | 1020 |
| gagttatcag caataacatt agagtataga agagagtgcg aaaggggactc agtattacag | 1080 |
| tcattaacag cagtatcagg aaacggaata ggaaacttag aaacgctgg agacatagaa | 1140 |
| tgtcagcact tactaaggtt agaggacgga gcagagatag taagggggaag gacagagtgg | 1200 |
| aggccaaagt actcatcaaa ctttggaata atgggacaga taccagtaga gtctgca | 1257 |

<210> SEQ ID NO 77  
<211> LENGTH: 1215  
<212> TYPE: DNA  
<213> ORGANISM: Artificial Sequence  
<220> FEATURE:  
<223> OTHER INFORMATION: Codon optimized Jatropha curcas acyl-ACP thioesterase sequence

<400> SEQUENCE: 77

| atggcagtat ttacatacag aatagcaatg ttaccaataa gatgttcatc atcaaactca | 60 |
| acaaattcac actcacacga cccaaaccaa cagaatttac acaagataaa gataaacgga | 120 |
| tcagcttcag caatgatgcc attaaaggta gacttaccat catcattaac aataacatca | 180 |
| gtagcaccag tagtagagaa cttatcttta acaaaagagc agacaaggca gaacatacca | 240 |

```
acaaagaagc agtatataga cccacatagg cagggactaa tagtagagga gggtgtagga      300
tacaggcaga cagtagtaat aagatcatac gaggtaggac cagacaagac agcaacatta      360
gagataatac tatgcttatt acaagagaca gcattaaacc acgtatggtt atcaggatta      420
ctatcaaacg gatttggagc aacacacgga atggtaagaa ataacctaat atgggtagta      480
tcaaagttac aggtacaggt agaccagtac ccaatatggg gagaggtagt agagatagac      540
acatgggtag gagcatctgg aaagaacgga atgagaaggg attggttagt aaggtcacag      600
gcaactggac aggttttcgc aagggcaaca agtacatggg taatgatgaa tgagaaaaca      660
agaaggctat caaagatgcc agaggaagta agggcagaga tagcaccatg gttcatagag      720
aagcaagcaa taaagaaga agtaccagag aagatagcaa agttagacga taaggcaagg      780
```

```
acaaagaagc agtatataga cccacatagg cagggactaa tagtagagga gggtgtagga      300
tacaggcaga cagtagtaat aagatcatac gaggtaggac cagacaagac agcaacatta      360
gagataatac tatgcttatt acaagagaca gcattaaacc acgtatggtt atcaggatta      420
ctatcaaacg gatttggagc aacacacgga atggtaagaa ataacctaat atgggtagta      480
tcaaagttac aggtacaggt agaccagtac ccaatatggg gagaggtagt agagatagac      540
acatgggtag gagcatctgg aaagaacgga atgagaaggg attggttagt aaggtcacag      600
gcaactggac aggttttcgc aagggcaaca agtacatggg taatgatgaa tgagaaaaca      660
agaaggctat caaagatgcc agaggaagta agggcagaga tagcaccatg gttcatagag      720
aagcaagcaa taaagaaga agtaccagag aagatagcaa agttagacga taaggcaagg      780
tatgtagtaa caaacttaaa gcctaagagg tcagatttag acatgaatca acatgtaaac      840
aacgtaaaat acgtaaggtg gatgttagag acattaccag accagttctt cgagaaccac      900
cagttaagtg gaataacttt agagtataag agagagtgcg gatcatcaga tatagtagag      960
tcattatgcg agccagatga agaagaggga ataataaaca caggattaaa gcagaacaac     1020
gacaagtcat tattcaatgg attctcatta ccatcagaga taatgaaagg aaacggattc     1080
ttatcatcat tagaaaagac accattaaag tacacacact tattagtagc aaagggaaag     1140
acacagtcag aggaaatagt aaggggaaag acaatatgga agaaaaagtt actaacaaca     1200
atgccatttt cacca                                                     1215

<210> SEQ ID NO 78
<211> LENGTH: 1044
<212> TYPE: DNA
<213> ORGANISM: Artificial Sequence
<220> FEATURE:
<223> OTHER INFORMATION: Codon optimized Jatropha curcas acyl-ACP
      thioesterase sequence

<400> SEQUENCE: 78
atggtatcaa cagcaatatc attttcacta ttaccaataa agttaataaa agaagagaca       60
agaatggcat cagcagatag gagaaagaac tcaatagtaa agaattcgg acacttcaca      120 tgcagatgtg cagcaataga gaagagaata caaaagttaa acaacttctt aatagacgga      180
ggattcggat cattagagca aaatggatta atatataggc agaacatatt cataaggtca      240
ttcgagatag gattcgacag aaagttatca ttagcagcat taactaattt cttacaggat      300
acagcattaa accacgtaag aatgatagga ttactagctg caggatttgg atcaacacca      360
gagatgtcaa agaaagactt aatatgggta ttatgcacat tacagatatt agtagacagg      420
cacccatctt ggttagacgc agtagaggta gacacatgga tgtaccccatc aggacagaac      480 ggacagggaa gggactggtt agtaagggac gcaaagacag gaaagccatt agcacaggca      540
tcaagtgtaa tggtattatt aaacaaaaag acaggaagc tatcaaagtt cacagaagag      600
ataagggacg agatagcacc acacatgatg atggactgca cccaataat aaattctagg      660 aagatgttac cattcgatgt aaatacagca gattacgcaa ggacaggatt aacaccaggt      720
tggaacgatt tagacttaaa tcagcatgta accatgtac agtacataaa ctggatatta      780
cagaacgtat taaggtcact aatacagcat cacaagttat cagatataac attagagtac      840
agaaaggaat gcgacataaa ctcaatacta cagtttctat caaagatagt taagaatgga      900
tcaaaccact caacagacac aaataactta atagagttag accactcatt actattagag      960
aacggatcag agatagcaag ggcaaacaca atatggaagc caagagaagt aaacaacttt     1020
```
aagaacgcag tatatacacc agca                                              1044

<210> SEQ ID NO 79
<211> LENGTH: 1071
<212> TYPE: DNA
<213> ORGANISM: Artificial Sequence
<220> FEATURE:
<223> OTHER INFORMATION: Codon optimized Jatropha curcas acyl-ACP
      thioesterase sequence

<400> SEQUENCE: 79

```
atggcatcaa ctgcaatatc attcttaagt ataccaataa agttaataaa agaagagatg     60
agaatggcat ctgcaggaag gagaaagaac acaatagcag cagagttcgg acattttaca    120
ttcggatcag caacagtaga gaaaaaagta cagaagtcaa ataacttcct aatagacgga    180
ggatttggat cattagagca gaacggatta atatacaggc agaacatatt tgtaaggtca    240
tttgagatag gattcgatag aaagttatca ttagcagcat taacaaactt cttacaggac    300
acagcattaa accactgcag aatgatagga ttactagcag agggattcgg atcaacacca    360
gagatgataa agaaagattt aatatgggta ttatgtacat tacagatatt agtagacgga    420
tatccaagtt ggctagacgt agtagaggta gatacatgga tgtacccatc aggacaaaac    480
ggattaggta ggggatggtt agtaagggac ggaaagacag gaaggtcatt agcacagtca    540
tcatcagtaa tggtatcatt caataagaaa acaggaaac tatcaaagtt agcaaaggag    600
ataagggacg agatagcacc acacatgatg gactgcgacc caataatgaa caagaactca    660
agaaagatat taccattcga cgtaaataca gctgattatg caaggacagg tttaacacca    720
ggatggaacg aattagactt aaaccaacac gtaaatcacg tacagtacat aaactggata    780
ttacagaatg taaggccatc attagttcag catcacaagt tatcagcaat tacattagag    840
tacagaaaag agtgcgacat gaattctata ctacagtcat tatcaaggat agtaaagaac    900
ggaggaaacg attcaacaga caagaacaac gtaatagagt tagaccactt cttactatta    960
gagaacggat cagagatagc aagggcaaac acaatatgga agccaagaga agtaaacaac   1020
tttaagaatg tagtacactc accagcagaa gagaacatat catcaatgaa t            1071
```

<210> SEQ ID NO 80
<211> LENGTH: 396
<212> TYPE: DNA
<213> ORGANISM: Artificial Sequence
<220> FEATURE:
<223> OTHER INFORMATION: Codon optimized E. Coli FadM sequence

<400> SEQUENCE: 80

```
atgcagacac agataaaggt aaggggatat cacttagacg tataccaaca cgtaaacaac     60
gcaaggtact tagagttctt agaagaagca agatgggatg gattagagaa ctcagattca    120
ttccagtgga tgacagcaca taacatagca tttgttgtag taaacataaa tataaactac    180
agaaggccag cagtattatc agacctatta acaataacat cacagttaca gcagttaaat    240
ggaaagtcag gaatactatc acaggtaata acattagagc cagagggaca ggtagtagca    300
gacgcactaa taacattcgt atgcatagac ttaaagacac aaaaggcatt agcattagag    360
ggagagttaa gggagaaatt agagcagatg gtaaag                              396
```

<210> SEQ ID NO 81
<211> LENGTH: 957
<212> TYPE: DNA
<213> ORGANISM: Artificial Sequence

```
<220> FEATURE:
<223> OTHER INFORMATION: Codon optimized E. Coli AccA sequence

<400> SEQUENCE: 81
atgtcattaa acttcttaga tttcgagcag ccaatagcag agttagaggc aaagatagac      60
tcattaacag cagtatcaag gcaagatgag aagttagaca taaacataga cgaagaagta     120
cataggttaa gggagaagtc agtagagtta acaagaaaga tattcgcaga cttaggagca     180
tggcagatag cacagctagc aaggcaccca cagaggccat acacattaga ctatgtaagg     240
ttagcattcg acgagttcga tgagcttgca ggagacaggg catacgcaga cgataaggca     300
atagtaggag gaatagcaag gttagacgga aggccagtaa tgataatagg acaccaaaag     360
ggaagggaga caaaagagaa gataagaaga aactttggaa tgcctgctcc agagggatac     420
agaaaggcat taaggttaat gcagatggca gaaaggttta gatgccaat aataacattc      480 atagacacac caggagcata cccaggagta ggagcagagg aaaggggaca gagtgaggca     540
atagcaagaa acttaaggga aatgtcaagg ttaggtgtac cagtagtatg cacagtaata     600
ggagagggag gatctggagg agcattagca ataggagtag gtgacaaggt aaacatgtta     660
cagtactcaa catattcagt aatatccaca gagggatgcg catcaatact atggaaatca     720
gcagataagg caccattagc tgcagaggca atgggaataa tagcaccaag gctaaaagaa     780
ctaaagttaa tagactcaat aataccagag ccattaggag gagcacacag aaatccagag     840
gcaatggcag catcattaaa ggcacagcta ttagcagatt tagcagactt agatgtatta     900
tcaacagagg acttaaagaa tagaagatac cagaggttaa tgtcatacgg atatgca       957

<210> SEQ ID NO 82
<211> LENGTH: 468
<212> TYPE: DNA
<213> ORGANISM: Artificial Sequence
<220> FEATURE:
<223> OTHER INFORMATION: Codon optimized E. Coli AccB sequence

<400> SEQUENCE: 82
atggacataa gaaagataaa gaaattaata gagttagtag aagagtcagg aatatcagag      60
ttagaaatat cagagggaga ggaatcagta agaatatcaa gggcagctcc agcagcatca     120
ttcccagtaa tgcaacaggc atacgcagca ccaatgatgc agcagcctgc acagagtaac     180
gcagcagcac cagcaacagt accatcaatg gaagcaccag cagcagcaga gatatctgga     240
cacatagtaa ggtcaccaat ggtaggaaca ttctatagga caccatcacc agacgcaaag     300
gcattccatg aggtaggaca aaaggtaaac gttggagata cattatgcat agtagaggca     360
atgaagatga tgaatcagat agaggcagat aagtcaggaa cagtaaaggc aatactagta     420
gagtcaggac agccagtaga gtttgacgag ccattagtag taatagag                 468

<210> SEQ ID NO 83
<211> LENGTH: 1347
<212> TYPE: DNA
<213> ORGANISM: Artificial Sequence
<220> FEATURE:
<223> OTHER INFORMATION: Codon optimized E. Coli AccC sequence

<400> SEQUENCE: 83
atgttagaca agatagtaat agcaaatagg ggagagatag cattaagaat actaagggca      60
tgcaaagagt taggaataaa gacagtagct gtacactcat cagcagacag ggacttaaaa     120
catgtattac tagcagatga gacagtttgt ataggaccag caccatcagt aaagtcatac     180
```

```
ttaaacatac cagcaataat atcagcagca gagataacag gagcagtagc aatacaccca    240
ggatacggat tcttatcaga aaacgcaaat ttcgcagagc aagtagagag atcaggattc    300
atattcatag gaccaaaggc agagacaata aggctaatgg gagacaaggt atcagcaata    360
gcagcaatga agaaagctgg agtaccatgc gtaccaggat cagacggacc attaggtgat    420
gacatggata agaatagggc aatagcaaaa aggataggat acccagtaat aataaaggca    480
agtggaggag gtggaggaag gggaatgaga gtagtaaggg gagatgcaga gttagcacag    540
tcaatatcaa tgacaagggc agaggcaaag gcagcattct caaatgacat ggtatacatg    600
gagaagtact tagagaaccc aaggcacgta gagatacagg tattagcaga cggacaggga    660
aacgcaatat acttagcaga gagggactgc tcaatgcaga aaggcaccag aaagtagta     720 gaagaagcac cagctccagg aataacacca gagttaagaa gatacatagg agagaggtgc    780
gcaaaggcat gcgtagacat aggatatagg ggagcaggaa catttgagtt cttattcgag    840
aacggagagt tttacttcat agagatgaac acaaggatac aggtagagca cccagtaaca    900
gagatgataa caggagtaga cttaataaag gaacagttaa ggattgcagc aggacagcca    960
ttatctataa agcaagaaga agtacacgta agggacatg cagtagagtg caggataaac    1020
gcagaggatc ctaacacatt tctaccatca ccaggaaaga taacaagatt ccatgcacca   1080
ggaggattcg gagtaaggtg ggagtcacac atatatgcag gatacacagt accaccatat   1140
tacgattcaa tgataggtaa gctaatatgc tacggagaga acaggacgt agcaatagca    1200 agaatgaaga acgcattaca ggaattaata atagacggaa taaagacaaa tgtagattta   1260
cagataagga taatgaacga cgagaacttt cagcacggag aacaaacat acactattta   1320 gagaaaaagt taggattaca agagaag                                       1347
```

<210> SEQ ID NO 84
<211> LENGTH: 912
<212> TYPE: DNA
<213> ORGANISM: Artificial Sequence
<220> FEATURE:
<223> OTHER INFORMATION: Codon optimized E. Coli AccD sequence

<400> SEQUENCE: 84

```
atgtcatgga tagagaggat aaagtcaaac ataacaccaa caagaaaggc atcaataccct    60 gagggagtat ggacaaagtg cgactcatgc ggacaggtac tatataggc agaattagag   120 agaaacttag aggtatgccc aaagtgcgat catcacatga gaatgacagc aaggaatagg   180
ttacactcat tattagatga aggatcatta gtagagttag atcagagtt agagccaaag   240 gacgtactaa agtttaggga cagtaagaag tacaaggaca ggttagcatc agcacagaaa   300
gagacaggag agaaagacgc attagtagta atgaagggaa cattatacgg aatgccagta   360
gtagcagcag catttgagtt cgcattcatg ggaggatcaa tgggatcagt agtaggagca   420
aggttcgtaa gggcagtaga gcaagcttta gaggacaact gcccattaat atgtttctca   480
gcatctggag gtgcaagaat gcaagaagca ttaatgtcat taatgcagat ggcaaagaca   540
tcagcagcat tagcaaaaat gcaggaaagg ggactaccat acatatcagt attaacagat   600
ccaacaatgg gaggagtatc agcatcattc gcatgtttag gagacttaaa catagctgag   660
ccaaaggcac taataggatt cgcaggacca agggtaatag agcagacagt aaggagaag    720 ttaccaccag gatttcagag gtcagagttc ttaatagaaa agggagcaat agacatgata   780
gttagaaggc cagagatgag attaaagtta gcatcaaatc tagcaaagtt aatgaatta    840 ccagcaccaa acccagaggc accaagagag ggagtagtag taccaccagt accagatcag   900
```

| gaaccagagg ca | 912 |

<210> SEQ ID NO 85
<211> LENGTH: 1716
<212> TYPE: DNA
<213> ORGANISM: Artificial Sequence
<220> FEATURE:
<223> OTHER INFORMATION: Mutated Clostridium ljungdahlii FadD sequence

<400> SEQUENCE: 85

| atggatgaaa ttaaaataaa tgatagccaa aaagatagt atgaaaaaat gggctattgg | 60 |
| ggtaaaaaaa cactctaaga ttactggcat acgtcggtaa aaagtatag agataaggaa | 120 |
| tttgtagtag atgatagagg atatcgttac acctagggac aattggatga aaaagcaggt | 180 |
| attgttgctt cctattttct tagtattgga gtaaagcctc tagatgttat ttcttttcaa | 240 |
| ataccaatat ggagtgaatt tgtaattgtt agtattgcat gcatgaaggt ggggagctgt | 300 |
| tgttaaccca attggcatgt gctatagtgg tccgggaagt ttcatatctt ttgaatttat | 360 |
| gtaaaagtaa agtttttctc tgccctacat ggtacaataa gacaaattat gaaaaattga | 420 |
| ttctatcagt caaaaaggat gtaaaaagtt taaaacacat tgtattactt gacaatctta | 480 |
| aagaaaaaga agtaacagt attactttaa acatatatt atcatcatac ttttccttga | 540 |
| acataaaaga tgaggtaatg gttgacagta atgatgtagc agctatcctt tgcacatccg | 600 |
| gtactactgg atgtgcaaag ggagccatgc tgactcataa aacataata tttagtgaaa | 660 |
| aatactttaa taaggaactt ggcattacaa aagatgatat tatgtttatg ccggcacctt | 720 |
| taaatcatgc aactggcttt catcatggaa ttattgcacc tatgcttatt ggatcaaaag | 780 |
| tggttttaca gcagaagttt aaaagtaaaa aggcaataga acttatgaat agagaaaaat | 840 |
| gcacctggtc aatgggagct acaccattta tatatgatat tttgaaaaac attagagagg | 900 |
| atgaagttta ccttagttcg ttaaaatttt atctttgtgg tggagctgta gtaccagaag | 960 |
| aaatggtaag gcaagcctat gaatatgaaa taaaattatg tgaagtttat ggatctacag | 1020 |
| aaagtgttcc acatgtattt gtaagaccag atgaaaatat tgagttaaca tttggcactg | 1080 |
| caggaagggc tatggaaggc gtagaagtta aaattgtaga tgaaaataga aaagagatac | 1140 |
| tacctggaaa tctaggggaa gaagtatcga gaggtccaaa tgtatttgta ggatatatag | 1200 |
| gtgataaatc agctacaaat aaggtactgg atgatgaagg atggttttat agtggcgatt | 1260 |
| tatgtgtaag tgatataagt ggcaatatta atatcattgg gagaaaaaaa gacataattg | 1320 |
| ttagaggcgg tgaaaatctc aactcgaatc atataagtca gtatatttca aaatttccac | 1380 |
| taattaaaga tgaggcagtt attggaatgc ctgataagcg tcttggtgaa cgaatttgtg | 1440 |
| cttatgtcgt attgaaaaaa gaagttaatt ctctgaaatt agaagaactt ttagagtaca | 1500 |
| tggaaaagga aaaaatccct aaaaggtatt ggccggaaca cctggagatt atagataaaa | 1560 |
| ttcccagaac tgacagtgga aaggtgaaaa aaatttatt ggcaaaggat ttaaaagttc | 1620 |
| gaatgagtag acaggaggag tcaagttgga agggcgagaa ttcggtccaa gaagatcaag | 1680 |
| agaaacaaca aaaccaaggg ttgtgtgccc caataa | 1716 |

<210> SEQ ID NO 86
<211> LENGTH: 927
<212> TYPE: DNA
<213> ORGANISM: Artificial Sequence
<220> FEATURE:
<223> OTHER INFORMATION: Codon optimized E. Coli FabD sequence -continued

<400> SEQUENCE: 86

```
atgactcaat tcgcgttcgt ttttccaggg caaggttctc agaccgtagg tatgttagca    60
gatatggcag catcatatcc aattgtagag gaaacctttg cagaagcatc agcggcgtta   120
ggctatgact tatgggcgct tacccaacag ggcccagcag aggaacttaa taagacttgg   180
cagacccagc cagcgttact aaccgcatca gttgcgcttt atagagtttg gcagcaacag   240
ggcggcaagg cgccagcgat gatggcaggg cattcattag gtgagtattc agcgcttgtg   300
tgtgcgggcg tcattgactt cgcggacgcg gtgagactag ttgaaatgag aggtaagttc   360
atgcaagaag cagtaccaga gggtaccgga gcaatggcag ccattattgg gcttgacgat   420
gcgagtatag cgaaagcgtg tgaagaagcg gccgagggtc aggttgtgtc accagtcaat   480
ttcaattcac caggacaagt tgttattgcc ggtcataaag aagcggttga gagagctggc   540
gcagcatgta aagcagcggg agcaaagaga gcacttccat taccagtttc agttccttca   600
cattgtgcct taatgaagcc tgcggcggac aagttagcgg ttgagttagc gaagattacc   660
ttcaatgcgc caactgtacc agttgtcaat aatgttgacg ttaaatgtga aaccaatggc   720
gacgcgatta gagatgcact tgtgagacaa ctttataatc cagttcaatg gaccaaatca   780
gttgagtata tggcggcaca gggtgttgaa catctttatg aagtcggccc aggtaaagta   840
cttaccggcc ttaccaagag aattgtagac acccttactg cgtcagcgtt aaatgagcct   900
tcagcgatgg cggcagcgct tgagtta                                       927
```

<210> SEQ ID NO 87
<211> LENGTH: 549
<212> TYPE: DNA
<213> ORGANISM: Artificial Sequence
<220> FEATURE:
<223> OTHER INFORMATION: Codon optimized E. Coli TesA sequence with periplasmic targeting sequence removed

<400> SEQUENCE: 87

```
atggcagata ccttacttat tcttggcgac agtttatcag cgggttatag aatgtcagca    60
tcagcagcgt ggcctgcgtt actaaatgac aaatggcaat caaagacctc agttgttaat   120
gcatcaatat ctggtgacac ttcacaacag ggattagcga gacttccagc gttacttaag   180
cagcatcagc caagatgggt attagttgag cttggtggga tgacggcct tagaggtttc    240
caaccacagc aaaccgagca aaccttaaga cagattcttc aagatgtgaa agcggcgaat   300
gcggagcctc ttcttatgca gattagactt cctgcgaatt atggcagaag atataatgaa   360
gcgttttcag ccatttatcc aaagttagca aaagaattcg acgttccatt acttccattt   420
ttcatggaag aagtctatct aaagccacag tggatgcaag atgacggcat tcatccaaat   480
agagatgcac aaccattcat tgcggactgg atggcaaaac agcttcagcc attagtaaat   540
catgactca                                                           549
```

<210> SEQ ID NO 88
<211> LENGTH: 1146
<212> TYPE: DNA
<213> ORGANISM: Artificial Sequence
<220> FEATURE:
<223> OTHER INFORMATION: Codon optimized Cinnamomum camphorum thioesterase sequence

<400> SEQUENCE: 88

```
atggcaacca ccagtttagc gagtgcgttt tgttcaatga agccgttat gttagcaaga     60
gatgggagag gaatgaaacc aagatcatca gaccttcaac ttagagcggg caatgcgcag   120
```

```
acctcattaa agatgattaa tggtaccaaa ttctcatata ccgaatcatt aaagaaactt    180
ccagactggt caatgctttt cgcagttatt accactattt tctcagccgc ggaaaagcaa    240
tggaccaatt tagagtggaa acctaagcca atcctccac agttattaga tgaccatttc     300
ggtccacatg gtttagtatt cagaagaact tttgcgatta gatcttatga agttggccca    360
gacagatcaa cctcaatagt tgcggtcatg aatcatttac aagaagcagc gcttaatcat    420
gcgaaatcag ttggcattct aggcgacggt ttcggcacta cccttgaaat gtcaaagaga    480
gatcttattt gggttgtgaa gagaacccat gtagcagttg agagatatcc agcgtgggga    540
gataccgttg aagttgaatg ttgggttgga gcatcaggga ataatggtag acgacatgac    600
ttcttagtaa gagactgtaa aactggcgag attcttacca gatgtacttc actttcagta    660
atgatgaata ccagaaccag aagattatca aagattccag aagaagtgag aggtgagatt    720
ggtccagcgt ttattgataa tgttgcggtg aaagatgaag agattaagaa gccacaaaag    780
cttaatgatt caaccgcaga ctatattcag ggtggcctta ccctagatg gaatgactta    840 gacattaatc agcatgtcaa taatattaaa tatgtcgact ggattcttga aactgttcca    900
gactcaattt tcgagtcaca tcatatttca tcatttacca ttgaatatag aagagagtgt    960
accatggact cagtcctaca atcattaacc accgtttctg gcgggtcatc agaggcaggc   1020
cttgtgtgtg agcatcttct acagcttgag ggcggatcag aagttttaag agcgaaaacc   1080
gagtggaggc caaagcttac tgactcattc agaggtattt cagtaatacc agcggagtca   1140
tcagtt                                                              1146
```

<210> SEQ ID NO 89
<211> LENGTH: 1146
<212> TYPE: DNA
<213> ORGANISM: Artificial Sequence
<220> FEATURE:
<223> OTHER INFORMATION: Codon optimized Umbellularia californica
      thioesterase sequence

<400> SEQUENCE: 89

```
atggcaacta cttcattagc gtcagcattt tgttcaatga agccgtaat gttagcaaga     60 gatgggagag gaatgaagcc aagatcaagt gacttacagt taagagcggg taatgcgcca    120
acttcactta agatgataaa tggtaccaaa ttctcatata ccgaatcatt aaagagactt    180
ccagactggt caatgttatt cgcggtgatt accaccattt tctcagcggc cgagaaacaa    240
tggaccaatc tagagtggaa acctaagcca aaacttccac aactacttga cgaccatttt    300
ggcttacatg gtcttgtttt cagaagaacc tttgcgatta gatcttatga agttggccct    360
gacagatcaa cttctattct tgcggttatg aatcacatgc aagaagcaac tcttaatcat    420
gcaaagtcag ttggtattct tggtgacggt ttcgggacca ctcttgaaat gtcaaagaga    480
gacttaatgt gggtagtaag aagaactcat gtcgcggttg aaagatatcc aacctgggga    540
gacaccgttg aggttgaatg ttggattggt gcgtcaggca ataatggcat gagaagagac    600
tttcttgtga gagattgtaa gaccggagag attcttacca gatgtacctc actttcagtt    660
cttatgaata cccgtaccag aagattatca accatacctg acgaagtgag aggcgaaatt    720
gggccagcgt tcattgacaa tgttgcggtt aaagatgatg agattaaaaa gcttcaaaag    780
cttaatgact caaccgcaga ctatattcag ggcggcttaa ccccaagatg gaatgacctt    840
gacgttaatc agcatgtcaa taatctaaaa tatgtagcgt gggttttcga aaccgttcca    900
gactcaattt tcgaatcaca tcatatttca tcattcacct tagagtatag aagagaatgt    960
```

```
accagagatt cagttttaag gtcattaacc accgtaagtg gtggttcatc agaggcaggc    1020
cttgtctgtg atcatctttt acagttagag ggcggatcag aggtgcttag agcgagaacc    1080
gagtggcgac caaagttaac tgattcattc agaggcattt cagttattcc agcggagcca    1140
agagtt                                                               1146

<210> SEQ ID NO 90
<211> LENGTH: 750
<212> TYPE: DNA
<213> ORGANISM: Artificial Sequence
<220> FEATURE:
<223> OTHER INFORMATION: Codon optimized Streptococcus pyogenes acyl-ACP
      thioesterase sequence

<400> SEQUENCE: 90
atgggcttat catatcaaga gagttaacc ttaccatttg aattatgtga tgttaagtca       60
gacattaaac ttccattact tttagactat tgtcttatgg tttcaggcag acagtcagtg     120
cagcttggta gatcaaataa taatcttta gtcgactata aacttgtatg gatagttact      180
gactatgaga ttaccattca tagattacca catttccaag aaaccattac cattgaaacc     240
aaagcgctaa gttataataa gttctttttgt tatagacaat ctatatttta tgaccaagag    300
ggctgtcttt tagttgacat tctatcatat ttcgcgcttc ttaatccaga taccagaaag    360
gttgcaacta ttccagagga cttagtcgcc ccattcgaga ctgactttgt taagaaatta    420
catagagttc caaaaatgcc tttacttgag cagtcaattg acagagacta ttatgtaaga    480
tatttcgata ttgacatgaa tggacatgtt aataattcaa gtatcttga ctggatgtat      540 gatgttttag gctgtcaatt ccttaagacc catcagccac ttaagatgac ccttaaatat    600
gtgaaagaag tatcacctgg tggtcaaatt acctcatcat atcatcttga ccagttgacc    660
tcatatcatc agattatatc agatgggcag cttaatgcac aggcgatgat tgaatgggaga    720 gcgattaagc aaaccgagtc tgaaaccgat                                     750

<210> SEQ ID NO 91
<211> LENGTH: 1191
<212> TYPE: DNA
<213> ORGANISM: Artificial Sequence
<220> FEATURE:
<223> OTHER INFORMATION: Codon optimized Ricinus communis palmitoyl-acyl
      carrier protein thioesterase sequence

<400> SEQUENCE: 91
atggggacct gttcatatac cattaccctt ccaattcgat gtttatcaaa ttcaaatggc      60
catcatgatc cacataagca gaatcttaat aagataaaga taaatggcgc gtcaactagt     120
accagaccac ttaagttaga cgcaccttca caaaccgttg gtgttgcgac catttatcta    180
gcatcagttt cagaaaatct taccccttacc aaagaagtca tgagacagaa tattccaacc    240
aagaaacagt atattgaccc acatagacaa gggttaatga ttgagggtgg agttggttat    300
agacaaacta ttgtcattag aagttatgaa gttggcccag acaaaaccgc gactttagag    360
tcaattcttt atcttttaca ggaaaccgcc ttaaatcatg tatggctttc aggtctactt    420
tcaaatggct tcggggcgac ccatggcatg gtaaagaata atttgattg ggtagtgtct     480 aagcttcagg ttcaagtgga tcattatcca atttggggag aggttgtaga gattgacacc    540
tgggttagag catcaggtaa gaatggtatg aaaagagact ggcttattag atcacaagca    600
accggccatg tatttgttag agcgacctca acttgggtta tgatgaatga gaaaaccaga    660
```

| | |
|---|---|
| agattatcaa agatgccaga agaagtcaga gcggagattt caccatggtt cattgaaaag | 720 |
| caagcgatta agaagaagt gccagacaaa attgcaaagt tagacgacaa ggcgagatat | 780 |
| gttatttcaa atctaaaacc taaaagatca gaccttgata tgaatcatca tgtgaataat | 840 |
| gtcaaatatg ttagatggat gcttgagatt ttaccagatc atttcttaga gtctcatcag | 900 |
| ttatcaggca taactatgga gtatagaaga gaatgtggat cagcagatat tgttcaatca | 960 |
| ttatgtgagc ctgacggtga cgagattctt caaatgaca ttcctgttct taatggtttc | 1020 |
| tcacttgcgt cagaaccatt aatggaaggc aatggtttcc ttgtaccatt agataaggtt | 1080 |
| ccattaaagt atacccatct tttacttacc aaaggcgagt cacagaatga agagattgtt | 1140 |
| agaggaaaaa ccatttggaa gaagaaactt tgtactatgc cattttcaac c | 1191 |

<210> SEQ ID NO 92
<211> LENGTH: 1176
<212> TYPE: DNA
<213> ORGANISM: Artificial Sequence
<220> FEATURE:
<223> OTHER INFORMATION: Codon optimized Ricinus communis palmitoyl-acyl carrier protein thioesterase sequence

<400> SEQUENCE: 92

| | |
|---|---|
| atggcatcaa agggctcaat tagattatat tttccatgtg acttcagaaa tactttacag | 60 |
| aaaaagaata tgaaaatgga catggtaatg gcgagatcag gattctcata ttcacttaat | 120 |
| ccaattgcgc caaagattcc aagattctat gttgtcgcta atgcgtcaaa tccacagaga | 180 |
| gttgatacca ttaatggcaa aaaagttaat ggtatacatg ttgcagagtc atcaaattct | 240 |
| tatgcggatc agaataagat gaatgcaacc gcgggtttag tcttagacgg caatgtagat | 300 |
| catcagccac ttcataagtg gcttttaggt agattcgttg acgaaagact tgtttattca | 360 |
| caaaccttca ttattagaag ttatgagatt ggtccagata agaccgcgac tatggaaacc | 420 |
| ttaatgaatt tacttcaaga aaccgcactt aatcatgtta cctcatcagg ccttgcggga | 480 |
| gatggttttg gtgcgactag agagatgtca ctaagaaaac taatttgggt ggtaactaga | 540 |
| attcatattc aagtccagag gtattcatgt tgggggatg tggttgaaat agacacctgg | 600 |
| gttgacggcg caggcaagaa tggaatgaga agagactgga ttattagaga ctataatacc | 660 |
| aaagaaataa ttactagagc aacctcaacc tgggtcatta tgaatagaga aactagaaag | 720 |
| ctttcaaaga tgccagagca agttagacaa gagttagttc cattctatac caatagaatt | 780 |
| gcaattgcga aagagaataa tgacgttgag aaaattgaca agttaaccga cgaaaccgcg | 840 |
| gagagaattc gatcagggct tgcgcctaga tggtcagaca tggacgccaa tcaacatgtg | 900 |
| aataatgtta gtatattggg ctggattctt gaatcagtac ctattaatgt acttgaggac | 960 |
| tataatctta cctcaatgac ccttgagtat agaagagaat gtagacagtc aaatcttta | 1020 |
| gagtcattaa ccagtaccac cgaacattca aataataatt cttgtaatag aaaggcccat | 1080 |
| ttagaatata cccatttact tagaatgcaa gcggataaag cggaaattgt tagagcaaga | 1140 |
| actgagtggc agtcaaagtc aaatagaaaa accatt | 1176 |

<210> SEQ ID NO 93
<211> LENGTH: 1257
<212> TYPE: DNA
<213> ORGANISM: Artificial Sequence
<220> FEATURE:
<223> OTHER INFORMATION: Codon optimized Ricinus communis palmitoyl-acyl carrier protein thioesterase sequence

<400> SEQUENCE: 93

```
atggtggcga ccgcagcagc agcaacctca tcattttcc cagtcccatc acaatcagcc    60
gacgcgaatt tcgacaaagc accagcgtca cttggcggca ttaaactaaa atcaacttca   120
tgttctagag gattacaggt taaagcaaat gcacaagcgc ctccaaagat aaatggatca   180
tcagttggtt tcaccacttc agtagaaacc gttaagaatg acggtgatat gcctttacct   240
ccaccaccaa gaaccttcat taatcagtta ccagactggt ctatgttact tgcggccatt   300
accaccattt tcttagcggc tgaaaagcag tggatgatgc ttgattggaa gccacgtaga   360
ccagacatgc ttattgatcc atttggcatt ggaagaattg tccaagacgg ttaatatttt   420
agacagaatt tctcaattag aagttatgag attggtgcag acagaaccgc gtcaattgag   480
actttaatga atcatcttca agaaaccgcg ttaaatcatg ttaaaaccgc gggtcttttta  540
ggtgacggtt tcggttcaac tccagaaatg agtaaaagaa atctaatttg ggttgtcacc   600
agaatgcaag ttttagtaga cagatatcca acctggggtg atgttgttca ggttgatact   660
tgggtttcaa aatctggtaa gaatggcatg agaagagact ggtgtgtgag agactcaaga   720
accggcgaaa cccttacccg agcgtcatca gtatgggtaa tgatgaataa gcttaccaga   780
agattatcaa agattccaga agaagtgaga ggcgaaattg agccatattt ccttaattca   840
gacccaattg tagacgaaga ttcaagaaag cttcctaaac ttgacgactc aaatgcggac   900
tatgttagaa aaggtttaac ccctagatgg tcagatcttg acataaatca acatgtgaat   960
aatgttaagt atattggttg gattcttgag tcagcgccat taccaattct agagtcacat  1020
gaactttcag cgattaccct tgagtataga agagaatgtg ggagagactc agttcttcag  1080
tcacttaccg cggtttcagg caatggcatt ggcaatcttg gcaatgcggg ggatattgag  1140
tgtcagcatt tacttagatt agaagatgga gcagagattg ttagaggtag aactgagtgg  1200
aggccaaagt attcatcaaa tttcggcatt atgggccaaa ttccagtcga gtcagcg    1257
```

<210> SEQ ID NO 94
<211> LENGTH: 1215
<212> TYPE: DNA
<213> ORGANISM: Artificial Sequence
<220> FEATURE:
<223> OTHER INFORMATION: Codon optimized Jatropha curcas acyl-ACP
      thioesterase sequence

<400> SEQUENCE: 94

```
atggcagtat tcacctatag aattgcgatg ttaccaatta gatgttcatc atcaaattca    60
accaattcac attcacatga cccaaatcaa cagaatttac ataagattaa gattaatggc   120
tcagcgtcag cgatgatgcc tcttaaggtt gatttaccaa gttcattgac gattacctca   180
gttgcaccag ttgtagagaa tctttcatta actaaagaac aaaccagaca gaatattcca   240
accaagaagc agtatattga cccacataga caaggtctta ttgtcgaaga gggcgttggt   300
tatagacaga ccgtcgttat tagatcttat gaagttggcc ctgacaaaac cgcaaccctt   360
gagattatac tttgtctact tcaagagact gcgttaaatc atgtttggtt atcaggctta   420
cttttcaaatg gttttggggc gacccatgga atggtgagaa ataatcttat tgggttgtt    480
tcaaaacttc aggtacaagt tgatcaatat ccaatttggg gcgaagttgt cgagattgac   540
acttgggttg gcgcgagtgg caagaatggt atgcgaagag actggcttgt tagatcacag   600
gcgaccggcc aggtatttgc aagggccacc tcaacctggg ttatgatgaa tgagaaaact   660
agaagattat caaaaatgcc agaagaagtg agagcggaaa ttgcgccatg gttcattgag   720
aagcaagcga ttaaagaaga agtgccagag aagattgcaa aactagacga taaggcgaga   780
```

-continued

```
tatgtagtta ccaatcttaa gcctaaaaga tcagaccttg acatgaatca gcatgtgaat        840
aatgtcaaat atgttagatg gatgcttgaa accttaccag atcaattctt cgagaatcat        900
cagttatcag gtattacttt agagtataag agagaatgtg gatcatcaga tatagtagag        960
tcattatgtg agccagacga agaggaaggg attataaata ccggacttaa gcagaataat       1020
gacaaatcac tattcaatgg tttctcactt ccatcagaga ttatggaagg taatggtttc       1080
ctttcatcat tagaaaagac ccctcttaag tatactcatc ttttagttgc aaaagggaaa       1140
acccaatctg aggaaattgt tagaggcaag accatttgga aaagaaatt acttaccacc        1200 atgccatttt cacca                                                        1215

<210> SEQ ID NO 95
<211> LENGTH: 1044
<212> TYPE: DNA
<213> ORGANISM: Artificial Sequence
<220> FEATURE:
<223> OTHER INFORMATION: Codon optimized Jatropha curcas acyl-ACP
      thioesterase sequence

<400> SEQUENCE: 95
atggtttcaa ccgcgatttc attttcactt ttaccaatta agttaattaa agaagaaact         60
agaatggcct cagcggacag aagaaagaat tcaattgtaa agaattcgg tcatttcacc         120 tgtagatgtg cagcgattga aaagagaatt caaaaactta taatttctt aatagacggc         180 ggcttcggct cattagagca aaatggtctt atatatagac agaatatttt cattagatca         240
ttcgagattg gattcgacag aaagcttca ttagcagcgt tgaccaattt ccttcaggac          300
accgcgctta tcatgttag aatgattggc ttacttgcag cgggtttcgg cagtactcca         360
gaaatgtcaa agaaagacct tatttgggtt ttatgtacct tacagattct tgttgacaga         420
catccttcat ggttagatgc agttgaggtc gacacctgga tgtatccatc aggccagaat         480
gggcaaggta gagactggct tgttagagat gcgaaaaccg gaaagccact tgcgcaggca         540
tcttcagtta tggttctatt aaataaaaag accagaaaac tttctaagtt taccgaagag         600
attagagatg aaattgcgcc acatatgatg atggactgta atccaattat taattcaaga         660
aaaatgctac catttgacgt gaatactgcg gattatgcaa gaaccggtct tacccccagt         720
tggaatgacc ttgaccttaa tcagcatgta aatcatgtcc aatatattaa ttggattta          780 caaaatgttt taagatcact tattcaacat cataagttat cagatattac cttagagtat        840
agaaaagagt gtgacataaa ttcaattctt cagttccttt caaagattgt gaaaatggg         900 tcaaatcatt caaccgatac caataatcta attgagttag accattcact tcttttagaa        960
aatggctcag agattgcgcg agcgaatact atttggaagc caagagaagt aaataatttt       1020
aagaatgcag tttataccc tgcc                                                1044

<210> SEQ ID NO 96
<211> LENGTH: 1071
<212> TYPE: DNA
<213> ORGANISM: Artificial Sequence
<220> FEATURE:
<223> OTHER INFORMATION: Codon optimized Jatropha curcas acyl-ACP
      thioesterase sequence

<400> SEQUENCE: 96
atggcatcaa ccgcgattag tttcctttca attccaatta agcttattaa agaagagatg         60
agaatggcgt cagcgggaag aagaaagaat actattgcag cagaattcgg ccatttcacc        120
```

```
ttcggctcag cgactgttga gaaaaaagtc caaaagtcaa ataatttctt aattgatggc      180
gggtttggct cattagaaca gaatgggtta atatatagac agaatatttt cgtgaggtca      240
ttcgagattg gttttgaccg aaagttatca ttagcagcgc ttaccaattt tctacaggac      300
actgcgctta atcattgtag aatgattggc ttattagccg aggggtttcgg atcaaccccca    360 gaaatgatta agaaagacct tatttgggtt ctttgtaccc ttcaaattct tgttgacgga      420
tatccatcat ggcttgacgt tgttgaggtc gacacctgga tgtatccttc aggtcaaaat      480
ggtcttggca gaggttggtt agtaagagat ggcaagactg gcagatcatt agcgcagtca      540
tcatcagtta tggtgtcatt caataagaaa accagaaaac tttctaagtt agcgaaagaa      600
attagagatg agattgcacc acacatgatg gattgtgacc caattatgaa taagaattca      660
agaaagatac ttccattcga tgtaaatacc gcagactatg cgagaaccgg ccttaccccca    720 ggttggaatg aattagactt aaatcagcat gttaatcatg tccagtatat taattggatt     780
ttacaaaatg ttagccttc acttgttcaa catcataagc tttcagcgat taccttagaa      840
tatagaaaag agtgtgacat gaattcaatt ctacaatcac tttcaagaat tgttaagaat     900
ggtgggaatg atagtaccga caagaataat gttattgagt tagaccatttt tcttcttcta    960 gagaatggtt cagaaattgc gagagcgaat accatttgga aaccaagaga agtaaataat     1020
ttcaaaaatg tagtgcattc accagcagaa gagaatatat cttcaatgaa t              1071

<210> SEQ ID NO 97
<211> LENGTH: 396
<212> TYPE: DNA
<213> ORGANISM: Artificial Sequence
<220> FEATURE:
<223> OTHER INFORMATION: Codon optimized E. Coli FadM sequence

<400> SEQUENCE: 97
atgcaaactc agattaaggt tagaggctat catctagacg tttatcaaca tgtgaataat       60
gcgagatatc ttgagttcct tgaagaagcc agatgggacg gtttagagaa ttcagattca      120
tttcagtgga tgaccgcaca taatattgca ttcgtagtgg tcaatattaa tataaattat      180
agacgaccag cggtcttatc agaccttttta accattacct cacaacttca acagttaaat     240
ggaaagtcag ggattctttc acaggttatt acccttgaac cagagggtca ggttgtagca      300
gatgcgctta ttaccttcgt ttgtattgac cttaaaactc aaaaagcgtt agcgcttgaa      360
ggcgagttaa gagaaaagtt agagcagatg gttaaa                                396

<210> SEQ ID NO 98
<211> LENGTH: 957
<212> TYPE: DNA
<213> ORGANISM: Artificial Sequence
<220> FEATURE:
<223> OTHER INFORMATION: Codon optimized E. Coli AccA sequence

<400> SEQUENCE: 98
atgtcattaa atttcttaga ctttgaacaa ccaatagcag aacttgaagc gaaaattgat       60
tcattaaccg cagtttcaag acaagatgaa aagttagaca ttaatataga cgaagaagtc      120
catagactta gagaaaaatc agttgagtta actagaaaga ttttcgcaga ccttggtgca      180
tggcagattg cgcaacttgc aagacatcca caaagaccat ataccttaga ctatgtaaga      240
ttagcatttg acgagttcga cgagcttgcg ggtgaccgag cgtatgcgga cgataaagca      300
attgttggtg gcattgccag attagacgga aggccagtta tgattattgg acatcagaaa      360
gggagagaga ctaaggaaaa gattagaaga aatttcggca tgccagcacc agaggggctat    420
```

```
agaaaggcac ttagacttat gcagatggcg gaaagattca agatgccaat tataaccttc    480
attgataccc ctggagcgta tccaggcgtt ggcgccgaag agagaggcca atcagaggcg    540
attgcgagaa atcttagaga gatgtcaaga ctaggtgtgc ctgtagtatg taccgttatt    600
ggcgagggtg gaagtggcgg tgcccttgcg attgggttg gtgacaaagt gaatatgtta     660
cagtattcaa cctattcagt catttcacct gagggctgtg cgtcaattct ttggaaatca    720
gcggacaaag cgccattagc ggcagaggcg atggggatta ttgcaccaag acttaaagaa    780
ctaaagctta ttgattcaat tattccagag ccacttggtg gtgcgcatag aaatccagaa    840
gcgatggcag cgtcattaaa ggcgcagtta ttagcggatc tagcggactt agacgttctt    900
tcaaccgaag atcttaagaa tagaagatat cagagactta tgtcttatgg ttatgca       957
```

<210> SEQ ID NO 99
<211> LENGTH: 468
<212> TYPE: DNA
<213> ORGANISM: Artificial Sequence
<220> FEATURE:
<223> OTHER INFORMATION: Codon optimized E. Coli AccB sequence

<400> SEQUENCE: 99

```
atggatatta aaagataaa gaaactaatt gagttagtcg aagagagtgg tatatcagag    60
ttagaaattt cagagggtga agaatcagtt agaatttcaa gagcggcacc agcggcctct    120
ttcccagtca tgcagcaagc gtatgcggca ccaatgatgc agcaaccagc ccagtcaaat    180
gcggcagcgc cagcgaccgt accatcaatg gaagcgccag cagcagcgga gatttcaggc    240
catattgtta gatcacctat ggttggtacc ttctatagaa ccccttcacc agacgcgaaa    300
gcgtttattg aagtgggaca aaaggttaat gtaggcgata ccctttgtat tgttgaggca    360
atgaaaatga tgaatcagat tgaagcggac aaatcaggca ctgttaaggc aattcttgta    420
gagtcagggc aaccagttga gttcgacgaa ccacttgtgg ttattgaa                 468
```

<210> SEQ ID NO 100
<211> LENGTH: 1347
<212> TYPE: DNA
<213> ORGANISM: Artificial Sequence
<220> FEATURE:
<223> OTHER INFORMATION: Codon optimized E. Coli AccC sequence

<400> SEQUENCE: 100

```
atgttagaca agattgttat tgcaaataga ggggaaattg cgcttagaat tcttagagcg    60
tgtaaagaat taggcattaa gactgttgca gttcattcat cagcagacag agatcttaaa    120
catgttttac ttgcggacga aaccgtttgt attggtccag caccatcagt aaagtcatat    180
cttaatattc cagccattat ttcagccgcg gagattaccg gagcggtagc gattcatcca    240
ggttatggct tcttatcaga gaatgcgaat ttcgcagaac aagttgagag atcaggattc    300
attttcattg gtccaaaggc agaaaccatt agattaatgg cgacaaggt ttcagcgatt    360 gcggcgatga aaaaggcagg cgtcccatgt gttccaggct cagatggccc attaggtgac    420
gatatggaca gaatagagc catagcgaaa agaataggt atccagtaat tataaaggcg    480 tctggggggtg gcggtggtag aggtatgaga gtagtcagag cgacgcaga gctagcacaa    540 tcaatttcaa tgaccagagc ggaagcaaaa gcggcattct caaatgacat ggtgtatatg    600
gagaagtatt tagagaatcc aagacatgtg gagattcaag ttcttgcgga cggccagggt    660
aatgcgattt atcttgcgga aagagactgt agtatgcaga gaaggcatca gaaagttgtt    720
```

| | |
|---|---|
| gaagaagcac cagcgccagg tattacccct gaacttagaa gatatatagg cgagagatgt | 780 |
| gcaaaggcgt gtgttgacat tggttataga ggggcaggga cctttgagtt tcttttgag | 840 |
| aatggagagt tctatttcat tgaaatgaat accagaattc aagttgaaca tcctgttacc | 900 |
| gagatgatta ccggcgtgga cttaattaaa gagcaattaa gaattgcagc gggccagcca | 960 |
| ctttcaatta agcaagaaga agtccatgtt agaggacatg cggtcgagtg tagaattaat | 1020 |
| gcggaagatc ctaatacttt cttaccatca ccaggcaaga ttaccagatt ccatgcacct | 1080 |
| ggtggtttcg gtgtaagatg ggaatcacat atttatgcgg gctatactgt tccaccatat | 1140 |
| tatgactcaa tgattggtaa acttatttgt tatggagaga atagagatgt agcgattgcg | 1200 |
| agaatgaaaa atgctttaca agaactaatt attgacggta ttaagaccaa tgtggatctt | 1260 |
| cagattcgaa ttatgaatga tgagaatttt cagcatggcg gcaccaatat acattatctt | 1320 |
| gagaagaaac ttggattaca ggaaaaa | 1347 |

<210> SEQ ID NO 101
<211> LENGTH: 912
<212> TYPE: DNA
<213> ORGANISM: Artificial Sequence
<220> FEATURE:
<223> OTHER INFORMATION: Codon optimized E. Coli AccD sequence

<400> SEQUENCE: 101

| | |
|---|---|
| atgtcatgga tagaaagaat taagtcaaat attaccccaa ccagaaaggc gtcaattcca | 60 |
| gagggcgtat ggaccaagtg tgactcatgt ggtcaggttc tttatagagc cgaattagaa | 120 |
| agaaatcttg aggtttgtcc aaaatgtgac catcacatga aatgaccgc aagaaataga | 180 |
| ttacattcac ttttagacga aggctcactt gtggaattag gctcagagct tgaaccaaaa | 240 |
| gacgttctta agttcagaga cagtaagaag tataaagata gattagcatc agcacagaaa | 300 |
| gagactgggg agaaagatgc gttagtggtc atgaaaggta ccttatatgg aatgcctgtc | 360 |
| gttgcagctg cgttcgaatt cgcgtttatg ggcggttcaa tgggttcagt tgtaggcgcg | 420 |
| agattcgtta gagcagttga acaggcgtta gaagataatt gtccactaat ttgttttca | 480 |
| gcgtctggtg gtgcaagaat gcaagaagca ctaatgtcac ttatgcaaat ggcgaaaact | 540 |
| tcagcggcgc ttgcaaagat gcaagagaga gggttaccat atatttcagt tcttaccgac | 600 |
| ccaaccatgg ggggtgtctc agcgtcattc gcgatgttag cgacttaaa tattgccgag | 660 |
| ccaaaagcac ttattggctt cgcgggacca agagtgattg aacagaccgt tagggaaaag | 720 |
| cttccacctg gatttcagag atcagagttc cttattgaaa aaggcgcgat tgatatgata | 780 |
| gttagacgac cagagatgag attaaagctt gcgtcaattc ttgcaaagtt aatgaatctt | 840 |
| ccagcgccta atccgaaagc accaagagag ggtgttgtag tacctccagt tccagaccaa | 900 |
| gagccagagg cg | 912 |

<210> SEQ ID NO 102
<211> LENGTH: 568
<212> TYPE: DNA
<213> ORGANISM: Artificial Sequence
<220> FEATURE:
<223> OTHER INFORMATION: Codon optimized E. Coli TesA with periplasmic
      targeting sequence removed

<400> SEQUENCE: 102

| | |
|---|---|
| ggtctctaat ggcagacaca cttttgatct tgggcgactc actttccgcg ggctatcgta | 60 |
| tgagtgcgtc cgcggcgtgg cccgcgctgc tgaacgacaa gtggcagagc aagacctccg | 120 |

```
tcgtcaacgc gtccatctcg ggcgacacga gccagcaggg actggcccgc ctcccggcgc    180
tgctcaagca gcatcagcca cgctgggtgc tcgtcgagct gggtggcaac gacgggctcc    240
gcggcttcca accgcagcag accgaacaga ccctccggca aattctccaa gacgtcaaag    300
cggccaacgc ggagcccctg ctgatgcaga tccgcctgcc ggcgaactac ggtcggcgtt    360
ataatgaggc gttcagcgcc atctatccga agctggccaa ggaattcgac gtgcccctcc    420
tcccgttttt catggaagaa gtgtacctca agcccagtg gatgcaagac gacggcatcc     480
acccgaatcg cgacgcgcag ccgttcatcg cggactggat ggcgaagcag ctgcagccgc    540
tcgtaaacca cgactcgtaa aagagacc                                      568
```

<210> SEQ ID NO 103
<211> LENGTH: 568
<212> TYPE: DNA
<213> ORGANISM: Artificial Sequence
<220> FEATURE:
<223> OTHER INFORMATION: Codon optimized E. Coli TesA with periplasmic
      targeting sequence removed

<400> SEQUENCE: 103

```
ggtctctaat ggctgatacc ctcttgattc ttggtgattc ccttagcgcc ggctaccgca    60
tgtccgcgag cgccgcatgg ccggcgctgc tgaatgacaa gtggcagtcc aagacctcgg    120
tcgtcaatgc gagcatcagc ggcgacacct cgcagcaggg cctcgcgcgg ctgccggccc    180
tcctgaagca acatcagccg cgctgggtac tcgtggagct cggcggcaat gatgggctgc    240
gtggcttcca gccccaacag accgagcaga cgttgaggca gatcctccaa gacgtgaagg    300
cagcgaatgc ggagcctctc ctcatgcaga tccggctgcc cgcgaattat ggccgccgtt    360
acaacgaggc cttctcggcg atctatccga agctcgcgaa agagttcgac gtcccgctgc    420
tgcccttctt tatggaggag gtgtacctga agccgcaatg gatgcaggat gacggcatcc    480
acccgaaccg ggacgcgcag cccttcatcg ccgattggat ggcgaagcag ctgcagccgc    540
tggttaatca tgacagttaa aagagacc                                      568
```

<210> SEQ ID NO 104
<211> LENGTH: 568
<212> TYPE: DNA
<213> ORGANISM: Artificial Sequence
<220> FEATURE:
<223> OTHER INFORMATION: Codon optimized E. Coli TesA with periplasmic
      targeting sequence removed

<400> SEQUENCE: 104

```
ggtctctaat ggccgatacc ctgctgatcc tcggcgattc acttagcgct ggataccgca    60
tgagcgcctc ggctgcgtgg cctgcactcc tcaacgacaa gtggcagagc aagacctcgg    120
tggtcaacgc gtccatttcg ggcgacacca gtcagcaggg cctcgccagg ctgcctgccc    180
tgctgaagca acatcagccg cgctgggtcc tggtcgagct tggcggcaac gacggcctcc    240
gggggttcca gccgcaacag acggagcaga cgttgcggca gattctccag gatgtaaagg    300
cggcgaatgc cgagccgctc ctgatgcaga tcaggctccc ggccaactat ggtcgccgct    360
ataacgaggc gttctccgca atctaccccca agctggcaaa agaattcgac gtgccgctgc    420
tgccattttt catggaagaa gtgtacctca agccgcagtg gatgcaagat gatgggtatcc   480 accccaaccg ggacgcccaa cccttcatcg ccgactggat ggcgaagcag ctgcagcccc    540
ttgtcaatca cgactcctaa aagagacc                                      568
```